(12) United States Patent
Yasunaga et al.

(10) Patent No.: US 8,234,838 B2
(45) Date of Patent: Aug. 7, 2012

(54) MEDICINE DISPENSING SYSTEM AND MEDICINE DISPENSING DEVICE

(75) Inventors: Itsuo Yasunaga, Toyonaka (JP); Chisei Asaoka, Toyonaka (JP); Norifumi Oike, Toyonaka (JP); Kensuke Kaminishi, Toyonaka (JP); Masahiko Kasuya, Toyonaka (JP); Nakaji Takeda, Toyonaka (JP); Hiromichi Tsuda, Toyonaka (JP); Yasuyuki Morita, Toyonaka (JP); Shinya Taira, Toyonaka (JP); Tomohiro Sugimoto, Toyonaka (JP); Naomichi Toyota, Toyonaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 225 days.

(21) Appl. No.: 12/765,741

(22) Filed: Apr. 22, 2010

(65) Prior Publication Data
US 2010/0287880 A1 Nov. 18, 2010

Related U.S. Application Data

(63) Continuation-in-part of application No. PCT/JP2008/069208, filed on Oct. 23, 2008.

(30) Foreign Application Priority Data

| Oct. 23, 2007 | (JP) | 2007-274931 |
| Oct. 23, 2007 | (JP) | 2007-274932 |
| Oct. 23, 2007 | (JP) | 2007-274933 |
| Oct. 23, 2007 | (JP) | 2007-274934 |
| Jul. 23, 2008 | (JP) | 2008-190195 |
| Sep. 19, 2008 | (JP) | 2008-240590 |
| Oct. 10, 2008 | (JP) | 2008-264662 |

(51) Int. Cl.
*B65B 35/54* (2006.01)
*B65H 3/08* (2006.01)

(52) U.S. Cl. .......... 53/55; 53/154; 53/167; 53/237; 221/123; 221/133; 221/278

(58) Field of Classification Search .......... 53/55, 154, 53/167, 237, 551; 221/123, 130–133, 278
See application file for complete search history.

(56) References Cited

U.S. PATENT DOCUMENTS
5,097,652 A * 3/1992 Inamura et al. .......... 53/154
(Continued)

FOREIGN PATENT DOCUMENTS
JP 61-273301 A 12/1986
(Continued)

OTHER PUBLICATIONS
U.S. Appl. No. 13/364,125, filed Feb. 1, 2012, Yasunaga.
(Continued)

*Primary Examiner* — Stephen F Gerrity
(74) *Attorney, Agent, or Firm* — Jones Day; Christopher C. Bolten

(57) ABSTRACT

There is provided a medicine dispensing system configured such that a medicine dispensing device includes a sub unit having a function to dispense medicine that is connected to a medicine dispensing device that includes a main unit having a function of packing medicines. There is also provided a medicine dispensing device that can be appropriately integrated with such a medicine dispensing system. The medicine dispensing system includes, in some embodiments a main unit, a sub unit and a transfer device connecting the main unit and the sub unit. The medicine dispensing system transfers the medicine dispensed in the sub unit to the main unit by means of a transfer device and dispenses the medicine at a medicine packing part together with the medicine dispensed from a main storage part in the main unit.

25 Claims, 62 Drawing Sheets

U.S. PATENT DOCUMENTS

| | | | |
|---|---|---|---|
| 5,709,063 A | 1/1998 | Yuyama et al. | |
| 5,787,678 A * | 8/1998 | Koike et al. | 53/154 |
| 5,930,145 A | 7/1999 | Yuyama et al. | |
| 6,145,700 A | 11/2000 | Takahashi et al. | |
| 6,405,893 B1 | 6/2002 | Tobe et al. | |
| 6,449,921 B1 * | 9/2002 | Kim | 53/154 |
| 6,510,668 B2 * | 1/2003 | Kim | 53/154 |
| 6,690,998 B1 * | 2/2004 | Yuyama | 53/154 |
| 6,772,907 B2 * | 8/2004 | Kim | 53/154 |
| 6,792,736 B1 * | 9/2004 | Takahashi et al. | 53/237 |
| 7,080,755 B2 | 7/2006 | Handfield et al. | |
| 7,277,776 B2 | 10/2007 | Kim | |
| 7,293,672 B2 * | 11/2007 | Mori et al. | 53/154 |
| 7,455,163 B2 * | 11/2008 | Yuyama et al. | 53/154 |
| 7,690,529 B2 * | 4/2010 | Kim | 221/133 |
| 7,747,345 B2 | 6/2010 | Ohmura et al. | |
| 7,827,764 B2 * | 11/2010 | Yuyama et al. | 53/237 |
| 2008/0029530 A1 | 2/2008 | Yuyama et al. | |
| 2008/0173664 A1 * | 7/2008 | Kim | 221/133 |

FOREIGN PATENT DOCUMENTS

| | | |
|---|---|---|
| JP | 62-032037 | 2/1987 |
| JP | 4-179624 A | 6/1992 |
| JP | 4-317714 A | 11/1992 |
| JP | 7-15655 | 3/1995 |
| JP | 2807931 B | 7/1998 |
| JP | 11-226086 A | 8/1999 |
| JP | 11-278402 A | 10/1999 |
| JP | 2001-276183 A | 10/2001 |
| JP | 2002-370703 A | 12/2002 |
| JP | 2006-130307 | 5/2006 |
| JP | 2007-202932 A | 8/2007 |

OTHER PUBLICATIONS

U.S. Appl. No. 13/364,199, filed Feb. 1, 2012, Yasunaga.
U.S. Appl. No. 13/364,210, filed Feb. 1, 2012, Yasunaga.
Non-final Office action for U.S. Appl. No. 13/364,210, mailed Apr. 13, 2012.

* cited by examiner

FIG. 10
(a)
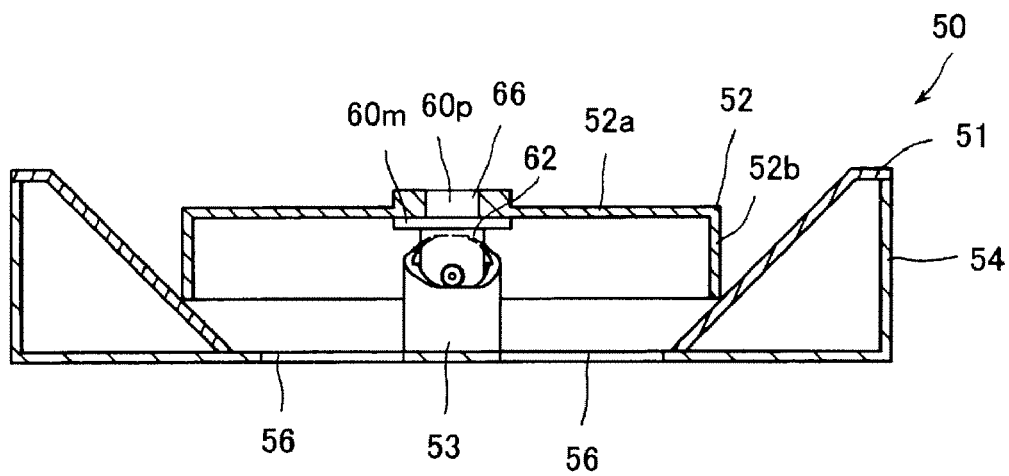
(b)
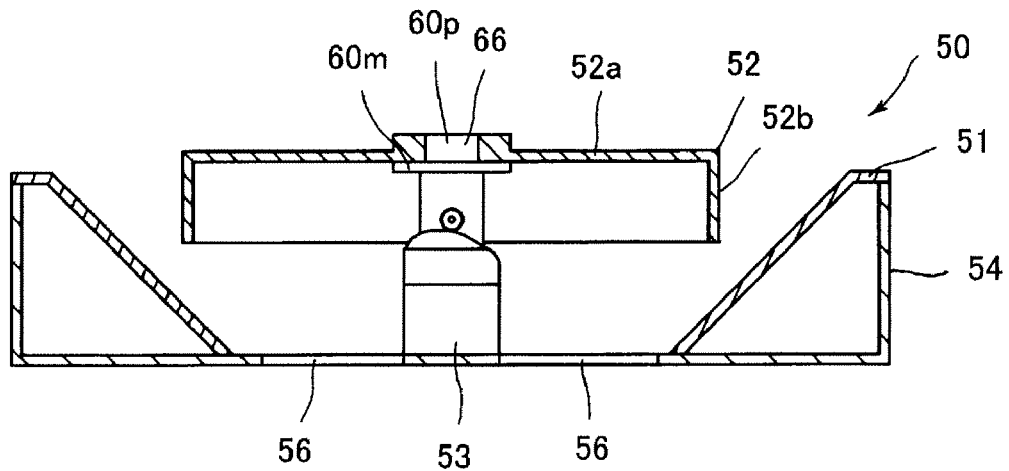

FIG. 19
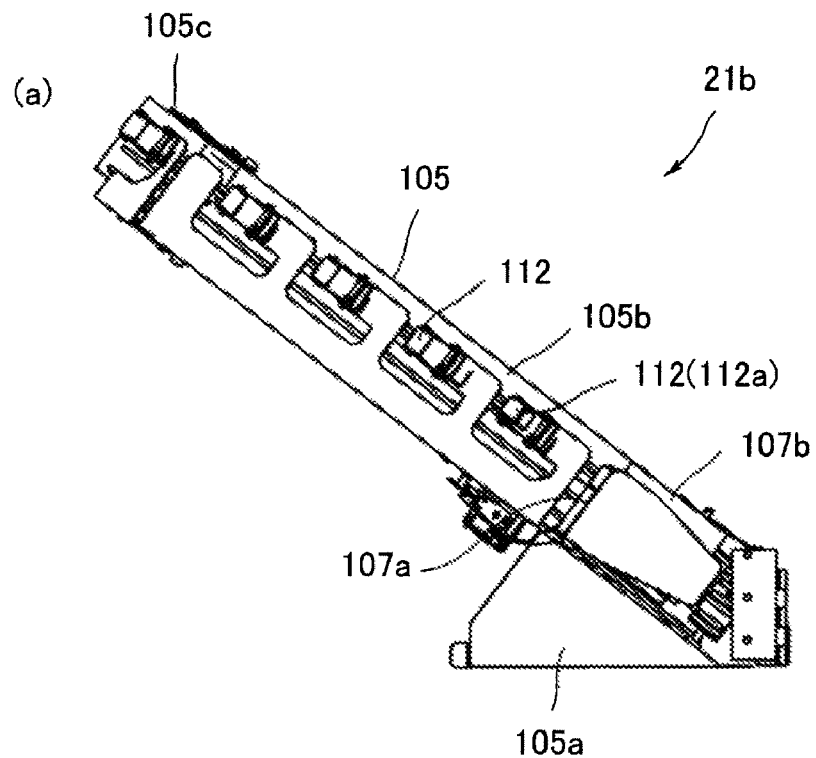
(a)
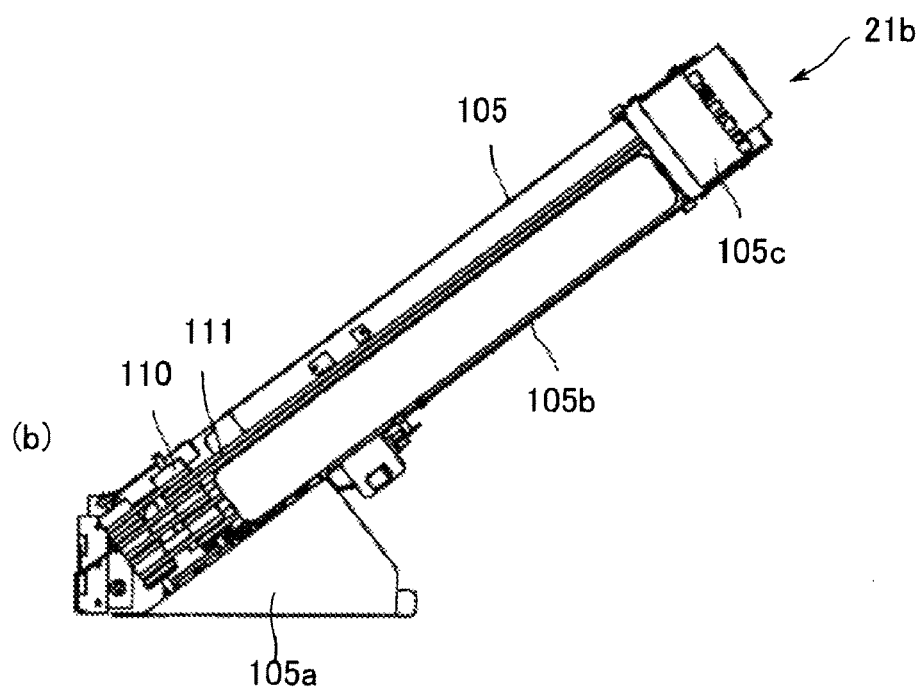
(b)

FIG. 20
(a)
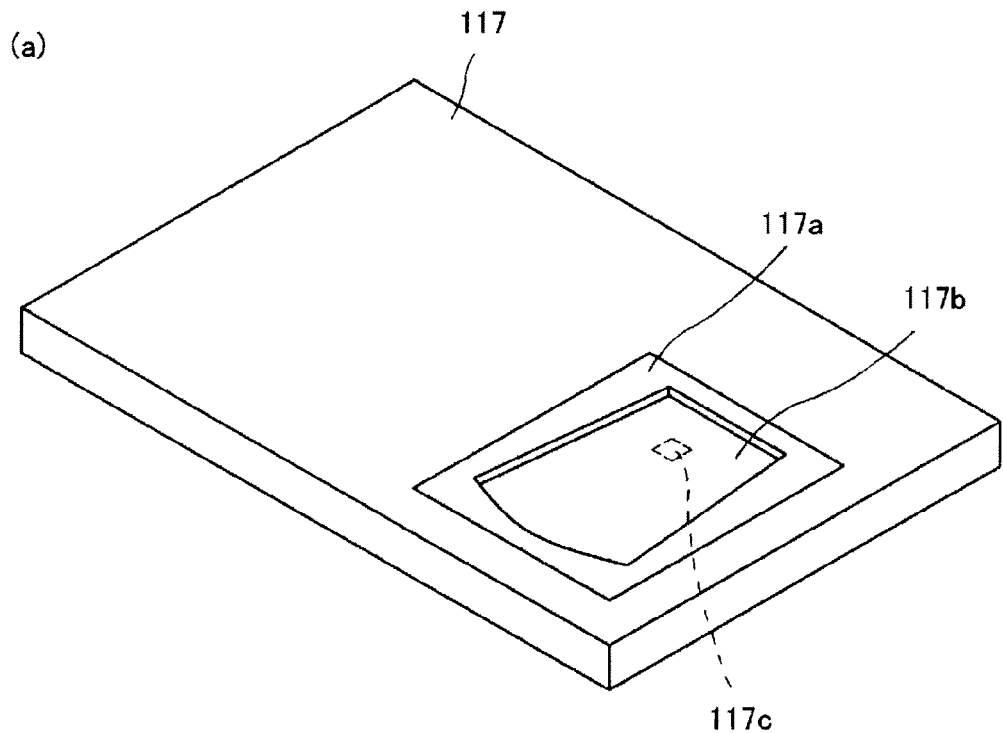
(b)
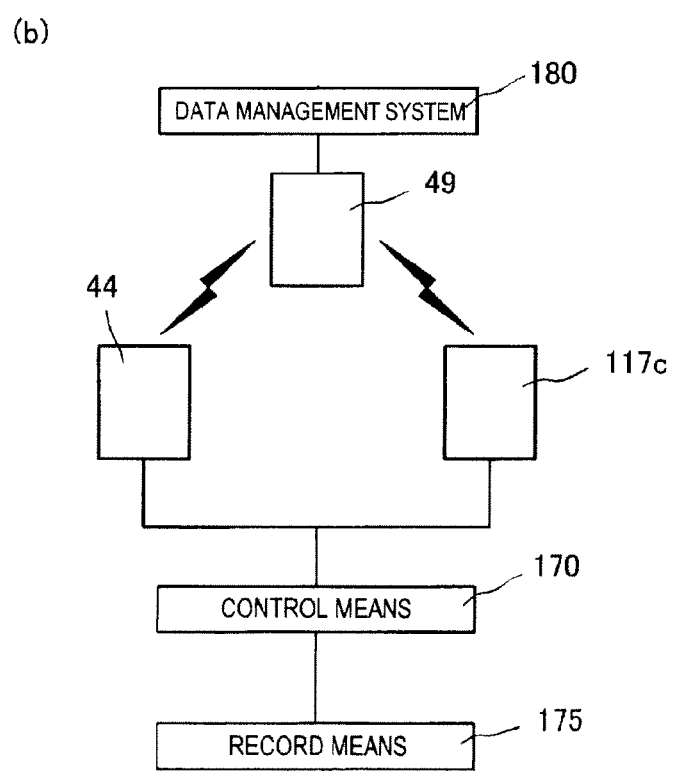

FIG. 21
(a)
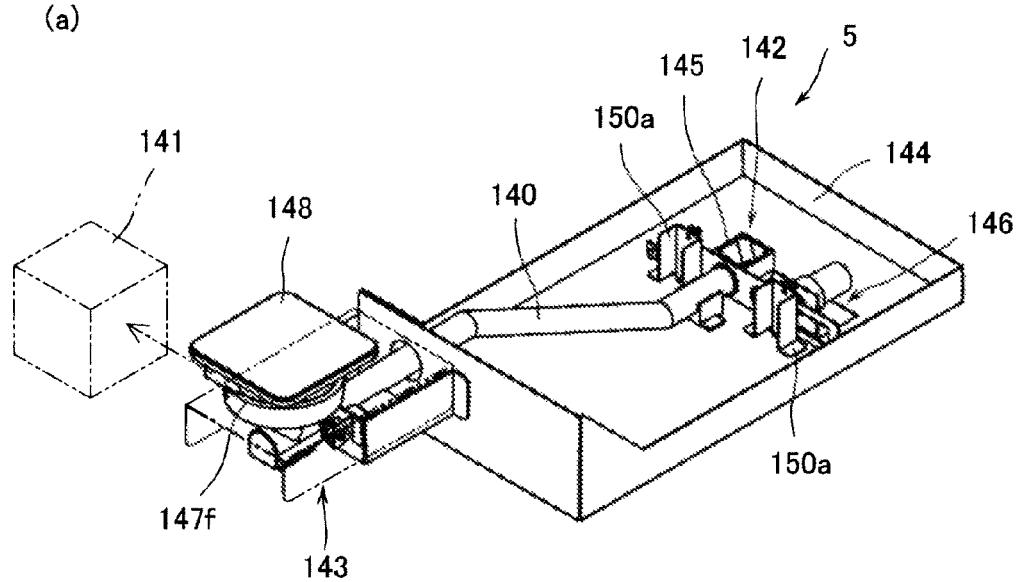
(b)
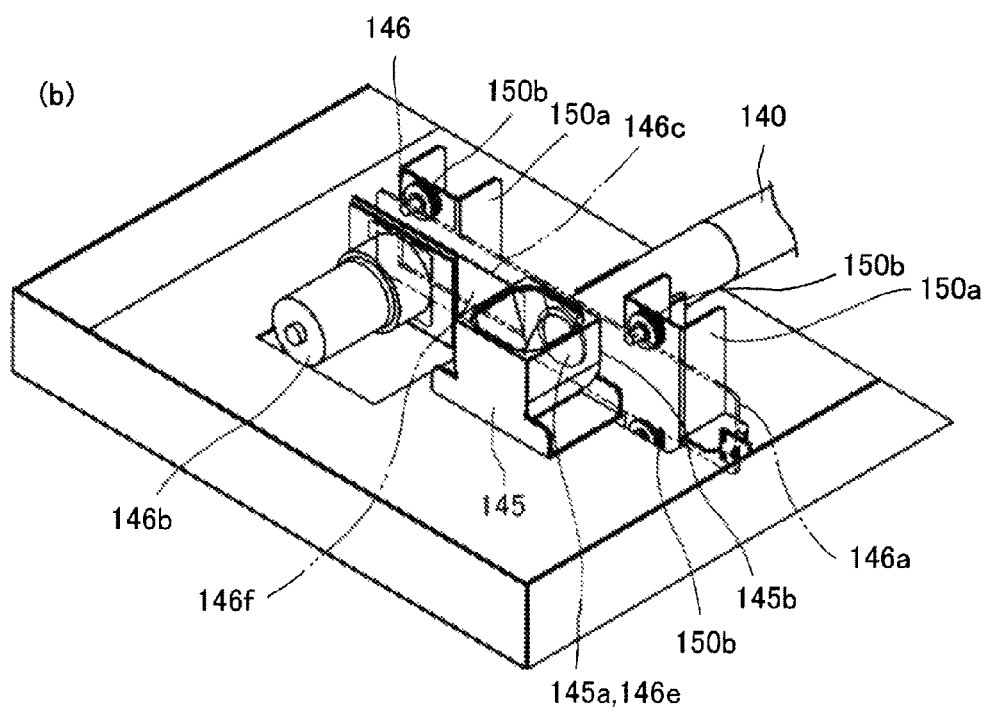

FIG. 22D

WAITING. PACKING OPERATION CAN BE PERFORMED.

STOP
OPEN/CLOSE DTA
SET DTA
CALL MEDICINE NAME
RELEASE
MAINTENANCE

OPERATOR: YUYAMA, TARO
MEDICINE NAME(CASSETTE): BUFFERIN
MEDICINE NAME(BARCODE): ALFAROL
TABLET NUMBER:
INQUIRY OK
START FILLING
RETURN

PACK NUMBER
ID:
EXCHANGE COUPON No.:
PAPER-REMAINING AMOUNT
DTA RESERVATION No.: 0
TEMPERATURE: 100°C
COMMUNICATION: ○

FIG. 23
(a)
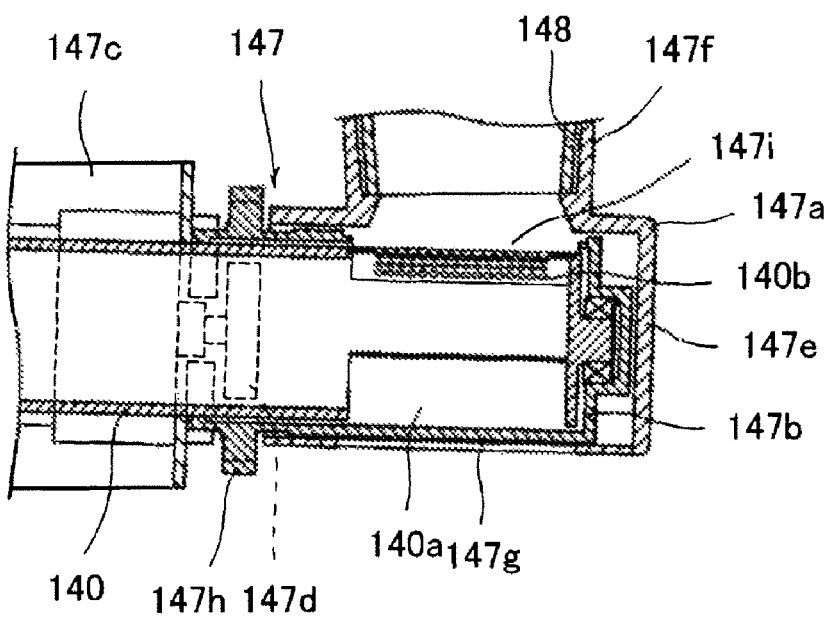
(b)
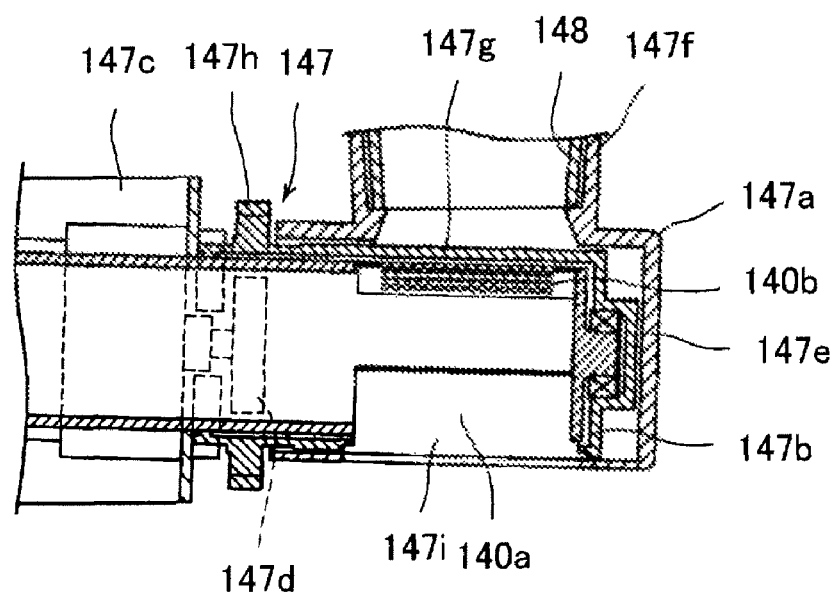

FIG. 25
(a)
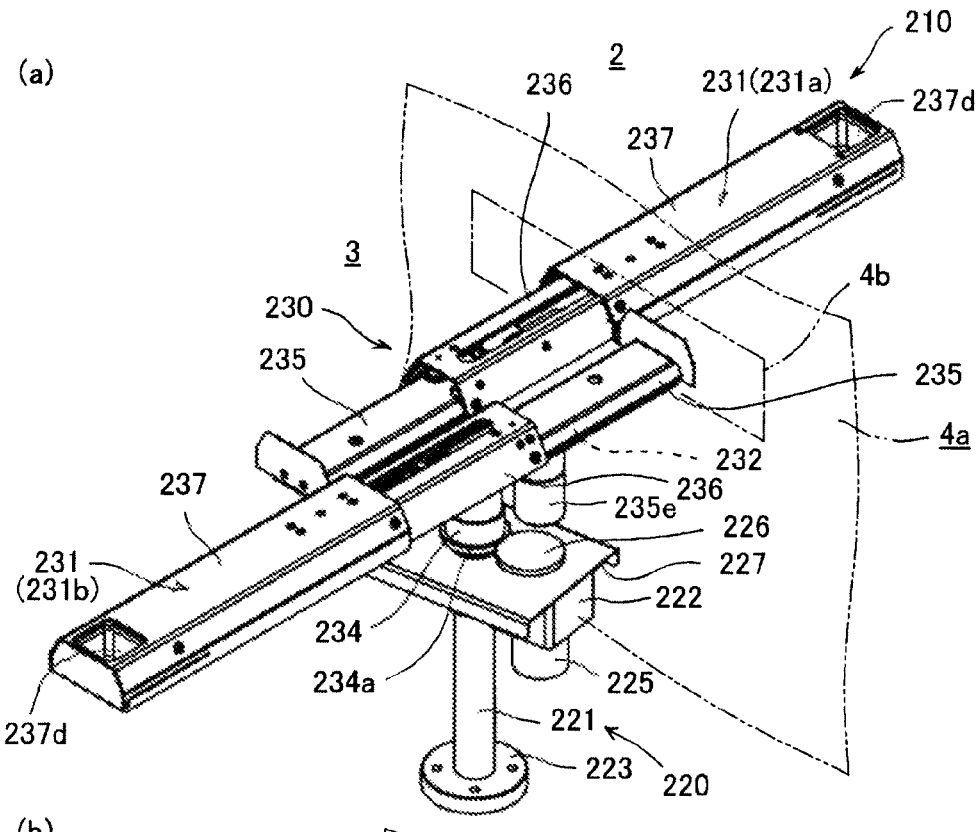
(b)
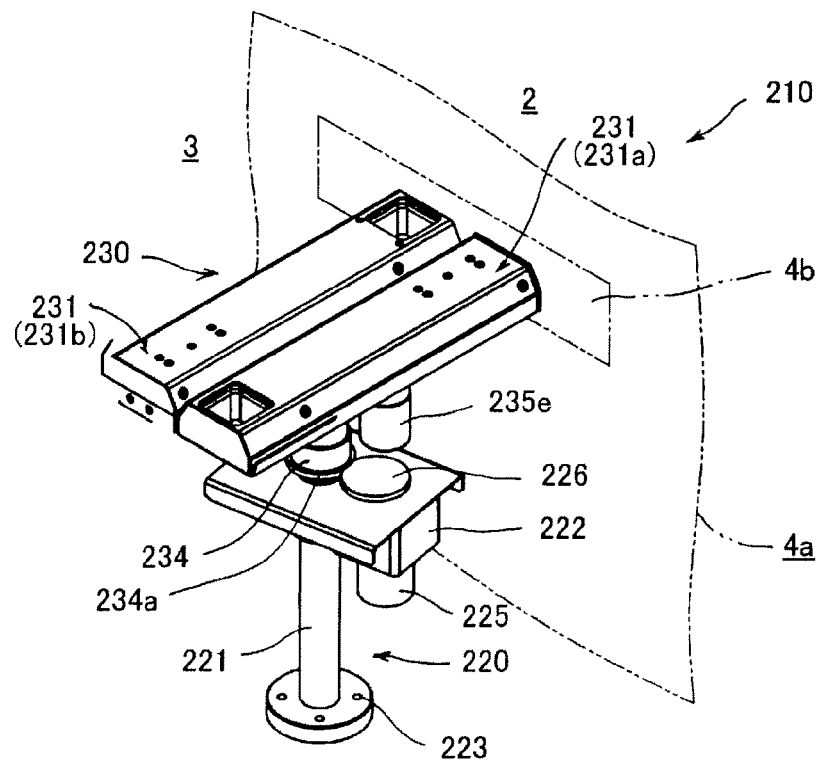

FIG. 29
(a)
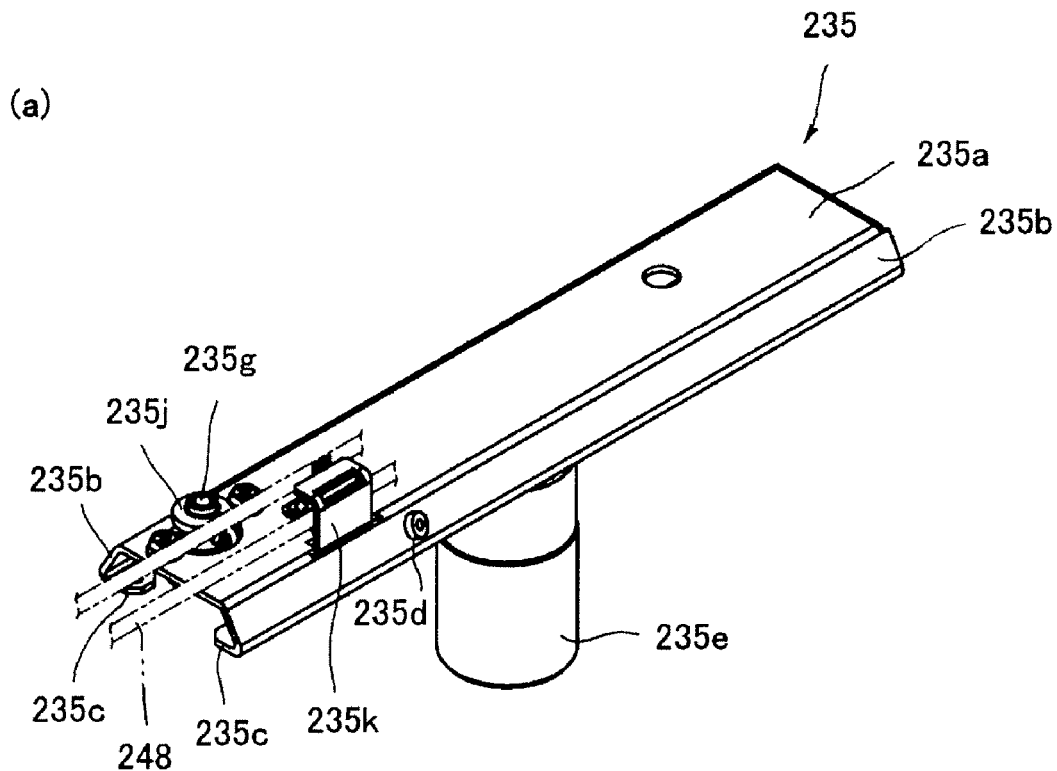
(b)
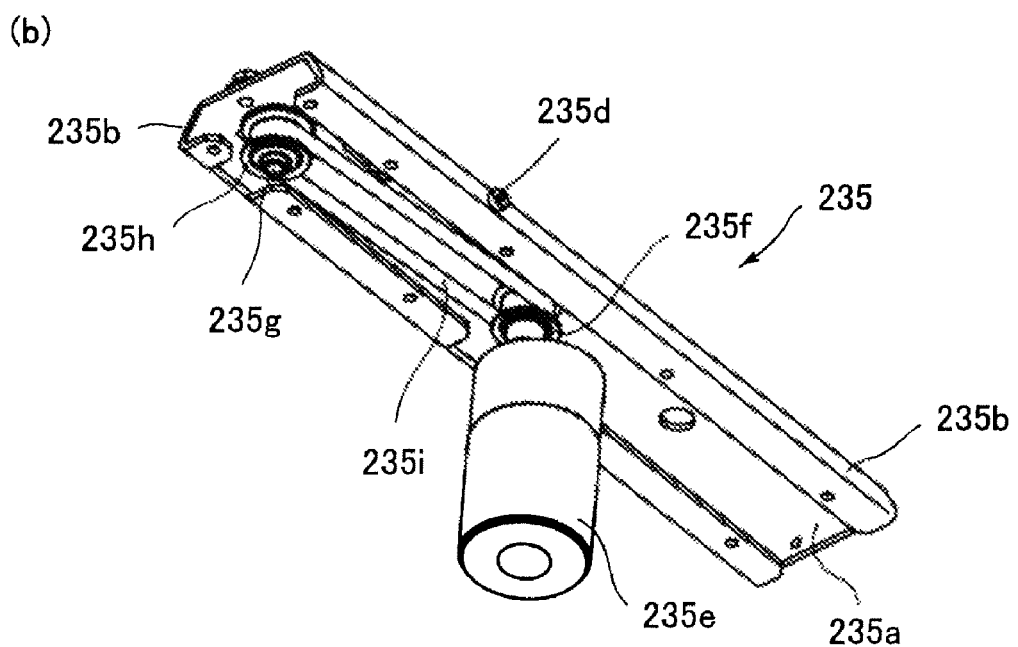

FIG. 40
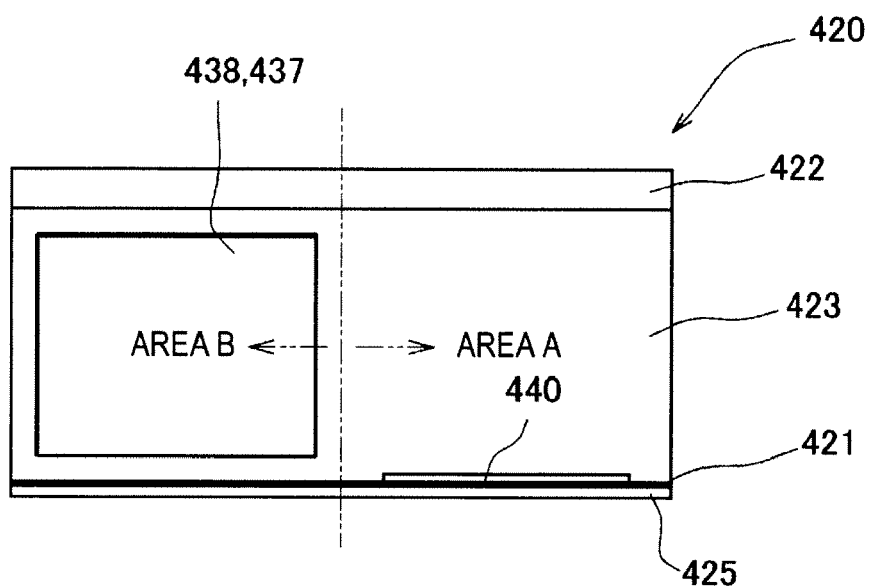
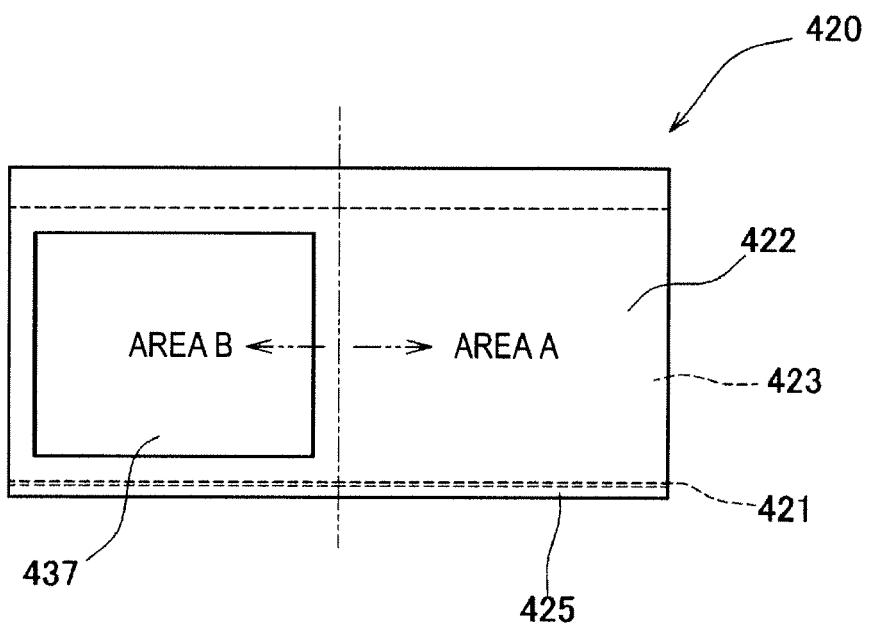

FIG. 56

CASSETTE IS MOUNTED AT A WRONG PLACE

| SHELF NO. | MEDICINE NAME |
|---|---|
| 1 | ALFAROL |
| 4 | BUFFERIN 5mg |
| 15 | AKINATE TABLET |
| 33 | TOUGHMAC |
| 45 | NAUZELIN TABLET |
| 78 | SERMION TABLET |
| 100 | CINAL TABLET |
| 184 | EPADEL |
| 287 | VITAMEDIN |
| 301 | MYONAL |

PACK NUMBER 10

ID: 0000000001
YUYAMA, TARO
EXCHANGE COUPON No.: 1234
THREE TIMES PER DAY
21-DAYS DOSE
CONTINUATION CASSETTE

PAPER-REMAINING AMOUNT

DTA RESERVATION No.: 0 | TEMPERATURE: 100°C | COMMUNICATION: ○

STOP | OPEN/CLOSE DTA | SET DTA | CALL CASSETTE | RELEASE | TO PRESCRIPTION

MEDICINE DISPENSING SYSTEM AND MEDICINE DISPENSING DEVICE

CROSS-REFERENCE TO RELATED APPLICATIONS

This application is a continuation-in-part under 35 U.S.C. §§120 and 365(c) of International Patent Application No. PCT/JP2008/069208, filed Oct. 23, 2008, the entire contents of which are incorporated by reference herein, which claims the benefit of the following applications, the entire contents of each of which are incorporated by reference herein:

Japanese Patent Application No. 2007-274931, filed Oct. 23, 2007,
Japanese Patent Application No. 2007-274932, filed Oct. 23, 2007,
Japanese Patent Application No. 2007-274933, filed Oct. 23, 2007,
Japanese Patent Application No. 2007-274934, filed Oct. 23, 2007,
Japanese Patent Application No. 2008-190195, filed Jul. 23, 2008,
Japanese Patent Application No. 2008-240590, filed Sep. 19, 2008, and
Japanese Patent Application No. 2008-264662, filed Oct. 10, 2008.

TECHNICAL FIELD

The present invention relates to a medicine dispensing system constructed by adding a sub unit to a main unit. Further, the present invention relates to a medicine dispensing device for such a sub unit.

BACKGROUND ART

There exists in the art a medicine dispensing device as disclosed in the below-mentioned reference Patent Document 1. A prior art medicine dispensing device has a storage part for storing a plurality kinds of medicines. Such a prior art medicine dispensing device is constructed to pack medicines removed from the storage part according to prescriptions and dispense the same.

Patent Document 1: Japanese Laid-Open Patent Application No. 2001-276183

SUMMARY OF THE INVENTION

In a prior art medicine dispensing device, the storage part is configured to accommodate a plurality kinds of medicines. However, with an increase in the kinds of medicines to be dealt with, more kinds of medicines than those accommodated by the storage part must be dealt with. Installing a plurality of prior art medicine dispensing devices can address such a need. However, there is a problem with such solution in that each medicine dispensing device packs medicines in a different manner. Further, installing a plurality of medicine dispensing devices has another problem in that it needs a larger installation area resulting in higher maintenance costs.

In one embodiment, a medicine dispensing system is configured such that a medicine dispensing device includes a sub unit having a function of dispensing medicines that is connected to a medicine dispensing device that includes a main unit having a function of packing medicines. The present invention also seeks to provide a medicine dispensing device that can be appropriately employed to such a medicine dispensing system.

In another embodiment, a medicine dispensing system includes a main unit; one or more sub units; and a transfer device configured to connect the main unit and the sub units. The main unit includes: a main storage part configured to store and dispense a plurality kinds of medicines; and a packing part configured to pack the medicine dispensed from the main storage part. The sub unit includes a sub storage part configured to store and dispense a plurality kinds of medicines. The transfer device transfers the medicine dispensed from the sub storage part toward the main unit. The packing part of the main unit packs and dispenses the medicine.

The medicine dispensing system of the present invention includes the main unit and the sub unit and can transfer the medicine dispensed from the sub storage part provided in the sub unit toward the main unit using the transfer device. Further, in the medicine dispensing system of the present invention, the main unit has the packing part. The main unit can pack not only the medicine dispensed from the main storage part of the main unit, but also the medicine from the sub storage part of the sub unit at the pack part. Thus, the medicine dispensing system of the present invention can deal with many kinds of medicines and a large quantity of medicine through use of the sub unit when compared to utilizing the main unit alone.

Further, the packing part of the main unit is capable of packing the medicine dispensed in the sub unit. Thus, the medicines dispensed from both the main unit and the sub unit can be packed into equal medicine packs or containers. Further, the medicine dispensing system of the present invention does not need a packing part to be included in the sub unit. Thus, not providing a packing part to the sub unit allows the sub unit to be compact or to be configured to accommodate more kinds of medicines and a larger quantity of medicine. Moreover, this can minimally decrease the installation area of the medicine dispensing system as well as the maintenance task thereof.

Further, the transfer device of the medicine dispensing system may have the pipe line connecting the main unit and the sub unit and the transfer means configured to suck or pressure-send the medicine staying in the pipe line from the sub unit toward the main unit.

According to such configuration, the medicines dispensed from the sub storage part in the sub unit may be easily transferred to the main unit.

The transfer device, which the medicine dispensing system of some embodiments includes, is configured to suck or pressure-send medicines existing in the pipe line by means of the medicine transfer means. Thus, according to the above-described transfer device, medicines can be rapidly transferred from the sub unit toward the main unit. Further, the above-described transfer device is capable of a transfer path of the medicines by appropriately adjusting the shape of the pipe line. Thus, the medicine dispensing system of in an embodiment has a higher degree of freedom in arrangement on the main unit and the sub unit.

Further, the transfer path of the transfer means can be set by appropriately adjusting the pipe line. Thus, it is possible to appropriately set the dispensing position of the medicine transferred by the transfer device in the main unit and the delivery position of delivering the medicine to be transferred to the transfer device. Accordingly, layout and configuration of members or components making up the main unit and the sub unit can be adjusted independently and respectively. Specifically, in the medicine dispensing system of one embodiment, the layout and configuration of the sub storage part of the sub unit can be adjusted to be adapted to the medicine storage or the medicine dispensing independently of the layout and configuration of the main storage part, a medicine awaiting part, the packing part, etc. Thus, in the medicine dispensing system of the present invention, it is possible to optimize the layout and configuration of the main unit and the sub unit.

Further, the transfer device may have a medicine delivering part configured to receive and dispense a medicine. The medicine delivering part may be configured to turn about a turning shaft and expand and contract in a direction orthogonal to the turning shaft.

The transfer device, in some embodiments, has the medicine delivering part configured to receive and dispense a medicine. The medicine delivering part is configured to turn about the turning shaft and expand and contract in the direction orthogonal to the turning shaft. Thus, the medicine dispensing system in some embodiments is capable of receiving the medicine dispensed in the sub unit and delivering the same to the main unit by appropriately turning the medicine delivering part or expanding and contracting the medicine delivering part according to the arrangement of the main unit and the sub unit.

The medicine dispensing system of the present invention can appropriately adjust the arrangement of the main unit and the sub unit within a range wherein the medicine can be delivered by the transfer means. Thus, the medicine dispensing system of the present invention has a higher degree of freedom in the arrangement of the main unit and the sub unit. Further, the medicine delivering part is capable of turning and expanding and contracting in the direction orthogonal to the turning shaft. Thus, the medicine delivering part can turn as contracted and therefore a space necessary for turning of the medicine delivering part can be minimized. Accordingly, the present invention can contribute saving space in the medicine dispensing system.

Further, the transfer device may include a medicine delivery container configured to receive and dispense a medicine; and a drive mechanism configured to move the medicine delivery container between the main unit and the sub unit. The drive mechanism may include a conveying part configured to reciprocate the medicine delivering part; a direction adjusting means configured to adjust a direction of the conveying means relative to the main unit and the sub unit by turning the conveying means.

The transfer device, which is employed in the present invention, is configured to reciprocate the medicine delivery container for receiving and dispensing a medicine in the conveying part and to adjust the direction thereof relative to the main unit and the sub unit by turning the conveying part. Thus, in the medicine dispensing system of the present invention, the medicine dispensed in the sub unit can be received into the medicine delivering part by adjusting the inclined direction of the delivering part such that the medicine dispensed from the sub storage part of the sub unit is situated in a position where the medicine can be received. Further, the medicine dispensed in the sub unit can be delivered to the main unit by adjusting an inclination of a conveyance path such that the medicine delivery container reaches a position where the medicine is delivered in the main storage part after the medicine is received in the medicine delivering part, and then by moving the medicine delivering part to the main unit.

The medicine dispensing system in some embodiments can appropriately adjust the arrangement of the main unit and the sub unit within a range wherein the medicine can be delivered by the transfer means. Thus, the medicine dispensing system can appropriately adjust the arrangement of the main unit and the sub unit.

Further, the transfer device may include a forward pipe line connecting the main storage part and the sub storage part; an airflow producing means producing airflow from the sub unit toward the main unit within the forward pipe line; an exhaust pipe line connected to the main storage part; a suction and exhaust means sucking and exhausting through the exhaust pipe line from an inside portion of the main storage part to an outside portion thereof; and a shutter disposed between the forward pipe line and the exhaust pipe line and the main storage part. The transfer device may be configured to perform the following: a medicine transferring operation for moving a medicine to the main storage part by operating the airflow producing means in a closed state where the forward pipe line is closed by the shutter; and a medicine introducing operation for introducing a medicine from the forward pipe line to the main storage part by operating the airflow producing means in a communication state where the shutter is opened and the forward pipe line, the exhaust pipe line and the main storage part are in communication with one another.

The medicine dispensing system can transfer medicine from the sub storage part toward the main storage part through the medicine transferring operation and thereafter can introduce the medicine transferred in such a manner to the main storage part through the medicine introducing operation. Thus, the medicine dispensing system of the present invention can deliver the medicine from the sub storage part to the main storage part by repeating the above-described medicine transferring operation and medicine introducing operations.

Further, in the medicine dispensing system of the present invention, since the operation for transferring the medicine between the main unit and the sub unit and the operation for introducing the medicine in the main unit are separately performed, the velocity of the airflow flowing within the forward pipe line during transfer of the medicine may be not so fast. Thus, in the medicine dispensing system of on embodiment, the medicines transferred from the main unit to the sub unit can be prevented from severely colliding with each other, breaking or chipping during their transfer.

In the above-described medicine dispensing system, the shutter may include a forward obstruction portion for obstructing a space between the forward pipe line and the main storage part; and a buffer means provided at the forward obstruction portion and configured to buffer an impact caused by a collision of the medicines proceeding within the forward pipe line.

With the above-described construction, the buffer means buffers the impact caused by a collision of the medicines with the shutter in the medicine transferring operation. Thus, the medicine dispensing system of the present invention can surely prevent the medicines from breaking or chipping due to collisions with the shutter in the medicine transferring operation.

The above-described medicine dispensing system may include a partitioning means configured to partition an internal space of the main storage part. Further, the medicine dispensing system may be configured such that when the shutter becomes opened, both the exhaust pipe line and the forward pipe line become in communication with a space, which is formed according to a division caused by the partitioning means.

The above-described medicine dispensing system can decrease the volume of the space, with which, when the shutter becomes opened, both the exhaust pipe line and the forward pipe line become in communication with each other, by partitioning the internal space of the main storage part through the partitioning means. Thus, the above-described medicine dispensing system does not need to excessively enlarge the exhaust capacity of the suction and exhaust means in order to introduce the medicine from the forward pipe line to the main storage part in the medicine introducing operation. Further, according to the above-described configuration, the exhaust capacity of the suction and exhaust means can be restricted. Thus, when the medicines are introduced to the main storage part, it is possible to prevent the medicines from colliding into one another and colliding with an inner peripheral surface of the main storage part or to buffer the impact resulting from such collision. Further, it is possible to more certainly prevent occurrence of the breakage or chipping of the medicines along with the medicine transfer.

In the above-described medicine dispensing system, it is preferred that the velocity of airflow flowing to transfer the medicine toward the main unit in the medicine transferring operation is slower than that of the airflow flowing to introduce the medicine to the main unit in the medicine introducing operation.

According to such configuration, it is possible to certainly prevent the medicine transferred from the sub unit through the medicine transferring operation from colliding with the shutter to thereby break.

In the above-described medicine dispensing system, the exhaust pipe line may connect the main storage part and the sub storage part.

The above-described medicine dispensing system may include a filter provided at a halfway portion of a flow line wherein airflow is produced concomitantly with transferring the medicine between the sub storage part and the main storage part; an airflow amount detecting means configured to detect an airflow amount in the flow line concomitantly with transferring the medicine from the main storage part to the sub storage part; and a clogging judging means configured to judge a clogging of the filter based on the airflow amount detected by the airflow amount detecting means.

According to such configuration, the clogging of the filter can be easily and certainly detected and thus maintenance of the filter can be performed at an appropriate time.

In case of employing such configuration, when it is doubtful whether the filter is clogged due to a decrease in the airflow amount detected by the airflow amount detecting means, the clogging judging means may judge the clogging of the filter and then the operation for transferring the medicine may be immediately stopped. If so, the medicine stops in the middle of the forward pipe line, thereby leading to troubles in the dispensing operation. Therefore, although the filter could be possibly clogged, it is preferred that the medicine dispensing system is configured to transfer the medicine to the main storage part.

Further, it is more preferable that the medicine dispensing system is configured to transfer the medicine to the main storage part by increasing the output of the airflow producing means and/or the suction and exhaust means when there is a decrease in the airflow amount detected by the airflow amount detecting means, and to judge the clogging of the filter by the clogging detecting means upon when there is an increase in the output of the airflow producing means and/or the suction and exhaust means.

When the medicine dispensing system is configured as indicated above, it is possible in some embodiments to transfer the medicine to the main storage part prior to judging the clogging of the filter by increasing the output of the airflow producing means or the suction and exhaust means. Thus, according to such configuration, it is possible to prevent problems during the dispensing operation, which may occur because the medicines stop in the middle of the forward pipe line due to the clogging of the filter.

The above-described medicine dispensing system may include a filter provided at a halfway portion of a flow line wherein airflow is produced concomitantly with transferring the medicine between the sub storage part and the main storage part; an airflow amount detecting means configured to detect an airflow amount in the flow line concomitantly with transferring the medicine from the main storage part to the sub storage part; and a notifying means. The medicine dispensing system may be configured to transfer the medicine to the main storage part by increasing the output of the airflow producing means and/or the suction and exhaust means upon a condition of decrease in the airflow amount detected by the airflow amount detecting means, and to notify the clogging of the filter by the notifying means.

Where the medicine dispensing system is configured as indicated above, when it is assumed that the filter is clogged due to a decrease in the airflow amount detected by the airflow amount detecting means, the medicine under the transferring operation is transferred, in some embodiments, to the main storage part and at the same time, the clogging of the filter is immediately notified, thereby urging users to take suitable measures.

Further, according to the present invention, the transfer device may include a forward pipe line connecting the main storage part and the sub storage part; an airflow producing means configured to produce an air flow within the forward pipe line from the sub unit toward the main unit; and a delivery part connected to the forward pipe line and configured to receive and dispense the medicine transferred from the sub unit through the forward pipe line in the main unit. The delivery part may include a delivery container, to which the forward pipe line is connected, and a shutter. The delivery container may include an internal space, which is configured such that the medicine transferred through the forward pipe line freely falls therein, and a dispensing opening disposed at a bottom portion of the delivery container to dispense the medicine. The shutter may be configured to be changed between a dispensing-allowed state where the medicine is allowed to be dispensed from the dispensing opening, and a dispensing-unallowed state.

In the medicine dispensing system of another embodiment, the medicine dispensed from the sub storage part may be transferred to the main storage part and may be received in the delivering part in advance, by having the shutter being in the dispensing-unallowed state where the medicine is not dispensed from the dispensing opening formed at the bottom of the delivering part and by operating the airflow producing means. Thereafter, the medicine received in the delivering part may be dispensed for a purpose of packing it by operating the shutter and converting it in the dispensing-unallowed state where the medicine is dispensed from the dispensing opening. Thus, the medicine dispensing system of the present invention may pack the medicine dispensed from the main storage part as well as the medicine dispensed from the sub storage part at the packing part provided in the main unit.

Meanwhile, in case the forward pipe line is connected to the delivering part as described above, since the medicine transferred from the sub unit is moved within the delivery container due to the airflow flowing from the forward pipe line into the delivery container, there could be a possibility that the medicine does not freely drop toward the bottom of the delivery container formed with the dispensing opening.

Accordingly, according to the present invention provided considering such knowledge, the delivery container may include an exhaust hole for exhausting an airflow flowing in through the forward pipe line and the exhaust hole may be positioned downwardly of a connection position between the delivery container and the forward pipe line.

In the medicine dispensing system of the present invention, since the exhaust hole is positioned downwardly of the connection position between the delivery container and the forward pipe line, the airflow flowing into the delivery container through the forward pipe line is allowed to flow downwardly. Thus, the medicine introduced into the delivery container through the forward pipe line also drops smoothly along with the airflow flowing downwardly within the delivery container.

In the above-described medicine dispensing system, the delivery container may include a side portion (A) connected to the forward pipe line; and a pair of opposed side portions (B, C) crossing to the side portions. The exhaust hole may be provided at each of the pair of the side portions (B, C).

Where the medicine dispensing system is configured as such, the airflow flowing into the delivery container through the forward pipe line is allowed to bifurcately flow to the exhaust holes provided at the side portions (B, C) and thus the medicine smoothly drops within the delivery container.

When the medicine is introduced into the delivering part along with the airflow flowing through the forward pipe line as described above, there could be a possibility that the medicine collides against an inner wall surface of the delivery container from the force of the airflow. Thus, the above-described medicine dispensing system is configured to minimize the impact on the medicine caused by its collision.

Accordingly, considering such knowledge, a buffer means configured to buffer an impact caused by collision of the medicine may be provided within the delivery container. The forward pipe line may be connected to a side portion of the delivery container, and the buffer means may be disposed opposite to the side portion to which the forward pipe line is connected.

In the medicine dispensing system of the present invention, the buffer means is disposed within the delivery container opposite to the side portion to which the forward pipe line is connected. Thus, when the medicine introduced into the delivery container from the forward pipe line flows on the force of the airflow and collides against the buffer means, the impact caused thereby is buffered and the possibility of breakage or chipping of the medicine is reduced.

Further, the shutter may be configured to change an inclination thereof in the delivery container. The shutter may go into the dispensing-unallowed state where the medicine is not dispensed from the dispensing opening when the shutter is situated to obliquely traverse the internal space of the delivery container. And, the shutter may go into the dispensing-allowed state where the medicine is dispensed from the dispensing opening by changing the inclination of the shutter from the dispensing-unallowed state.

In the dispensing-unallowed state where the medicine is not dispensed from the dispensing opening, the shutter is inclined within the delivery container. Thus, according to such configuration, a dropping distance of the medicine within the delivery container can be shortened and the medicine dropping down toward the shutter can be guided to the bottom side along the shutter, thereby minimizing the impact exerted on the medicine.

In the above-described medicine dispensing system, the delivery container may be configured to be divided into two or more sub container bodies.

According to such configuration, since the delivery container is divided into each sub container body, cleaning the inside of the delivery container and the maintenance thereof can be easily performed.

If the airflow is produced to flow toward the delivering part to transfer the medicine from the sub unit to the main unit as described above, it is preferable to devise some means so that dust cannot blow in undesired locations due to the airflow exhausted from the delivering part.

Accordingly, the delivery part may further include an outer container, in which the delivery container may be disposed. The delivery container may include an exhaust part for exhausting an airflow exhausted from the delivery container into the outer container outwardly of the outer container.

In some embodiments, the delivery container is disposed in the outer container and the airflow exhausted from the delivery part can be exhausted through the exhausting part into an internal space of the outer container. Thus, it is possible to prevent the dusts from blowing under the influence caused by the exhausted airflow.

Further, in other embodiments, the exhausting part may include a primary filter; and a secondary filter disposed downstream of the primary filter in an exhaust flow direction, the secondary filter having meshes finer than the primary filter.

In the medicine dispensing system of the present invention, since the primary filter and the secondary filter are provided at the exhausting part, when dusts is contained in the airflow exhausted from the delivering part to the outer container, such dust can be prevented from leaking outwardly of the outer container. Further, in the medicine dispensing system of the present invention, the primary filter with sparse meshes is disposed upstream of the secondary filter having fine meshes in the exhaust flow direction, thereby enlarging a service life of the secondary filter with fine meshes.

Further, in the above-described medicine dispensing system, a piping constituting the forward pipe line may preferably comprise a hard material in order to prevent jamming caused by the medicine in the middle thereof. Meanwhile, when the forward pipe line comprising a piping of a hard material is directly connected to the delivering part, a joint portion between the forward pipe line and the delivering part can be broken due to some stress acting thereon. Thus, in the above-described medicine dispensing system, it is preferable to devise some means to cope with such a problem.

Accordingly, the delivery container and the forward pipe line may be connected to each other via a flexible joint pipe.

According to such configuration, when some stress acts on the forward pipe line, such stress is absorbed or mitigated through the joint pipe constituting the joint portion between the delivering part and the forward pipe line, thereby preventing the joint portion between the delivering part and the forward pipe line from being broken.

In the above-described medicine dispensing, while a transfer operation of medicine from the sub unit to the main unit is completed and thereafter a next transfer operation is done, the shutter may go into the dispensing-allowed state and the airflow producing means may operate, thereby performing a sweeping operation for sweeping a medicine transfer passage formed in the transfer device.

According to such configuration, the medicine transfer passage formed in the transfer device can be maintained cleanly with ease.

According to another embodiment, a medicine dispensing device for a sub unit for constructing a medicine dispensing system includes a main unit and one or more sub units, the main unit and the sub unit being configured to dispense a predetermined medicine by a predetermined quantity; and a transfer device, wherein a medicine dispensed in the sub unit is transferred by the transfer device to the main unit and is dispensed in the main unit. The medicine dispensing device may include a sub storage part configured to store and dispense a plurality kinds of medicines; and a transfer device configured to transfer a medicine dispensed from the sub storage part toward the main unit.

The medicine dispensing device includes the transfer device and is configured to dispense medicine from the sub storage part toward the main storage part by means of the transfer device. Thus, a medicine dispensing system may be constructed, wherein the medicine stored in the sub storage part can be dispensed in the main unit, by employing the medicine dispensing device of the present invention as the sub unit and combining such a sub unit with the main unit.

Further, in the medicine dispensing device of the present invention, the transfer device may have the pipe line connecting the main unit and the sub unit and the transfer means configured to suck or pressure-send the medicine staying in the pipe line from the sub unit toward the main unit.

The medicine dispensing device can be a part of a medicine dispensing system, wherein the medicine dispensed from the sub storage part is fed to the main unit and can be dispensed in the main unit, by connecting the pipe line to the main unit.

Further, since the above-described medicine dispensing device transfers the medicine by sucking or pressure-sending the medicine, a transfer path of the medicines can be appropriately set by appropriately arranging the pipe line. Thus, the medicine dispensing device may in some embodiments have a higher degree of freedom in arrangement on the main unit.

Further, the transfer device may have a medicine delivering part configured to receive and dispense a medicine dispensed from the sub storage part. The medicine delivering part may be configured to turn about a turning shaft and expand and contract in a direction orthogonal to the turning shaft.

The medicine dispensing device is configured such that the medicine delivering part turns about the turning shaft or expands and contracts in the direction orthogonal to the turning shaft. Thus, in case of combining the medicine dispensing device of the present invention with the main unit to construct a medicine dispensing system, the medicine delivering part can obtain its movable range and the medicine dispensed from the sub storage part to the medicine delivering part can be transferred to the main unit and be dispensed therefrom.

Further, the medicine delivering part is capable of expanding and contracting in the direction orthogonal to the turning shaft. Thus, the medicine dispensing device of the present invention can turn the medicine delivering part as contracted. Therefore a space necessary for turning of the medicine delivering part can be minimized.

Further, the transfer device may include a medicine delivery container configured to receive a medicine dispensed from the sub storage part and to dispense the medicine to a medicine preparing part for the medicine; and a drive mechanism configured to move the medicine delivery container between itself and the main unit. The drive mechanism may include a conveying part configured to reciprocate the medicine delivering part; a direction adjusting means configured to adjust a direction of the conveying means relative to the main unit by turning the conveying part.

The transfer device, which is employed in the medicine dispensing device, has the drive mechanism and is configured to reciprocate the medicine delivery container between the main unit and itself and to adjust the direction of the conveying part relative to the main unit. Thus, the medicine dispensing device appropriately operates the transfer device to place the medicine delivery container in a position suitable for receiving the medicine dispensed in the sub unit and in a position where the medicine must be dispensed in the main unit.

Further, the transfer device includes a forward pipe line in communication with the sub storage part and configured to be connected to the main storage part provided in the main unit; an airflow producing means producing airflow from the sub unit toward the main unit within the forward pipe line; an exhaust pipe line configured to be connected to the main storage part; a suction and exhaust means configured to suck and exhaust through the exhaust pipe line from inside the main storage part to an outside portion thereof; and a shutter configured to close at least one of the forward pipe line and the exhaust pipe line. The transfer device may be configured to perform the following: a medicine transferring operation for moving a medicine to the main storage part by operating the airflow producing means in a closed state where the forward pipe line is closed by the shutter; and a medicine introducing operation for introducing medicine from the forward pipe line to the main storage part by operating the suction and exhaust means in a communication state where the shutter is opened and the forward pipe line, the exhaust pipe line and the main storage part are in communication with one another.

The medicine dispensing device can transfer a medicine by means of airflow flowing from the sub storage part toward the main storage part through the medicine transferring operation and thereafter can introduce the medicine into the main storage part through the medicine introducing operation. Thus, the medicine dispensing system of the present invention can deliver the medicine from the sub storage part to the main storage part by repeating the medicine transferring operation and medicine introducing operation.

Further, in the medicine dispensing device, the medicine transferring operation for transferring the medicine by means of the airflow and the medicine introducing operation for introducing the medicine into the main storage part can be separately performed. Thus, in the medicine transferring operation, the airflow may flow within the forward pipe line at a velocity sufficient enough to transfer the medicine in the vicinity of the main storage part. The velocity of the airflow flowing within the forward pipe line in the medicine transferring operation does not need to become excessively fast. Thus, in the medicine dispensing system, the medicines transferred from the main unit to the sub unit can be prevented from severely colliding with each other, breaking or chipping during their transfer operation.

In the above-described medicine dispensing device, the shutter may include a forward obstruction portion for obstructing the forward pipe line; and a buffer means provided at the forward obstruction portion and configured to buffer an impact caused by collision of the medicines proceeding within the forward pipe line.

In case of providing the buffer means as described above, the impact caused by the collision between the shutter and the medicines transferred through the medicine transferring operation can be buffered. Thus, according to the above-described embodiment, the medicine dispensing device can surely prevent the medicines from breaking or chipping due to collision between the medicine and the shutter concomitantly with the medicine transferring operation.

The above-described medicine dispensing device may include a partitioning means configured to partition an internal space of the main storage part. Further, the medicine dispensing device may be configured such that when the shutter becomes opened, both the exhaust pipe line and the forward pipe line become in communication with a space, which is formed according to a division caused by the partitioning means.

According to such configuration, by partitioning the internal space of the main storage part through the partitioning means, the volume of the space, with which, when the shutter becomes opened, both the exhaust pipe line and the forward pipe line become in communication, can be decreased. Thus, although the suction and exhaust means does not have an excessively high exhaust capacity, the above-described medicine dispensing device can introduce the medicine transferred through the forward pipe line into the main storage part in the medicine introducing operation. Further, according to the above-described embodiment, the exhaust capacity of the suction and exhaust means can be minimized. Thus, when the medicines are introduced into the main storage part, it is possible to prevent the medicines from colliding into one another and to prevent occurrence of the breakage or chipping of the medicines.

In the above-described medicine dispensing system, a velocity of the airflow flowing within the forward pipe line by operation of the airflow producing means may be slower than that of the exhaust concomitantly with operation of the suction and exhaust means.

According to such configuration, it is possible to certainly prevent the medicine transferred from the sub unit through the medicine transferring operation from colliding with the shutter to thereby break.

In the above-described medicine dispensing device, the exhaust pipe line may be connected to the sub storage part.

The above-described medicine dispensing device may include a filter provided at a halfway portion of a flow line wherein an airflow is produced concomitantly with transferring the medicine between the sub storage part and the main storage part; an airflow amount detecting means configured to detect an airflow amount in the flow line concomitantly with transferring the medicine from the main storage part to the sub storage part; and a clogging judging means configured to judge a clogging of the filter based on the airflow amount detected by the airflow amount detecting means.

According to such configuration, the clogging of the filter can be easily and certainly detected and thus maintenance of the filter can be performed at an appropriate timing.

Further, it is preferred that the above-described medicine dispensing device is configured to transfer the medicine to the main storage part by increasing the output of the airflow producing means and/or the suction and exhaust means upon a condition of decrease in the airflow amount detected by the airflow amount detecting means, and to judge the clogging of the filter by the clogging detecting means upon a condition of increase in the output of the airflow producing means and/or the suction and exhaust means.

Where the medicine dispensing system is configured as such, it is possible to avoid that the medicine under transfer is transferred to the main storage part and stays in the medicine transfer path by increasing the output of the airflow producing means or the suction and exhaust means prior to judging the clogging of the filter. Thus, according to such configuration, it is possible to prevent the troubles in the dispensing operation, which may occur because the medicine is completely transferred to the main storage part in the clogging of the filter.

The above-described medicine dispensing device may include a filter provided at a halfway portion of a flow line wherein an airflow is produced concomitantly with transferring the medicine between the sub storage part and the main storage part; an airflow amount detecting means configured to detect an airflow amount in the flow line concomitantly with transferring the medicine from the main storage part to the sub storage part; and a notifying means. The medicine dispensing device may be configured to transfer the medicine to the main storage part by increasing the output of the airflow producing means and/or the suction and exhaust means upon a condition of decrease in the airflow amount detected by the airflow amount detecting means, and to notify the clogging of the filter by the notifying means.

According to such configuration, when it is assumed that the filter is clogged due to a decrease in the airflow amount detected by the airflow amount detecting means, the medicine under the transferring operation is certainly transferred to the main storage part and at the same time, the clogging of the filter is immediately notified, thereby urging users to take suitable measures.

Further, according to the medicine dispensing device one embodiment, the transfer device may include a forward pipe line in communication with the sub storage part and configured to be connected to the main storage part; an airflow producing means configured to produce an air flow within the forward pipe line from the sub unit toward the main unit; and a delivery part connected to the forward pipe line and configured to receive and dispense the medicine transferred from the sub unit through the forward pipe line at the main unit. The delivery part may include a delivery container, to which the forward pipe line is connected, and a shutter. The delivery container may include an internal space, which is configured such that the medicine transferred through the forward pipe line freely falls therein, and a dispensing opening disposed at a bottom thereof to dispense the medicine. The shutter may be configured to be changed between a dispensing-allowed state where the medicine is allowed to be dispensed from the dispensing opening, and a dispensing-unallowed state.

In the medicine dispensing device of the present invention, the medicine dispensed from the sub storage part is transferred to the main storage part by having the shutter be in the dispensing-unallowed state where the medicine is not dispensed and by operating the airflow producing means. Thereby, the medicine transferred to the main unit is first received in the delivering part, and thereafter the medicine can be dispensed from the delivering part by converting the shutter. Thus, a medicine dispensing system may be constructed, wherein the medicine stored in the sub storage part can be dispensed in the main unit, by employing the medicine dispensing device as the sub unit and combining such a sub unit with the main unit.

In the above-described medicine dispensing device, it is preferred that the delivery container may include an exhaust hole for exhausting an airflow flowing in through the forward pipe line and the exhaust hole may be positioned downwardly of a connection position between the delivery container and the forward pipe line.

According to such configuration, the airflow flowing into the delivery container through the forward pipe line is allowed to flow downwardly. Also, the medicine introduced into the delivery container through the forward pipe line can drop smoothly along with the airflow.

In the above-described medicine dispensing device, the delivery container may include a side portion (A) connected to the forward pipe line; and a pair of opposed side portions (B, C) crossing to the side portions. The exhaust hole may be provided at each of the pair of the side portions (B, C).

Where the medicine dispensing device is configured as such, the airflow flowing into the delivery container through the forward pipe line is allowed to bifurcately flow to the exhaust holes provided at the side portions (B, C). Thus, the medicine can drop more smoothly within the delivery container.

In the above-described medicine dispensing device, it is preferred that a buffer means configured to buffer an impact caused by the collision of the medicine may be provided within the delivery container. It is preferred that the forward pipe line may be connected to a side portion of the delivery container, and that the buffer means may be disposed opposite to the side portion to which the forward pipe line is connected.

Where the medicine dispensing device is configured as such, when the medicine is introduced into the delivery container from the forward pipe line to the extent that it collides against the buffer means, the impact exerted to the medicine due to collision can be decreased and the medicine can be prevented from breaking or chipping.

In the medicine dispensing device of some embodiments, the shutter may be configured to change an inclination thereof within an internal space of the delivery container. The shutter may become into the dispensing-unallowed state where the medicine is not dispensed from the dispensing opening when the shutter is situated to obliquely traverse the internal space of the delivery container. And, the shutter may become into the dispensing-allowed state where the medicine is dispensed from the dispensing opening by changing the inclination of the shutter from the dispensing-unallowed state.

Where the medicine dispensing device is configured as such, since the shutter is inclined within the delivery container in the dispensing-unallowed state where the medicine is not dispensed from the dispensing opening, a dropping distance of the medicine within the delivery container can be shortened. Further, the medicine can be guided to the bottom side along the shutter. Thus, according to such configuration, the impact exerted on the medicine due to dropping of the medicine within the delivery container can be minimized.

The delivery container, which the medicine dispensing device of the present invention employs, may be configured to be divided into two or more sub container bodies.

Where the medicine dispensing device is configured as such, since the delivery container is divided into each sub container body, cleaning the inside of the delivery container and maintenance thereof can be easily performed.

In the above-described medicine dispensing device, the delivery part may further include an outer container, in which the delivery container may be disposed. The delivery container may include an exhausting part for exhausting an airflow exhausted from the delivery container into the outer container outwardly of the outer container.

According to such configuration, the airflow exhausted from the delivery part into the outer container can be exhausted through the exhausting part outwardly of the outer container. Thus, according to such configuration, the airflow produced concomitantly with transferring the medicine can be exhausted through the exhausting part. Also, it is possible to prevent dust from blowing under the influence caused by the exhausted airflow.

In the above-described medicine dispensing device, the exhausting part may preferably include a primary filter; and a secondary filter disposed downstream of the primary filter in an exhaust flow direction, the secondary filter having meshes finer than the primary filter.

According to such configuration, when the dust is contained in the airflow exhausted from the delivering part to the outer container, such dust can be prevented from leaking outwardly of the outer container. Further, as described above, the primary filter with sparse meshes is disposed upstream of the secondary filter with fine meshes in the exhaust flow direction, thereby enlarging a service life of the secondary filter with fine meshes.

In the above-described medicine dispensing device, the delivery container and the forward pipe line may be connected to each other via a flexible joint pipe.

According to such configuration, when some stress acts on the forward pipe line, such stress is absorbed or mitigated through the joint pipe constituting a joint portion between the delivering part and the forward pipe line, thereby preventing the joint portion between the delivering part and the forward pipe line from being broken.

In the above-described medicine dispensing device, it is preferred that the shutter may go into the dispensing-allowed state and the airflow producing means may be operated until a transfer operation of a medicine from the sub unit to the main unit is completed and a next transfer operation is done thereafter, thereby performing a sweeping operation for sweeping a medicine transfer passage formed in the transfer device.

According to such configuration, the medicine transfer passage formed in the transfer device can be maintained cleanly with ease.

Further, in an alternate embodiment a medicine dispensing device is provided, which is configured to rapidly and reliably detect abnormality in packing paper sheet transfer in a packing paper sheet conveying part, and a medicine dispensing system including the same. Further, a medicine dispensing device and a medicine dispensing system is provided, which are configured to obtain a packed medicine at a desired position in a packing part.

In one embodiment a medicine dispensing device includes a storage part configured to store and dispense a medicine; a packing part configured to pack the medicine dispensed from the storage part into a packing paper sheet; and a packing paper sheet conveying part configured to convey a packing paper sheet into which the medicine is packed by the packing part. The packing paper sheet conveying part includes a packing paper sheet conveying means configured to convey the packing paper sheet along a predetermined conveyance path through contact with the packing paper sheet; and a detecting means configured to contact the packing paper sheet passing through the transfer path and operate independently of the packing paper sheet conveying means. It is detected upon a condition of not operating of the detecting means during operation of the packing paper sheet conveying means whether abnormality in transferring a packing paper sheet occurs.

The medicine dispensing device of the second present invention includes, at the packing paper sheet conveying part, the detecting means contacting the packing paper sheet and operating independently of the packing paper sheet conveying means. The medicine dispensing device can detect whether or not the packing paper sheet transfer is normal by the detecting means. Further, the medicine dispensing device of the present invention can rapidly and precisely detect an abnormality in the packing paper sheet transfer. Thus, the medicine dispensing device can perform appropriate measures such as stopping the packing paper sheet transfer, or stopping to dispense medicines to the packing paper sheet. It is possible to minimize the amount of the packing paper sheet or the medicine, which become unnecessary when there is an abnormality in the packing paper sheet transfer.

Further, another embodiment is configured to rapidly and precisely perform an analysis to prevent the occurrence of wasted packing paper sheets, and a medicine dispensing system including the same.

Further the detecting means may include a roller independently rotatable of the packing paper sheet conveying means; and a rotation detecting means configured to detect a rotation of the roller.

According to such configuration, there can be provided a medicine dispensing device which can detect an abnormality in packing paper sheet transfer based on whether the rotation of the roller is detected by the rotation detecting means.

Further, the packing paper sheet conveying part may be configured to bend the conveyance path of the packing paper sheet.

According to such configuration, there can be provided a medicine dispensing device, which can remove the medicine packed in the packing part at a desired position by appropriately bending the conveyance path in the packing paper sheet conveying part.

In the medicine dispensing device according to the above-described embodiment, in order to rapidly detect the abnormality in packing paper sheet transfer, an abnormality in packing paper sheet transfer can be detected in a position as far upstream as possible in a conveyance direction of the packing paper sheet where the occurrence of the abnormality in packing paper sheet transfer can be accurately detected. Specifically, the abnormality in packing paper sheet transfer can be detected in a position as far upstream as possible in the conveyance direction of the packing paper sheet where a conveyance force acts on the packing paper sheet.

Thus, the detecting means may be situated upstream in the conveyance direction of the packing paper sheet in the packing paper sheet conveying means.

According to such configuration, there can be provided a medicine dispensing device, which can rapidly and accurately grasp an abnormality in packing paper sheet transfer when it occurs.

Further, the packing paper sheet conveying part may include a packing part for packing medicine. The packing paper sheet conveying means may be provided downstream in the conveyance direction of the packing paper sheet relative to the packing part. The packing paper sheet conveying means may include a receiving part receiving a packing paper sheet conveyed from the packing part; and a conveying part downstream of the conveying of the packing paper sheet received in the receiving part. The detecting means may be disposed near a boundary between the receiving part and the conveying part.

In the medicine dispensing device, the receiving part receiving the packing paper sheet is provided in the packing paper sheet conveying means. In the conveying part, a conveyance force acts on the packing paper sheet received in the receiving part to convey the packing paper sheet. Thus, where the detecting means is disposed near the boundary between the receiving part and the conveying part, similar to the medicine dispensing device of the present invention, an abnormality in packing paper sheet transfer can be rapidly and accurately detected.

Further, there is provided a medicine dispensing system including a main unit; one or more sub units; and a transfer device configured to connect the main unit and the sub units. The main unit includes the above-described medicine dispensing device. The sub unit includes a sub storage part configured to store and dispense a plurality kinds of medicines. The transfer device transfers the medicine dispensed from the sub storage part toward the main unit. The packing part of the main unit packs and dispenses the medicine.

The medicine dispensing system may include the main unit and the sub unit. It is configured such that the medicine dispensed from the sub storage part provided in the sub unit is transferred to the main unit through the transfer device and is packed and dispensed together with the medicine dispensed in the main unit. However, when the packing paper sheet conveying part provided in the main unit cannot rapidly and accurately detect an abnormality in packing paper sheet transfer, the medicine dispensed in the main unit as well as the medicine dispensed in the sub unit are not allowed to be properly packed. As a result, when the medicines dispensed from both the main unit and the sub unit are allowed to be packed together as described in the medicine dispensing system of the present invention, not detecting the abnormality in packing paper sheet transfer rapidly and accurately raises problems in that the wasted amount of the packing paper sheet and the medicine becomes excessive.

Thus, a medicine dispensing device in some embodiments may be employed as the main unit. Thus, when an abnormality in packing paper sheet transfer is detected in the main unit, such abnormality can be rapidly and accurately detected. Further, an abnormality in packing paper sheet transfer can be detected rapidly and accurately in some embodiments, the medicine dispensing device can perform appropriate measures such as stopping the packing paper sheet transfer, or stopping to dispense medicines to the packing paper sheet in case of the occurrence of an abnormality in packing paper sheet transfer. Thus, the wasted amount of the packing paper sheet and the medicine can be minimized.

There can be provided in other embodiments, a medicine dispensing device, which is configured to rapidly and reliably detect an abnormality in packing paper sheet transfer in a packing paper sheet conveying part, and the medicine dispensing system including the same. Further, there can be provided a medicine dispensing device and a medicine dispensing system, which are configured to remove a medicine packed in the packing part at a desired position.

Next, another embodiment will be explained hereinafter. There exists in the art a medicine dispensing device as disclosed in the below-mentioned reference Patent Document 3. A prior art medicine dispensing device has a medicine dispensing means. Such a prior art medicine dispensing device is configured to pack medicines dispensed from the medicine dispensing means according to prescriptions into a packing paper sheet at a packing means. Further, as disclosed in Patent Document 3, the prior art medicine dispensing device includes a printing means and is configured to print necessary information such as contents of the packed medicine on the packing paper sheet through the printing means. (see Patent Document 3: Japanese Laid-Open Patent Application No. 2006-130307).

In a packing work performed by the prior art medicine dispensing device disclosed in the Patent Document 3, pharmacists monitor whether medicines to be fed to the packing part and to be packed therein are accurately packed. The prior art medicine dispensing device disclosed in the Patent Document 3 is configured to assume that the medicines to be packed are fed to the packing part at a time when the medicines to be fed to the packing part and to be packed therein are ready and then to perform a printing operation to a packing paper sheet through the printing means. Thus, in the packing work performed by the prior art medicine dispensing device disclosed in the Patent Document 3, it cannot be judged by looking over the information printed on the packing paper sheet whether the medicines to be packed are accurately packed. Thus, it has a problem in that the examination work becomes complicated. Further, it has another problem in that the packing paper sheet, to which the printing operation is performed after the medicines are already packed, appears to be under a normally packed state. Further, in the prior art medicine dispensing device, even if the medicines to be packed are not ready due to an abnormality in feeding medicines to the packing part, the printing operation is performed to a packing paper sheet, thereby wasting the packing paper sheet.

Thus, in one embodiment a medicine dispensing device, which is configured to rapidly and precisely perform an examination work and to prevent the occurrence of wasted packing paper sheets, and a medicine dispensing system including the same.

In one embodiment a medicine dispensing device includes a medicine dispensing means configured to dispense medicine according to a prescription; a medicine preparing means configured to receive a medicine dispensed from the medicine dispensing means and to dispense the same at a predetermined time; a packing means configured to pack medicine dispensed from the medicine preparing means into a packing paper sheet; a packing paper sheet feeding means configured to feed a packing paper sheet to the packing means; and a printing means configured to print predetermined information on a packing paper sheet fed from the packing paper sheet feeding means to the packing means. The printing means is disposed upstream of the packing means in a flow direction of the packing paper sheet fed by the packing paper sheet feeding means. The length of the path, through which a packing paper sheet passes between the printing means and the packing means, is n times the length of a packing paper sheet necessary for packing medicine for a single pack. The medicine preparing means includes a plurality of sections configured to gather the medicine dispensed from the medicine dispensing means for one pack respectively and is configured to dispense the medicines gathered in the plurality of sections in predetermined order. The printing means prints information corresponding to a section A of the plurality of sections on the packing paper sheet at a timing earlier, by a time period necessary for dispensing a medicine for a section n from the medicine preparing means, than a timing of dispensing a medicine gathered in the section A.

In another embodiment, the length of the path, through which the packing paper sheet passes between the printing means and the packing means, is set n times of the length of the packing paper sheet necessary for packing a medicine for one pack. Further, the medicine preparing means, which the medicine dispensing device of the present invention includes, includes a plurality of sections and is configured to dispense the medicine gathered in each of the sections in a predetermined order. Thus, in the medicine dispensing device of one embodiment, the medicine dispensed from the section A is packed into the packing paper sheet, which the printing means prints at a timing earlier, by a time period necessary for dispensing a medicine for the section n (i.e., equal to n packs) from the medicine preparing means toward the packing means, than a timing of dispensing a medicine gathered in the section A. That is, in the medicine dispensing device of this embodiment, a medicine to be packed is supplied to the section A at a timing prior to performing the print operation corresponding to the section A to the packing paper sheet. Further, a timing when the medicine gathered in the section A is dispensed to the packing part and a timing when a section of a packing paper sheet with the information corresponding to the section A printed thereon reaches the packing part coincide. Thus, the medicine dispensing device in some embodiments performs printing to a packing paper sheet upon a condition that a medicine to be packed is supplied to the section A. Further, it can easily monitor whether or not a medicine to be packed is exactly supplied and resolve the problem of wasted packing paper sheets resulting from abnormality in feeding a medicine.

Further, in the above-described medicine dispensing device, a printing operation to the packing paper sheet may be performed by the printing means upon a condition that the medicine is fed into section A up to a time earlier by the time period necessary for dispensing a medicine for the section n from the medicine preparing means than the time of dispensing a medicine gathered in the section A of the plurality of sections in the medicine preparing means.

Further, in the above-described medicine dispensing device, the medicine is dispensed from the medicine dispensing means to section A at a time earlier by a time period more than the time period necessary for dispensing a medicine for the section n from the medicine preparing means than the time of dispensing a medicine gathered in section A in the medicine preparing means. Thus, the information corresponding to section A is printed on the packing paper sheet after the medicine is fed into section A. Thus, the medicine dispensing device can easily monitor whether or not a medicine to be packed is accurately packed and resolve the waste of a packing paper sheet resulting from an abnormality in feeding a medicine.

Further a medicine dispensing device includes a medicine dispensing means configured to dispense a medicine according to a prescription; a medicine preparing means configured to receive a medicine dispensed from the medicine dispensing means and to dispense the same at a predetermined time; a packing means configured to pack a medicine dispensed from the medicine preparing means into a packing paper sheet; a packing paper sheet feeding means configured to feed a packing paper sheet to the packing means; and a printing means configured to print predetermined information on a packing paper sheet fed from the packing paper sheet feeding means to the packing means. The printing means is disposed upstream of the packing means in a flow direction of the packing paper sheet fed by the packing paper sheet feeding means. The medicine preparing means includes a plurality of sections configured to gather the medicine for one pack dispensed from the medicine dispensing means respectively. The medicine preparing means is configured to dispense the medicines gathered in the plurality of sections in a predetermined order. A medicine is dispensed from the medicine dispensing means into one section A of the plurality of sections at a time earlier by a timing Z as early as a time period Y when the packing paper sheet fed by the packing paper sheet feeding means moves from a position corresponding to the printing means to the packing means, than a timing X when the medicine in the section A is dispensed from the medicine dispensing means toward the packing means. Information corresponding to section A is printed on the packing paper sheet at the time Z by the printing means.

In the above-described medicine dispensing device, medicine is fed into section A of the medicine preparing means at a time earlier than the time Z. Further, the information corresponding to section A is printed on the packing paper sheet by the printing means at the time Z as early as the time period Y when the packing paper sheet fed by the packing paper sheet feeding means moves from the position corresponding to the printing means to the packing means, from the timing X when the medicine in section A is dispensed from the medicine dispensing means toward the packing means. That is, the information corresponding to section A is printed on a portion of the packing paper sheet, which is used for packing the medicine in section A, at the same time as, or later than a time for feeding the medicine into section A. Thus, the medicine dispensing device can perform the printing operation to the medicine dispensing device after ascertaining that the medicine to be packed is exactly fed into the section. Further, the medicine dispensing device can easily monitor whether or not the medicine to be packed is exactly fed and resolve the waste of a packing paper sheet resulting from an abnormality in feeding a medicine.

Further, the printing operation to the packing paper sheet may be performed upon a condition that the medicine is fed into section A at a time earlier than the time Z.

With such configuration, if the printing operation to the packing paper sheet is not performed, it can be judged that the medicine is not fed exactly before the time Z. Thus, examining whether or not the medicine is exactly packed can become easy. Further, according to such configuration, if the medicine is not fed into the section A before the time Z, the printing operation to the packing paper sheet stops, thereby preventing the occurrence of the wasted packing paper sheet in advance.

Further, a print purporting that the medicine to be packed runs short may be made on the packing paper sheet by the printing means upon a condition that the medicine to be packed is not inputted to section A until the time earlier than the time Z.

According to such configuration, it is ascertained through only looking over the print made on the packing paper sheet that the medicine to be packed runs short. Thus, the examination work can be performed more easily and reliably.

Further, in the above-described medicine dispensing device, the medicine preparing means may include a section forming body having a plurality of sections arranged circumferentially; and a dispensing opening. The section forming body may be configured to move relative to the dispensing opening. When the section reaches a position corresponding to the dispensing opening, the medicine gathered in the section may be disposed through the dispensing opening.

Further, a medicine dispensing device comprises: a medicine dispensing means configured to dispense a medicine according to a prescription; a medicine preparing means configured to receive a medicine dispensed from the medicine dispensing means and to dispense the same at a predetermined time; a packing means configured to pack a medicine dispensed from the medicine preparing means into a packing paper sheet; a packing paper sheet feeding means configured to feed a packing paper sheet to the packing means; and a printing means configured to print a predetermined information on a packing paper sheet fed from the packing paper sheet feeding means to the packing means. The printing means is disposed upstream of the packing means in a flow direction of the packing paper sheet fed by the packing paper sheet feeding means. The medicine preparing means comprises: a rotatable section forming body; an opening for dispensing a medicine from the medicine preparing means; and a hole to which the medicine dispensed from the medicine dispensing means is inputted. The section forming body includes a plurality of sections in a circumferential direction. The section is configured to gather a medicine for one pack. When the section forming body rotates and each of the sections reaches a position corresponding to the hole, the medicine is inputted to the section through the hole. When the section forming body rotates and each of the sections reaches a position corresponding to the opening, the medicine in the section is dispensed. The hole is formed in a position upstream of the opening in a rotating direction of the section forming body.

In the above-described medicine dispensing device, a length of a path, through which a packing paper sheet passes between the printing means and the packing means, is n times of a length of a packing paper sheet necessary for packing a medicine for one pack. The hole is formed in a position upstream of the opening by more than n sections in the rotating direction of the section forming body.

Further, the medicine dispensing means capable of dispensing a medicine according to a prescription includes: a main storage part; a manual distributing unit; a collecting hopper for feeding a medicine dispensed from the main storage part; and a manual distributing hopper for feeding a medicine dispensed from the manual distributing unit. The hole to which the medicine dispensed from the medicine dispensing means is inputted comprises: a hole for connection to the collecting hopper and a hole for connection to the manual distributing hopper. The hole for connection to the collecting hopper and the hole for connection to the manual distributing hopper are apart from each other in the circumferential direction. The hole for connection to the collecting hopper and the hole for connection to the manual distributing hopper are formed in a position upstream of the opening for dispensing a medicine from the medicine preparing means by more than n sections in the rotating direction of the section forming body.

Further, the medicine preparing means comprises: a shutter provided in each of the sections of the medicine preparing means; a dispensing opening for dispensing a medicine from the medicine dispensing means; and a contactor provided near the opening. When each of the sections reaches a position corresponding to the dispensing opening, the shutter provided in each of the sections is pressed by contact to the contactor and then opened, thereby dispensing the medicine in each of the sections.

Further, the above-described medicine dispensing device further comprises a medicine standby part provided between the medicine preparing means and the medicine dispensing means. The medicine standby part includes: a funnel-shaped standby hopper; a movable lid; and a lid moving mechanism. The movable lid moves upward and downward by an operation of the lid moving mechanism to open and close a discharging opening formed in the standby hopper.

Further, there is provided a medicine dispensing system that includes a main unit; one or more sub units; and a transfer device configured to connect the main unit and the sub units. The main unit includes the above-described medicine dispensing device. The sub unit includes a sub storage part configured to store and dispense a plurality kinds of medicines. The transfer device transfers the medicine dispensed from the sub storage part toward the main unit and feeds the medicine into the section provided in the medicine preparing means. The packing means of the main unit packs and dispenses the medicine.

The medicine dispensing system includes the main unit and the sub unit. It is configured such that the medicine dispensed in the sub unit is transferred to the medicine preparing means provided in the main unit and is packed and dispensed together with the medicine dispensed in the main unit by the packing means. However, in the medicine dispensing system, there is a possibility that an abnormality in dispensing medicine to the medicine preparing means occurs in the main unit. In addition, there is another possibility that an abnormality in dispensing medicine occurs in the sub unit, and that troubles take place during transferring a medicine to the medicine preparing means through the transfer device. As such, where the main unit is provided, the medicine dispensing system may have many factors associated with the abnormality in dispensing medicine to the medicine preparing means. Accordingly, similar to the above-described medicine dispensing device of the present invention, it is preferred that the above-described medicine dispensing system may have some means so that it can easily monitor whether a packing operation is accurately performed and prevent the packing paper sheet from wasting concomitantly with the abnormality in dispensing a medicine to the medicine preparing means.

Thus, the medicine dispensing system, which is provided based on such knowledge, employs the above-described medicine dispensing device as the main unit. Thus, the medicine dispensing system can prevent the packing paper sheet from being wasting in conjunction with an abnormality in dispensing a medicine to the medicine preparing means.

According to another embodiment, there can be provided a medicine dispensing device, which is configured to easily and accurately perform the examination work regarding whether or not packing medicine is accurately performed and to prevent the packing paper sheet from wasting even if the medicine to be dispensed becomes unready due to an abnormality in feeding a medicine to the packing part. Further, there can be provided a medicine dispensing system that includes such a medicine dispensing device.

Further, in the above-described medicine dispensing system, the medicine preparing means of the main unit includes: a rotatable section forming body; an opening for dispensing a medicine from the medicine preparing means; and a hole to which the medicine dispensed from the medicine dispensing means is inputted. The section forming body includes a plurality of sections in a circumferential direction, the section being configured to gather a medicine for one pack. When the section forming body rotates and each of the sections reaches a position corresponding to the hole, the medicine is inputted to the section through the hole. When the section forming body rotates and each of the sections reaches a position corresponding to the opening, the medicine in the section is dispensed. The main unit has a main storage part and a manual distributing unit as the medicine dispensing means configured to dispense a medicine according to a prescription and the main unit comprises a collecting hopper for feeding a medicine dispensed from the main storage part and a sub collecting hopper for feeding a medicine dispensed from the sub storage part. The medicine preparing means comprises a hole for connection to the collecting hopper and a hole for connection to the sub collecting hopper at a position corresponding to each of the sections of the section forming body, the hole for connection to the collecting hopper and the hole for connection to the sub collecting hopper being apart from each other in the circumferential direction. The medicines fed by the collecting hopper and the sub collecting hopper are inputted to each of the sections through the holes. The hole for connection to the collecting hopper and the hole for connection to the sub collecting hopper are formed in a position upstream of the opening for dispensing a medicine from the medicine preparing means in the rotating direction of the section forming body.

Further, a length of a path, through which a packing paper sheet passes between the printing means and the packing means provided in the main unit, is n times of a length of a packing paper sheet necessary for packing a medicine for one pack. The hole is formed in a position upstream of the opening by more than n sections in the rotating direction of the section forming body.

Next, another embodiment will be explained hereinafter. There exists in the art a medicine dispensing device as disclosed in the below-mentioned reference Patent Document 4. A prior art medicine dispensing device includes a plurality of medicine feeding containers configured to store medicine in a storage part and dispense the medicine. Such a prior art medicine dispensing device is configured to dispense the medicine from each of the medicine feeding container by the amount corresponding to a prescription and pack the same. (see Patent Document 4: Japanese Laid-Open Patent Application No. 2001-276183).

The prior art medicine dispensing device is used in such a manner that each of the medicine feeding containers accommodates different kinds of medicines. However, the prior art medicine dispensing device is not configured to simply and accurately grasp characteristic data of each medicine feeding container, such as a date and time when the medicine feeding container is filled with medicines, a user filling the medicine feeding container, data related to medicines accommodated in the medicine feeding container, etc. Further, as the number of the medicine feeding containers increases with an increase in the kinds of medicines to be dealt with, such a tendency becomes strong. Thus, the relevant art requires a medicine dispensing device configured to simply and accurately grasp characteristic data of each medicine feeding container. Similarly, a medicine dispensing system, which is constructed by combining a plurality of medicine dispensing devices, is required to be configured to simply and accurately grasp characteristic data of each medicine feeding container.

Thus, to satisfy the aforementioned demand, it is an object of the present invention to provide a medicine dispensing device and a medicine dispensing system, which are configured to simply and accurately grasp characteristic data of each medicine feeding container.

In order to accomplish the above objects, there is provided a medicine dispensing device, which includes a medicine feeding container configured to store a medicine, the medicine feeding container including an information recordable medium; a container mounting part configured to mount the medicine feeding container; and a control means. The medicine is allowed to be dispensed by mounting the medicine feeding container to the container mounting part. The control means is configured to perform a data communication for a characteristic data of the medicine feeding container with the information recordable medium of the medicine feeding container.

According to such configuration, there is provided the medicine dispensing device, which can perform the data communication for the characteristic data between the control means and the medicine feeding container having the information recordable medium and can simply and accurately grasp the characteristic data.

Further, a medicine dispensing device, which is provided based on the same knowledge, may include a storage means configured to store and dispense medicine; and a control means configured to data-communicate with an information recordable medium. The storage means may include a plurality of attachable/detachable medicine feeding containers configured to store and dispense the medicine. The information recordable medium may be provided in some or all of the medicine feeding containers. A data communication for the characteristic data of the medicine feeding container may be performed between the information recordable medium of the medicine feeding container and the control means.

The above-described medicine dispensing device includes a storage means configured to store and dispense medicine; and a control means configured to data-communicate with the information recordable medium. Herein, the storage means includes a shelf or drum, in which a plurality of medicine feeding container are removably provided (for example, this may be referred to as a main storage part or a sub storage part in embodiments described below). Further, in the medicine dispensing device, a plurality of medicine feeding containers configured to store and dispense a medicine are removably provided in the storage means, which includes a shelf or drum. Herein, the medicine feeding container corresponds to a feeder container in the below-described embodiments and a container capable of dispensing the medicine accommodated therein. The above-described storage means, which includes the medicine feeding container, can dispense the medicine dispensed from the medicine feeding container for the purpose of packing the same.

With the above-described constitution, there can be provided a medicine dispensing device, which can data communicate with the control means with respect to the characteristic data of each of the medicine feeding containers with the information recordable medium and thus can simply and accurately grasp the characteristic data.

Further, the control means may be configured to data communicate with an operator information recordable medium recording an operator information specifying an operator. The operator information read from the operator information recordable medium through the data communication may be recorded into the information recordable medium.

According to such constitution, information on an operator, who performs tasks relevant to the medicine feeding container, such as filling the medicine feeding container with medicines, may be recorded into the information recordable medium of each of the medicine feeding containers.

Further, the medicine dispensing device may be configured to operate in a plurality of operation modes. The operation mode may change in a predetermined operation mode selected from a plurality of operation modes upon a condition that the data communication is allowed between the control means and the information recordable medium of the medicine feeding container removed from a container mounting part.

In the medicine dispensing device, the operation mode changes upon a condition that the data communication is allowed between the control means and the information recordable medium of the medicine feeding container. That is, it can be used as a trigger for changing the operation modes that the information recordable medium provided in each of medicine feeding container is allowed to data communicate with the control means. Thus, efforts required to change the operation modes can be minimized and misoperation can be prevented.

Further, the medicine dispensing device may include a mark reading means for reading an identification mark assigned to each of the kinds of medicine. The kinds of medicine may be specified by the control means based on the identification mark read by the mark reading means. Information on the kinds of medicine may be recorded into the information recordable medium through data communication between the control means and the information recordable medium of the medicine feeding container removed from the container mounting part.

According to such configuration, if the mark reading means reads the identification mark assigned to each of the kinds of medicine when filling the medicine feeding container removed from the container mounting part with a medicine, the information on the kind of such a medicine can be recorded into the information recordable medium of the medicine feeding container through data communication. Thus, according to the medicine dispensing device of one embodiment, when the medicine feeding container is filled with a medicine, the information on the kinds of medicine can be easily and reliably recorded into the information recordable medium.

The medicine dispensing device according to this embodiment may further include a cassette placing part configured to place the medicine feeding container removed from the container mounting part; and an interface means wiredly or wirelessly connected to the control means. When the medicine feeding container is placed on the cassette placing part, the data communication between the information recordable medium of the medicine feeding container and the control means may be allowed via the interface means.

According to such configuration, efforts required to enable the data communication between the information recordable medium and the control means after removing the medicine feeding container from the container mounting part can be minimally saved.

Further, the medicine dispensing device may further include an interface means wiredly or wirelessly connected to the control means. The interface means may be configured to read and record data as not in contact with the information recordable medium.

According to such configuration, efforts required to enable the data communication between the information recordable medium and the control means after removing the medicine feeding container from the container mounting part can be saved.

The above-described medicine dispensing device can data-communicate with the information recordable medium of each of the medicine feeding containers with respect to the characteristic data of the medicine feeding container. Thus, the medicine dispensing device can be configured to dispense medicines for purposes of packing the same even if the medicine feeding container accommodating a predetermined medicine is situated at any location in the storage means. However, some medicine of the plurality kinds of medicines is prone to bound, roll over, break or chip due to drop impact at a dispensing portion while dispensed from the medicine feeding container. In case of dealing with such a medicine, it must be dealt with in a different manner from those for other medicines (for example, adjustment in dispensing timing regarding bound or roll, means for mitigating drop impact, etc.) so as not to cause an abnormality in dispensing medicine. Accordingly, the medicine feeding container accommodating medicine having such a particular characteristics is attached to a location capable of resolving the foregoing matter.

Further, medicines may be sequentially dispensed based on prescription data inputted to the control means and a plurality of the container mounting parts configured to mount the medicine feeding container may be provided. The control means may include: a correspondence relationship storing part regulating and storing a correspondence relationship between the plurality of the container mounting parts and the medicine feeding container to be attached to the plurality of container mounting parts; and a judging part. The judging part may be configured to perform an error judgment operation for judging the following states, by comparing the correspondence relation storing part and the characteristic data of the medicine feeding container obtained from the data communication with the information recordable medium of the medicine feeding container mounted on the container mounting part: a right mount state where the medicine feeding container is properly mounted on the container mount part coinciding with the correspondence relationship regulated in the correspondence relationship storing part; and a erroneous mount state where the medicine feeding container is erroneously mounted on the container mounting part against the correspondence relationship regulated in the correspondence relationship storing part. Dispensing the medicines may continue from other medicine feeding containers excluding an erroneously-mounted medicine feeding container upon a condition that it is judged by the error judgment operation that there is the erroneously mounted medicine feeding container, and that a medicine accommodated in the erroneously mounted medicine feeding container is not a medicine to be dispensed according to the prescription data. Dispensing the medicines may stop upon a condition that it is judged by the error judgment operation that there is the erroneously mounted medicine feeding container, and that a medicine accommodated in the erroneously mounted medicine feeding container is a medicine to be dispensed according to the prescription data.

In the medicine dispensing device configured as such, the judging part of the control means performs the error judgment operation. Based on the correspondence relationship between the container mounting part and the medicine feeding container, which is regulated in the correspondence relationship storing part, it can be judged whether the medicine feeding container is properly mounted or erroneously mounted on the container mounting part dedicated for said medicine feeding container. Further, in the medicine dispensing device of the present invention, where the medicine feeding container is erroneously mounted and such a medicine feeding container does not accommodate a medicine to be dispensed, even if dispensing a medicine does not stop in other medicine feeding containers, problems such as bound, roll, breakage, chipping, etc. of medicines do not occur. And, stopping to dispense a medicine leads to loss of work efficiency. Accordingly, in the medicine dispensing device of some embodiments, where the erroneously mounted medicine feeding container does not accommodate a medicine to be dispensed, dispensing a medicine continues and the erroneously mounted medicine feeding container can be dismounted without stopping to dispense a medicine. Accordingly, even if the erroneously mounted medicine feeding container exists, the loss of work efficiency resulting therefrom can be minimized.

By contrast, where the erroneously mounted medicine feeding container exists and such a medicine feeding container accommodates a medicine to be dispensed, continuing to dispense a medicine causes the aforementioned problems such as bound, roll, breakage, chipping, etc. of medicines. Accordingly, in such a case, the medicine dispensing device of in some embodiments is configured to stop to dispense a medicine. Thus, according to the medicine dispensing device in some embodiments, it is possible to prevent medicines from being dispensed from the erroneously mounted medicine feeding container.

Further, it is preferred that medicines prone to bound, roll over, break or chip due to drop impact at the dispensing portion are dispensed at a side as low as possible.

Thus, in the above-described medicine dispensing device provided based on such knowledge, the storage means may include a plurality of the container mounting parts configured to mount the medicine feeding container. The container mounting parts may be vertically arranged. It may be judged through the error judgment operation whether a medicine feeding container to be mounted on a container mounting part provided below a predetermined height is erroneously mounted on a container mounting part provided in a position above the predetermined height.

According to such configuration, it can be prevented that the medicine feeding container accommodating the medicine to be dispensed at a side as low as possible (i.e. the aforementioned medicine causing problems such as bound, roll, breakage or chipping concomitantly with drop) is erroneously mounted on the container mounting part situated in a position above the predetermined height.

Further, the above-described medicine dispensing device provided based on the same knowledge, the container mounting part configured to mount the medicine feeding container may be disposed in each of a plurality of container mounting regions defined along a height direction. The correspondence relationship storing part may regulate the correspondence relationship between the container mounting part and the medicine feeding container to be attached to the container mounting part as a relationship relative to the container mounting region located at a height corresponding to an upper attachment limit of a medicine feeding container that is determined according to a kind of medicine. The erroneous mount state may be judged through the error judgment operation when a medicine feeding container is mounted on a container mounting part of a container mounting region locating beyond a container mounting region located at a height corresponding to the upper attachment limit. The right mount state may be judged through the error judgment operation when a medicine feeding container is mounted on a container mounting part of a container mounting region located at a height below the upper attachment limit.

In the medicine dispensing device, the correspondence relationship storing part can regulate the correspondence relationship between the container mounting regions and the height corresponding to the upper attachment limit of the medicine feeding container at a plurality of steps in view of that bound, roll, breakage or chipping occurs at what level concomitantly with drop. Further, the erroneous mount state can be judged through the error judgment operation based on such a regulation, when a medicine feeding container is mounted on a container mounting part of a container mounting region located upward beyond a container mounting region located at a height corresponding to the upper attachment limit. Thus, it is possible to prevent the occurrence of trouble such as an abnormality in dispensing a medicine resulting from the erroneous mount state.

Further, the control means may be configured to perform a search operation for searching and selecting a container mounting part, on which the medicine feeding container judged to be in the erroneous mount state through the error judgment operation must be mounted.

According to such configuration, it can be easily determined through the search operation on which container mounting part the erroneously mounted medicine feeding container must be mounted.

Further, a search condition may be determined based on the characteristic data of the medicine feeding container obtained by the data communication with the information recordable medium, which the medicine feeding container judged to be in the erroneous mount state through the error judgment operation includes.

According to such configuration, even if an operator does not separately input a search condition in the search operation, the container mounting part on which the erroneously mounted medicine feeding container must be mounted can be selected. Thus, convenience in the search operation can be enhanced.

In the above-described invention, the storage means may be configured to move each of the container mounting parts to an attachment/detachment work position where an attachment/detachment work of the medicine feeding container can be performed. The container mounting part selected through the search operation may be moved to the attachment/detachment work position.

In such a medicine dispensing device, a container mounting part located at a proper position, in which the erroneously mounted medicine feeding container must be properly attached, is moved to the attachment/detachment work position. Thus, convenience in attaching the medicine feeding container in the proper position can be enhanced.

Further, there is provided a medicine dispensing system that includes a main unit; one or more sub units; and a transfer device configured to connect the main unit and the sub units. The main unit includes the above-described medicine dispensing device. The sub unit includes a sub storage means configured to store and dispense a plurality kinds of medicines. The sub storage means includes a plurality of attachable/detachable medicine feeding containers configured to store and dispense a medicine. The transfer device transfers the medicine dispensed from the sub storage means toward the main unit. The medicine is dispensed in the main unit.

Such a medicine dispensing system includes the main unit and the sub unit. A plurality of medicine feeding containers are removably attached to both the storage means of the main unit and the sub storage means of the sub unit. Accordingly, the medicine dispensing system has a large number of medicine feeding containers and thus needs to be configured to even more easily and reliably control the characteristic data of each of the medicine feeding containers. Thus, the medicine dispensing system, which is provided based on such knowledge, includes the above-described medicine dispensing device as the main unit. As a result, the medicine dispensing system can simply and accurately grasp and control the characteristic data through the data communication between the control means provided in the main unit and the information recordable medium of each of the medicine feeding containers provided in the main unit and the sub unit.

Thus, there can be provided a medicine dispensing device and a medicine dispensing system, which are configured to simply and accurately grasp the characteristic data of each medicine feeding container.

According to another embodiment there can be provided a medicine dispensing system, which is configured such that a medicine dispensing device that includes a sub unit having a function of dispensing medicines is connected to a medicine dispensing device that includes a main unit having a function of packing medicines. Further, there can be provided a medicine dispensing device that can be appropriately employed to such a medicine dispensing system.

Also, according to other embodiments, there can be provided a medicine dispensing device, which is configured to rapidly and reliably detect abnormality in packing paper sheet transfer in a packing paper sheet conveying part, and a medicine dispensing system including the same. Further, there can be provided a medicine dispensing device and a medicine dispensing system, which are configured to remove a packed medicine at a desired position in a packing part.

Further, there can be provided a medicine dispensing device, which is configured to rapidly and precisely perform an examination work regarding whether or not packing a medicine is accurately performed and to prevent occurrence of a wasted packing paper sheet even if a medicine to be dispensed becomes unready due to abnormality in feeding a medicine to a packing part. Further, there can be provided a medicine dispensing system comprising such a medicine dispensing device.

Furthermore, there can be provided a medicine dispensing device and a medicine dispensing system, which are configured to simply and accurately grasp a characteristic data of each medicine feeding container.

BRIEF DESCRIPTION OF THE DRAWINGS

FIG. 10(a) is a sectional view showing that a discharging opening of the medicine awaiting mechanism part is closed. FIG. 10(b) is a sectional view showing that the discharging opening is open.

FIG. 19(a) is a rear view of the conveying means. FIG. 19(b) is a front view of the conveying means.

FIG. 20(a) is a perspective view showing a work table. FIG. 20(b) is a block diagram showing the features of a data management system.

FIG. 21(a) is a perspective view showing a transfer device viewed from a medicine dispensing part. FIG. 21(b) is a perspective view showing the transfer device viewed from a medicine receiving part.

FIGS. 22C and 22D are front views showing an interface for displaying a characteristic information of a container.

FIG. 23 is a sectional view showing the medicine dispensing part of the transfer device shown in FIG. 21. FIG. 23(a) is a sectional view showing transferring a medicine. FIG. 23(b) is a sectional view showing dispensing a medicine.

FIG. 25 is a perspective view showing a variation of the transfer device. FIG. 25(a) is a perspective view showing that a medicine delivering unit of a transfer device according to a variation is expanded. FIG. 25(b) is a perspective view showing that the medicine delivering unit is contracted.

FIG. 29(a) is an upper perspective view of a sliding base of the medicine delivering unit of the transfer device shown in FIG. 25. FIG. 29(b) is a lower perspective view of the sliding base.

FIG. 37(a) illustrates that an area A of a shutter is located in the medicine dispensing part. FIG. 37(b) illustrates that an area B of the shutter is not located in the medicine dispensing part.

FIG. 40(a) is a view taken along an arrow X in FIG. 39. FIG. 40(b) is a view taken along an arrow Y in FIG. 39.

FIG. 56 is a front view showing a display of the manipulating panel when a message for urging erroneous mount solution is emitted.

DESCRIPTION OF REFERENCE NUMERALS

1 . . . Medicine Dispensing System
2 . . . Main Unit (Medicine Dispensing Device)
3 . . . Sub Unit (Medicine Dispensing Device)
5 . . . Transfer Device
20 . . . Main Storage Part
120 . . . Sub Storage Part
140 . . . Pipe Line
141 . . . Suction means (Transfer Means)
210 . . . Transfer Device
231 . . . Medicine Delivering Unit (Medicine Delivering Part)
234 . . . Turning Shaft
300 . . . Transfer Device
312 . . . Drive Unit (Direction Adjusting Means)
330 . . . Turning Part (Conveying Part)
340 . . . Medicine Container (Medicine Delivery container)
400 . . . Transfer Device
401 . . . Medicine Receiving Part (Sub Storage Part)
402 . . . Medicine Dispensing Part (Main Storage Part)
403 . . . Forward Pipe Line
405 . . . Blower (Airflow Producing Means)
408 . . . Pump (Suction and exhaust means)
410 . . . Exhaust Pipe Line
420 . . . Shutter
423 . . . Inclined Surface (Partitioning means)
440 . . . Filter
441 . . . Buffer (Buffer Means)
442 . . . Forward Isolation Portion
500 . . . Transfer Device
502 . . . Forward Pipe Line
504 . . . Blower (Airflow Producing Means)
510 . . . Medicine Dispensing Part (Delivering Part)
512 . . . Delivery container
512a . . . Side Portion (Side Portion A)
512b . . . Side Portion (Side Portion B)
512c . . . Side Portion (Side Portion C)
514 . . . Shutter
516 . . . Internal Space
518 . . . Bottom Portion
520 . . . Dispensing Opening
522 . . . Buffer Means
524 . . . Upper Sub Container Body (Sub Container Body)
524p . . . Exhaust Hole
526 . . . Lower Sub Container Body (Sub Container Body)
526p . . . Exhaust Hole
530 . . . Outer Container
532 . . . Exhaust Part
534 . . . Primary Filter
536 . . . Secondary Filter
540 . . . Joint Pipe

DETAILED DESCRIPTION

Figure 1:
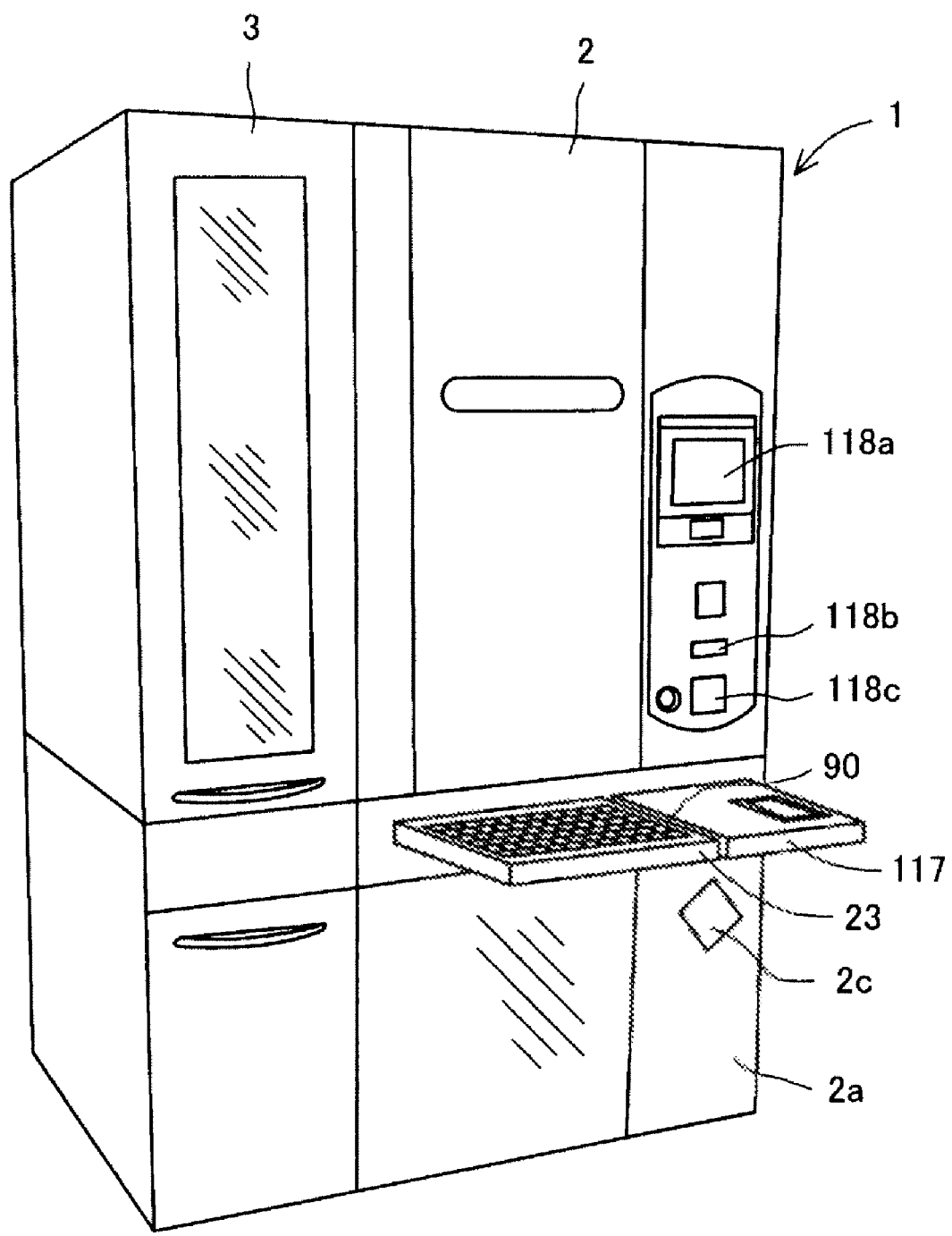
FIG. 1 is a perspective view showing a medicine dispensing system according to one embodiment of the present invention.

A medicine dispensing system 1, a main unit (medicine dispensing device) 2 and a sub unit (medicine dispensing device) 3 according to one embodiment of the present invention will be described in detail with reference to the accompanying drawings. As shown in FIG. 1, the medicine dispensing system 1 has the main unit 2 and the sub unit 3. The main unit 2 forms a basic section of the medicine dispensing system 1. Further, the sub unit 3 may be used in combination with the main unit 2. The medicine dispensing system 1 has a transfer device 5 operated between the main unit 2 and the sub unit 3. In the medicine dispensing system 1 according to the present embodiment, the transfer device 5 is disposed in the sub unit 3. The transfer device is configured to transfer the medicine dispensed in the sub unit 3 toward the main unit 2.

Figure 2:
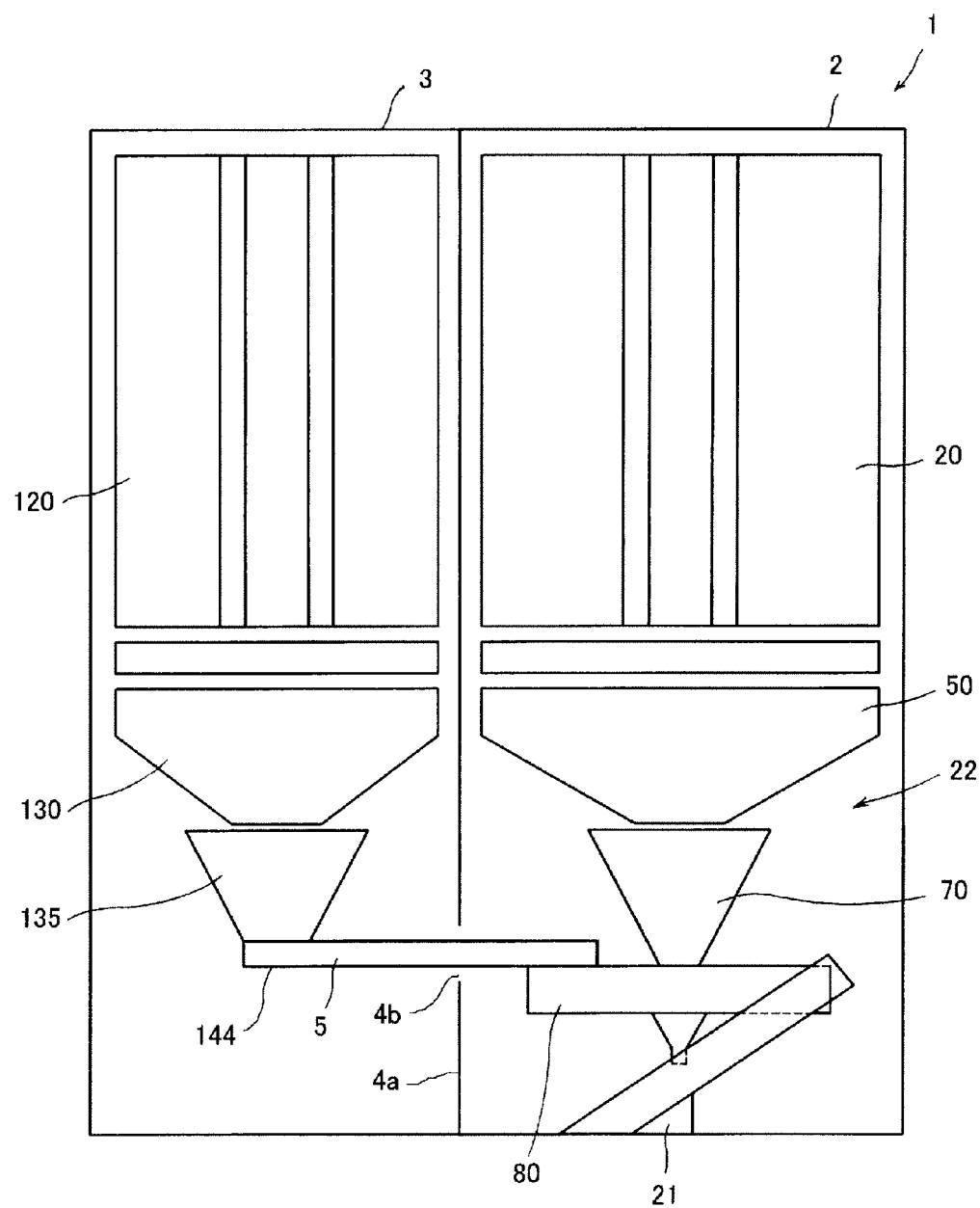
FIG. 2 is a front view schematically showing the internal structure of the medicine dispensing system shown in FIG. 1.

More specifically, as shown in FIG. 2, the main unit 2 includes a main storage part 20 and a medicine packing part 21. A medicine path 22 connecting the main storage part and the medicine packing part is formed in the main unit. A medicine standby mechanism part 50 and a medicine preparing part 80, which will be described in detail below, form a middle section of the medicine path 22. Further, as shown in FIG. 1, the main unit 2 includes a manual distributing unit 23 independent from the main storage part 20. Medicines to be prescribed can be also fed into the manual distributing unit 23. That is, the main unit 2 includes the main storage part 20 and the manual distributing unit 23 as a medicine dispensing means capable of dispensing the medicines according to a prescription.

Figure 4:
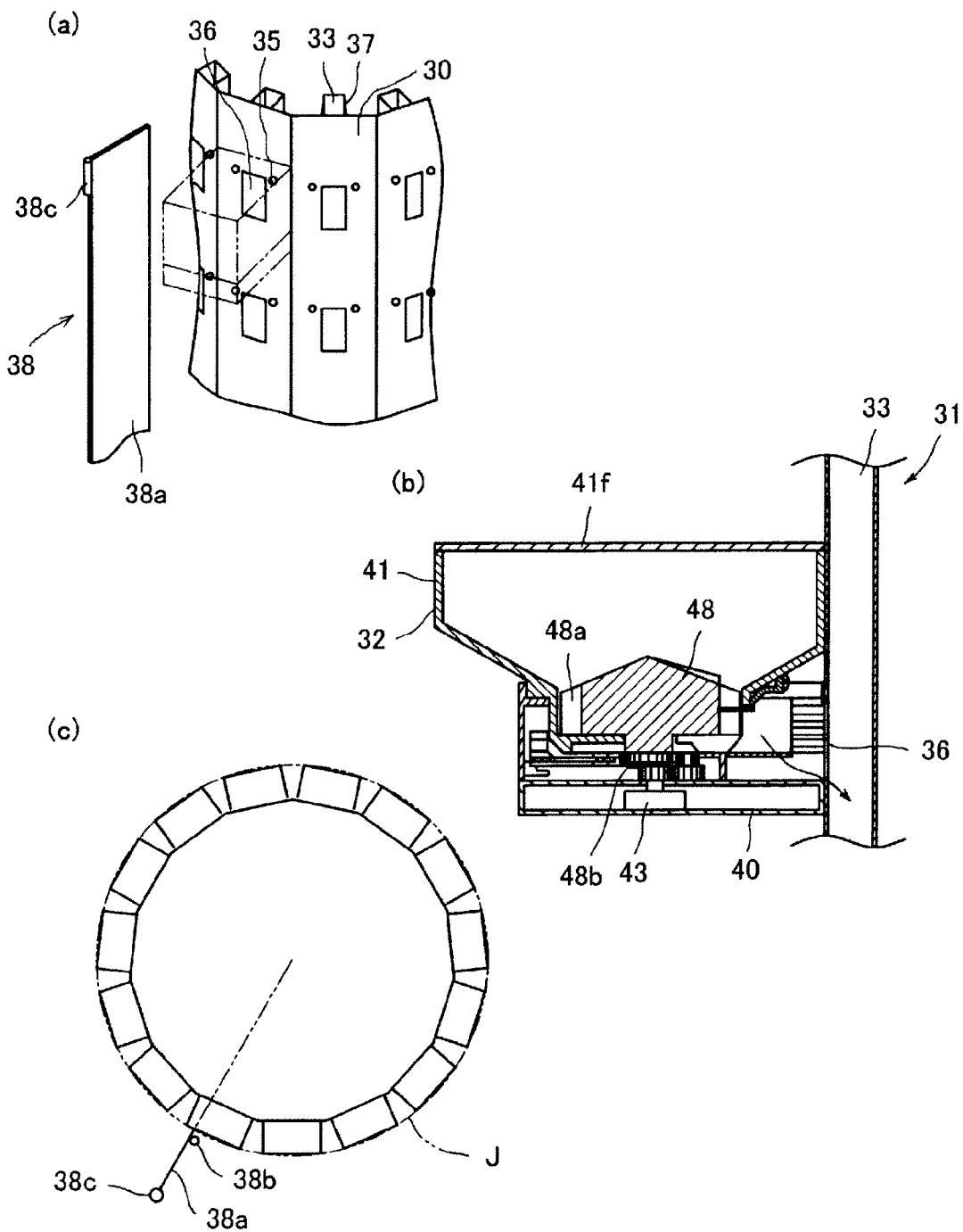
FIG. 4(a) is a partially enlarged perspective view showing a structure of a drum.
FIG. 4(b) is a sectional view showing that a cassette is attached to the drum.
FIG. 4(c) illustrates a positional relationship between a main storage part and an irregular set detecting means.

The main storage part 20 has a drum 31 having a plurality of vertically elongated plate members 30 that are circumferentially arranged as shown in FIG. 4(*a*). The main storage part is configured such that a plurality of cassettes 32 for accommodating tablets are attached to an outer peripheral surface of the drum 31 as shown in FIG. 4(*b*). In the plate members 30, a plurality of cassette attaching holes 35, for attaching the cassette 32, and openings 36 communicating with a dispensing path 33 are formed along a length direction (upward and downward direction) to correspond to an attachment position of the cassettes 32. In the main storage part 20 employed in the present embodiment, a plurality of the cassettes 32 are juxtaposed along a lengthwise direction (upward and downward direction) of the plate member 30 as well as around the circumference of the drum 31.

Each of the plate members 30 is attached through a hinge to a frame that makes up a framework of the drum 31 at its upper end portion. When performing maintenance on the main storage part 20, each of the plate members is maintained in a raised state by lifting a lower end portion of each of the plate members 30 and the drum 31 can be opened.

Further, as shown in FIG. 4, an inner side (an inner peripheral surface) of the drum 31 is provided with the dispensing path 33. The dispensing path 33 serves as a path for feeding the medicines dispensed from the cassette 32 to a further downstream side. More specifically, to a rear side of the plate member 30, that is, a surface facing the inside of the drum 31 is provided with a guide member 37. The guide member 37 has an approximately U-shaped cross-section and is an elongated member similar to the plate member 30. The guide member 37 is fixed to the rear side of the plate member 30 and an approximate center portion of the plate member 30 in a widthwise direction thereof (in a circumferential direction of the drum 31). Thus, the dispensing path 33, which extends straight along a lengthwise direction of the plate member 30 (i.e., along an upward and downward direction), is formed between the guide member 37 and the rear surface of the plate member 30.

As shown in FIGS. 4(*b*) and 5, a main portion of the cassette 32 includes a motor base (container mounting part) 40 and a feeder container (medicine feeding container) 41. The motor base 40 includes a motor 43. An output shaft 45 is attached to the motor to upwardly project from the motor base 40. Also, the output shaft 45 is provided with a gear 46. Further, the motor base 40 contains a reader-writer (an interface means) 44. The reader-writer 44 corresponds to a communication mechanism referred to as an RFID (Radio Frequency Identification). The reader-writer is configured to communicate with a tag 49 provided in the feeder container 41 (this will be described in detail below) to read and write a data necessary for the tag 49.

Figure 5:
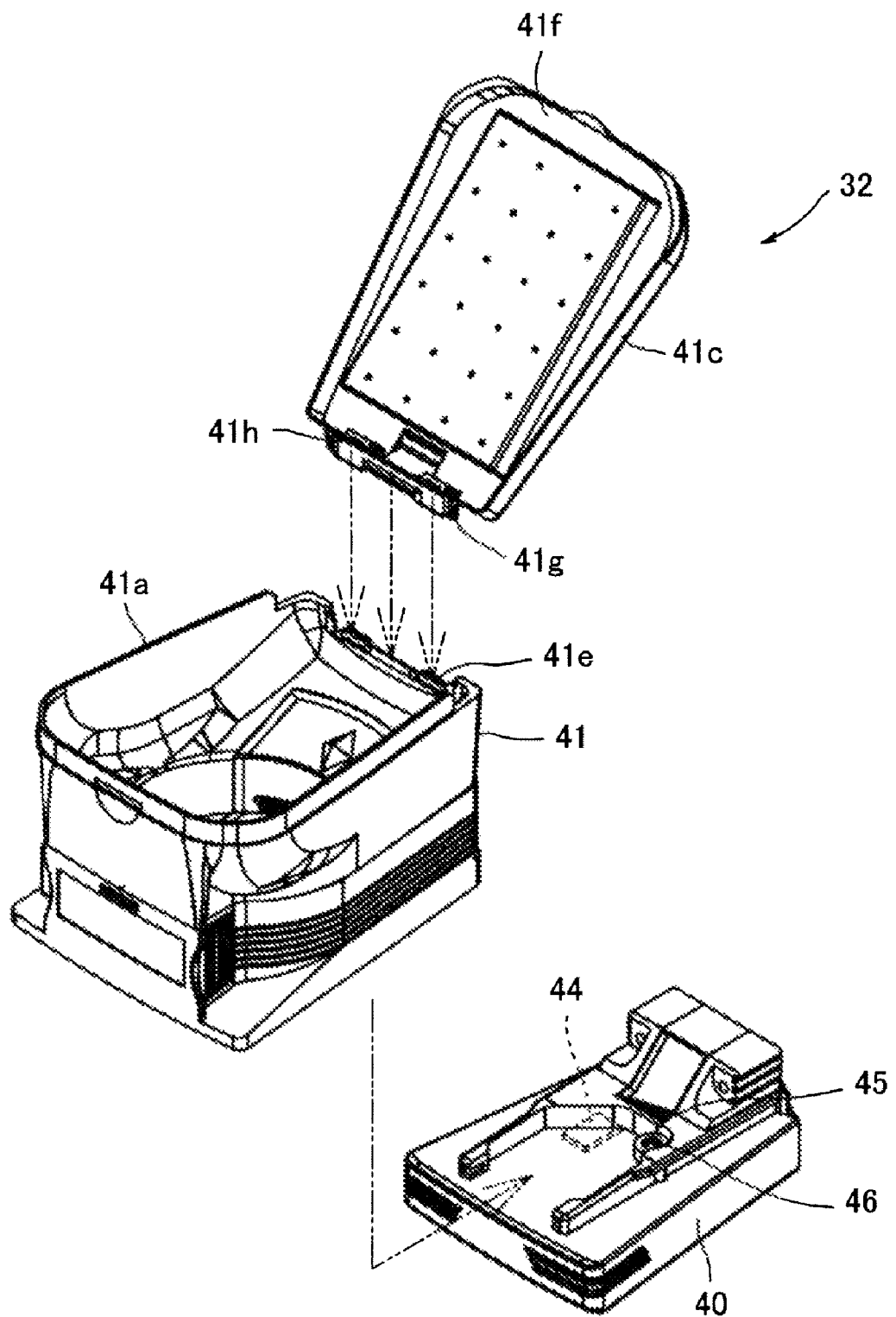
FIG. 5 is an exploded perspective view of a cassette.
Figure 6:
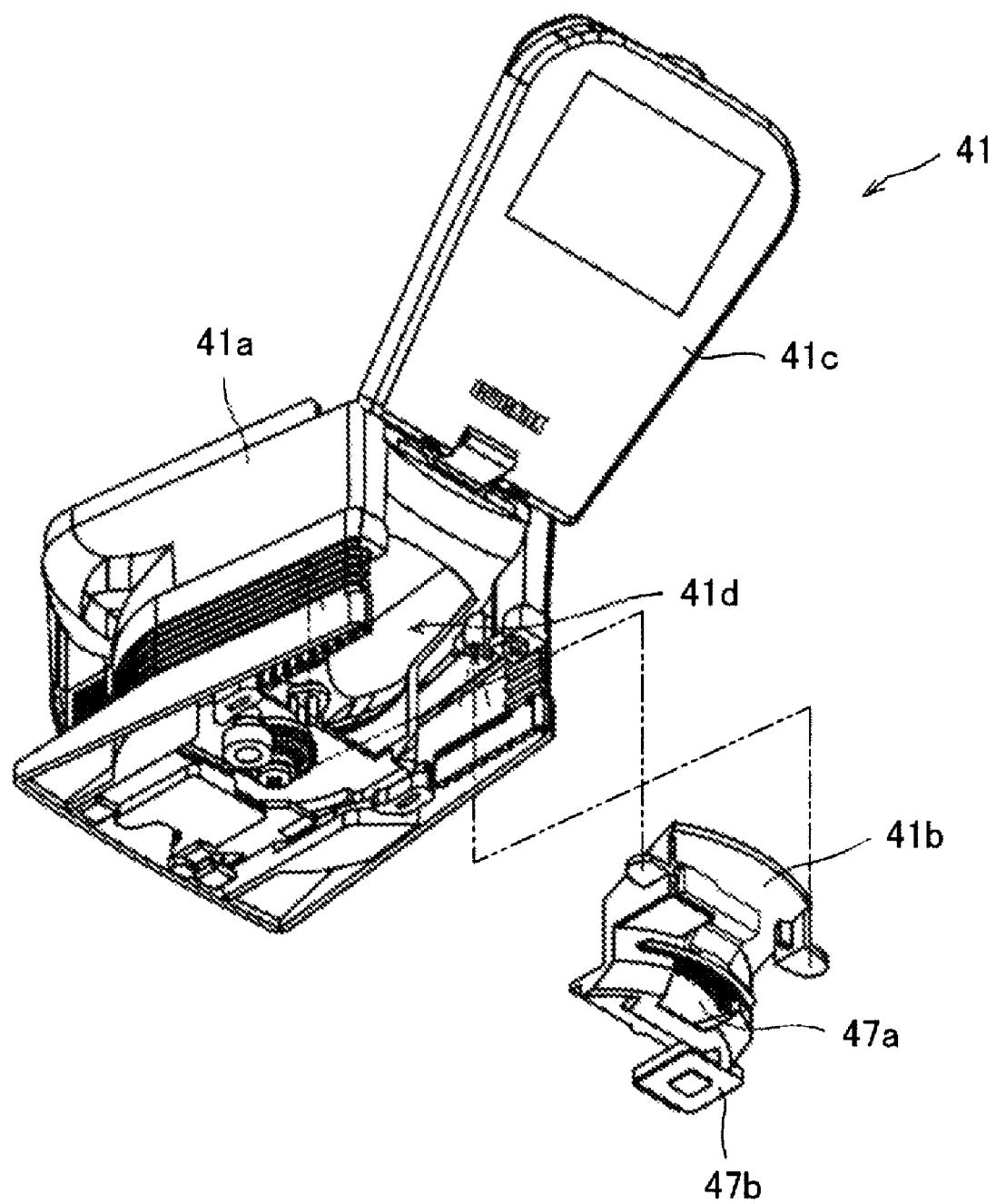
FIG. 6 is an exploded perspective view of a feeder container.

The feeder container 41 is disposed above the motor base 40 and is configured to be detachable relative to the motor base 40. As shown in FIGS. 5 and 6, the feeder container 41 is a hollow container formed by mounting an opening attachment 41*b* and a lid attachment 41*c* on a container body portion 41*a*. The feeder container is configured to be capable of accommodating medicines therein. As shown in FIG. 6, the container body portion 41 has an opening attachment mounting portion 41*d* capable of mounting the opening attachment 41*b* at its back side (i.e., a side facing toward the drum 31 when the feeder container 41 is attached to the motor bases 40 mounted on the drum 31).

The opening attachment 41*b* is configured to be mounted to the opening attachment mounting portion 41*d* of the container body portion 41*a*. The opening attachment 41*b* has an opening 47*a* for discharging the medicines accommodated in the feeder container 41 and a tag attaching portion 47*b*. In the feeder container 41 employed in the present embodiment, various kinds of the opening attachments 41*b* with different sizes of openings 47*a* are prepared. Thus, according to a size of the medicine to be accommodated in the container body portion 41*a*, a suitable opening attachment can be selected and mounted. The tag attaching portion 47*b* is formed at a lower side of the opening attachment 41*b* in a cantilever shape. When the opening attachment 41*b* is mounted to the opening attachment mounting portion 41*d*, the tag attaching portion 47*b* becomes parallel to a bottom surface of the container body portion 41*a*.

The lid attachment 41*c* is configured to close an open portion of an upper end side of the container body portion 41*a*. The lid attachment 41*c* has a lid portion 41*f*, a clip potion 41*g* and a hinge portion 41*h*. The lid portion 41*f* and the clip portion 41*g* are bendably connected to each other through the hinge portion 41*h*. The lid attachment 41*c* is mounted by fitting a lid attachment mounting portion 41*e* provided at an upper end of the container body portion 41*a* to the clip portion 41*g*. The feeder container 41 can open the container body portion 41*a* by erecting the lid portion 41*f* as shown in FIGS. 5 and 6 and can close the container body portion 41*a* by laying down the lid portion as shown in FIG. 4(*b*).

As shown in FIG. 4(*b*), a rotor 48 is disposed in the feeder container 41. A plurality of grooves 48 extending in an upward and downward direction are circumferentially formed at an outer periphery of the rotor 48 at an approximately equal interval. The rotor 48 is configured to freely rotate in the feeder container 41. As the rotor rotates, the grooves 48*a* reach a position of an opening 47*a* formed at a back side of the feeder container 41 one after another. In the present embodiment, various kinds of the rotors 48 with different widths of grooves 48*a* are prepared. Thus, according to the size of the medicine to be accommodated in the container body portion 41*a*, a suitable rotor may be selected and mounted. That is, in the present embodiment, a width (a length in a circumferential direction of the rotor 48) and depth (a length along a diameter of the rotor 48) of the groove 48*a* is sized such that one of the medicines accommodated in the container body portion 41a can pass through the groove one by one.

The rotor 48 is connected to a gear 48b exposed on a bottom surface of the feeder container 41. When the feeder container 41 is mounted on the motor base 40, the gear 48b is allowed to mesh with a gear 46 of the motor base 40. As a result, as the motor 43 provided in the motor base 40 operates, the rotor 48 rotates within the feeder container 41 as much as a rotation quantity of the output shaft 45. Thus, the cassette 32 is configured to appropriately adjust a quantity of the medicines dispensed from the opening 47a of the feeder container 41 by adjusting the amount of rotation of the output shaft 45 of the motor 43.

When the opening attachment 41b and the lid attachment 41c are attached as described above, the tag attaching portion 47b comes to a position which becomes a bottom surface of the feeder container 41. The tag attaching portion 47b is provided with a tag (an information recordable medium) 49. In the present embodiment, as the tag 49, an RFID tag or an RFID chip is employed as the tag 49. Various data including an identification data of the feeder container 41 and the kinds of medicines to be accommodated in the feeder container 41 can be transmitted to and received from the tag 49. The data of the tag can be renewed or written.

Further, as shown in FIG. 4(a) and FIG. 4(c), an abnormal set detecting means 38 is provided at an outer side of the drum 31. The abnormal set detecting means 38 includes a contact plate 38a and a switch 38b. The abnormal set detecting means 38 is configured to detect an abnormal attachment of the cassette 32 to the drum 31 based on whether or not the switch 38b is turned on.

Configuration of the abnormal set detecting means 38 will be described in detail as follows. As shown in FIG. 4(a), the contact plate 38a is an elongated plate body. The contact plate 38a is disposed along a height direction of the drum 31. The contact plate 38a is shaft-supported on a housing of the main unit 2 through a hinge 38c in a cantilever shape. An end of the contact plate facing toward the drum 31 is a free end. That is, the contact plate 38a is supported by the hinge 38c so as to be capable of swinging relative to a tangential direction of the drum 31. Further, the switch 38b is disposed in a position where the contact plate 38a contacts the switch as the contact plate 38a swings. If the contact plate 38a contacts the switch 38b, then a contact of the switch is pressed down and thus the switch is turned on.

As shown in FIG. 4(c), when assuming a trajectory J, which ends of the cassettes 32 form while passing along with a rotation of the drum 31 with the cassettes 32 attached thereto, the contact plate 38a is positioned slightly apart from the trajectory J in a direction of a diameter of the drum 31 in a position where the ends of the cassettes reach. Thus, when the cassette 32 is not securely mounted on the drum 31 and therefore projects outwardly in a direction of a diameter of the drum 31, the cassette 32 is brought into contact with the contact plate 38a along with the rotation of the drum 31 and therefore the contact plate 38a swings about the hinge 38c. As a result, the contact plate 38a bumps against the switch 38b and the switch is turned on. Thus, the abnormal attachment of the cassette 32 is detected.

Figure 3:
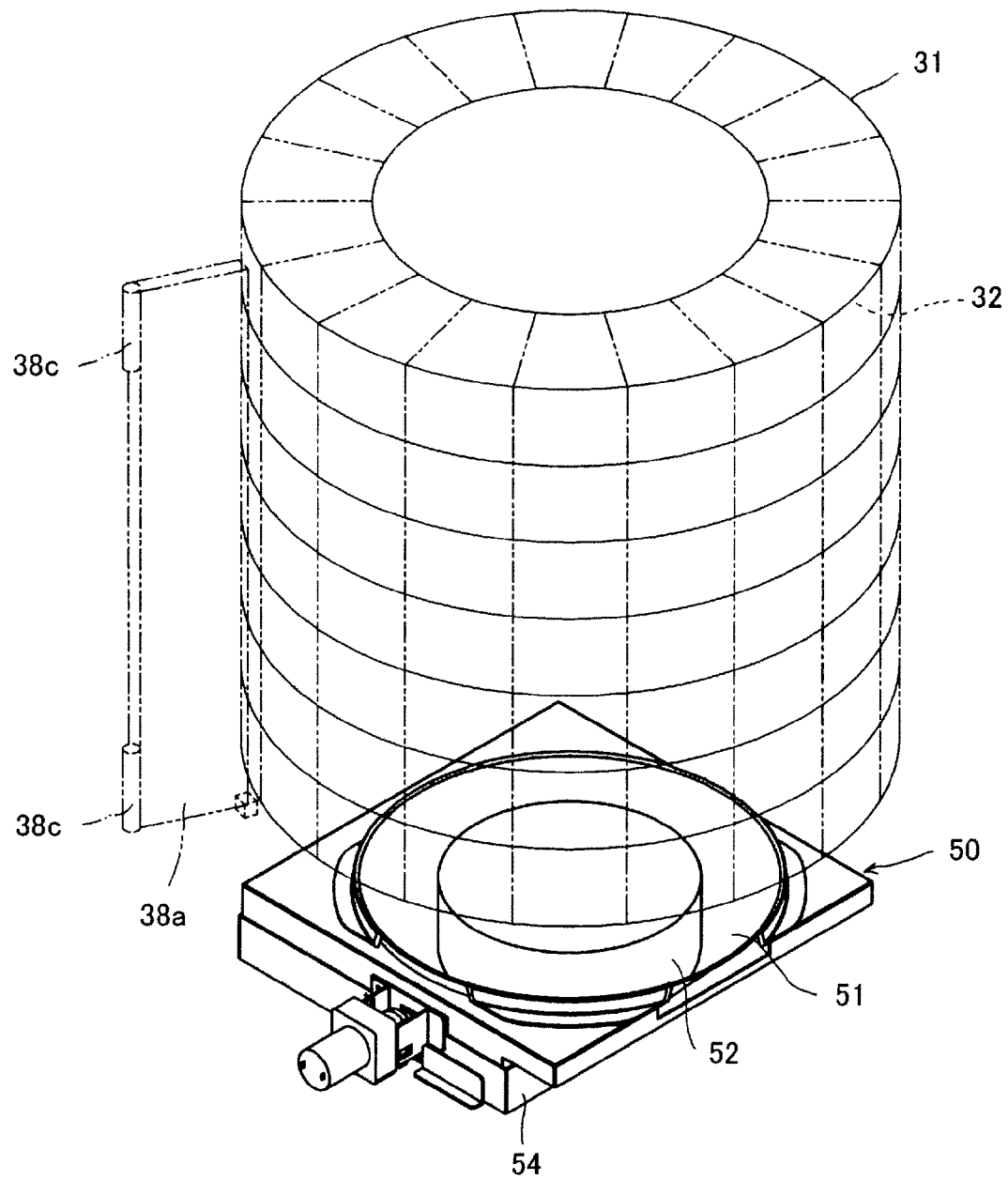
FIG. 3 is a perspective view showing a structure near a main storage part of a main unit.
Figure 7:
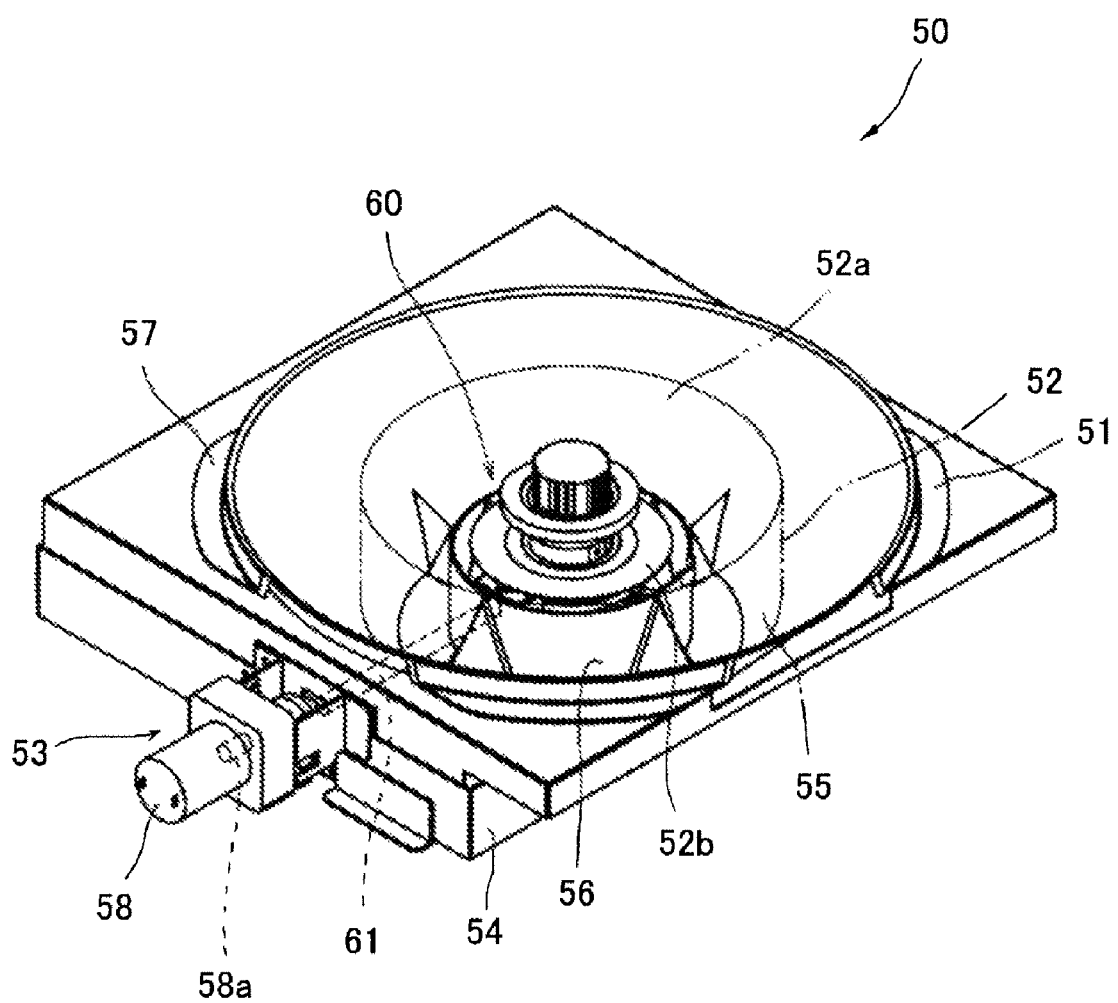
FIG. 7 is a perspective view showing a medicine awaiting mechanism part.

As shown in FIGS. 2 and 3, the medicine standby mechanism part 50 is disposed below the above-described drum 31. As shown in FIGS. 3 and 7, the medicine standby mechanism part 50 includes, as a main part thereof, a funnel-shaped standby hopper 51, a movable lid 52 and a lid moving mechanism 53. The standby hopper 51 is attached to a box body 54 of the medicine standby mechanism part 50. The movable lid 52 is mounted on the lid moving mechanism 53 attached to the standby hopper 51.

More specifically, as shown in FIG. 7, the standby hopper 51 has a mechanism positioning part 55 for disposing the lid moving mechanism 53 in its center portion. A plurality of discharging openings 56 are formed in a position surrounding the mechanism positioning part 55. Further, a flange 57 is formed along an outer edge portion of the standby hopper 51. The standby hopper 51 is fixed to the box body 54 by screw-fixing the flange 57 to the box body.

The lid moving mechanism 53 is configured to move the movable lid 52 in an upward and downward direction relative to the standby hopper 51. The lid moving mechanism 53 has a motor 58 as a power source, a mechanism part 60 operable by a power from the motor 58, and a power transmitting shaft 61 for transmitting the power of the motor 58 to the mechanism part 60. The motor 58 is positioned such that a rotating shaft 58a is approximately vertical to a side surface of the box body 54 and projects toward an inside portion of the box body 54.

Figure 8:
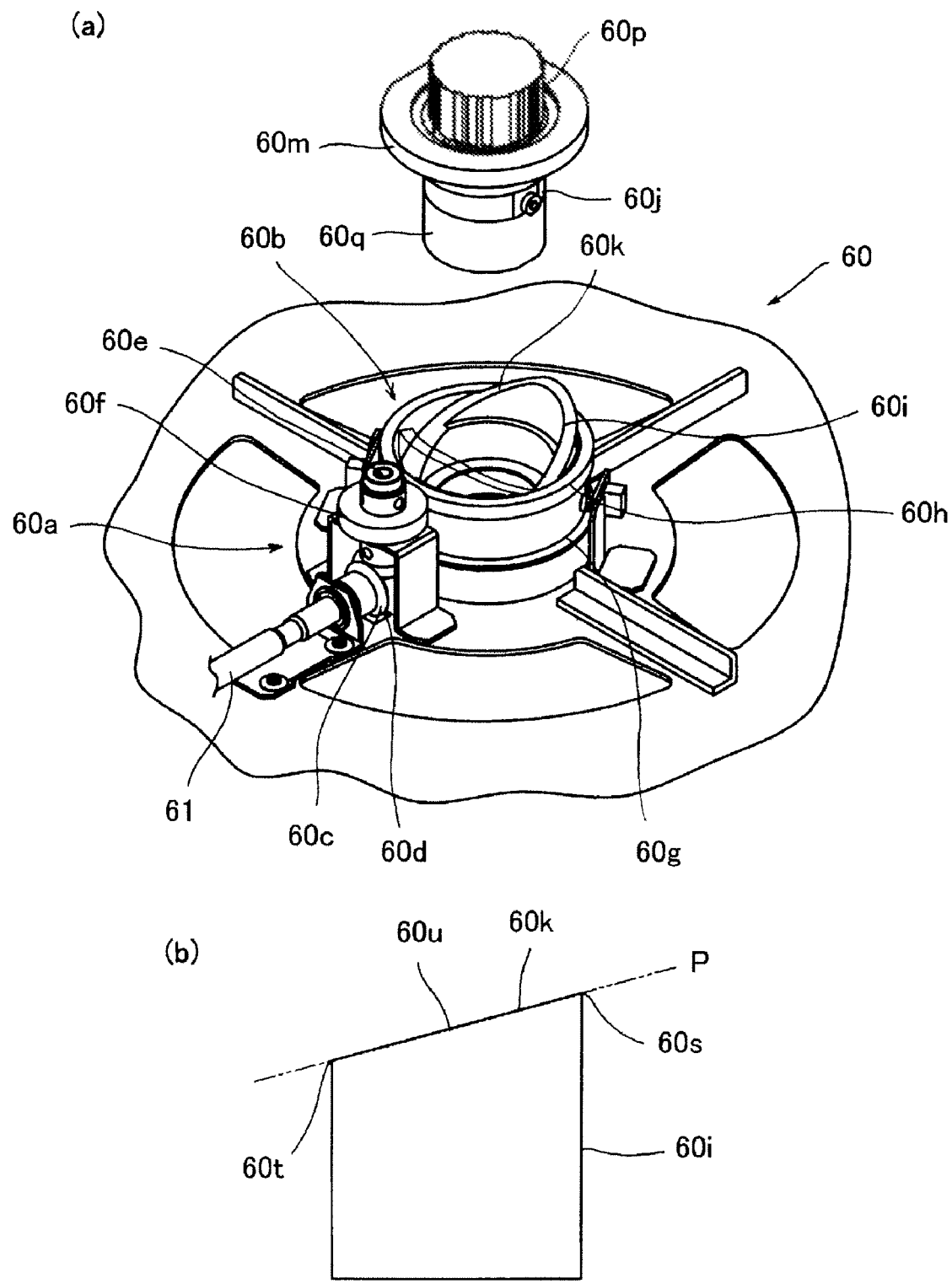
FIG. 8 is a perspective view showing a mechanism part.

As shown in FIG. 8, the mechanism part 60 includes a drive part 60a operable by the power of the motor 58 and a driven part 60b operable by the power from the drive part 60a. The drive part 60a has a bevel gear 60c coupled to a leading end of the power transmitting shaft 61 and a bevel gear 60d disposed so as to mesh therewith. The bevel gear 60d is coupled to one end of a rotating shaft 60e uprightly erected vertically to the power transmitting shaft 61. Further, a drive gear 60f is coupled to the other end of the rotating shaft 60e and configured to be integrally rotatable with the bevel gear 60d. Thus, if a rotation power is transmitted from the motor 58 through the power transmitting shaft 61, the drive gear 60f rotates about the rotating shaft 60e.

Meanwhile, the driven part 60b has a rotating cylinder member 60g, a driven gear 60h, a cam 60i and a slide shaft 60j. The rotating cylinder member 60g is a cylindrical member. The rotating cylinder member is positioned with its axial center at an approximate center of the mechanism positioning part 55 and is supported so as to rotate about the axial center. The drive gear 60h has a ring shape. The drive gear 60h is an outwardly-toothed gear with its outer diameter approximately equal to the rotating cylinder member 60g. The drive gear 60h is fixed on an upper end of the rotating cylinder member 60g. Further, the drive gear 60h is meshed with the drive gear 60f installed in the drive part 60a. Thus, if the drive gear 60f rotates by the power of the motor 58, the power is transmitted to the drive gear 60f, thereby rotating the rotating cylinder member 60g about its axial center.

The cam 60i is a so-called end cam. An end face 60k of the cam has a shape which is formed by cutting a cylinder at a plane P intersecting its generator. More specifically, as shown in FIG. 8(b), when assuming the plane P passes the end face 60k and the cam 60i is disposed with the end face 60k facing upward, the end face 60k has an upper end 60s located at an uppermost side and a lower end 60t located at a lowermost side. The end face is shaped such that an intermediate portion 60u gently connects the upper end 60s and the lower end 60t.

The cam 60i is disposed inside the rotating cylinder member 60g with the end face 60k facing upward. The cam 60i is integrated with the rotating cylinder member 60g to rotate along with the rotating cylinder member 60g. The slide shaft 60j is a shaft body connected to the movable lid 52. The slide shaft is divided into a smaller diameter portion 60p and a larger diameter portion 60q by a flange portion 60m provided at one end side in a lengthwise direction. The smaller diameter portion 60*p* is located more closely to the end side of the slide shaft 60*j* than the flange portion 60*m* and has a diameter smaller than other portions.

The larger diameter portion 60*q* forms a main portion of the slide shaft 60*j*. The slide shaft 60*j* is configured to freely slide in an axial direction relative to the cam 60*i* (i.e., an upward and downward direction) by inserting the larger diameter portion 60*q* into the cam 60*i*. A roller 60*r* is rotatably coupled to a peripheral surface of the larger diameter portion 60*q* and an intermediate portion in a lengthwise direction of the larger diameter portion 60*q*. The roller 60*r* is in contact with the end face 60*k* of the cam 60*i* when the slide shaft 60*j* is inserted into the cam 60*i* with the larger diameter portion 60*q* facing downward. Thus, as the cam 60*i* rotates about its axial center, the roller 60*r* rolls on the end face 60*k* and the slide shaft 60*j* moves in an upward and downward direction to conform with an undulation of the end face 60*k*.

The slide shaft 60*j* is integrated with the movable lid 52 by inserting the smaller diameter portion 60*p* into a recess 66 formed at an approximate center of the movable lid 52 and screw-fixing the flange portion 60*m* to the movable lid 52. More specifically, the movable lid 52 is a disk-shaped member having an approximate circular lid top surface 52*a* and a lid peripheral surface 52*b* for surrounding an outer periphery of the lid top surface. The recess 66 is formed at an approximate center portion of the lid top surface 52*a* inside the movable lid 52. The movable lid 52 is integrated with the slide shaft 60*j* by inserting the smaller diameter portion 60*p* of the slide shaft 60*j* into the recess 66 and screw-securing between the lid top surface 52*a* and the flange portion 60*m*.

The movable lid 52 moves in an upward and downward direction by operation of the above-described lid moving mechanism 53 to thereby open and close each of the discharging openings 56 formed in the standby hopper 51. More specifically, in the lid moving mechanism 53, as the rotating cylinder member 60*g* rotates by operation of the motor, the cam 60*i* relatively rotates about the axial center relative to the slide shaft 60*j*. As a result, the roller 60*r* coupled to the slide shaft 60*j* moves in an upward and downward direction to conform with the undulation of the end face 60*k* while rolling along the end face 60*k* of the cam 60*i*. Accordingly, the slide shaft 60*j* and the movable lid 52 integrated thereto slide upward and downward relative to the cam 60*i*.

Figure 9:
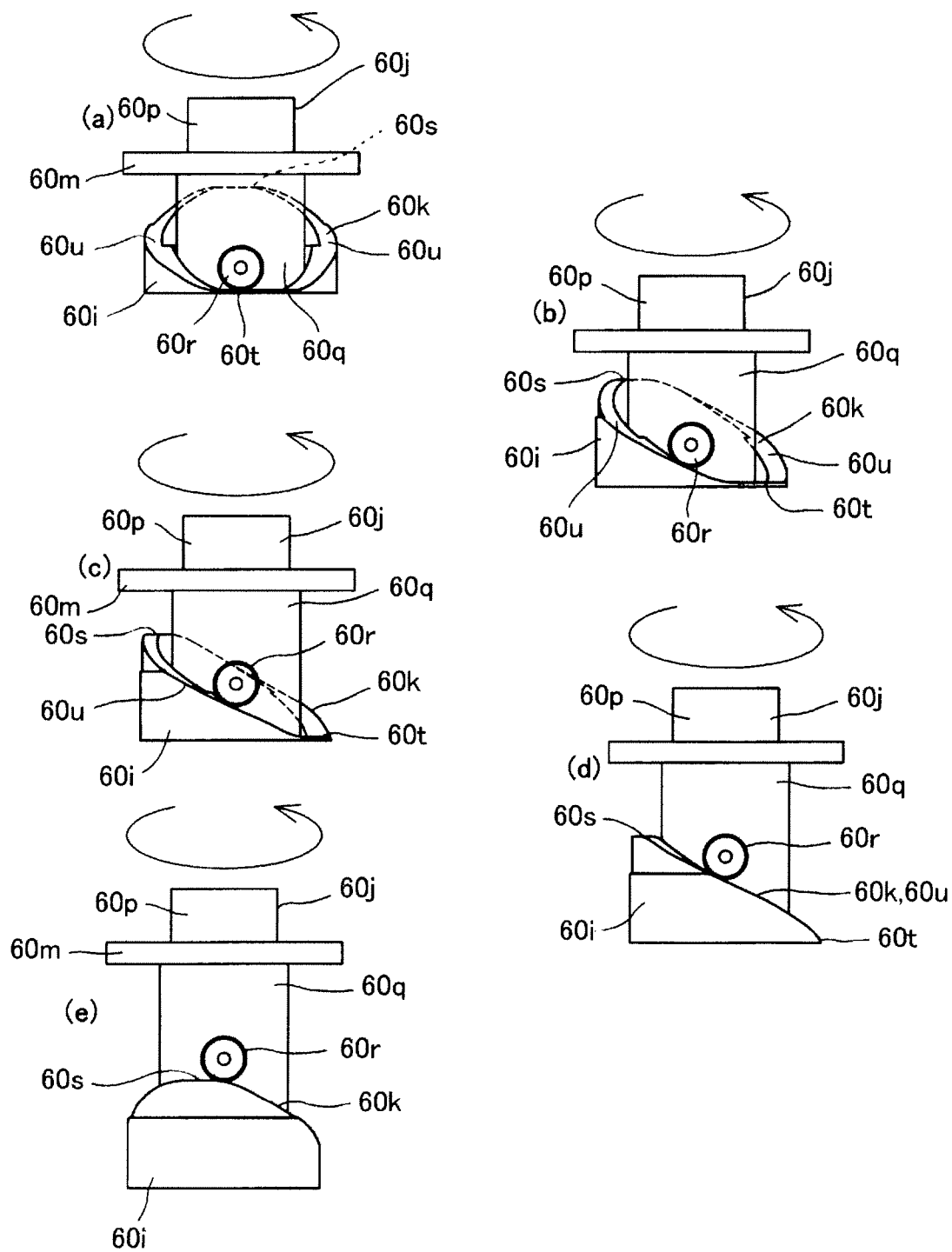
FIGS. 9(a) to 9(d) are side views sequentially showing a vertical movement of a slide shaft.

Still more specifically, as shown in FIG. 9(*a*), when the roller 60*r* coupled to the larger diameter portion 60*q* of the slide shaft 60*j* is in contact with a position corresponding to the lower end 60*t* of the cam 60*i*, the slide shaft 60*j* is in a lowermost position in the cam 60*i*. In this case, as shown in FIG. 10(*a*), the movable lid 52 is in a state where a lid connecting cylinder 62 of the mechanism part 60 is lowered and a lower end of the lid peripheral surface 52*b* is in contact with an inner peripheral surface of the standby hopper 51. In such a state, since each of the discharging openings 56 formed in the standby hopper 51 is surrounded and blocked by the lid peripheral surface 52*b*, the medicines inputted into the standby hopper 51 can be gathered.

Meanwhile, if the motor 58 provided in the lid moving mechanism 53 operates, the rotating cylinder member 60*g* and the cam 60*i* integrated thereto start to rotate as indicated by an arrow in FIG. 9. As a result, as shown in FIG. 9(*b*), the intermediate portion 60*u* of the end face 60*k* comes to a position corresponding to the roller 60*r*. In this case, as described above, the slide shaft 60*j* is configured to freely slide upwardly and downwardly relative to the cam 60*i*. Thus, if the intermediate portion 60*u* comes to the position corresponding to the roller 60*r* by the rotation of the cam 60*i*, the slide shaft 60*j* is pushed upwardly. As a result, the movable lid 52 integrated to the slide shaft 60*j* is gradually pushed upward, thereby forming a gap between the lower end of the lid peripheral surface 52*b* and the inner peripheral surface of the standby hopper 51 as shown in FIG. 10(*b*).

Thereafter, the cam 60*i* further rotates. As shown in FIG. 9(*c*) and FIG. 9(*d*), as the intermediate portion 60*u* comes to the position corresponding to the roller 60*r*, a height in the end face 60*k* becomes gradually higher and thus the movable lid 52 is further pushed upwardly. As a result, the gap between the lower end of the movable lid 52 integrated to the slide shaft 60*j* and the inner peripheral surface of the standby hopper 51 becomes larger. Further, if the cam 60*i* rotates until the upper end 60*s* of the end face 60*k* comes to the position corresponding to the roller 60*r*, then the gap between the lid peripheral surface 52*b* and the inner peripheral surface of the standby hopper 51 is allowed to maximally open, thereby providing a state where the medicines can sufficiently pass through, that is, a state where each of the discharging openings 56 is opened.

As shown in FIG. 2, a collecting hopper 70 is provided below the medicine standby mechanism part 50. The collecting hopper 70 is situated so as to connect the medicine standby mechanism part 50 and a medicine preparing part 80 (this will be described in detail below).

Further, as described above, the main unit 2 includes the manual distributing unit 23. As shown in FIG. 1, the manual distributing unit 23 has a plurality of measures 90 arranged in a matrix form therein. Each of the measures in some embodiments is capable of accommodating multiple medicines per pack. The medicine delivering unit is configured to be drawn out from the housing of the main unit 2. An upper side of each of the measures 90 is opened. The medicine delivering unit 23 is configured to be appropriately drawn out from the housing of the main unit 2 so that the medicines for one pack can be fed into each of the measures 90. When accommodated in the housing of the main unit 2, the manual distributing unit 23 can dispense the medicines by opening a bottom side of each of the measures 90.

In a state where the manual distributing unit 23 is accommodated in the housing of the main unit 2, a manual distributing hopper 91 is disposed below the manual distributing unit 23. The manual distributing hopper 91 is configured to feed the medicines dispensed from each of the measures 90 of the manual distributing unit 23 to the medicine preparing part 80.

Figure 11:
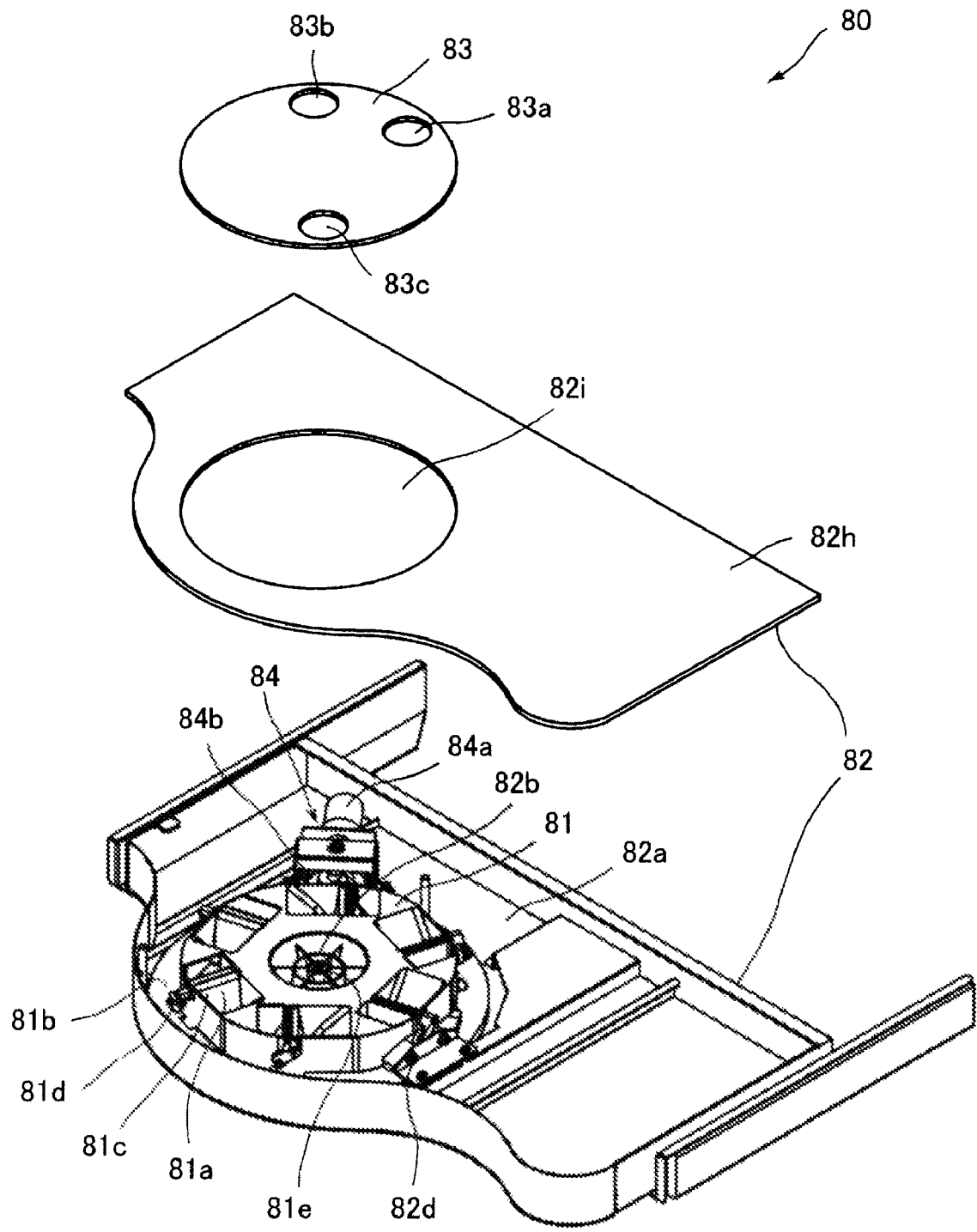
FIG. 11 is an exploded perspective view showing a medicine preparing part.
Figure 12:
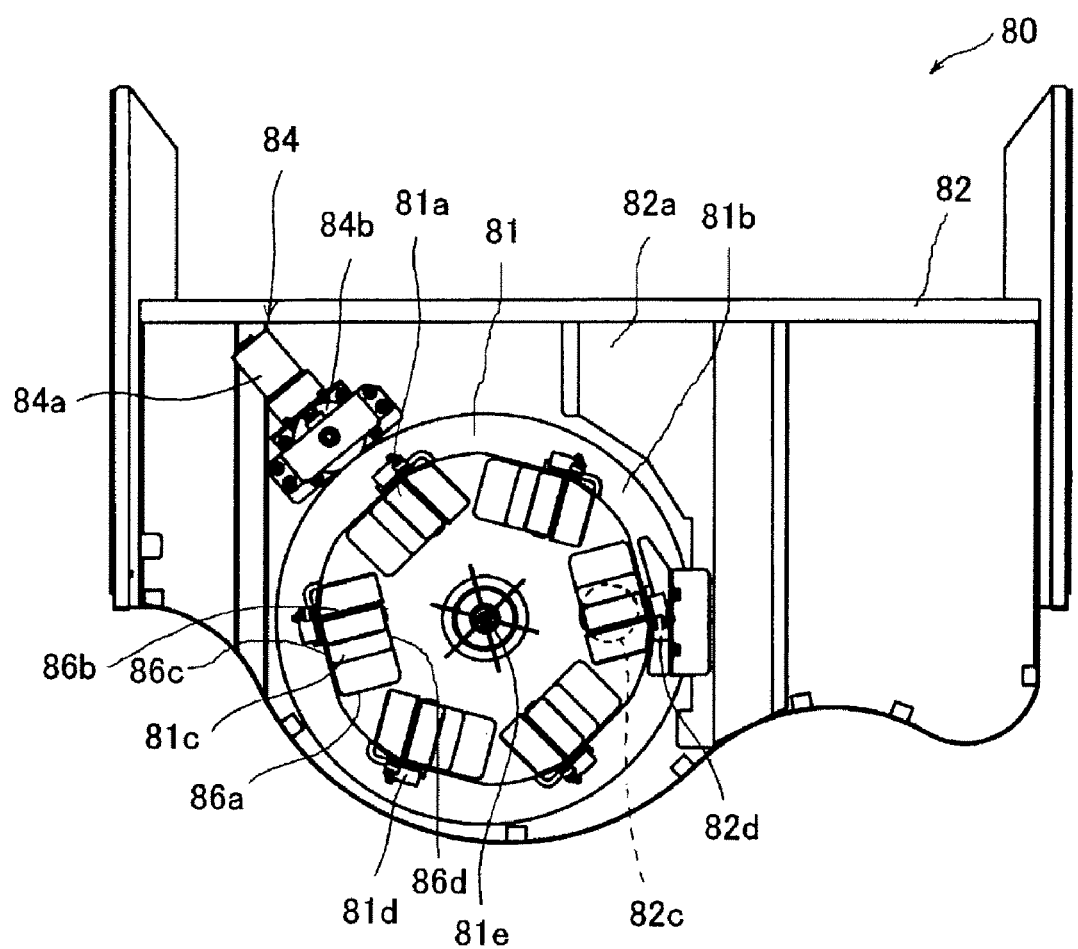
FIG. 12 is a top plan view showing the internal structure of the medicine preparing part.

The medicine preparing part 80 is configured to gather and prepare the medicines for one pack fed from the above described standby hopper 51 and the manual distributing hopper 91 and to sequentially discharge the same to a further downstream side. The medicine preparing part 80 is disposed below the medicine gathering mechanism portion 50 and the manual distributing unit 23. As shown in FIGS. 11 and 12, the medicine preparing part 80 has a disk-shaped section forming body 81, a medicine preparing part body 82 and a lid 83. The section forming body 81 has sections 81*a* for gathering the medicines. The section forming body 81 employed in the present embodiment has a plurality of the sections 81*a* (six sections in the present embodiment) in a circumferential direction. Each of the sections 81*a* is opened at a top surface of the section forming body 81. Further, each of the sections 81*a* has a shutter 81*c*, which can be opened and closed independently. The shutter 81*c* is blocked at normal times, but is opened if a lever 81*d* provided at a lateral side of each of the sections 81*a* is pressed.

More specifically, as shown in FIG. 12, each of the sections 81*a* is surrounded by the following: a front wall portion 86*a* at one end side in a circumferential direction of the section forming body 81; a rear wall portion 86b at the other side in the circumferential direction and peripheral wall portions 86c, 86d at outer and inner sides in a diametrical direction of the section forming body 81. The front wall portion 86a is inclined toward an inside of the section 81a from a top surface of the section forming body 81 toward a bottom surface thereof. Further, a stepped portion 86e is formed in a portion of the front wall portion 86a at a bottom surface of the section forming body 81. The rear wall portion 86b approximately vertically extends from the top surface of the section forming body 81 toward its bottom surface up to a middle portion and then is inclined toward an outside of the section 81a from the middle portion to the bottom surface.

The shutter 81c has a plate shape. One end (hereinafter, this may be referred to as a proximal end) of the shutter 81c is swingably shaft-supported by a support shaft 86f in a position of the real wall portion 86b and the top surface of the section forming body 81. The other end (hereinafter, this may be referred to as a leading end) of the shutter 81c faces toward the front wall portion 86a and the bottom surface of the section forming body 81. That is, the shutter 81c is inclined in a downward direction in an inner space of the section 81a as going from the proximal end to the leading end. The shutter 81c is biased by a biasing means (not shown) such as a spring coupled to the leading end pressed so that the leading end can face upwardly. Further, at normal times, the leading end of the shutter 81a is closed to the stepped portion 86e of the front wall portion 86a. Thus, the section 81a is blocked at the bottom surface of the section forming body 81. The lever 81d is integrated with the shutter 81a by the support shaft 86f. The lever 81d is configured to be pivot about the support shaft 86f while maintaining at a constant angle relative to the shutter 81c. A roller 86g is freely rotatably coupled to the lever 81d.

As shown in FIGS. 11 and 12, a flange portion 81b projecting diametrically outwardly is provided at the bottom surface of the above-described section forming body 81. The flange portion 81b has a plurality of gear teeth at its outer periphery and thus has an outwardly-toothed gear shape. A through hole 81e is formed in a center portion of the section forming body 81 so as to pass through in thickness of the section forming body 81, that is, between the top surface and the bottom surface.

The medicine preparing part body 82 has an accommodating part 82a capable of accommodating the section forming body 81. A support shaft 82b projecting upwardly is disposed in an approximate center of the accommodating part 82a. The above-described section forming body 81 is mounted in the accommodating part 82a in such a manner that the top surface faces upward and the support shaft 82 is inserted through the through hole 81e. Thus, the section forming body 81 is accommodated within the accommodating part 82a while rotatable about the support shaft 82b.

Further, a drive mechanism 84 is provided in the medicine preparing part body 82. The drive mechanism 84 includes a motor 84a and a gear 84b rotatable by power from the motor 84a. The gear 84b is meshed with the gear formed in the flange portion 81b of the section forming body 81 accommodated in the accommodating part 82a. Thus, if the motor 84a operates, the power is transmitted through the gear 84b to the section forming body 81 and thus the section forming body 81 rotates about the support shaft 82b.

As shown in FIG. 12, an opening 82c for dispensing the medicines is formed at a bottom surface of the medicine preparing part body 82. The opening 82c is formed in a position where it can communicate with each of the sections 81a provided in the section forming body 81. Further, a lever contactor 82d is provided in a position adjacent to the opening 82c. More specifically, the lever contactor 82d has a block shape. The lever contactor 82d is, in some embodiments, made up of an ascending-inclined portion 82e, a horizontal portion 82f and a descending-inclined portion 82g as shown by a tow-dot chain line in FIG. 13. An upper surface of the lever contactor 82d is inclined in the ascending-inclined portion 82e and the descending-inclined portion 82g, while horizontal in the horizontal portion 82f. The upper surface of the lever contactor 82d is upwardly inclined in the ascending-inclined portion 82e as going toward the horizontal portion 82f. The upper surface of the lever contactor 82d is downwardly inclined in the descending-inclined portion 82g as being spaced apart from the horizontal portion 82f. The lever contactor 82d is positioned such that the ascending-inclined portion 82e faces upstream in a rotation direction of the section forming body 81 and the descending-inclined portion 82g faces downstream in the rotation direction.

Figure 13:
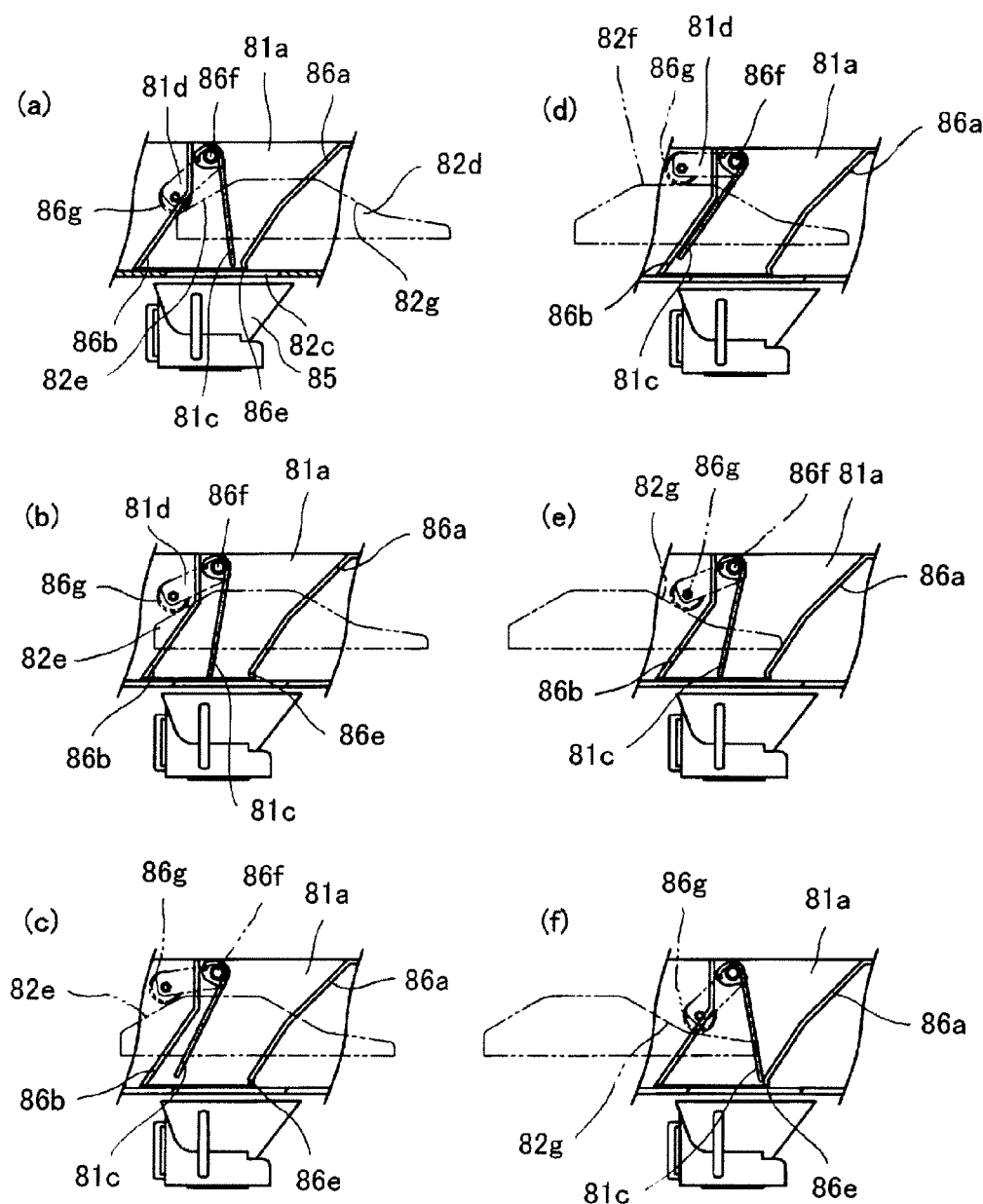
FIGS. 13(a) to 13(f) are sectional views sequentially showing operating processes of a shutter provided in a section forming body.

The lever contactor 82d is positioned in the medicine preparing part body 82 in a position where the lever contactor 82d contacts the lever 81d provided at a later side of each of the sections 81a when the section forming body 81 rotates. Thus, as shown in FIG. 13, if the section forming body 81 rotates and thus each of the levers 81d contacts the lever contactor 82d, then the shutter 81c connected to the lever 81d is opened. More specifically, when the lever 81d comes to a position where the lever contactor 82d is provided by the rotation of the section forming body 81, the roller 86g coupled to the leading end of the lever 81d is allowed to ride on the ascending-inclined portion 82e as shown in FIG. 13(a). If the section forming body 81 further rotates from such a state, the roller 86g rolls on the ascending-inclined portion 82e and an inclination of the lever 81d becomes closer to an approximately horizontal state as shown in FIG. 13(b).

In this case, as described above, the lever 81d is configured to be rotatable about the support shaft 86f while maintaining at a constant angle relative to the shutter 81c. Thus, if the inclination of the lever 81d changes as described above, the shutter 81c rotates about the support shaft 86f by such change and the leading end of the shutter 81c becomes gradually close to the rear wall portion 86b. Thus, the bottom surface of section 81a gradually becomes open.

If the rotation of the section forming body 81 proceeds as described above, the opening extent of the shutter 81c becomes gradually large as shown in FIG. 13(c). Thereafter, if the section forming body 81 further rotates and the roller 86g coupled to the leading end of the lever 81d is positioned as shown in FIG. 13(d), the shutter 81c becomes in contact with the rear wall portion 86b of section 81a and thus the shutter 81c becomes fully open.

If the rotation of the section forming body 81 further proceeds from a full open state of the shutter 81c and the roller 86g reaches the descending-inclined portion 82g as shown in FIG. 13(e), the shutter 81c is biased and the leading end of the shutter 81c becomes gradually close to the front wall portion 86a of section 81a. Thus, the bottom surface of section 81a gradually becomes closed by the shutter 81c. And, if the roller 86g passes over a halfway point of the descending-inclined portion 82g, the leading end of the shutter 81a contacts the stepped portion 86e formed in the front wall portion 86a and the bottom surface of section 81a becomes blocked by shutter 81c as shown in FIG. 13(f).

The section forming body 81 is accommodated in the medicine preparing part body 82 so as to operate as described above. Meanwhile, a packing hopper 85 is provided in a position corresponding to the opening 82c of the bottom surface of the medicine preparing part body 82. The packing hopper 85 is provided so as to feed the medicines dispensed from the opening 82c toward the medicine packing part 21 (this will be described in detail below). Thus, if each of the sections 81a comes to a position corresponding to the opening 82c in the medicine preparing part body 82, the lever 81d provided in section 81a is pressed and the shutter 81 is opened. As a result, the medicines gathered in section 81a are dispensed toward the medicine packing part 21.

Further, as shown in FIG. 11, an approximately circular opening 82i is formed in a top plate 82h forming the top surface of the medicine preparing part body 82 so as to correspond to the section forming body 81. Further, the lid 83 is provided so as to block the opening 82i. The lid 83 has three holes 83a to 83c. The holes 83a to 83c are configured to be connected to the collecting hopper 70, the manual distributing hopper 91 and the sub collecting hopper 87 (this will be described in detail below). The holes 83a to 83c are formed in a position corresponding to each of the sections 81a of the section forming body 81 accommodated in the accommodating part 82a. Thus, the medicine preparing part 80 is configured to be capable of inputting the medicines through the holes 83a to 83c into each of the sections 81a provided in the medicine preparing part body 82.

Figure 14:
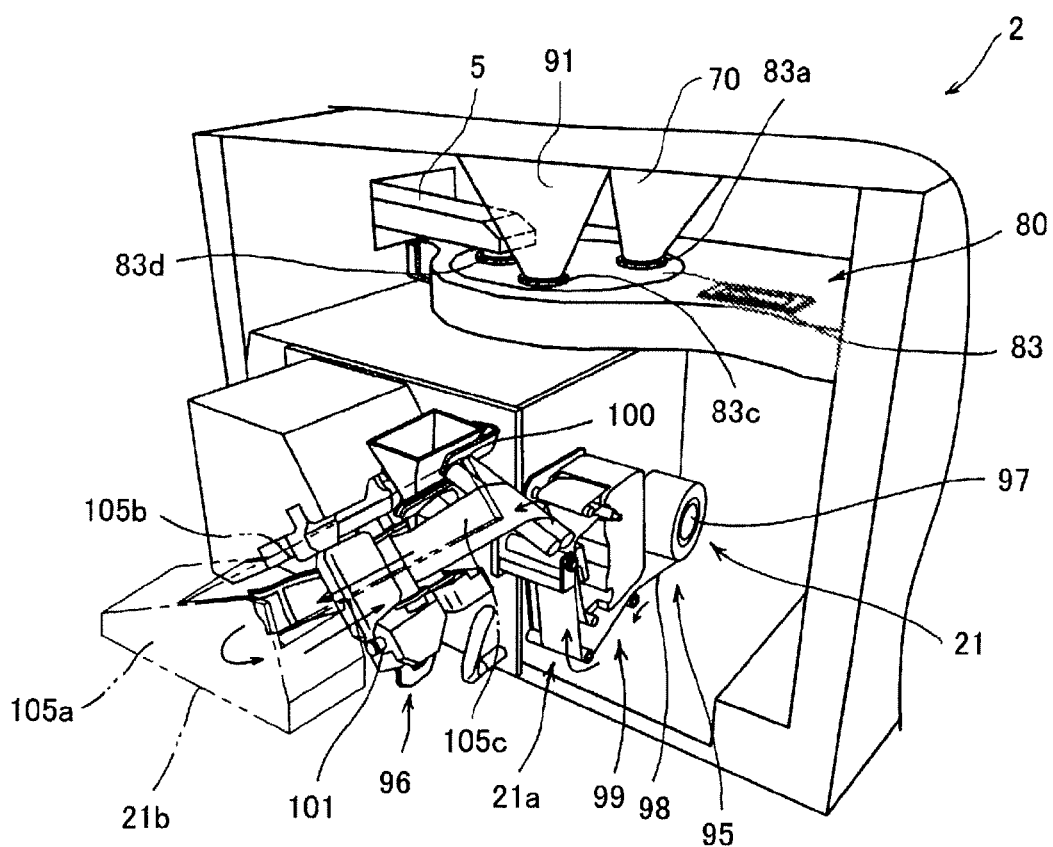
FIG. 14 is a perspective view showing structure near a medicine preparing part and a medicine packing part of the main unit.
Figure 15:
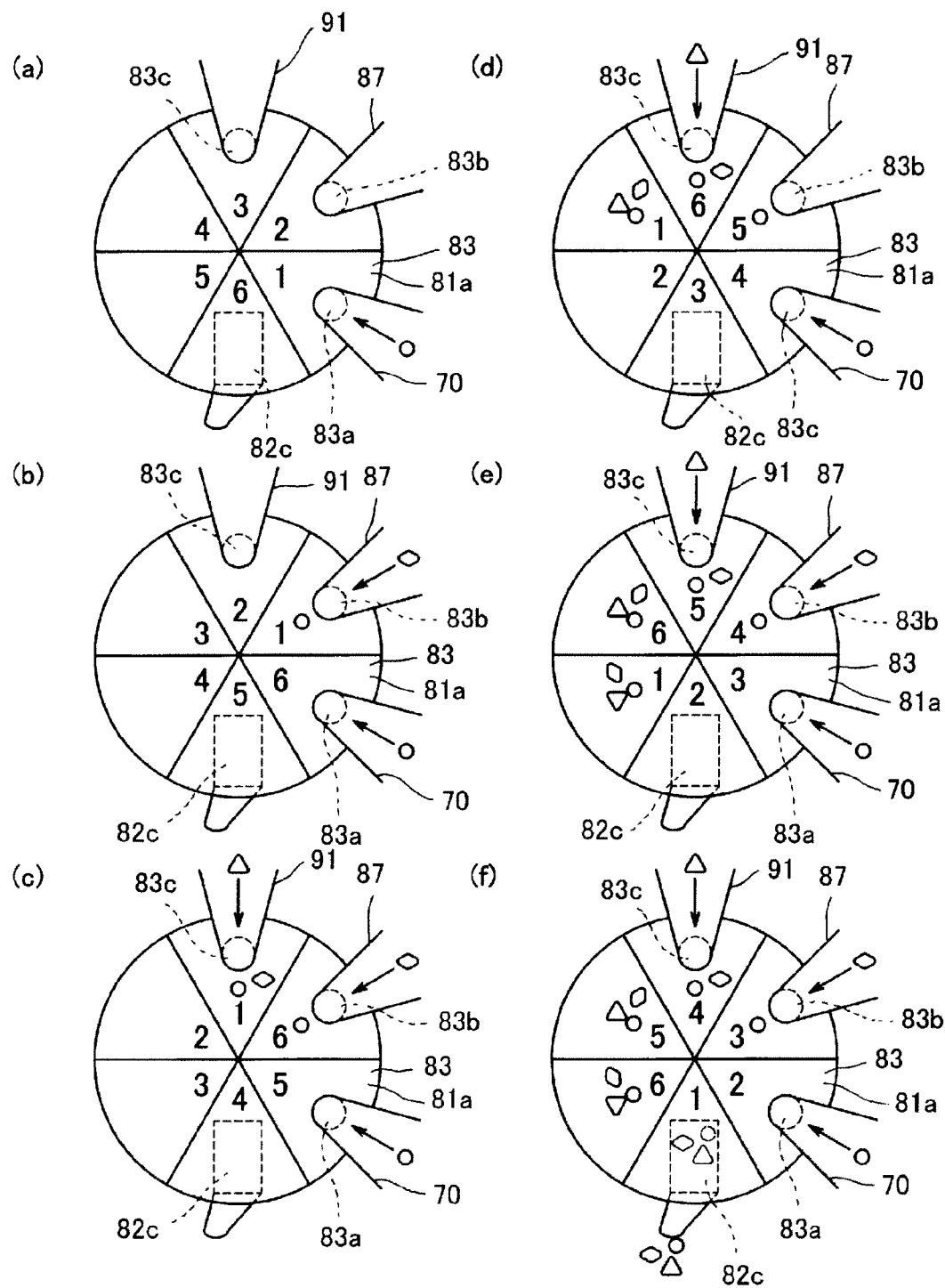
FIGS. 15(a) to 15(f) schematically illustrates that medicines are fed into the section forming body.

More specifically, as shown in FIG. 14, the collecting hopper 70 is connected to the hole 83a formed in the lid 83. As shown in FIG. 15, when viewed from the top surface, the hole 83a is formed in a position deviated by one section 81a, which makes up the section forming body 81, in a counterclockwise direction (a left-hand direction) from a position of the opening 82c formed in the medicine preparing part body 82 for dispensing the medicines. That is, when assuming that one section 81a provided in the section forming body 81 coexists with the opening 82c, the hole 83a is formed in a position where the medicines can be inputted into section 81a counterclockwise in a circumferential direction of the section forming body 81 from section 81a corresponding to the opening 82c.

As will be described in detail below, the sub collecting hopper 87 for feeding the medicines, which are transferred from the sub unit 3 through the transfer device 5, to the medicine preparing part 80 is connected to the hole 83b. The hole 83b is formed in a position counterclockwise deviated from the opening 82c of the medicine preparing part body 82 by two sections 81a constituting the section forming body 81. That is, when assuming that section 81a is positioned so as to correspond to the opening 82c, the hole 83b is formed in a position where the medicines can be inputted into section 81a counterclockwise adjacent to the section 81a. Further, the manual distributing hopper 91 is connected to the hole 83c. The hole 83c is formed in a position clockwise (in a right-hand direction) from the opening 82c of the medicine preparing part body 82 by three sections 81a.

As shown in FIG. 14, the medicine packing part 21 is provided below the above-described medicine preparing part 80. The medicine packing part 21 includes a packing means 21a and a conveying means 21b. The packing means 21a includes a sheet transferring mechanism 95, a pack forming mechanism 96 and a printing part 99. The sheet transferring mechanism 95 is configured to unwind a packing paper sheet 98, which includes a thermally fused elongated sheet and has a sheet form wound around a roll shaft 97, and to transfer it to the pack forming mechanism 96. The packing paper sheet 98 unwound by the sheet transferring mechanism 95 is sequentially transferred along a path extending through the pack forming mechanism 96 to the printing part 99 as indicated by an arrow in FIG. 14 and is then fed to the conveying means 21b. The pack forming mechanism 96 has a sheet supporting part 99, a guide member 100 and a partition forming device 101. The pack forming mechanism 96 is configured to bend the packing paper sheet 98 transferred from the sheet transferring mechanism 95 into two portions at its approximate halfway portion in a shorter direction (width direction) and compresses the bent packing paper sheet 98 into a pouch shape.

The guide member 100 is provided upstream in a flowing direction of the packing paper sheet 98 from the packing hopper 85 provided in the bottom surface of the medicine preparing part body 82 halfway in the flowing direction of the packing paper sheet 98. The guide member 100 has functions of not only serving as a guide of the packing paper sheet 98 but also bending the elongated packing paper sheet 98 into two portions at an approximate halfway portion in a width direction. The partition forming device 101 is disposed downstream in the flowing direction of the packing paper sheet 98 from the above-described packing hopper 85. The partition forming device 101 can compress a portion of one end side (downstream side) in a lengthwise direction of the bifold packing paper sheet 98, which is previously bent by the guide member 100, into a semi-pouch shape or compress and close an opening portion of the semi-pouch shaped packing paper sheet 98 into a pouch shape.

The printing part 99 is configured to perform a print on the packing paper sheet 98 transferred by the sheet transferring mechanism 95. As shown in FIG. 14, the printing part 99 is positioned downstream in the flowing direction of the packing paper sheet 98 from the medicine packing part 21 and upstream in the flowing direction of the packing paper sheet 98 from the pack forming mechanism 96. A length of the packing paper sheet 98 existing between the positions of the printing part 99 and the pack forming mechanism 96 is n times (three times in the present embodiment) greater than a length of a medicine pack formed by compressing the packing paper sheet 98.

Figure 16:
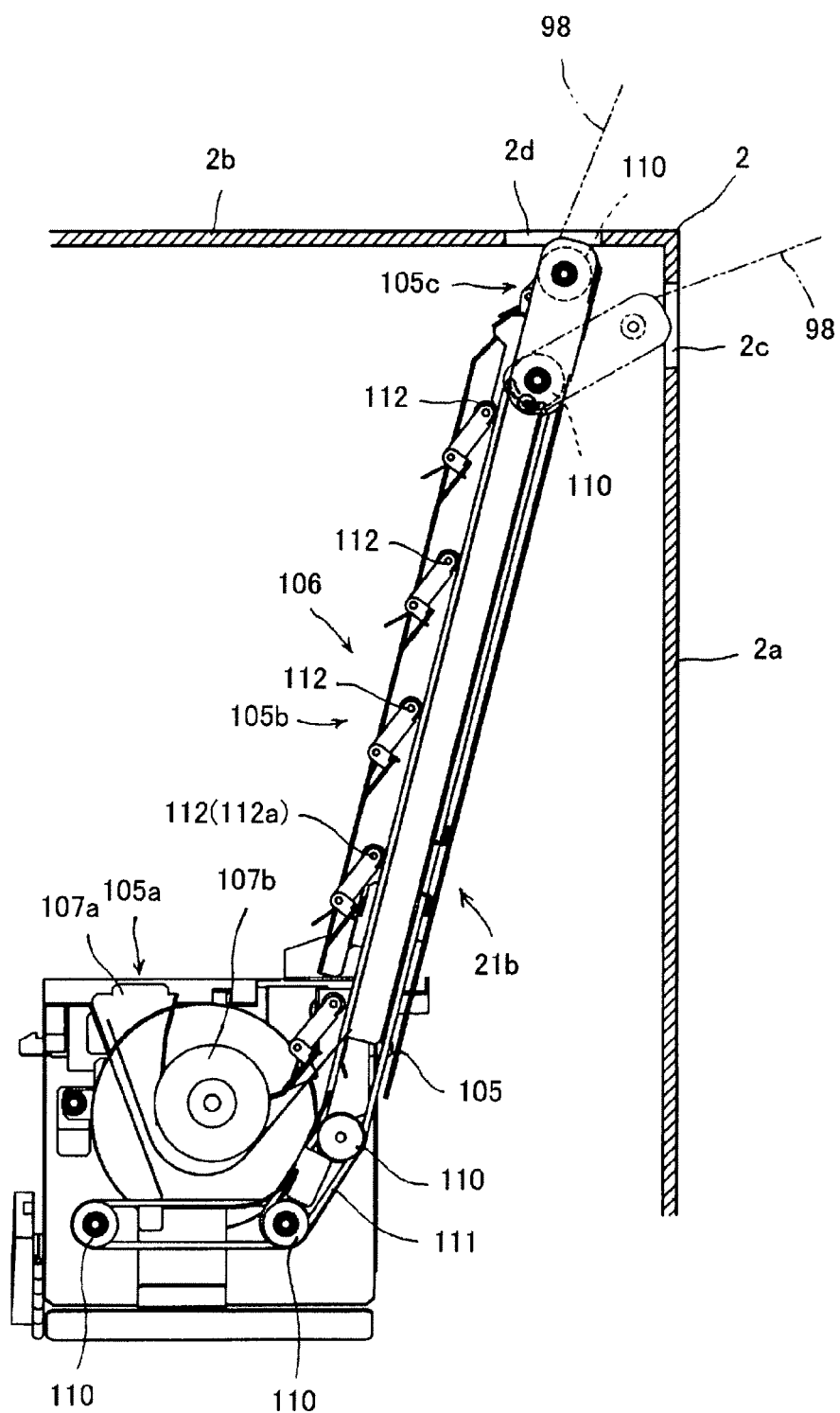
FIG. 16 is a sectional view showing arrangement of a conveying means in the main unit.
Figure 17:
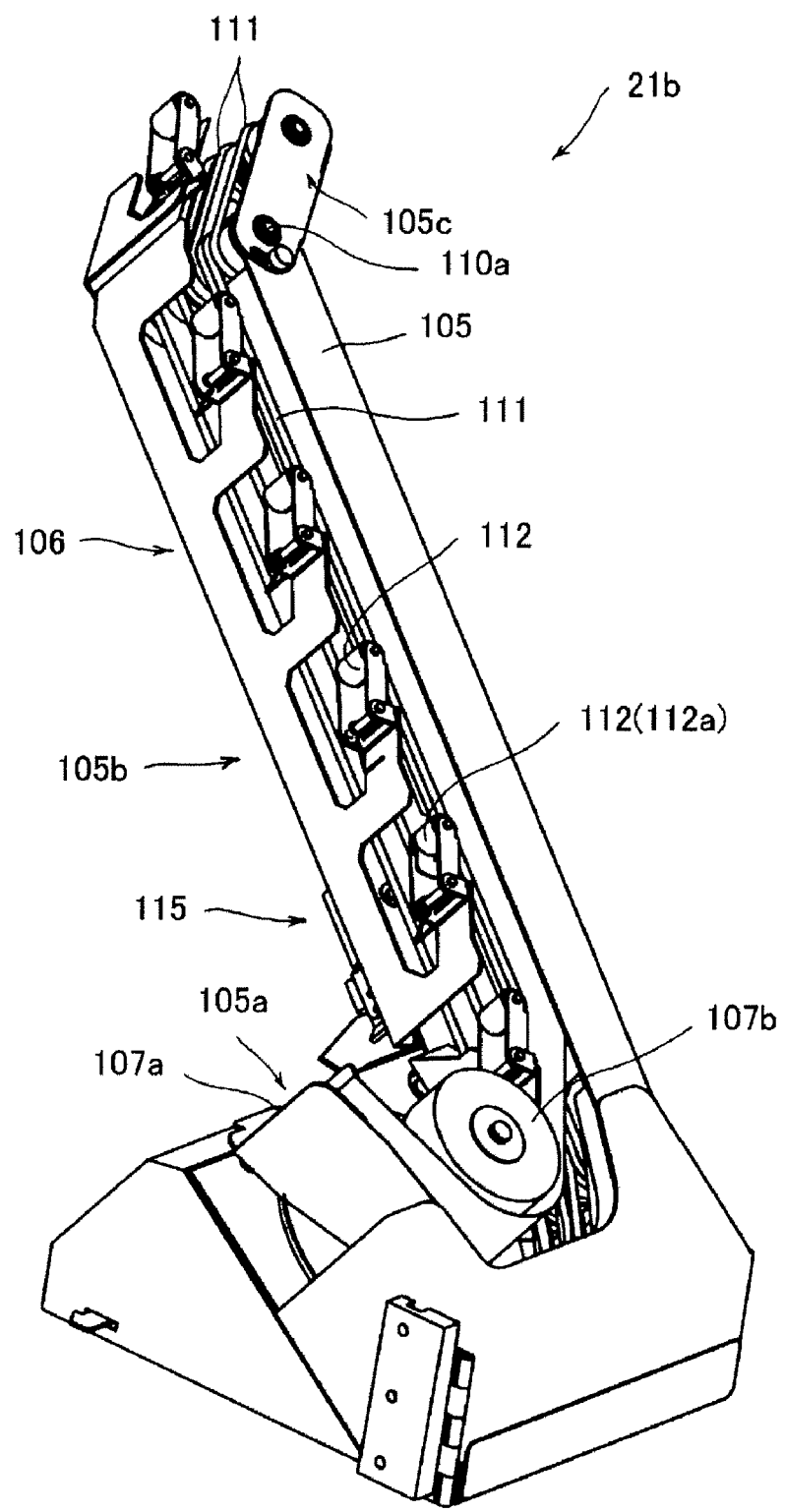
FIG. 17 is a perspective view showing the conveying means.

As shown in FIG. 16, the conveying means 21b is configured to convey the packing paper sheet 98 with the medicines packed therein in the packing means 21a toward dispensing openings 2c, 2d formed in a front panel 2a or a side panel 2b of the main unit 2. As shown in FIG. 17, the conveying means 21b has a casing 105. A conveying mechanism 106 is equipped in the casing 105. The conveying means 21b includes a receiving portion 105a, a straight portion 105b and a bent portion 105c. As shown in FIGS. 14, 17 and 19, the conveying means 21b is disposed in a manner that the receiving portion 105a is positioned at a bottom surface in the housing of the main unit 2 and a portion from the straight portion 105b to the bent portion 105c erects obliquely upwardly from the receiving opening 105.

The conveying means 21b has a serial conveying path of the packing paper sheet 98 from the receiving portion 105a through the straight portion 105b to the bent portion 105c. As shown in FIGS. 16 and 19, drive rollers 110 are provided in several places along the conveying path formed in the conveying means 21b. More specifically, the drive rollers 110 are freely rotatably provided in the following places: an entrance to the receiving portion 105a; the vicinity of a boundary between the receiving portion 105a and the straight portion 105b; and the vicinity of a boundary between the straight portion 105b and the bent portion 105c; and a leading end side of the bent portion 105c. In the conveying means 21b, belts 111 are wound between neighboring drive rollers 110 so as to transmit a power from a motor (not shown). In the present embodiment, four belts 111 are provided at a predetermined interval in a lengthwise direction of each drive roller 110.

The receiving portion 105a is configured to receive the packing paper sheet 98 with the medicines packed by the packing means 21a and to change a transfer direction of the packing paper sheet 98, which is transferred obliquely downward, into an obliquely upward direction. The receiving opening 105 has a receiving opening 107a for receiving the packing paper sheet 98 and a guide roller 107b provided therein. The receiving portion 105a is disposed in a position where the receiving opening 107a can receive the serial packing paper sheet 98 formed by packing the medicines in the packing means 21a.

The casing 105 is configured to allow the packing paper sheet 98 to pass through between the guide roller 107b and the above-described drive roller 110 and the belt 111 suspended thereto at a portion corresponding to the receiving portion 105a. Further, the receiving portion 105a is curved along the guide roller 107b and connected to the straight portion 105b. Thus, if the packing paper sheet 98 is introduced through the receiving opening 107a into the receiving portion 105a in the conveying means 21b, then the packing paper sheet 98 is guided by the guide roller 107b and is brought into contact with the drive roller 110 and the belt 111 and then the packing paper sheet 98 is transferred toward the straight portion 105b.

A plurality of pressing rollers 112 are provided at a boundary between the receiving portion 105a and the straight portion 105b, the straight portion 105b and the bent portion 105c. The pressing rollers 112 are disposed at a predetermined interval with the neighboring one in a lengthwise direction of the straight portion 105b. Further, when assuming a conveyance plane H of the packing paper sheet 98 formed by the drive roller 110 and the belt 111, the pressing roller 112 presses the conveyance plane H with such a pressure force as the belt 11 slightly flexes. Further, the pressing roller 112 is biased toward the conveyance plane H. Thus, if the packing paper sheet 98 is introduced through the receiving portion 105a, the packing paper sheet 98 is under pressure toward the conveyance plane H by the pressing roller 112 and the packing paper sheet 98 receives a power from the drive roller 110 and the belt 111 to be transferred downstream.

In this case, as described above, a plurality of the pressing rollers 112 are provided in the conveying means 21a. Meanwhile, as shown in FIG. 18(b), a sub roller 115a is provided at a lateral side of the pressing roller 112 closer to the receiving portion 105a (hereinafter, where necessary, this may be referred to as the pressing roller 112a). The sub roller 115a constitutes a transfer abnormality detecting mechanism (detecting means) 115 for detecting a transfer abnormality of the packing paper sheet 98. The sub roller is provided so as to be rotatable independently of the pressing roller 112a.

Figure 18:
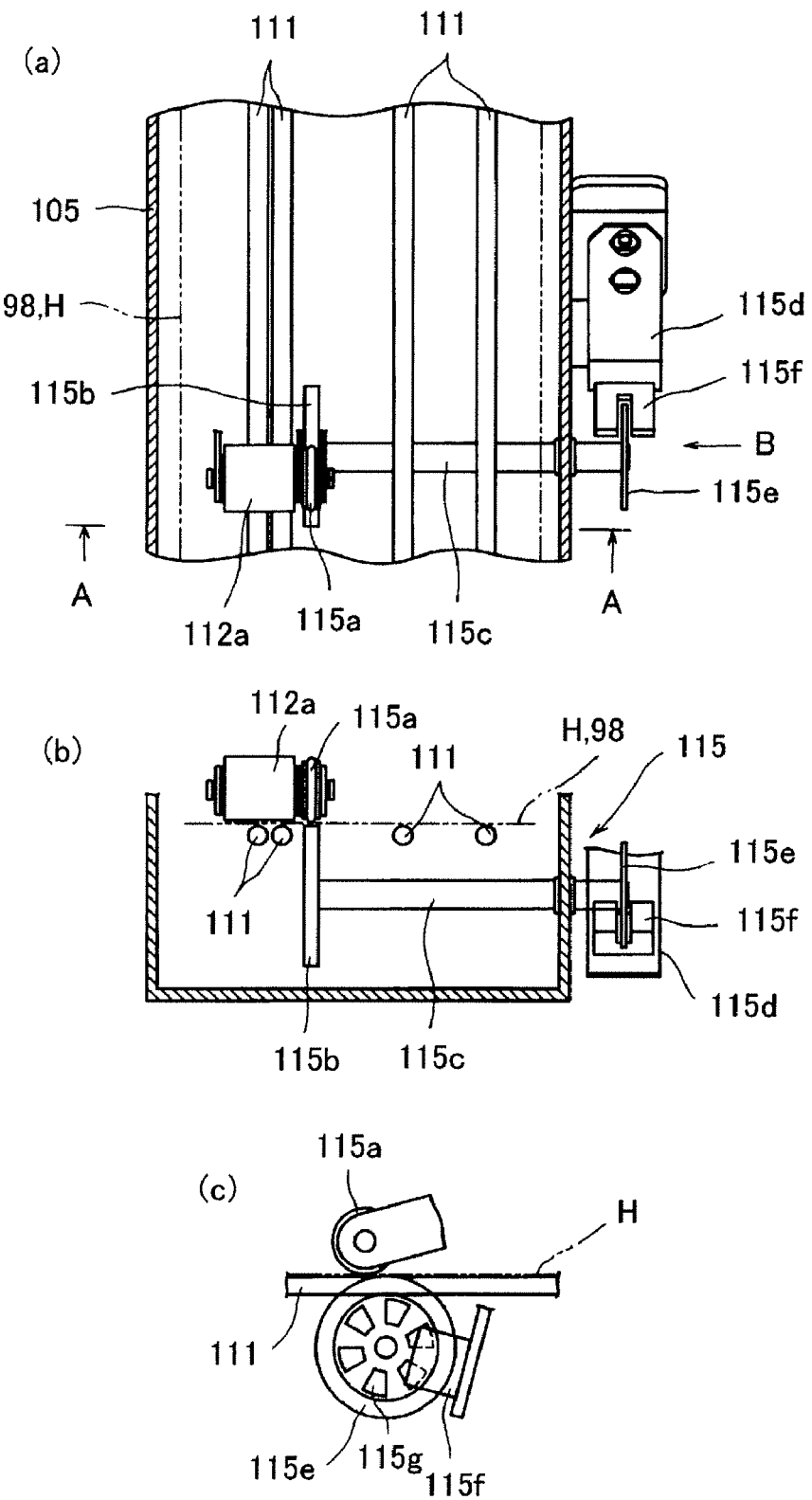
FIG. 18(a) is a sectional view showing that an abnormality detecting mechanism is attached to a transfer means.
FIG. 18(b) is a section view taken along the ling A-A in FIG. 18(a).
FIG. 18(c) is a view viewed along an arrow B in FIG. 18(a).

As shown in FIG. 18, the abnormality detecting mechanism 115 has a pinch roller (detecting means) 115b, a shaft 115c and a rotary encoder (rotary detecting means) 115d in addition to the above-described sub roller 115a. The pinch roller 115b is disposed such that the above-described conveyance plane H is interposed between the pinch roller and the sub roller 115a. The pinch roller 115b is coupled to one end of the shaft 115c and is rotatable integrally with the shaft 115c. Thus, if the packing paper sheet 98 passes along the conveyance plane H, the pinch roller 115b and the shaft 115c integrally rotate since they are pushed by the packing paper sheet 98.

In this case, as described above, the sub roller 115a is configured to be rotatable independently of the pressing roller 112a. Thus, although the belt 11 operates and the pressing roller 112a rotates by the power from the belt 111, the sub roller 115a does not rotate. Thus, the sub roller 115a and the pinch roller 115b do not rotate as far as the packing paper sheet 98 does not pass therebetween.

As shown in FIGS. 18(b) and 18(c), the rotary encoder 115d has an encoder disc 115e with a plurality of slits 115g circumferentially formed and a photo interrupter 115f like a conventional one. Further, the encoder disc 115e is integrally coupled to the other end of the above-described shaft 115c. Thus, the encoder disc 115e rotates along with the pinch roller 115b. Accordingly, when the packing paper sheet 98 passes through a position where the pressing roller 112a is provided, a rotation is detected by the rotary encoder 115d. On the contrary, when the pinch roller 115b does not rotate since the packing paper sheet 98 causes a transfer abnormality of the packing paper sheet such as a paper jam, a rotation is not detected in the rotary decoder 115d.

As shown in FIG. 17, the bent portion 105c is connected to the straight portion 105b through a support shaft 110a of the drive roller 110 provided at a distal end of the straight portion 105b. The bent portion can bend about the support shaft 110a relative to the straight portion 105b. As shown in FIG. 16, when the bent portion 105c extends straight out to follow the straight portion 105b, its leading end faces toward the dispensing opening 2d formed in the side panel 2b of the main unit 2. Meanwhile, when the bent portion 105c is bent toward the front panel 2a relative to the straight portion 105b, its leading end faces toward the dispensing opening 2c.

As shown in FIG. 1, the main unit 2 has a worktable 117 at a later side of the above-described manual distributing unit 23. Where necessary, the worktable 117 can be drawn out from a main body of the main unit 2 or pushed into the main body of the main unit to be accommodated therein. As shown in FIG. 20, the worktable 117 has a container placing portion 117a capable of placing the feeder container 41 which constitutes the above-described cassette 32. The container placing portion 117a has a recess 117b which is concave to correspond to a shape of the bottom surface of the feeder container 41. Further, when the bottom surface of the feeder container 41 is fitted into the recess 117b, the reader-writer 117c is positioned in a position opposite tag 49 in the bottoms side of the feeder container 41. The reader-writer 117c corresponds to a communication mechanism referred to as a RFID (Radio Frequency Identification). The reader-writer can read and write necessary data by communication with the tag 49.

As shown in FIG. 1, an operation panel 118a for operating the medicine dispensing system 1, a barcode reader 118b and a journal printer 118c are provided at a front side of the main unit 2. The barcode reader 118b is capable of reading barcodes written on an original medicine box. Further, the journal printer 118c is provided in order to print prescription records of medicines done by the medicine dispensing system 1. According to the medicine dispensing system 1, the barcodes are read by the barcode reader 118b to thereby operate the drum 31 so that the cassette 32 provided in order to accommodate the medicines corresponding to the barcodes can come to the front side.

As shown in FIGS. 1 and 2, the medicine dispensing system 1 according to the present embodiment is configured to add the sub unit 3 to the main unit 2 configured as above. The sub unit 3 includes a sub storage part 120 capable of accommodating and appropriately dispensing medicines, which has the same configuration as the main storage part 20 of the above-described main unit 2. That is, in the medicine dispensing system 1 according to the present embodiment, the sub storage part 120 constitutes the medicine dispensing means together with the main storage part 20 and the manual distributing unit 23 at the main unit 2. Further, a sub medicine standby part 130, which has the same configuration of the medicine standby mechanism part 50 provided in the main unit 2, is provided below the sub storage part 120. Also, a sub hopper 135 is disposed below the sub medicine standby part 130. Thus, medicines dispensed from the sub medicine standby part 130 can be fed through the sub hopper 135 to the transfer device 5, which will be described in detail below.

The sub unit 3 is configured to select the cassette 32 accommodating the medicines according to the prescription from a plurality of the cassettes 32 provided in the sub storage part 120, to operate the cassette 32 and to dispense the medicines as much as a required quantity. Further, the sub unit 3 can gather the medicines dispensed from the sub storage part 120 one pack at a time in the sub main storage part 130 and dispense the same one after another through the sub hopper 135 to the transfer device 5.

The transfer device 5 is configured to transfer the medicines from the sub unit 3 constituting the sub unit toward the main unit 2 constituting the main unit. As shown in FIG. 21, the transfer device 5 has a pipe line 140 and a suction means (transfer means) 141. Each component member based on the pipe line 140 are set on in a support 144. As shown in FIG. 2, the transfer device 5 is positioned in a manner that the support 144 is inserted through a communication opening 4b formed in a wall surface 4a existing at a boundary between the main unit 2 and the sub unit 3 to lie across the main unit 2 and the sub unit 3.

Configuration of the transfer device 5 will be described in detail below. A medicine receiving part 142 is provided at one end of the pipe line 140, while a medicine dispensing part 143 is provided at the other side. The suction means 141 is pipe-connected to a suction means connecting portion 148 provided at the other side of the pipe line 140, i.e., in a position of the medicine dispensing part 143. Further, the suction means connecting portion 148 serves as a joint for connecting the pipe line 140 and a pipe connected to the suction means 141. Thus, the transfer device 5 is configured to suck the medicines existing in the medicine receiving part 142 in the pipe line 140 to the medicine dispensing part 143 when the suction means 141 operates.

The medicine receiving part 142 is provided with a measure 145 for receiving the medicines and an inlet shutter mechanism 146. As shown in FIG. 21, the measure 145 has an opening at a top surface. The medicines transferred through the sub hopper 135 provided at the sub unit 3 can be inputted through the opening to an inside portion of the measure 145. Meanwhile, the measure 145 has a medicine dispensing opening 145a at a side portion 145b. Further, in a position opposite the opening 145a, the one end of the pipe line 140 is disposed through a shutter plate 146a constituting the inlet shutter mechanism 146.

In addition to the shutter plate 146a, the inlet shutter mechanism 146 has a motor 146b for operating the shutter plate 146a. A pinion (not shown) is coupled to an output shaft of the motor 146b. Meanwhile, the shutter plate 146a has a rectangular opening 146f opened in a rectangular shape. One edge of the rectangular opening 146f is serrated, thereby forming a rack 146c extending in a lengthwise direction of the shutter plate 146a. Further, the shutter plate 146a has an opening 146e in a position adjacent to the rectangular opening 146f in a lengthwise direction. The opening 146e has an approximately circular opening shape and is formed in an appropriate center portion of the shutter plate 146a. An opening diameter of the opening 146e is approximately equal to an opening diameter of the pipe line 140.

The shutter plate 146a is disposed to follow the side portion 145b of the measure 145. The motor 146b is provided in a position adjacent to the shutter plate 146a. The pinion coupled to the output shaft of the motor 146b is positioned within the rectangular opening 146f of the shutter plate 146a and is meshed with the rack 146c. Meanwhile, braces 150a are provided in positions adjacent to both lateral sides of the pipe line 140. Two rollers 150b are vertically and rotatably provided in the respective braces 150a. The shutter plate 146a is supported as fitted between the rollers 150b vertically juxtaposed in each brace 150a. Thus, if the pinion (not shown) rotates by an operation of the motor 146b, the shutter plate 146a slides along the side portion 145b of the measure 145.

If the shutter plate 146a slides by the operation of the motor 146b up to a position where the opening 145a of the measure 145 coexist with the opening 146e of the shutter plate 146e, then the measure 145 is allowed to communicate with the pipe line 140. On the contrary, as shown in FIG. 21(b), if the openings 145a, 146e are in a positions deviated from each other, that is, if a portion of the shutter plate 146a opposed to the rectangular opening 146f through the opening 146e comes to a position corresponding to the opening 145a of the measure 145, then the opening 145a becomes blocked by the shutter plate 146a.

The medicine dispensing part 143 is a part for dispensing the medicines conveyed from the medicine receiving part 142 through the pipe line 140. The medicine dispensing part 14 has an outlet shutter mechanism 147. As shown in FIG. 23, the end of the pipe line 140 is blocked at the medicine dispensing part 143. A large number of fine openings 140b are formed in a periphery of the pipe line 140 at an upper side in an assemble state of the pipe line. Further, a dispensing opening 140a is formed in the periphery of the pipe line 140 at a side opposed to a portion where the fine opening 140b is formed.

As shown in FIG. 23, the outlet shutter mechanism 147 has a jacket 147a, a shutter tube 147b, a motor 147c and a gear 147d. The jacket 147a has a tube-shaped jacket body 147e and a branch portion 147f. One end of the jacket body 147e is blocked and is mounted on the end of the pipe line 140. The jacket body 147e and the branch portion 147f communicate with each other. In the jacket body 147e, the above-described fine openings 140b face toward the branch portion 147f. The end of the pipe line 140 is inserted to the jacket body. Further, as shown in FIG. 21, the suction means connecting portion 148 is connected to the branch portion 147f.

The shutter tube 147b has a tube portion 147g and a gear 147h provided in an outer periphery of the tube portion. The tube portion and the gear 147h are integrally formed. The tube portion 147g is positioned between the outer periphery of the pipe line 140 and an inner periphery of the jacket body 147e and rotatable therebetween in a circumferential direction of the pipe line 140. Further, the tube portion 147g is provided with an opening 147i having the same size and shape as the dispensing opening 140a formed in the end of the pipe line 140. The gear 147h is provided at one end of the tube portion 147g and exposed outwardly of the jacket body 147e.

As shown in FIG. 23, the motor 147c is disposed along the pipe line 140. A gear 147d provided in a leading end of a rotating shaft of the motor 147c is meshed with the gear 147h integrally provided in the shutter tube 147b. Thus, if the motor 147c operates, the shutter tube 147b circumferentially rotates relative to the pipe line 140.

If the shutter tube 147b rotates and the opening 147i formed in the shutter tube 147b comes to the fine opening 140b of the pipe line 140 as shown in FIG. 23(a), the dispensing opening 140a becomes blocked by the peripheral surface of the shutter tube 147b. Thus, if the suction means 141 operates in such a state, then air in the pipe line 140 is sucked through the fine openings 140b and thus airflow flowing from the medicine receiving part 142 to the medicine dispensing part 143 is produced. Meanwhile, if the shutter tube 147b rotates and the opening 147*i* formed in the tube portion 147*g* approximately coincide with the dispensing opening 140*a* of the jacket body 147*e* to thereby communicate with each other as shown in FIG. 23(*b*). The medicines having come to the end of the pipe line 140 are allowed to be downwardly disposed. Further, the fine openings 140*b* become blocked.

Next, operations of the medicine dispensing system 1 according to the present embodiment will be described in detail below. The medicine dispensing system 1 can pack the medicines according to the prescription into the packing paper sheet 98 one pack at a time and dispense the same by the cooperation of main unit 2 and the sub unit 3. More specifically, the medicine dispensing system 1 is in some embodiments configured to dispense the medicines in the main storage part 20 or the manual distributing unit 23 provided in the main unit 2 or the medicines in the sub storage part 120 provided in the sub unit 3 according to the prescription one pack at a time to the medicine preparing part 80 in the main unit 2 and then pack the medicines at the medicine packing part 21 and dispense the same.

Still more specifically, in case where medicines are prescribed by the medicine dispensing system 1, when the medicines to be dispensed are in the main storage part 20 of the main unit 2, the motor 43 of the cassette 32 accommodating such medicines operates. As a result, the medicines accommodated in the feeder container 41 are dispensed one pack at a time. The medicines dispensed from the feeder container 41 drop downward through the dispensing path 33 provided in the inside of the drum 31 and are gathered in the standby hopper 51 of the medicine standby mechanism part 50. As such, when the medicines in the main unit 2 corresponding to a prescription for one pack are gathered in the standby hopper 51, the lid moving mechanism 53 operates and the movable lid 52 is lifted upward. Thus, the lower end of the lid peripheral surface 52*b* of the movable lid 52 is spaced apart from the inner peripheral surface of the standby hopper 51 and thus the medicines blocked by the lid peripheral surface 52*b* fall down toward the discharging opening 56. The medicines reaching the discharging opening 56 are dispensed through the collecting hopper 70 provided below the standby hopper 51 to the medicine preparing part 80.

Meanwhile, when the medicines to be dispensed are in the manual distributing unit 23 of the main unit 2, the medicines are dispensed one pack at a time from the manual distributing unit 23 as well. The medicines dispensed from the manual distributing unit 23 are fed through the manual distributing hopper 91 to the medicine preparing part 80.

Further, when the medicines to be dispensed are in the sub storage part 120 of the sub unit 3, the medicines are dispensed from the sub storage part 120 to the sub medicine standby part 130, similar to a case where medicines are in the main storage part 20 of the main unit 2. That is, when medicines in the cassette 32 provided in the sub storage part 120 are prescribed, the medicines accommodated in the feeder container 41 are dispensed one pack at a time as described above and then gathered in the standby hopper 51 of the sub medicine standby part (medicine standby mechanism part) 130. When the medicines to be prescribed from each of the cassettes 32 provided in the sub storage part 120 are gathered in the medicine standby part 130, the lid moving mechanism 53 of the sub medicine standby part 130 operates and thus the movable lid 52 is lifted upward. Thus, the medicines gathered in the sub medicine standby part 130 are dispensed through the discharging opening 56 and the sub hopper 135 to the measure 145 of the transfer device 5.

When the medicines are dispensed to the measure 145, the motor 146*b* of the inlet shutter mechanism 146 provided in the vicinity of the medicine receiving part 142 operates to slide the shutter plate 146*a* and the suction means 141 operates. Further, in the medicine dispensing part 143, the dispensing opening 140*a* of the pipe line 140 is blocked by the peripheral surface of the shutter tube 147*b*, while the opening 147*i* formed in the peripheral surface of the shutter tube 147*b* communicates with the fine openings 140*b* formed in the peripheral surface of the pipe line 140. Then, if the opening 146*e* of the shutter plate 146*a* communicates with the openings 145*a* formed in the side portion 145*b* of the measure 145, the medicines dispensed in the measure 145 are drawn into the pipe line 140. Thereafter, the motor 146*b* operates in a reverse direction to the above-described embodiment and the opening 145*a* of the measure 145 is blocked by the shutter plate 146*a*.

The medicines drawn into the pipe line 140 as described above further move toward the medicine dispensing part 143 in the pipe line 140. If the medicines reach the medicine dispensing part 143, the suction means 141 is stopped. Then, the outlet shutter mechanism 147 provided in the vicinity of the medicine dispensing part 143 operates to open the dispensing opening 140*a*. That is, the motor 147*a* operates to rotate the shutter tube 147*b* in a circumferential direction and thus the opening 147*i* formed in the shutter tube 147*b* is allowed to communicate with the dispensing opening 140*a* of the pipe line 140. Thus, the medicines conveyed from the sub unit 3 are dispensed through the dispensing opening 140*a* to the sub collecting hopper 87. The medicines dispensed to the sub collecting hopper 87 are received in section 81*a* of the section forming body 81 provided in the medicine preparing part 80.

In the medicine dispensing system 1 according to the present embodiment, the medicines for one pack are dispensed from the main storage part 20, the manual distributing unit 23 and the sub storage part 120 are gathered in section 81*a* of the section forming body 81 provided in the medicine preparing part 80. After gathered therein, the medicines are dispensed to the medicine packing part 21. Further, as described above, in the medicine dispensing system 1, the collecting hopper 70, the manual distributing hopper 91 and the sub collecting hopper 87, which are provided in order to feed the medicines from each of the parts to the medicine preparing part 80, are provided in positions circumferentially deviated in the lid 83 of the medicine preparing part 80. Thus, in the medicine dispensing system 1, the timing for dispensing the medicines from the main storage part 20, the manual distributing unit 23 and the sub storage part 23 toward the medicine preparing part 80 are different.

More specifically, as for six sections 81*a* provided in the section forming body 81, when one section 81*a* corresponding to the hole 83*a* as indicated by "1" in FIG. 15(*a*) is set as a first section 81*a* (corresponding to section A), the other five sections 81*a* are arranged counterclockwise relative to the first section 81*a* as indicated by "2" to "6" in FIG. 15(*a*) when the section forming body 81 is viewed from the top down. When assuming that the sections 81*a* indicated by "2" to "6" in FIG. 15(*a*) are set as second to sixth sections 81*a*, the medicines to be dispensed are fed through the collecting hopper 70 from the main storage part 20 in a state shown in FIG. 15(*a*) (hereinafter, this may be referred to as a first rotation state). Thus, when the medicines are drawn into the first section 81*a*, the drive mechanism 84 operates and the section forming body 81 rotates counterclockwise by 60 degrees. As a result, the first section 81*a* comes to a position corresponding to the hole 83*b* as shown in FIG. 15(*b*) and the sixth section 81*a* comes to a position corresponding to the hole 83*a* (hereinafter, this may be referred to as a second rotation state).

In the second rotation state, in case there are medicines to be dispensed from the sub storage part 120 to the first section 81*a*, the transfer device 5 operates to supply the medicines. Further, in the second rotation state, in case there are medicines to be dispensed from the main storage part 20 to the sixth section 81*a*, such medicines are dispensed through the collecting hopper 70. If the medicines are dispensed from the main storage part 20 or the sub storage part 120 as described above then section forming body 81 sequentially rotates counterclockwise. The second rotation state changes into a state shown in FIG. 15(*c*) (hereinafter, this may be referred to as a third rotation state).

In the third rotation state, the first section 81*a* comes to a position corresponding to the hole 83*c*, to which the manual distributing hopper 91 is connected. In such a state, when there are medicines to be packed together with the medicines previously dispensed to the first section 81*a* in the manual distributing unit 23, those medicines are dispensed from the manual distributing unit 23 through the manual distributing hopper 91 to the first section 81*a*. Further, in the third rotation state, when there are medicines to be dispensed from the main storage part 20 to the fifth section 81*a* or medicines to be dispensed from the sub storage part 120 to the sixth section 81*a*, those medicines are dispensed through the collecting hopper 70 or the manual distributing hopper 91.

When dispensing the medicines to each of the sections 81*a* is completed in the third rotation state as described above, the third rotation state changes into a state shown in FIG. 15(*d*) (hereinafter, this may be referred to as a fourth rotation state) and a state shown in FIG. 15(*e*) (hereinafter, this may be referred to as a fifth rotation state). During such change, similar to the first to third states, the medicines dispensed from the main storage part 20, the sub storage part 120 and the manual distributing unit 23 are inputted into each of the sections 81*a*.

Then, when dispensing the medicines is completed in the fifth rotation state, the drive mechanism 84 operates to further rotate the section forming body 81 by 60 degrees in a clockwise direction. Thus, as shown in FIG. 15(*f*), the first section 81*a* comes to a position corresponding to the hole 82*c* formed in the bottom surface of the medicine preparing part body 82. At this time, the lever 81*d* provided in a position corresponding to the first section 81*a* is brought into contact with the lever contactor 82*d* provided in a position adjacent to the opening 82*c*, thereby opening the shutter 81*c*. Thus, while the section forming body 81 moves in a counterclockwise direction, all the medicines gathered in the first section 81*a* direction are dispensed through the packing hopper 85 to the medicine packing part 21.

The medicines dispensed from the medicine preparing part 80 to the medicine packing part 21 are accommodated in a medicine pack, which is previously formed into a semi-pouch shape by the packing paper sheet 98. Then, the medicine pack is sealed by the pack forming mechanism 96 and the packing paper sheet 98 is transferred by the sheet transferring mechanism 95 toward a further downstream side (toward an obliquely downward side).

In the medicine dispensing system 1 according to the present embodiment, predetermined information on the medicine is printed by the printing part 99 at a time (time Z) before the medicines dispensed from the medicine preparing part 80 is packed in the medicine packing part 21. More specifically, as described above, in the medicine packing part 21 employed in the present embodiment, a distance between the pack forming mechanism 96 and the printing part 99 is set as a length corresponding to three packs of a medicine pack. Thus, at a time (time Z) as early as a time period (time period Y) required to rotate the section forming body 81 as much as a quantity corresponding to three sections 81*a* from a time (time X) when the medicines are dispensed from the first section 81*a*, that is, in the above-described third rotation state, the information on the medicines in the third rotation state is printed by the printing part 99. In other words, at a time (time Z) as early as the time period required for dispensing the medicines from three sections 81*a* positioned upstream from the first section 81*a* in a rotation direction of the section forming body 81 from the timing when the medicines are dispensed from the first section 81*a*, the information on the medicines accommodated in the first section 81*a* is printed by the printing part 99.

While the section forming body 81 sequentially rotates as described above, the medicines accommodated in the first to sixth sections 81*a* are dispensed one after another to the medicine packing part 21 and then packed therein and the medicines are dispensed from the main storage part 20, the manual distributing unit 23 and the sub storage part 120 to the first to sixth sections 81*a*. The packing paper sheet 98, which is formed by packing the medicines as described above, is serially transferred to the conveying means 21*b* existing in the obliquely downward side. The packing paper sheet 98 transferred to the conveying means 21*b* enters an inside portion of the casing 105 from the receiving opening 107*a* formed in the receiving part 105*a*. Then, a proceeding direction of the packing paper sheet 98, which proceeds obliquely downward in the housing of the main unit 2, changes toward an oblique upward side due to a bend in a portion of the casing 105 corresponding to the receiving portion 105*a* or guide by the guide roller 107*b*. That is, the proceeding direction of the packing paper sheet 98 changes in the receiving portion 105*a*.

The packing paper sheet 98 entering the casing 105 is guided by the guide roller 107*b* and contacts the drive rollers 110 and the belts 111 wound thereto. Meanwhile, the drive rollers 110 and the belts 111 operate by the power from a motor (not shown) provided in the casing 105. Further, a plurality of the pressing rollers 112 are provided in a position opposed to the drive roller 110 and the belt 111. The pressing rollers 112 are biased toward the belt 111 and press the belt 111. Thus, if the packing paper sheet 98 is transferred from the receiving portion 105*a* toward the straight portion 105*b* to thereby enter between the belt 111 and the pressing roller 112, the packing paper sheet 98 becomes pressed toward the drive roller 110 and the belt 111 by the pressing roller 112. Accordingly, if the power is transmitted from the belt 111 to the packing paper sheet 98, the packing paper sheet 98 is conveyed along the straight portion 105 toward the bent portion 105*c* located obliquely upward.

The packing paper sheet 98, which reaches the bent portion 105*c* as described above, is further conveyed along the bent portion 105*c*. In this case, as described above, in the conveying means 21*b* employed in the present embodiment, the bent portion 105*c* may be continue in a straight direction toward the straight portion 105 with its leading end facing toward the side panel 2*b* or may be bent toward the front panel 2*a* of the main unit 2 relative to the straight portion 105*b*. Thus, when the bent portion 105*c* is continues in a straight direction towards the straight portion 105*b*, the packing paper sheet 98 conveyed along the straight portion 105*b* moves straight toward the side panel 2*b* and then is removed from the dispensing opening 2*d* to the outside of the main unit 2. Meanwhile, when the bent portion 105*c* is bent toward the front panel 2*a*, a conveying direction of the packing paper sheet 98 conveyed along the straight portion 105b is directed to the front panel 2a and therefore the packing paper sheet 98 is dispensed from the dispensing opening 2c.

In the medicine dispensing system 1 according to the present embodiment, abnormality in the medicine packing part 21 such as a paper jam of the packing paper sheet 98 can be detected by means of the abnormality detecting means 115. More specifically, the packing paper sheet 98 is conveyed by the conveying means 21b in the medicine packing part 21. However, if the abnormality in transferring the packing paper sheet occurs at the conveying means 21 or at the packing means 21a disposed more upstream than the conveying means 21b, then the flow of the packing paper sheet 98 is delayed in the conveying means 21b.

Meanwhile, in the conveying means 21b, the sub roller 115a is disposed near the pressing roller 112a, which is disposed upstream in the conveying direction of the packing paper sheet 98, that is, disposed adjacent to the receiving portion 105a, among the plurality of pressing rollers 112. The sub roller 115a is rotatable independently of the pressing roller. Further, the pinch roller 115a is disposed in a position opposed to the sub roller 115a. Thus, when the packing paper sheet 98 flows in the medicine packing part 21 without delays, the packing paper sheet 98 passes between the sub roller 115a and the pinch roller 115a and the pinch roller 115b is rotated by the packing paper sheet 98. On the contrary, when the flow of the packing paper sheet 98 in the medicine packing part 21 is stopped by any chance, the packing paper sheet 98 does not pass between the sub roller 115a and the pinch roller 115b and thus the pinch roller 115 does not rotate. Thus, by detecting by means of the rotary encoder 115d connected to the pinch roller 115b by shaft 115c whether or not the pinch roller 115b normally rotates, the abnormality in transferring the packing paper sheet 98 can be detected. When the abnormality in transferring the packing paper sheet 98 such as a paper jam is detected by the abnormality detecting mechanism 115, the medicine dispensing system 1 stops the above-described serial operations.

Further, the abnormal set detecting means 38 is provided in the main unit 2 and the sub unit 3 employed in the present embodiment. The abnormal set detecting means is configured to detecting a case where the cassette 32 is not securely mounted on the drum 31. More specifically, when the cassette 32 is pushed out from the trajectory J illustrated in FIG. 4(c) due to an abnormal mount, the cassette 32 bumps against the contact plate 38a, which constitutes the abnormal set detecting means, along with the rotation of the drum 31 to thereby swing the contact plate 38a to turn on the switch 38b. Thus, when the switch 38b is turned on, the medicine dispensing system 1 judges the abnormal mount of the cassette to thereby stop the above-described serial operations.

As described above, the medicine dispensing system 1 has the main unit 2 and the sub unit 3 and is configured to transfer the medicines dispensed from the sub storage part 120 provided in the sub unit 3 to the main unit 2 through the transfer device 5. Further, not only are the medicines dispensed in the main unit 2 but also the medicines dispensed in the sub unit 3 can be packed in the medicine packing part 21 provided in the main unit 2 together and then be dispensed. Thus various kinds of the medicines can be dealt with by providing the sub units 3.

In this case, as described above, in the medicine dispensing system 1, a large number of the cassettes 32 are provided installed not only in the main unit 2 but also in the sub unit 3. Thus, in some embodiments, the medicine dispensing system 1 is configured to accurately manage characteristic information on the feeder container 41 (hereinafter, this may be referred to as a characteristic container information), which constitutes each cassette 32. More specifically, it is preferred that the medicine dispensing system 1 is configured to record the characteristic container information such as data on the kind or quantity of the medicines accommodated in the feeder container 41 of each cassette 32, data on a supplement history related to a person performing a medicine supplement in each feeder container 41 and date and time of the medicine supplement, data on a usage history of each cassette, and the like into the tag 49. Further, the medicine dispensing system 1 may be configured to manage the medicines accommodated in each feeder container 41 or notify a user of a maintenance time of each cassette 32 based on the characteristic container information of each cassette recorded in the tag 49. Thus, in order to meet such a demand, as shown in FIG. 20, there is provided a data management system 180 configured to transmit and receive the data including the characteristic container information to and from the tag 49, to renew and write the data and to read the data from the tag 49, by a control means 170 provided for controlling the operations of the medicine dispensing system 1 and either the reader-writer 49 contained in the motor base 40 which constitutes each cassette 32 or the reader-writer 117c provided in the worktable 117. The data management system 180 manages the characteristic container information of each cassette 32. Hereinafter, a data management method performed by means of the data management system 180 in the medicine dispensing system 1 and the operations of the medicine dispensing system 1 will be described in detail below according to an order of medicine filling.

Figure 22A:
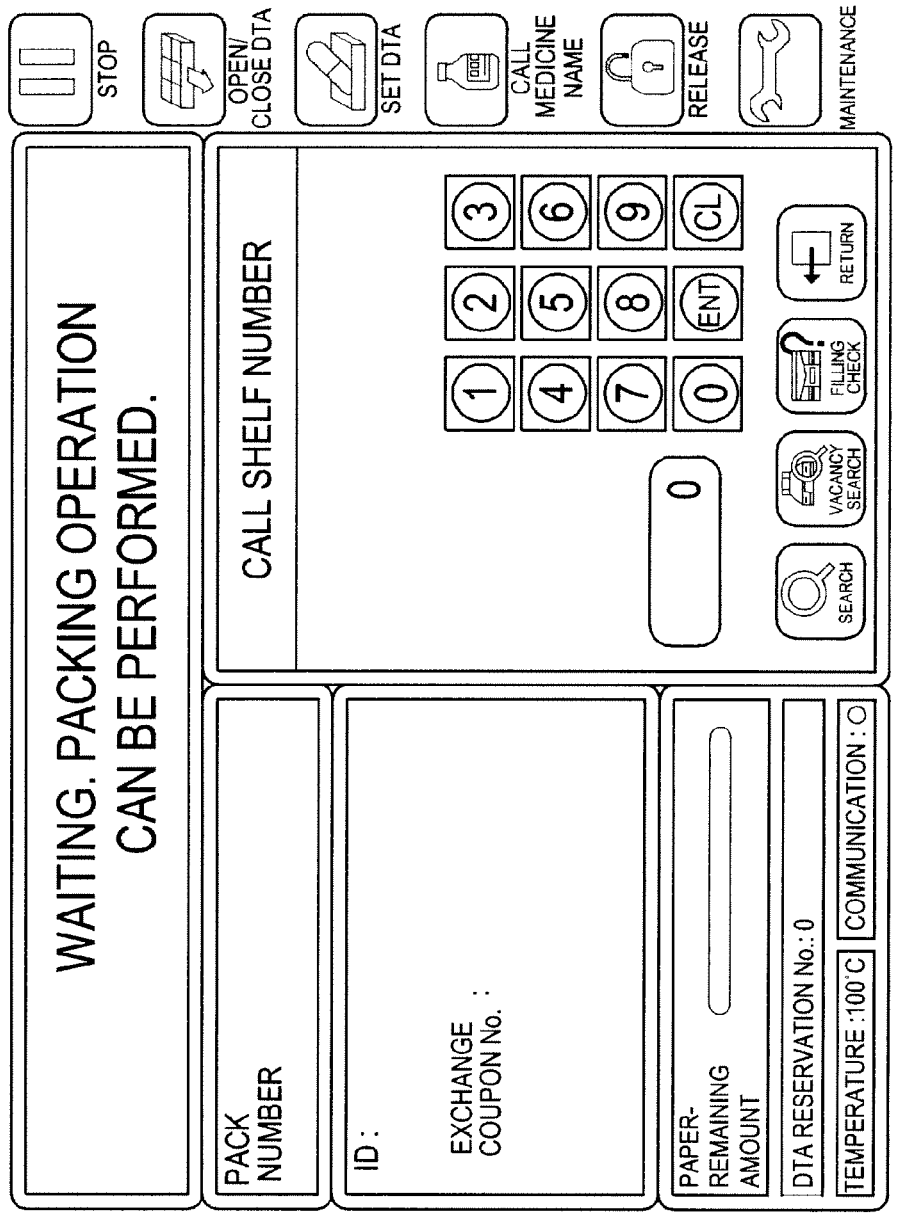
FIG. 22A is a front view showing an interface for calling a cassette.
Figure 22B:
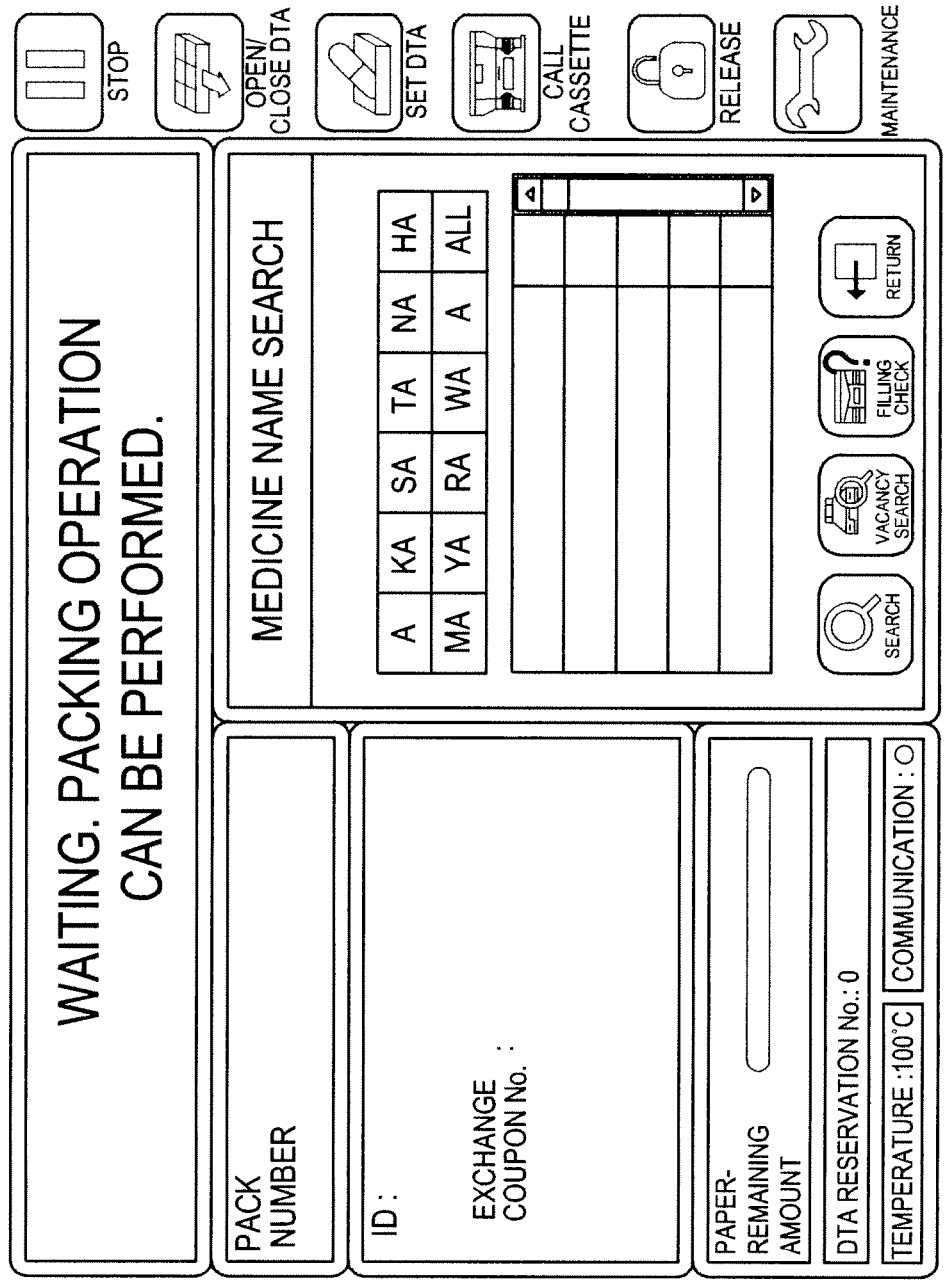
FIG. 22B is a front view showing an interface for calling a medicine name.

In the medicine dispensing system 1, the medicine filling for the main storage part 20 and the sub storage part 120 is performed by removing the feeder container 41 of each cassette 32 assigned to every medicine. In this case, when the cassette 32 accommodating medicines for medicine filling is in a place where a user can easily remove the feeder container 41, the feeder container 41 can be removed as it is. However, it may be in a place where a user cannot easily remove it. In such a case, the operation panel 118a is manipulated and an interface for calling the cassette shown in FIG. 22(a) is displayed. A number individually assigned to each cassette 32 is inputted through the interface and thus the feeder container 41 of the desired cassette 32 can come to a place where a user can easily remove the feeder container 41. Further, when the kind of medicines for medicine filling can be specified, the operation panel 118a is first manipulated and then an interface for calling a medicine name shown in FIG. 22(b) is displayed. In such a state, the medicine name can be inputted by manually inputting the kind of the medicines for medicine filling through the operation panel 118a or be inputted automatically by reading a particular barcode for each medicine assigned to the original medicine box by means of the barcode reader 118b. By dosing so, it is possible to move the feeder container 41 of the cassette 32 accommodating the medicines for medicine filling to a place where the user can easily remove the feeder container 41.

The feeder container 41 of the cassette 32 removed from the main storage part 20 or the sub storage part 120 as described above is positioned so as to be fitted in the recess 117b formed in the worktable 117. Then, the tag 49 provided at the bottom surface of the feeder container 41 comes to a position corresponding to the reader-writer 117c provided at the worktable 117. Thus, data communication becomes possible through the reader-writer 117c between the tag 49 and the control means 170 of the medicine dispensing system 1. Further, in such a stage, an interface for indicating the characteristic container information shown in FIG. 22(c) and FIG.

22(d) is displayed in the operation panel 118a provided at the front side of the main unit 2 and thus the characteristic container information is displayed. Thus, an operation mode of the medicine dispensing system 1 is changed from a general operation mode for packing and dispensing medicines according to a prescription to a medicine filling mode for filling the feeder container 41 with medicines.

If the operation mode of the medicine dispensing system 1 is changed into the medicine filling mode, the characteristic container information is read from the tag 49 of the feeder container 41 disposed on the worktable 117 through the reader-writer 117c. More specifically, except when there is no data in the tag 49 such as right after starting to use the feeder container 41, the characteristic container information such as data on the kind or quantity of the medicines accommodated in the feeder container 41 of each cassette 32, data on a supplement history related to a person carrying out a medicine supplement in each feeder container 41 and date and time of the medicine supplement, data on a usage history of each cassette, and the like is recorded in the tag 49. Thus, when the feeder container 41 is fitted to the recess 117b of the worktable 117, the characteristic container information including the above-described data is read from the tag 49 through the reader-writer 117c to the control means 170 of the medicine dispensing system 1. The data read from the tag 49 as described above is recorded by the control means 170 into a record means 175 including a conventional memory or a hard disk.

Figure 22C:
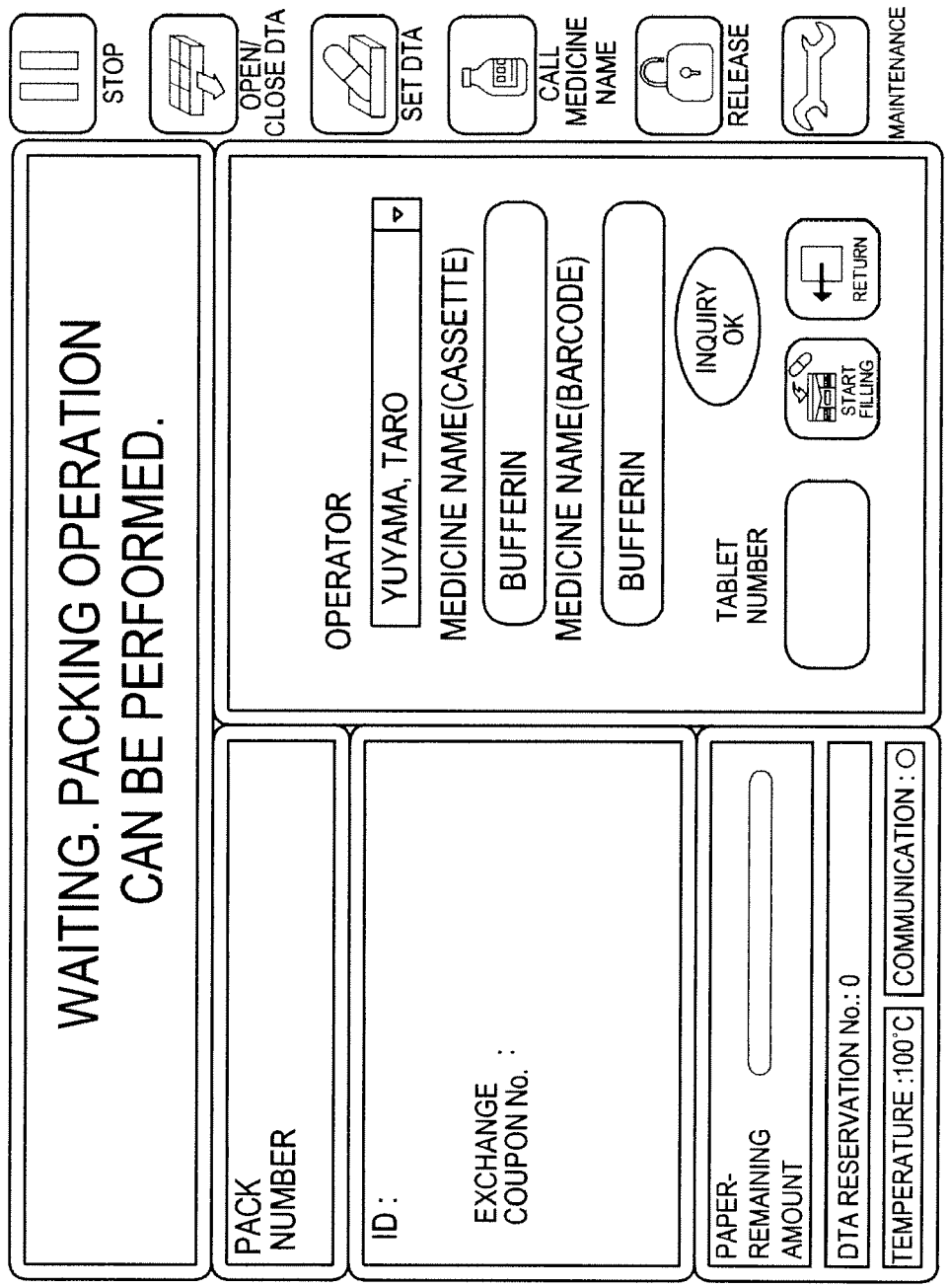

When a screen display is made as shown in FIG. 22(c) and FIG. 22(d), it is possible to input the information such as the kind or quantity of the medicines for medicine filling in the feeder container 41 and an operator's name carrying out the filling operation as the characteristic container information. Regarding inputting the kind of the medicines, the operator carrying out the filling operation can manually input information. Further, it is possible to specify the kind of the medicines in the control means 170 by reading the barcode, which is written on the original medicine box of the medicine for medicine filling, by means of the barcode reader (identification mark reading means) 118b. Further, it is possible to input the kind of the medicine by means of such an operation.

Further, for the operator's name carrying out the filling operation of the medicines, the operator can manually input like kinds of medicines. Further, in the present embodiment, for example, information for specifying the operator (operator specifying information), which is recorded in an employee card, an ID card, a ring or a wrist band assigned to each operator, is read by the barcode reader 118b or the reader-writer 117c. The operator's name may be automatically inputted to the control means 170 using this information.

Further, when the tag 49 provided in the bottom surface of the feeder container 41 is allowed to data-communicate with the control means 170 of the medicine dispensing system 1 through the reader-writer 117c, the characteristic container information on the usage history such as a total rotation quantity and a total rotation time of the rotor 48 provided in the feeder container 41 is read in the control means 170 in addition to the data related to the medicines accommodated in the feeder container 41 such as the kind or quantity of the medicines or the data related to the supplement history of the medicines to the feeder container 41. Based on the data related to the usage history of the cassette 32, the control means 170 judges whether the cassette 32 reaches a durable term or a maintenance time. Further, if it is ascertained that the cassette 32 reaches the durable term or that it is time for maintenance to be performed, a warning to that effect is displayed in the operation panel 118a.

In the medicine dispensing system 1 according to the present embodiment, if the feeder container 41 of each cassette 32 is filled with medicines as described above and is set in the motor base 40, then the data-communication is performed between the tag 49 of the feeder container 41 and the control means 170 through the reader-writer 44 provided in the motor base 40. Thus, a filling recording information that a feeder container 41 of which cassettes 32 among the cassettes 32 is filled with what medicines and how much the feeder container is filled is grasped by the control means 170 for each cassette 32. Thereafter, a dispensing history of the medicine in each cassette is written into the tag 49 through the reader-writer 44 on occasions. Thus, the control means 170 can grasp a remaining quantity of the medicines in the feeder container 41 of each cassette 32 based on the filling quantity in the feeder container 41 of each cassette 32 with the medicines and the dispensing history of the medicines written in the tag 49. Further, the medicine dispensing system 1 can grasp and manage statistical information such as when and how much any medicines are used based on the filling history or the dispensing history of the medicines grasped by the control means 170 as described above.

The above-described medicine dispensing system 1 has a function of continuously packing many predetermined medicines through an operation mode referred to as a group packing mode (i.e., a preliminary prescribing function), in addition to the function of packing medicines through the general operation mode where the medicines are prescribed based on the prescription inputted by a doctor or pharmacist. Thus, for example, it is possible to preliminarily pack many general-purpose medicines such as refrigerant medicines, analgesic medicines and stomach medicines per dosage. When the medicine dispensing system 1 operates in the group packing mode, the control means 170 confirms whether there is any cassette 32 accommodating the medicines to be packed among a large number of the cassettes 32 provided in the main storage part 20 or the sub storage part 120. In this case, when the feeder container 41 of each cassette 32 is replaced before the medicine dispensing system operates in the group packing mode, the characteristic container information recorded in the tag 49 provided in such a feeder container 41 is read through the reader-writer 44 contained in the motor base 40. Then, the control means 17 specifies the cassette 32 including the feeder container 41, which accommodates the medicines to be packed through the group packing mode, and then the medicines are dispensed from the cassette 32 by a predetermined quantity. The medicines dispensed from the cassette 32 are packed in the medicine packing part 21.

As described above, the medicine dispensing system 1 has a data management system 180 and is configured such that the tag 49 provided in every feeder container 41 of each cassette 32 and the control means 170 can data-communicate with each other through the reader-writer 118c and the characteristic container information characteristic in each feeder container 41 can be read from the tag 49 or written into the tag 49. Thus, it is possible to simply and accurately manage, renew and grasp the characteristic container information for each feeder container 41.

As described above, the reader-writer 44 is contained in the motor base 40 of each cassette and it is possible to data-communicate with the tag 49 provided in the feeder container 41 through the reader-writer without contact with the tag. Thus, in the medicine dispensing system 1, even if the feeder container 41 is mounted on the motor base 40, the data such as the dispensing history of the medicines recorded in the tag 49 can be appropriately renewed. This can be effectively used for a stock management of medicines. Further, it is illustrated in the above-described embodiment that the reader-writer 44 is provided in each cassette 32. The present invention should not be limited to such a configuration. The reader-writer 44 may be provided in some or all of the cassettes 32.

In the above-described embodiment, the reader-writer 44, 117*c* is provided in the cassette 32 or the worktable 117, which constitutes the medicine dispensing system 1, and it is possible to access to the tag 49 provided in the feeder container 41 and read and write the data from and into the tag through the reader-writer 44, 117*c*. However, the present invention should not be limited to such a configuration. More specifically, the present invention may be configured such that a device provided separately from the medicine dispensing system 1 accesses the tag 49 and reads and writes the data from and into the tag, and the data written in the tag 49 is read through the reader-writer 44 and 117*c* to the control means 170 to assist in medicine management.

Figure 24:
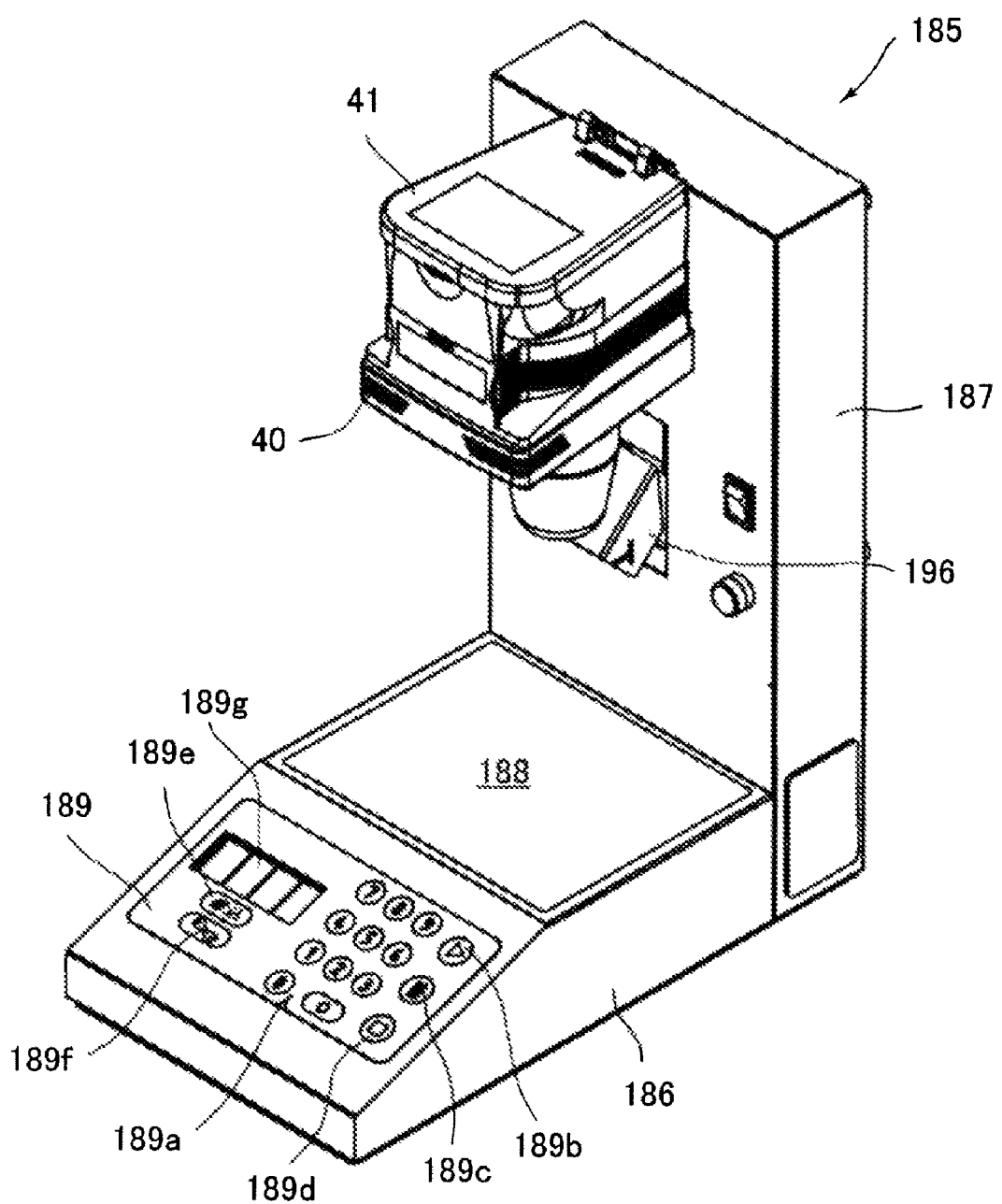
FIG. 24 is a perspective view showing a counter device.

More specifically, by way of an example of the above-described device provided separately from the medicine dispensing system 1, a counter device 195 shown in FIG. 24 can be employed. The counter device 185 has a body portion 186 and a container attaching portion 187. A control device (not shown) for controlling operations of the counter device 185 is provided in the body portion 186. Further, a container placing portion and an operation panel 189 are provided at a top surface of the body portion 186. The container placing portion is a portion for placing the container for accommodating medicines thereon. Further, the operation panel 189 is provided with buttons for inputting operation conditions or operation commands, such as a ten key 189*a* for inputting a quantity; a start button 189*b* for starting the operation; a temporary stop button 189*c* for temporarily stopping the operation; and a stop button 189*d* for stopping the operation. In addition to the above-described-mentioned buttons, the operation panel 189 is further provided with buttons such as a write button 189*e* and a maintenance button 189*f* and a display 189*g*.

The container attaching portion 187 is provided with an equivalent of the above-described motor base 40 of the cassette 32 and a dispensing opening 196. A feeder container 41, which is removed from the main storage part 20 or the sub storage part 120 of the medicine dispensing system 1, or which is separately prepared, can be mounted on the motor base 40. Medicines can be dispensed from the feeder container 41 by operating a motor 43 contained in the motor base 40. Further, a medicine path (not shown), through which the medicines dispensed from the feeder container 41 attached to the motor base 40 pass, is provided in the container attaching portion 187. Also, the medicine path communicates with the dispensing opening 196. Thus, the medicines, which are dispensed from the feeder container 41 to thereby pass through the medicine path, are discharged through the dispensing opening 196 toward the container placing portion 188. In the container attaching portion 187, more specifically, in a suitable place such as the above-described medicine path or the motor base 49, a counting means (not shown) configured to counting the number of the medicines dispensed from the feeder container 41 is provided.

The counter device 185 can be operated in a plurality of operation modes including a counting mode or a predetermined quantity dispensing mode. The counting mode is a mode for counting the number of the medicines accommodated in the feeder container 41 mounted on the motor base 40 by dispensing all the medicines 40 therein. The counter device 185 starts an operation according to the counting mode by pressing on the start button 189*b* when the feeder container 41 is mounted on the motor base 40. Further, the number of medicines, which is counted by the counting means (not shown) provided in the container attaching portion 187, is displayed in the display 189*g*.

The predetermined quantity dispensing mode is an operation mode for dispensing the medicine from the feeder container 41 mounted on the motor base 40 by a quantity which a user inputs and sets through the ten key pad 189*a*. The counter device 185 operates in the predetermined quantity dispensing mode when the quantity of the medicines to be dispensed from the feeder container 41 (set quantity Q) is inputted through the ten key pad 189*a* and then the start button 189*b* is pressed on. After the counter device 185 starts the operation according to the predetermined quantity dispensing mode, as the quantity of the dispensed medicines comes to the set quantity Q, the rotation of the motor 43 provided in the motor base 40 becomes slow to thereby reduce a dispensing speed of the medicines. In the counter device 185 according to the present embodiment, when the quantity of the dispensed medicines becomes Q−2, the dispensing speed of the medicines is reduced. Thus, excessively dispensing the medicines by an error is prevented.

After the counter device 185 operates in the above-described counting mode or the predetermined quantity dispensing mode, the operation information associated therewith can be written into the tag 49 provided in the bottom surface of the feeder container 41 through the reader-writer 44 provided in the motor base 40 by the counter device. More specifically, after the counter device 185 operates in the counting mode, if the write button 189*e* provided in the operation panel 189 is pressed on, then the counted number of the medicines is written into the tag 49. Further, after the counter device 185 operates in the predetermined quantity dispensing mode, if the write button 189*e* is pressed on, then the counted number of the medicines is written into the tag 49. Thus, in case the counter device 185 counts the quantity of the medicines in the feeder container 41 or counts and removes the medicines and the data associated therewith is written into the tag 49 and then the feeder container 41 is set in the main storage part 20 or the sub storage part 120 of the medicine dispensing system 1, the data written into the tag 49 by the counter device 185 can be effectively used to control the medicine dispensing system 1 or medicine management. More specifically, after the data is written in the tag 49 by the counter device 185 as described above, if the feeder container 41 is set in the main storage part 20 or the sub storage part 120 or the feeder container 41 is fitted to the recess 117*b* of the container placing portion 117*a* provided in the worktable 117, the data written into the tag 49 may be read through the reader-writer 44, 117*c* by the control means 170 or recorded on the record means 175. According to such configuration, the data obtained by setting the feeder container 41 in the counter device 185 can be effectively used for the operation control of the medicine dispensing system 1 or the stock management of medicines.

The counter device 185 is an example of the above-described device provided separately from the medicine dispensing system 1. Further, the counter device 185 itself serves as a medicine dispensing device for dispensing medicines. That is, the counter device (medicine dispensing device) 185 includes the feeder container 41 configured to store and dispense the medicines and a control means (not shown) configured to data-communicate with the tag 49 provided in the feeder container 41. The feeder container 41 is configured to be attachable and detachable. The counter device 185 can perform data-communication of the data characteristic for the feeder container 41 such as the quantity of the medicines in the feeder container 41 with the tag 49 provided in the feeder container 41 and the above-described control means. Accordingly, the counter device 185 corresponds to a medicine dispensing device provided separately from the medicine dispensing system 1.

Further, as described above, the medicine dispensing system 1 can read the information specifying the operator read from an employee card or an ID card, and easily and accurately record a person who performed the medicine supplement for the feeder container 41 of each cassette 32 into the tag 49 using such a data. It is illustrated in the above-described embodiment that the operator information is specified by items carried by the operator such as the employee card or the ID card or items assigned to each operator. However, the present invention should not be limited to such a configuration. For example, the operator information may be specified by a biometric certification such as a fingerprint. Further, the above-described embodiment employs a configuration wherein the operator information is read from any medium and the data for specifying the operator can be automatically inputted based on data associated therewith. However, the present invention should not be limited to such a configuration.

The operation mode of the medicine dispensing system 1 is changed into the medicine filling mode upon a condition that the feeder container 41 of the cassette 32 removed from the main storage part 20 or the sub storage part 120 is fitted to the recess 117b of the worktable 117 and data communication becomes possible through the reader-writer 117c between the tag 48 and the control means 170. That is, in the medicine dispensing system 1, it serves as a trigger for changing the operation mode to fit the feeder container 41 to the recess 117b of the worktable 117 and to enable the data-communication. Thus, according to the medicine dispensing system 1, when the operation mode is changed into the medicine filling mode, the operator does not need to perform complicated work. Further, it is illustrated in the above-described embodiment that the operation mode is changed by fitting the feeder container 41 to the recess 117b. However, the present invention should not be limited to such a configuration.

As described above, the medicine dispensing system 1 is capable of reading the identification mark, which is assigned to each kind of medicine, such as the barcode written on the original medicine box by means of a mark reading means configured to read identification marks such as the barcode reader 118b. Further, the information on the kind of medicine specified as described above is recorded into the tag 49 by the data-communication between the control means 170 and the tag 49 provided in the feeder container 41. Thus, the medicine dispensing system 1 does not need any effort such as an operator's manual input of the kind of medicines when the medicine dispensing system 1 operates in the medicine filling mode. Accordingly, the information on the kind of medicine can be more easily and accurately recorded into the tag 49. Further, it is illustrated in the above-described embodiment that the kind of the medicine is specified by reading the barcode assigned to each medicine by the barcode reader 118b and the data associated with such kind of medicine can be automatically inputted. However, the present invention should not be limited thereto. Further, the barcode reader 118b may read any barcodes including a one-dimensional barcode and a two-dimensional barcode. Further, it is illustrated in the above-described embodiment that the barcode reader 118b is capable of reading the barcode assigned to each kind of medicine. However, the present invention should not be limited to such a configuration. The present invention may employ an appropriate reader capable of reading a mark made by a color combination or reading the information recorded in an RFID tag instead of the barcode reader 118b.

As described above, in the medicine dispensing system 1, only by positioning the feeder container 41 in the recess 117b of the worktable 117, the data-communication becomes possible without any contact through the barcode reader 118b provided in a position corresponding to the recess 117b. Thus, in the medicine dispensing system 1, data-communication becomes possible between the tag 49 and the control means 170 without any effort, for example, such as connecting a wire to the feeder container 41, and serial operations such as renewing, writing and managing the characteristic container information on each feeder container 41 can be smoothly performed. Further, in the above-described embodiment, the RFID tag or the RFID reader-writer is employed as the tag 49 or the reader-writer 117c and thus reading the information recorded in the tag 49 and writing the information into the tag 49 can be performed without any contact. However, the present invention should not be limited to such a configuration. That is, the information may be read and written by using other kinds of information, recordable medium or reader-writer. Also, although the data-communication is possible without any contact, the data-communication may be performed through wire connection.

In the medicine dispensing system 1 according to the above-described embodiment, it is possible to read and write the data characteristic in each feeder container 41, which is recorded in the tag 49 provided in each feeder container 41. More specifically, the data such as the kind or quantity of the accommodated medicines and a name of an operator performing the medicine supplement. Thus, the medicine dispensing system 1 may be configured such that when the feeder container 41 filled with medicines is attached to the motor base 40 appropriately selected from the plurality of motor bases 40 previously provided in the main storage part 20 of the main unit 2 and the sub storage part 120 of the sub unit 3, the control means 170 specifies where the feeder container 41 accommodating the medicines required for packing and thus the medicines can be dispensed according to the kind and quantity corresponding to a prescription. That is, according to such a configuration, the medicine dispensing system 1 may be a device of a so-called free address type wherein the feeder container 41 can be mounted in any position, not of a so-called fixed address type wherein the mount position of each feeder container 41 is fixed.

Further, the medicine dispensing system 1 may be a device of a semi-fixed type wherein the motor base 40 configured to attach only the feeder container 41 for accommodating medicines with a particular property thereon is specified. More specifically, the medicine dispensing system 1 may handle various kinds of the medicines. However, depending on the kind of medicines, there are medicines prone to bound, roll, break or chip due to a drop impact at a place where they are dispensed from the feeder container 41. When dealing with the medicines with such properties (hereinafter, those medicines are referred to as specific medicines), a packing abnormality may occur unless a timing of packing the medicines is delayed until the medicines become stable without bounding or rolling or a means for buffering the drop impact is devised.

Figure 51:
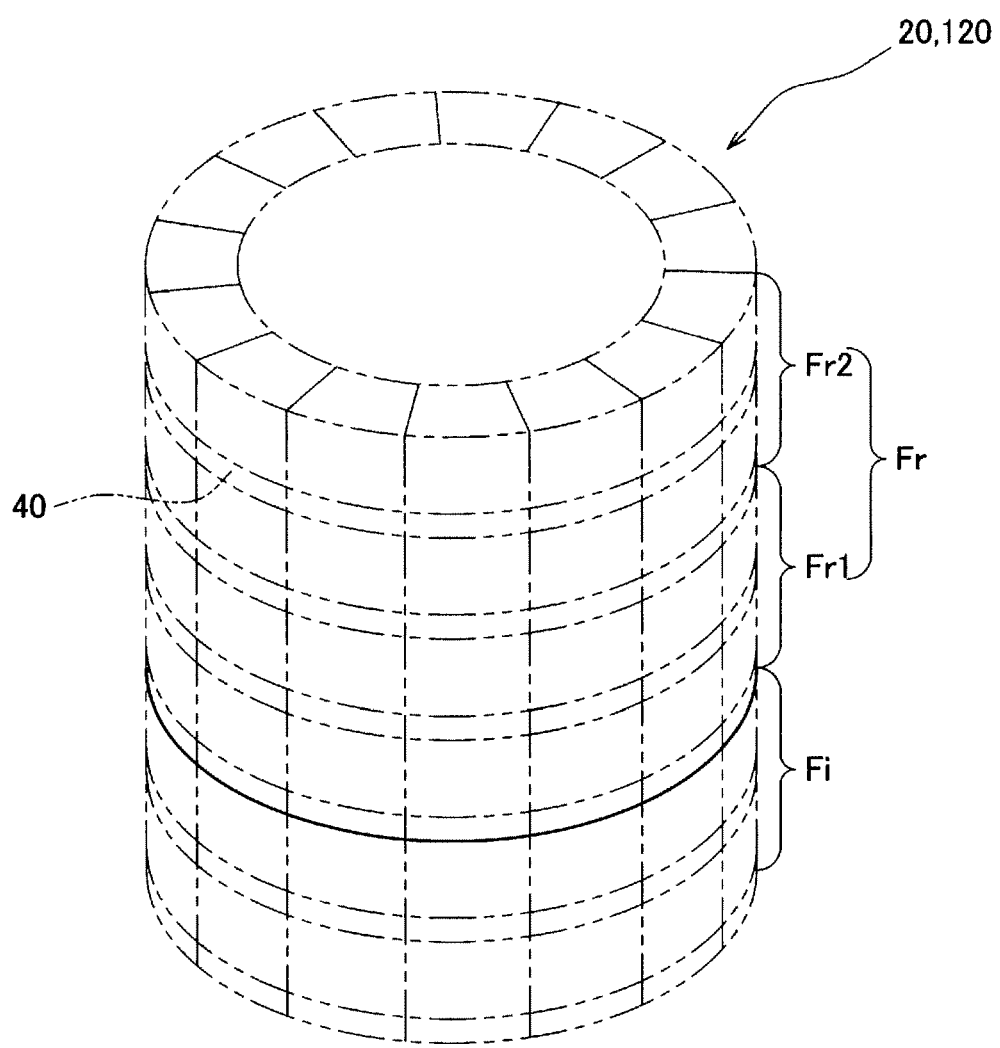
FIG. 51 is a perspective view schematically showing features of a main storage part and a sub storage part.

Preferably, the feeder container 41 for accommodating the medicines (specific medicines) prone to bound, roll, break or chip as described above is to be attached in a lower position of the main storage part 20 and the sub storage part 120 or in a position where the above-described concerns can be resolved. Accordingly, in case of the above-described concerns, the medicine dispensing system 1 may be a device in the above-described semi-fixed address type. More specifically, in case the motor bases 40 are upwardly and downwardly provided in six stages in the main storage part 20 and the sub storage part 120 as shown in FIG. 51, the medicine dispensing system 1 may regulate the feeder container 41 accommodating the medicines with concerns of bounding or rolling (specific medicines) and may in some embodiments be attached to the motor base 40 in a region from a bottom portion up to two stages (hereinafter, this may be referred to as fixed address region Fi).

Further, the medicine dispensing system 1 may regulate the feeder container 41 accommodating the medicines except that the specific medicines may be attached not only in the fixed address region Fi but also to the motor bases 40 in a region (hereinafter, this may be referred to as a free address region Fr) other than the region Fi. Also, as for the feeder container 41 which can be attached in the free address region Fr, its attachment arrangement may be regulated in a manner of subdividing into two or more groups. More specifically, as for the feeder container 41 accommodating the medicines other than the specific medicines and inappropriate to drop from a higher place, it may be regulated that such a feeder container 41 is attached in a region lower than a free address region Fr1 divided into two stages above the fixed address region Fi. And, as for the feeder container 41 accommodating the medicines with no concerns caused by dropping, it may be regulated that such a feeder container 41 is attached to the motor base 40 in a free address region Fr2 divided into two stages above the free address region Fr1. The above-described regulation for a correspondence relationship between the feeder container 41 and the motor base 40 in each region is built in a control means 190 in a manner of storing it in a memory means in the control means 190 as a container mounting database (correspondence relationship regulating part) 193 as shown in FIG. 52.

As described above, in case the regions of installing a large number of the motor bases 40 provided in the main storage part 20 or the sub storage part 120 are classified into a plurality of regions (container mounting region) such as the fixed address region Fi and the free address regions Fr (Fr1, Fr2) according to a height of the regions, the correspondence relationship between the motor base 40 and the feeder container 41 may be regulated as a relationship with the container mounting region at a height which becomes an upper attachment limit of the feeder container 41 determined depending on the kinds of the medicines accommodated in this feeder container 41. More specifically, the correspondence relationship between the motor base 40 and each feeder container 41 may be determined considering some or all of the following: a bound factor counted for a correlation between a drop height of the medicines accommodated in each feeder container 41 and a bound thereof; a rolling factor counted for a correlation between the drop height and the rolling; and a value of factor counted for a drop height wherein the breakage or chipping becomes equal to or less than a certain probability.

In the present embodiment, a correspondence label is attached on the feeder container 41 and the motor base 40 such that an operator performing detachment of the feeder container 41 can easily distinguish the regulations stored in the above-described container mounting database 193. More specifically, a specific label A colored in blue, for example, is attached on the motor base 40 in the fixed address region Fi and the feeder container 41 accommodating the specific medicines. Further, a specific label B colored in green, for example, is attached on the motor base 40 in the free address region Fr1. Also, the label B is attached on the feeder container 41 which may be attached in any of the free address region Fr1 and the fixed address region Fi. Likewise, a specific label C colored in white, for example, is attached on the motor base 40 in the free address region Fr1. Also, the label C is attached on the feeder container 41 which may be attached in any of the free address regions Fr1 and Fr2 and the fixed address region Fi. Thus, the operator can be intuitively aware to attach the feeder container 41 in a region with the same label as the label of the feeder container 41 to be attached or in a region lower than said region.

Figure 52:
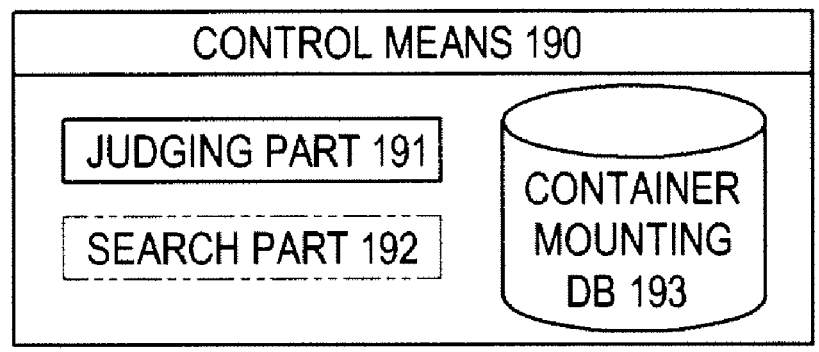
FIG. 52 is a block diagram showing a variation of a control means.

As described above, when the medicine dispensing system 1 is the device of the above-described semi-fixed address type, for example, the control means 190 shown in FIG. 52 may be employed instead of the above-described control means 170. Hereinafter, the medicine dispensing system 1 provided with the control means 190 will be explained focused on configurations and operations of the control means 190. Further, in the following description, in order to simplify the description, an example will be described wherein the region of the main storage part 20 or the sub storage part 120 is classified into two regions of the fixed address region Fi and the free address region Fr according to the height of the main storage part 20 or the sub storage part 120.

In addition to the function of the above-described control means 170, the control means 190 has a judging part 191 having a function of performing an error judgment operation for confirming whether the feeder container 41 to be set in the motor base 50 in the fixed address region Fi (hereinafter, this may be referred to as a specific feeder container 41x) is mounted on the wrong motor base 40. That is, when the feeder container 41 is attached to the motor base 40, the control means 190 allow the judging part 191 to perform the error judgment operation to thereby judge whether or not the attached feeder container 41 is the specific feeder container 41x. Also, the control means allows the judging part to perform the error judgment operation for judging an erroneous mount by confirming whether the specific feeder container 41x is erroneously mounted on the motor base 40 in the region other than the fixed address region Fi (hereinafter, this may be referred to as a free address region Fr). More specifically, in the free address region Fr1, divided into two stages above the fixed address region Fi, or in the free address region Fr2, divided into two stages above the free address region Fr1. Hereinafter, the error judgment operation will be described in detail.

Figure 53:
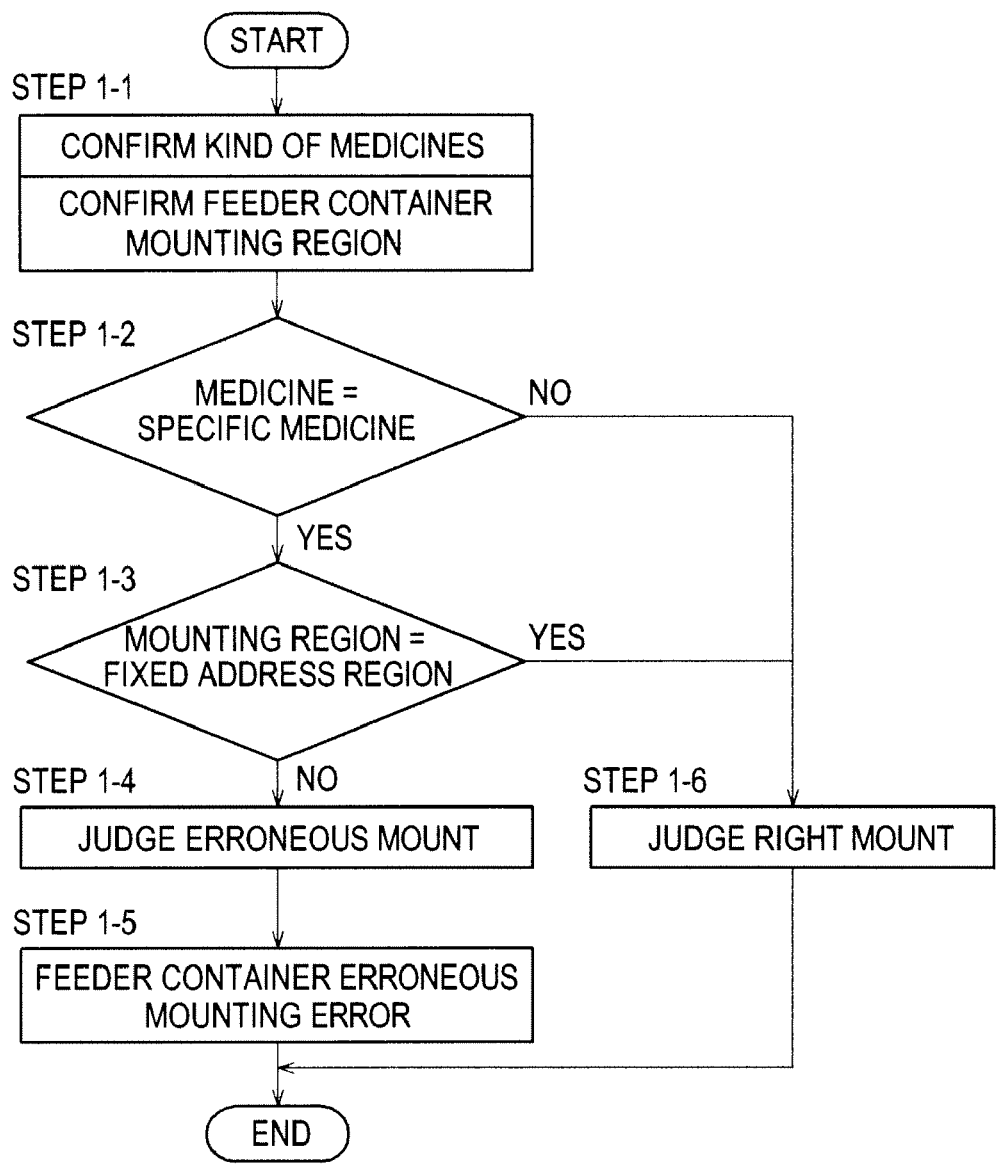
FIG. 53 is a flow chat showing an error judgment operation of a medicine dispensing system.

(Error judgment operation) In the medicine dispensing system 1 with the control means 190, when the feeder container 41 is mounted on the motor base 40, the error judgment operation is performed according to a control flow shown in FIG. 53. More specifically, if the erroneous mount judging operation begins, the judging part 191 confirms whether there is any feeder container 41 erroneously mounted against the regulation of the container mounting database 193 in Steps 1-1 to 1-3, based on the following: the above-described container mounting database 193; the region in which the motor base 40 with the feeder container 41 mounted thereon exists; and the kind of the medicines read from the tag 49 of the feeder container 41.

Even more specifically, first in Step 1-1, data-communication is performed between the control means 190 and the tag 49 of the feeder container 41 mounted on the motor base 40 by the reader-writer 44 provided in each of the motor bases 40 in the main storage part 20 or the sub storage part 120. Thus, the control means 190 specifies which region of the fixed address region Fi and the free address region Fr the motor base 40 with the feeder container 41 mounted thereon exists. Further, in addition to the above, the control means 190 confirms whether or not the feeder container 41 mounted on the motor base 40 is the specific feeder container 41x. That is, whether or not the medicines in the feeder container 41 are the specific medicines with the concerns of breakage or chipping. Then, the control flow proceeds to Step 1-2.

When the control flow proceeds to Step 1-2, the judging part 191 of the control means 190 confirms whether or not the medicines accommodated in the feeder container 41 confirmed in Step 1-1 are the specific medicines with the concerns of breakage or chipping. In this case, if the medicines are not the specific medicines, the feeder container 41 accommodating those medicines may be mounted on the motor base 40 in any of the fixed address region Fi and the free address region Fr. Thus, when it is checked in Step 1-2 that the kind of medicines is not the specific medicine, the control flow proceeds to Step 1-6 and it is judged that the feeder container 41 is mounted in a normal position (right mount state). Then, the control flow is ended.

Meanwhile, when it is checked in Step 1-2 that the medicines accommodated in the feeder container 41 provided in the main storage part 20 or the sub storage part 120 are the specific medicines, the control flow proceeds to Step 1-3. It is checked in Step 1-3 whether the motor base 40 provided with the feeder container 41 is in the fixed address region Fi of the main storage part 20 or the sub storage part 120. In this case, when the feeder container 41 is mounted on the motor base 40 in the fixed address region Fi, it is assumed that when the medicines in the feeder container 41 (the specific medicines) are dispensed, no problems due to the bound or breakage occurs. Accordingly, in this case, the control flow proceeds to Step 1-6 and it is judged that the feeder container 41 is mounted on the normal position. Then, the control flow is ended.

Meanwhile, when it is checked in Step 1-3 that the motor base 40 provided with the feeder container 41 is not in the fixed address region Fi but in the free address region Fr, there are concerns about the problems due to the bound or breakage by dispensing the medicines (the specific medicines) from this feeder container 41. Accordingly, in this case, the control flow proceeds to Step 1-4 and it is judged as the erroneous mount state that the feeder container 41 is not mounted in the normal position. Then, the control flow proceeds to Step 1-5 to perform a display for warning the erroneous mount state in the operating panel 118a provided in the front surface of the main body of the main unit 2 and the control flow is ended.

Figure 54:
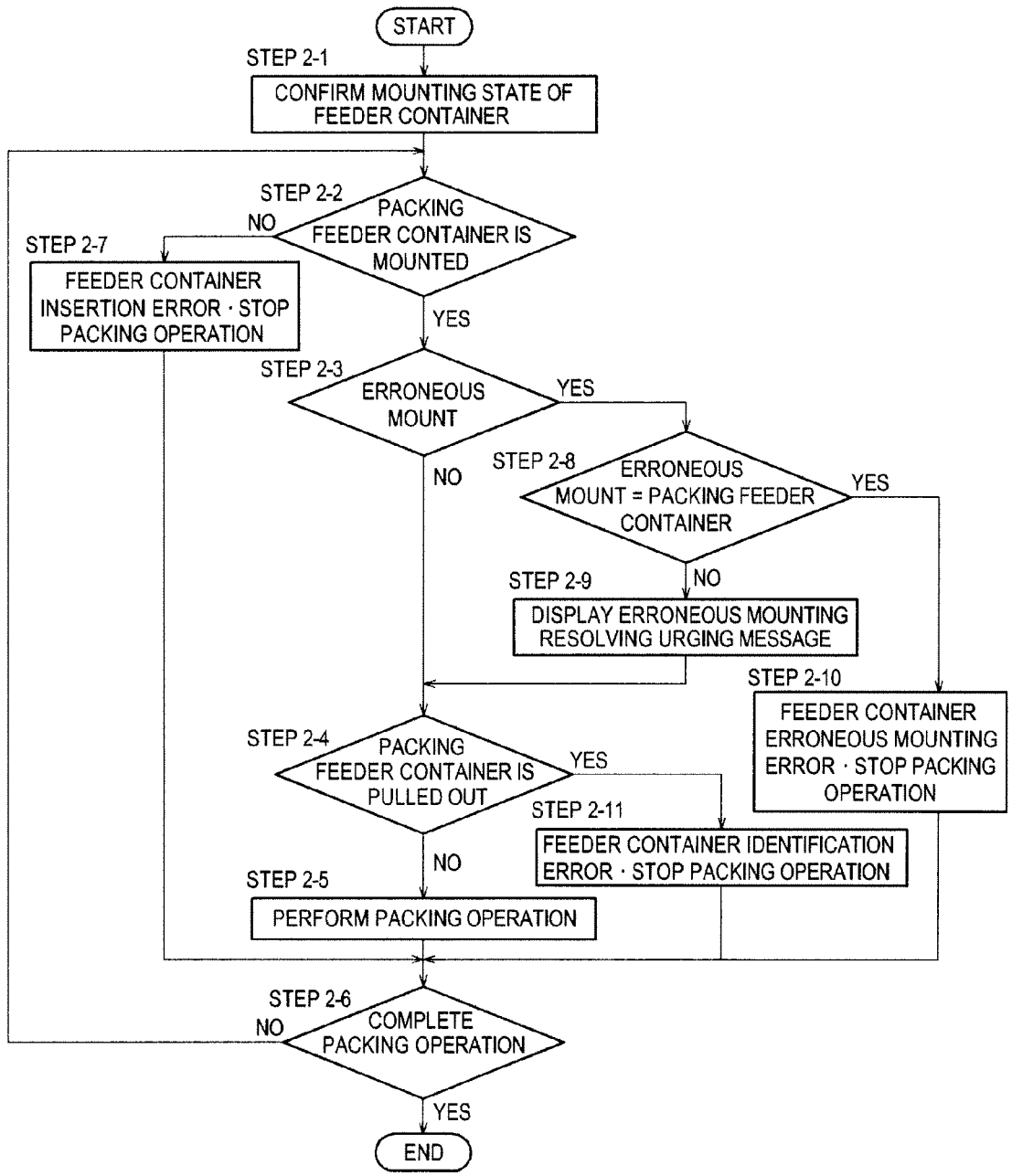
FIG. 54 is a flow chart showing operations of the medicine dispensing system.

In the medicine dispensing system 1 provided with the control means 190, a medicine packing operation under the general operation mode can be performed according to the control flow shown in FIG. 54 using judgment results from the above-described error judgment operation. Hereinafter, the packing operation under the general operation mode, which is performed using the judgment results from the error judgment operation, will be described.

Figure 55:
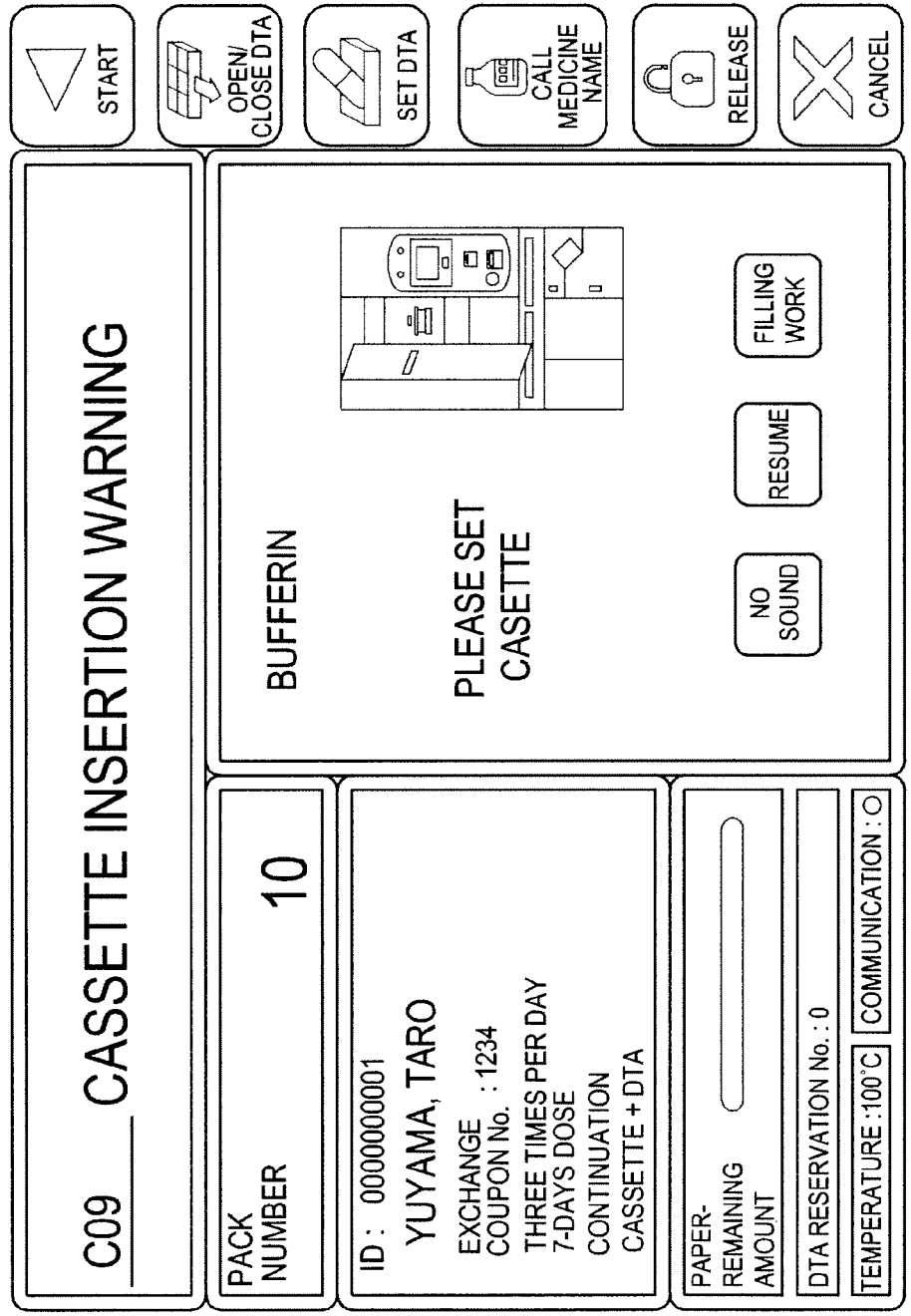
FIG. 55 is a front view showing a display of a manipulating panel when a feeder container insertion error occurs.
Figure 57:
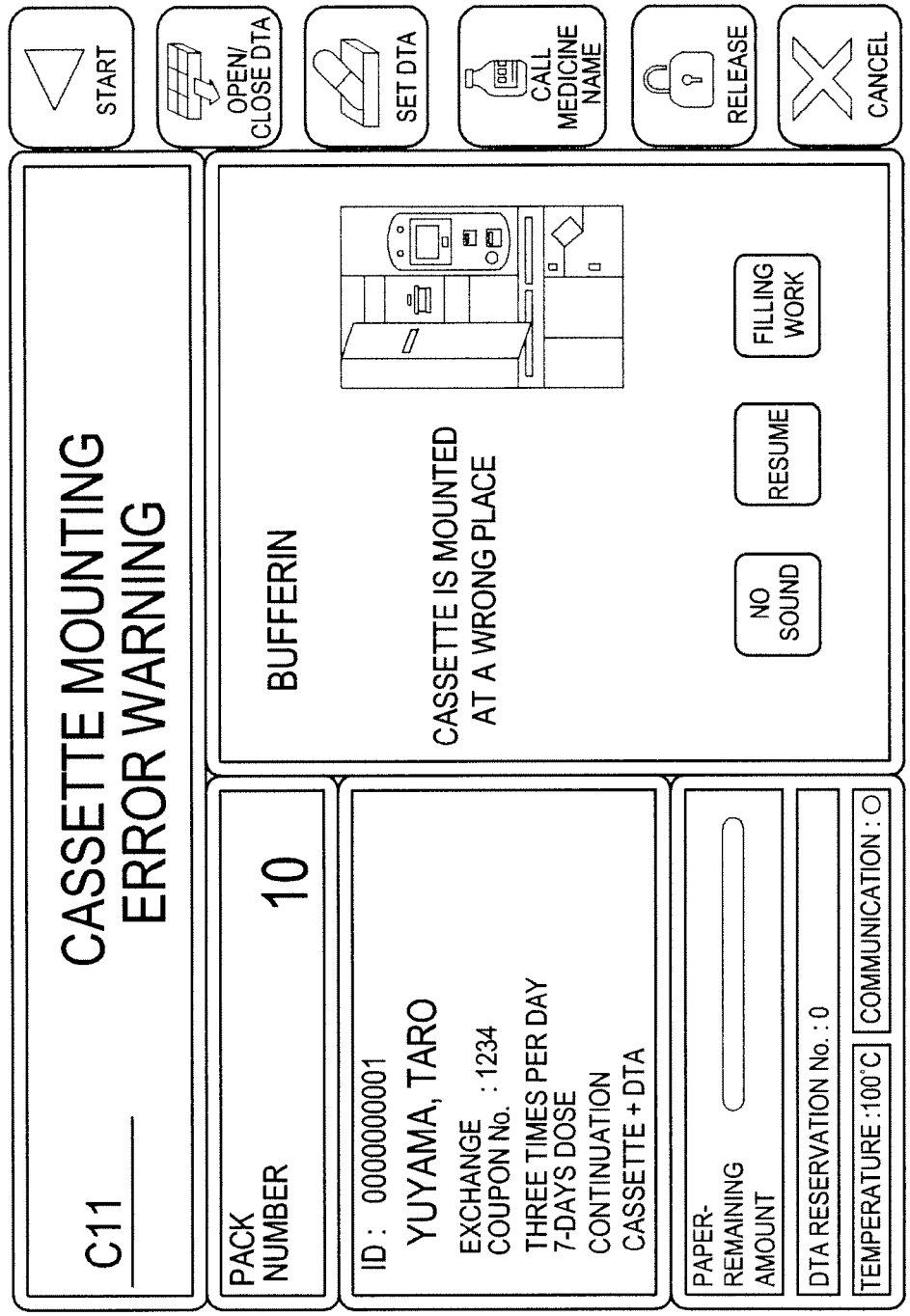
FIG. 57 is a front view showing a display of the manipulating panel when a feeder container mount error occurs.

(Packing operation using the judgment results from the error judgment operation) According to the medicine dispensing system 1 provided with the control means 190, if a prescription data for designating the kind, the quantity and the number of packs of the medicines to be packed is inputted to the control means 190, an operation under the general operation mode is started. If the operation under the general operation mode is started, the mounting state of the feeder container 41 for the motor base 40 provided in the drums of the main storage part 20 and the sub storage part 120 is confirmed in Step 2-1. Then, if the control flow proceeds to Step 2-2, it is checked whether the feeder container 41 accommodating the medicines to be packed according to the previously-inputted prescription data (hereinafter, this may be referred to as a packing feeder container 41y) is mounted on the main storage part 20 or the sub storage part 120. In this case, when the packing feeder containers 41y is empty, the control flow proceeds to Step 2-7 and an information indicating an error (a feeder container insertion error) is displayed in the operating panel 118a as shown in FIG. 55. Further, in Step 2-7, the packing operation is stopped. Then, the control flow proceeds to Step 2-6 which will be described below.

Meanwhile, when all the packing feeder containers 41y are mounted in Step 2-2, the control flow proceeds to Step 2-3. It is checked in Step 2-3 according to the above-described control flow shown in FIG. 53 whether not only the packing feeder container 41y but also all the feeder containers 41 mounted on the main storage part 20 and the sub storage part 120 are erroneously mounted. When the erroneous mounting is confirmed in Step 2-3, that is, when it is confirmed in Step 2-3 that the feeder container 41 (the specific feeder container 41x) accommodating the specific medicines having problems such as bound or breakage, which should be originally mounted in the fixed address region Fi, is mounted in the free address region Fr in the main storage part 20 or the sub storage part 120, the control flow proceeds to Step 2-8.

It is checked in Step 2-8 whether the erroneously-mounted feeder container 41 is a feeder container accommodating the medicines to be packed (the packing feeder container 41y). In this case, when the erroneously-mounted feeder container 41 corresponds to the packing feeder container 41y, continuing to dispense the medicines as it is can cause the problems such as packing abnormality resulting from bound or rolling of the medicines in the place where the medicines are dispensed or breakage and chipping of the medicines. Accordingly, in this case, the control flow proceeds to Step 2-10 and information indicating an error (a feeder container erroneous mounting error) purporting that the feeder container 41 (the specific feeder container 41x) is erroneously mounted in the free address region Fr is displayed in the operating panel 118a. Also, the packing operation is stopped until the erroneously-mounted feeder container 41 is mounted in the fixed address region Fi.

Meanwhile, when it is judged in Step 2-8 that the erroneously-mounted feeder container 41 does not correspond to the packing feeder container 41y, the medicines are not allowed to be dispensed from the erroneously-mounted feeder container 41 in the packing operation. Thus, although the packing operation continues as the feeder container 41 to be mounted in the fixed address region Fi is erroneously mounted, it is assumed that there is no problem due to the above-described bound, rolling, breakage and chipping of the medicines. Accordingly, in this case, a message for urging to resolve the erroneous mounting (an erroneous mounting resolving urging message) as shown in FIG. 56 is displayed in Step 2-9. Then, the control flow proceeds to Step 2-4 and the packing operation continues as the erroneous mounting resolving urging message is displayed in the operating panel 118a in Step 2-9.

Figure 58:
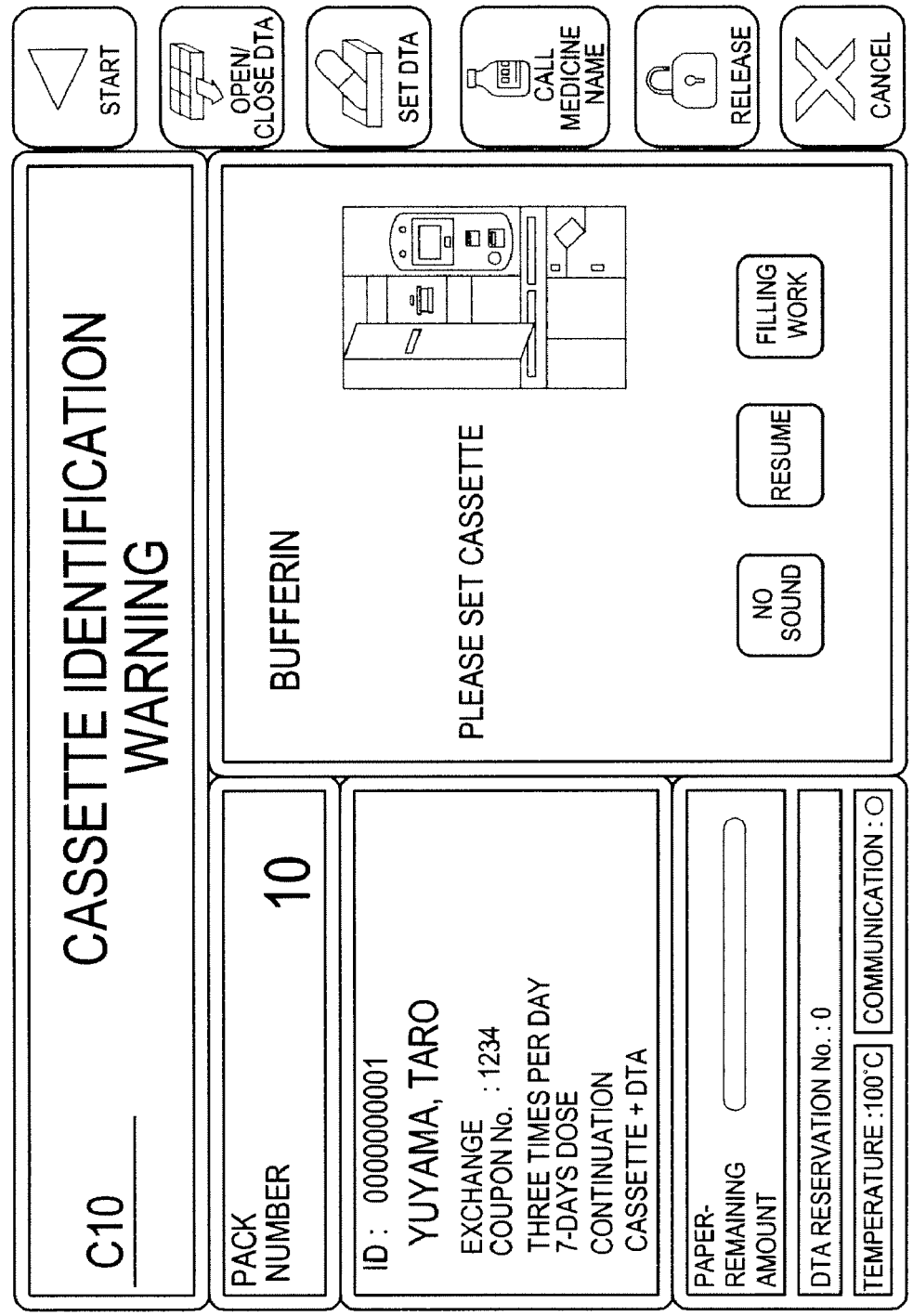
FIG. 58 is a front view showing a display of a manipulating panel when a feeder container identification error occurs.

When it is judged in Step 2-3 that no feeder container 41 is erroneously mounted, or when it is judged in Step 2-8 that the erroneously-mounted feeder container 41 does not correspond to the packing feeder container 41y, the control flow proceeds to Step 2-4. It is checked in Step 2-4 whether the packing feeder container 41y accommodating the medicines to be packed is pulled out while the control flow proceeds from said Step 2-1. In this case, when it is confirmed that the packing feed container 41y is pulled out, the control flow proceeds to Step 2-11 and an information indicating an error to this effect (a feeder container identification error) is displayed in the operating panel 118a as shown in FIG. 58. Also, the packing operation is stopped until the pulled-out packing feeder container 41y is mounted again. Meanwhile, when it is judged that the packing feeder container 41y is not pulled out, the control flow proceeds to Step 2-5 and the packing operation is performed. Then, the control flow proceeds to Step 2-6 and it is checked whether all the medicines to be packed according to the prescription data inputted at the time of starting the medicine packing operation under the general operation mode are packed. In this case, when packing the medicines to be packed according to the prescription data is not completed, the control flow returns to Step 2-2. Meanwhile, when packing all the medicines is completed, the control flow is ended.

As described above, in case the medicine dispensing system 1 employs the control means 190, the error judgment operation is performed according to the control flow shown in FIG. 53 and therefore it can be judged whether the feeder container 41 is erroneously mounted in the container mounting part where the feeder container 41 should not be mounted originally. Further, as shown in the control flow of FIG. 54, in the medicine dispensing system 1, when the feeder container 41 is erroneously mounted and such an erroneously-mounted feeder container 41 does not correspond to the feeder container accommodating the medicines to be packed (the packing feeder container 41y), dispensing the medicines continues due to no inconvenience in packing the medicines. Thus, the work efficiency in dispensing and packing the medicines is enhanced. Meanwhile, when the erroneously-mounted packing feeder container 41y accommodates the above-described medicines with the concerns of problems such as bound or breakage, dispensing and packing the medicine is stopped. Thus, where the medicine dispensing system 1 is configured as described above, although there is the erroneously-mounted feeder container 41, the packing abnormality caused by the problems such as bound or breakage of the medicines can be prevented while minimizing a loss in work efficiency.

In an example illustrated in the above-described embodiment, the motor bases 40 capable of mounting the feeder container 41 thereon are provided as divided into multiple stages in an upward and downward direction. Further, the motor bases are regulated in a two-stage region (the container mounting region) of the fixed address region Fi and the free address region Fr according to the height. Further, the corresponding relationship between the motor base 40 and the feeder container 41 to be attached thereto is regulated in the container mounting database 193 as the relationship with the container mounting region being at the height which becomes the upper attachment limit of the feeder container 41 determined according to the kinds of medicines. That is, a region which becomes the upper attachment limit of the feeder container 41 accommodating the specific medicines causing the problems such as bound or breakage is regulated as the fixed address region Fi. Further, a region which becomes the upper attachment limit of the feeder container 41 accommodating the medicines causing less problems such as bound or breakage is regulated as the free address region Fr.

However, the regulation (classification) for the relationship with the container mounting region being at the height which becomes the upper attachment limit of the feeder container 41 regulated in the container mounting database 193 should not be limited to the above-described. The region divided into multiple stages in an upward and downward direction where the motor bases 40 are provided may be regulated to be divided into still more stages according to the height. More specifically, the regions may be classified into three stages by classifying the free address region Fr into two regions Fr1, Fr2 as described above or may be classified into still more stages. In this case, the medicine dispensing system is configured such that the correspondence relationship between the motor base 40 and the feeder container 41 to be attached thereto is regulated in the container mounting database 193 as the relationship with the region (container mounting region) being at the height which becomes the upper attachment limit of a medicine feeding container determined according to the kinds of the medicines, and that it is judged as an erroneous mount state by the error judgment operation when the feeder container 41 is mounted on the motor base 40 in the container mounting region positioned above the container mounting region being at the height which becomes the upper attachment limit, and that it is judged as a right mount state by the error judgment operation when the feeder container 41 is mounted on the motor base 40 in the container mounting region being at the height equal to or less than said upper attachment limit. Accordingly, the attachment state of the feeder container 41 can be managed in more detail.

The height (the container mounting region) which becomes the upper attachment limit of the feeder container 41 may be previously determined based on the factors counted for the bound, rolling, breakage and chipping of the medicines due to drop of the medicines per each kind of the medicines or the classification of the medicines in each grade. The height (the container mounting region) which becomes the upper attachment limit may be determined by the control means 190 in an orderly manner according to the factor or grade.

Figure 59:
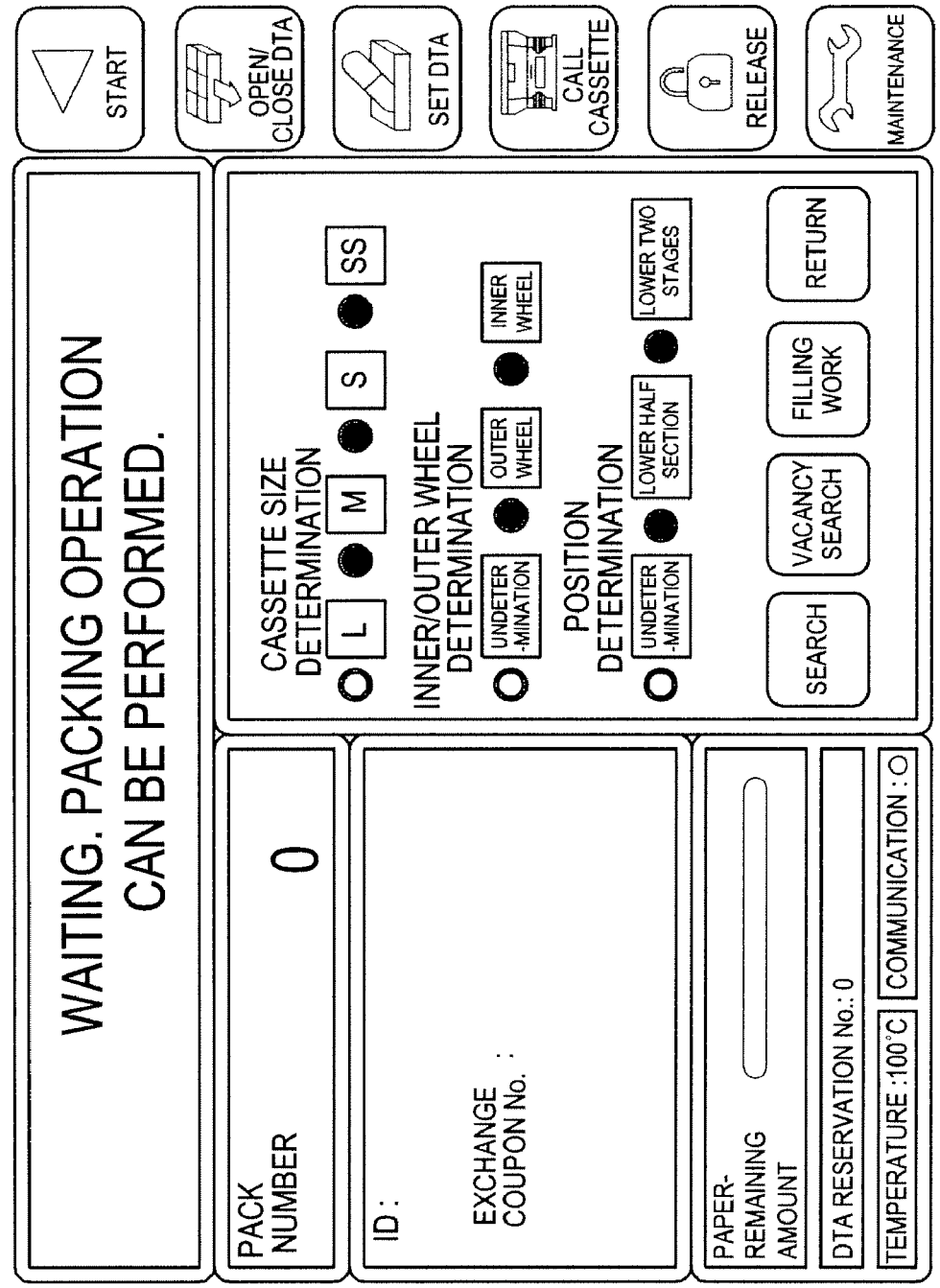
FIG. 59 is a front view showing a display of a manipulating panel when a search condition is set.

The above-described medicine dispensing system 1 may include a search part 192 having a searching function of searching and selecting the motor base 40 which must mount the feeder container 41 judged as the erroneous mount by the error judgment operation of the control means 190, as shown by a two-dot chain line in FIG. 52. More specifically, a search condition may be determined by reading the information recorded in the tag 49 through the data-communication between the tag 49 provided in the feeder container 41 and the reader-writer 117c by removing the feeder container 41 judged as the erroneous mount by the error judgment operation and fitting the feeder container to the recess 117b provided in the worktable 117 of the main unit 2. And, the motor base 40 suitable for mounting the feeder container 41 may be searched and selected by the search part 192. Further, as for the search condition, it is preferred to appropriately display the search condition in the operating panel 118a as shown in FIG. 59. Meanwhile, instead of determining the searching condition by reading the information of the erroneously-mounted feeder container 41 through the data-communication between the tag 49 and the reader-writer 117c, an operator may manually input the search condition through the operating panel 118a and the search part 192 may search the motor base based on the manually inputted search condition. In this case, for example, the search condition can be appropriately inputted by displaying a search condition determining screen shown in FIG. 59 in the operating panel 118a.

Further, when the position of the motor base 40 suitable for mounting the erroneously-mounted feeder container 41 is searched as described above, the main storage part 20 or the sub storage part 120 may be operated such that the selected motor base 40 comes to a position where an operator can perform the attachment/detachment work of the feeder container 41 (an attachment/detachment work position). According to such a configuration, the attachment/detachment work for the erroneously-mounted feeder container 41 becomes still easier.

As described above, in the present embodiment, the medicine dispensing system 1 is constructed by combining the main unit 2 and the sub unit 3 and a large number of the cassettes 32 are provided not only in the main storage part 20 but also in the sub storage part 120. Thus, when constructing the medicine dispensing system 1, it is preferred to read, write or manage the characteristic container information on the feeder container 41 of each of the cassettes 32 as described in the foregoing embodiment. Further, it is illustrated in the above-described embodiment that the medicine dispensing system 1 is constructed by combining the main unit 2 and the sub unit 3. However, the present invention should not be limited to such a configuration. The characteristic container information can be accurately read, written or managed when only a part corresponding to the main unit 2 is utilized as the medicine dispensing system.

In the medicine dispensing system 1, the sub unit 3 does not need the medicine packing part 21. Thus, the medicine dispensing system 1 can reduce the device configuration and minimize an installation area, when compared to a case of providing a plurality of equivalents of the medicine packing part to the main unit 2. Further, according to the configuration of the medicine dispensing system 1, a part corresponding to the medicine packing part 21 can be omitted in the sub unit 3 and thus the sub unit 3 can be configured to accommodate various kinds of medicines in a large quantity. Further, since the sub unit 3 does not need the medicine packing part 21, the medicine dispensing system 1 can simplify a device configuration or minimize efforts for maintenance.

Since the transfer device 5 employed in the medicine dispensing system 1 has the pipe line 140 for transferring the medicines and is configured to suck the medicines inputted therein, the medicines dispensed in the sub unit 3 can be smoothly conveyed toward the main unit 2. Further, since the transfer device 5 is configured to suck and convey the medicines, the medicines can be conveyed along any conveying path by appropriately curving the pipe line 140. Thus, the medicine dispensing system 1 has a high degree of freedom in a device configuration and layout of the main unit 2 and the sub unit 3.

Further, the above-described transfer device 5 is configured to suck and transfer the medicines inputted in the measures 145 of the medicine receiving part 142 connected to the pipe line 140 toward the medicine dispensing part 143. However, the present invention should not be limited to such a configuration. The transfer device 5 may be configured to pressure-transfer the medicines from the medicine receiving part 142 toward the medicine dispensing part 143. Further, the transfer device 5 includes the pipe line 140 of one channel. However, the present invention should not be limited to such a configuration. The conveying path of many channels including many pipe lines 140 may be employed.

In the medicine dispensing system 1 of the present embodiment, the tag 49 is provided in each of the cassettes 32 set in the main storage part 20 and the sub storage part 120. Also, the data can be transmitted to and received from the tag 49 and the data can be renewed or written in the tag by the reader-writer 117c provided in the worktable 117. Thus, the medicine dispensing system 1 can record various data such as data on the kind or quantity of the medicines accommodated in each cassette 32, data on a supplement history related to a person performing a medicine supplement in each cassette 41 and date and time of the medicine supplement, data on a usage history of each cassette, and the like into the tag 49. Further, the medicines accommodated in each cassette 32 can be managed or the user can be notified of a maintenance time of each cassette 32 based on the data recorded in the tag 49.

Further, it is illustrated in the above-described embodiment that the tag 49 is provided in the feeder container 41 of each cassette 32 and the reader-writers 44, 117c are provided in all the motor bases 40 or the worktable 117. However, the present invention should not be limited to such a configuration. That is, the medicine dispensing system 1 may be configured such that all the cassettes 32 do not have the tag 49 and some or all of the motor bases 49 do not have the reader-writers 44. Likewise, the medicine dispensing system 1 may not include the reader-writer 117c. Further, the medicine dispensing system 1 may be configured such that only some cassettes 32, for example, for managing the quantity of the medicines include the tag 49.

As described above, the feeder container 41 of the cassette 32 can adjust the size of the opening 47 for dispensing the medicines according to the size of the medicines to be accommodated by appropriately replacing the opening attachment 41b. Also, the rotor 48 of the feeder container 41 can be appropriately replaced with another one having a groove 48a sized to be suitable for the size of the medicines to be accommodated. Thus, the cassette 32 can deal with the medicines of various sizes by appropriately replacing the opening attachment 41b or the rotor 48.

Further, it is illustrated in the above-described embodiment that the opening attachment 41b or the rotor 48 can be appropriately replaced in the feeder container 41 according to the size of the medicines. However, the present invention should not be limited to such a configuration. More specifically, the opening 47a of a fixed size may be formed in the feeder container 41 or the rotor 48 may not be replaceable.

Also, in the medicine dispensing system 1, considering that the packing paper sheet 98 with the length corresponding to n packs of the medicine pack (three packs in the present embodiment) exists between the pack forming mechanism 96 and the printing part 99, the information on the medicines is printed by the printing part 99 at a time (time Z) as early as the time period (time period Y) required to rotate the section forming body 81 as much as a quantity corresponding to n sections 81a (three sections in the present embodiment) from the timing (timing X) when the medicines are dispensed through the opening 82c from the section 81a in the medicine preparing part 80. Further, at a time before the timing Z of printing to the packing paper sheet 98, the medicines dispensed from the main storage part 20 or the sub storage part 120 are inputted in the section 81a. That is, printing to the packing paper sheet 98 is performed in the medicine dispensing system 1 upon a condition that the medicines are dispensed from the main storage part 20, sub storage part 120 and the manual dispensing unit 23 to the medicine preparing part 80. Thus, when a dispensing abnormality of the medicines to the medicine preparing part 80 occurs, printing to the packing paper sheet 98 is not performed. Thus, the medicine dispensing part 1 can easily and accurately monitor whether a dispensing abnormality of the medicines from the main storage part 20, the sub storage part 120 and the manual dispensing unit 23 to the medicine preparing part 80, only by checking whether or not printing to the packing paper sheet 98 is performed. Further, according to the above-described configuration, when the medicines to be packed into the packing paper sheet 98 lack or do not exist, unnecessary printing is not performed to the packing paper sheet 98 and a waste of the packing paper sheet 98 to that extent can be prevented.

In the above-described embodiment, at the timing before the timing Z, the medicines are dispensed from all of the main storage part 20, the storage part 120 and the manual dispensing unit 23, which constitute the medicine dispensing means, and inputted in each section 81a. However, the present invention should not be limited to such a configuration. More specifically, the medicines dispensed from some of the main storage part 20, the sub storage part 120 and the manual dispensing unit 23, which constitute the medicine dispensing means, are dispensed into each section 81a at a time after the time Z. Even more specifically, for example, since the manual dispensing unit 23 is installed in order to pack the medicines inputted by the user's own hands, it is considered that abnormality in inputting the medicines from the manual dispensing unit 23 to each section 81a hardly occurs. Thus, in the aforementioned circumstance, the time of dispensing the medicines may be after the time Z with regard to some of parts constituting the medicine dispensing means.

The medicine dispensing system 1 according to the above-described embodiment includes the circular section forming body 81 with a plurality of the circumferentially-arranged sections 81a in the medicine preparing part 80 and is configured to dispense the medicines from each of the sections 81a by relatively rotating the section forming body 81 relative to the opening 82c. Thus, according to the above-described configuration, a space required for operating the section forming body 81 becomes minimized and thus the device configuration can be reduced. Further, the medicine preparing part 80 should not be limited to the above-described embodiment. For example, the medicine preparing part may be configured such that the section forming body 81 has a plurality of linearly-arranged sections 81a and the medicines are dispensed from each of the sections 81a one after another by linearly moving the section forming body 81 relative to the opening 82c.

Further, as described above, the medicine dispensing system 1 has the set abnormality detecting means 38 at the main unit 2 or the sub unit 3. The set abnormality detecting means 38 is not the same as the conventionally known optical sensor but employs a so-called mechanical configuration wherein the switch 38b is turned on when the cassette 32 bumps against the contact plate 38a along with the rotation of the drum 31 and the contact plate 38a swings thereby. Thus, according to the above-described set abnormality detecting means 38, the attachment abnormality of the cassette 32 can be accurately detected without an effect from a dust, when compared to a case of employing the optical sensor.

Also, it is illustrated that the medicine dispensing system 1 includes the set abnormality detecting means 38 of a mechanical type at both the main unit 2 and the sub unit 3. However, the present invention should not be limited to such a configuration. The set abnormality detecting means 38 may be provided at one side or the set abnormality detecting means 38 and known detecting means such as an optical sensor may be used together.

In the medicine dispensing system 1, the abnormality detecting mechanism 115 is provided in the conveying means 21b of the medicine packing part 21 and the transfer abnormality of the packing paper sheet such as a paper jam of the packing paper sheet 98 can be detected by the abnormality detecting mechanism 115. That is, the abnormality detecting mechanism 115 illustrated in the above-described embodiment has a pinch roller 115b rotatable independently of the conveying means 21b and a paper transfer abnormality can be detected based on whether the rotation of this pinch roller 115b is detected by the rotary encoder 115d during operation of the conveying means 21b. Thus, the medicine dispensing system 1 of the present invention can minimize the waste of the packing paper sheet 98 or the medicines due to the transfer abnormality of the packing paper sheet 98. Further, it is illustrated in the above-described embodiment that the abnormality detecting mechanism 115 is positioned in the straight portion 105b of the casing 105, which constitutes the conveying means 21b, and in a position upstream in the transfer direction of the packing paper sheet 98 in order to detect the transfer abnormality of the packing paper sheet in the medicine packing part 21 as fast as possible. However, the present invention should not be limited to such a configuration. The abnormality detecting mechanism 115 may be positioned in a position further downstream than the aforementioned position.

In the above-described embodiment, the medicine packing part 21 can appropriately bend the bent portion 105c positioned at the distal end portion of the casing 105, which constitutes the conveying means 21b, relative to the straight portion 105b. Thus, in the medicine dispensing system 1, the packing paper sheet 98 with the packed medicines can be removed from a better one of the dispensing openings 2c, 2d of the main unit 2. Further, the conveying means 21 is configured to appropriately bend the bent portion 105c. However, the conveying means may not have a part corresponding to the bent portion 105c. Also, it is illustrated in the above-described embodiment that the medicine dispensing system 1 is constructed by combining the main unit 2 and the sub unit 3. However, the present invention should not be limited to such a configuration. The main unit 2 may be used alone.

The above-described medicine dispensing system 1 may be configured such that the transfer device 5 is separately provided in addition to the main unit 2 and the sub unit 3 and the transfer device lies across the main and sub units. However, the transfer device 5 may be previously assembled with the sub unit 3 and, when necessary, the same may be connected to the main unit 2 to provide extension of installation. That is, the sub unit 3 may or may not include the transfer device 5 as a part of its configuration.

The transfer device 5 of a type of sucking and transferring the medicines dispensed in the sub unit 3 is illustrated in the above-described embodiment. However, the present invention should not be limited to such a configuration. For example, a transfer device 210 shown in FIG. 25 may be employed.

More specifically, the transfer device 210 is mainly comprised of a support part 220 and a drive part 230. As shown in FIG. 25, the support part 220 has a supporting shaft 221 and a base part 222. A supporting shaft 221 has a flange 223 provided at one end and can be erected approximately upright by screw-fixing the flange 223. The base part 222 serves as a turning means for turning the drive part 230 and is provided at the other end of the supporting shaft 221. The base part 222 includes a turn drive motor 225, a turn drive gear 226, and a seat plate 227. As shown in FIG. 25, the seat plate 227 is a plate body that is horizontal when the supporting shaft 221 is erected. Further, the turn drive motor 225 is positioned such that its rotating shaft approximately vertically passes through the seat plate 227 from a lower surface thereof. The turn drive gear 226 is connected to the rotating shaft of the turn drive motor 225 on an upper surface of the seat plate 227.

As shown in FIG. 25, the drive part 230 includes two sets of medicine delivering units 231 (medicine delivering part) and a supporting plate 232 supporting them at their lower sides. Further, a turning shaft 234 is erected at an approximate center of the supporting plate 232. The turning shaft 234 approximately vertically extends from the supporting plate 232 and is rotatably supported on the seat plate 227 of the base part 222 at its lower end. The turn driven gear 234a is integrally coupled to the lower end of the turning shaft 234. The turn driven gear 234a is meshed with the turn drive gear 226 of the base part 222. Thus, as the turn drive motor 225 provided in the base part 222 operates, the supporting plate 232 and the medicine delivering unit 231 provided thereon can turn integrally about the turning shaft 234.

Both of the medicine delivering units 231, 231 have an elongated shape and are supported parallel to each other by supporting plates attached to bottom surfaces thereof. The medicine delivering unit 231 includes a slide base 235 and first and second sliding bodies 236, 237 (first and second sliding portions). The slide base 235 and the first and second sliding bodies 236, 237 are elongated bodies and have approximately equal lengths. The slide base 235 is fixed on the seat plate 227 of the base part 222. In the present embodiment, as shown in FIG. 25, the sliding bases 235, 235 of the two sets of the medicine delivering units 231, 231 are fixed on the seat plate 227 and are arranged approximately parallel to each other.

Figure 26:
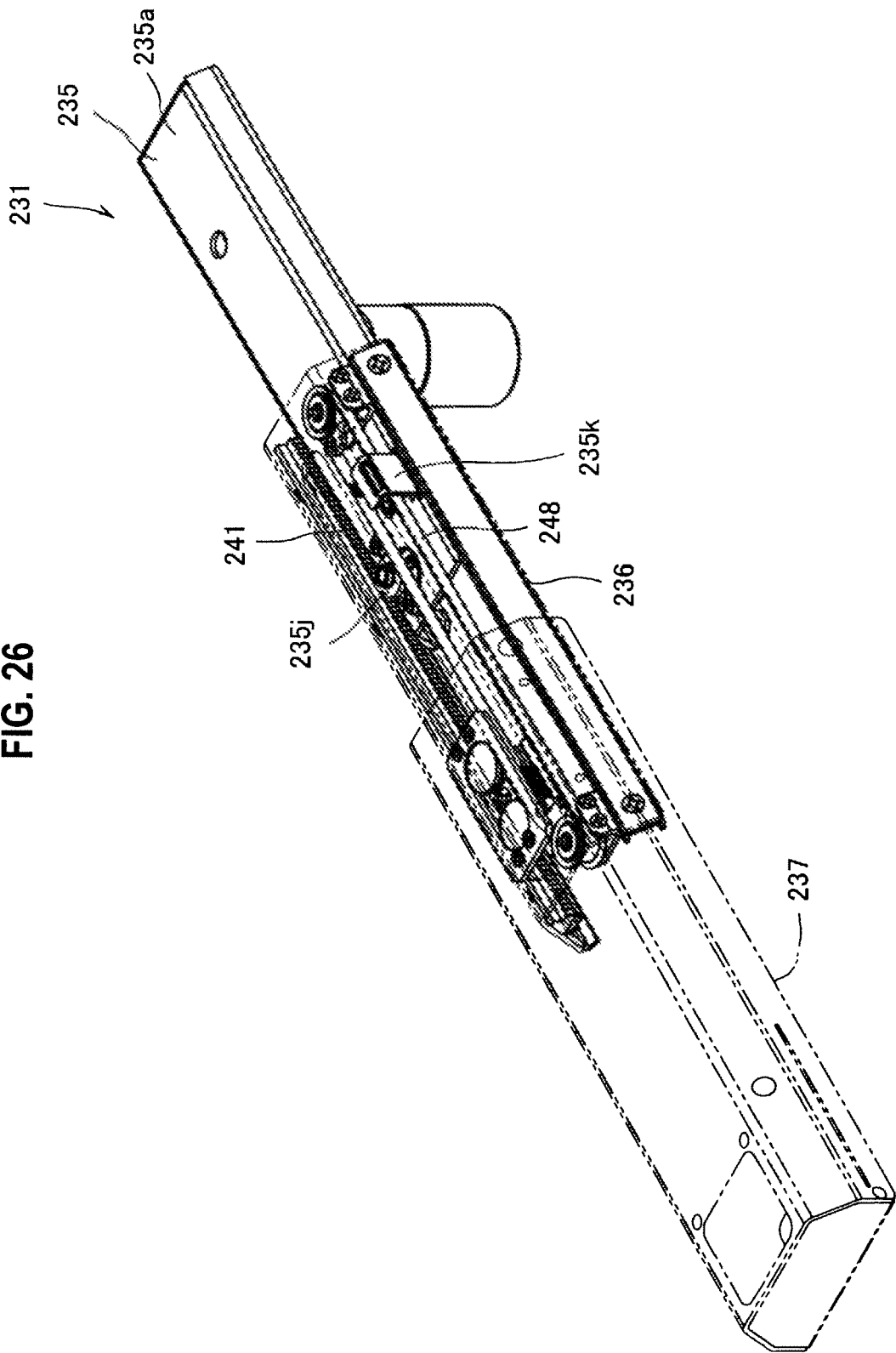
FIG. 26 is an upper perspective view of the medicine delivering unit of the transfer device shown in FIG. 25.
Figure 27:
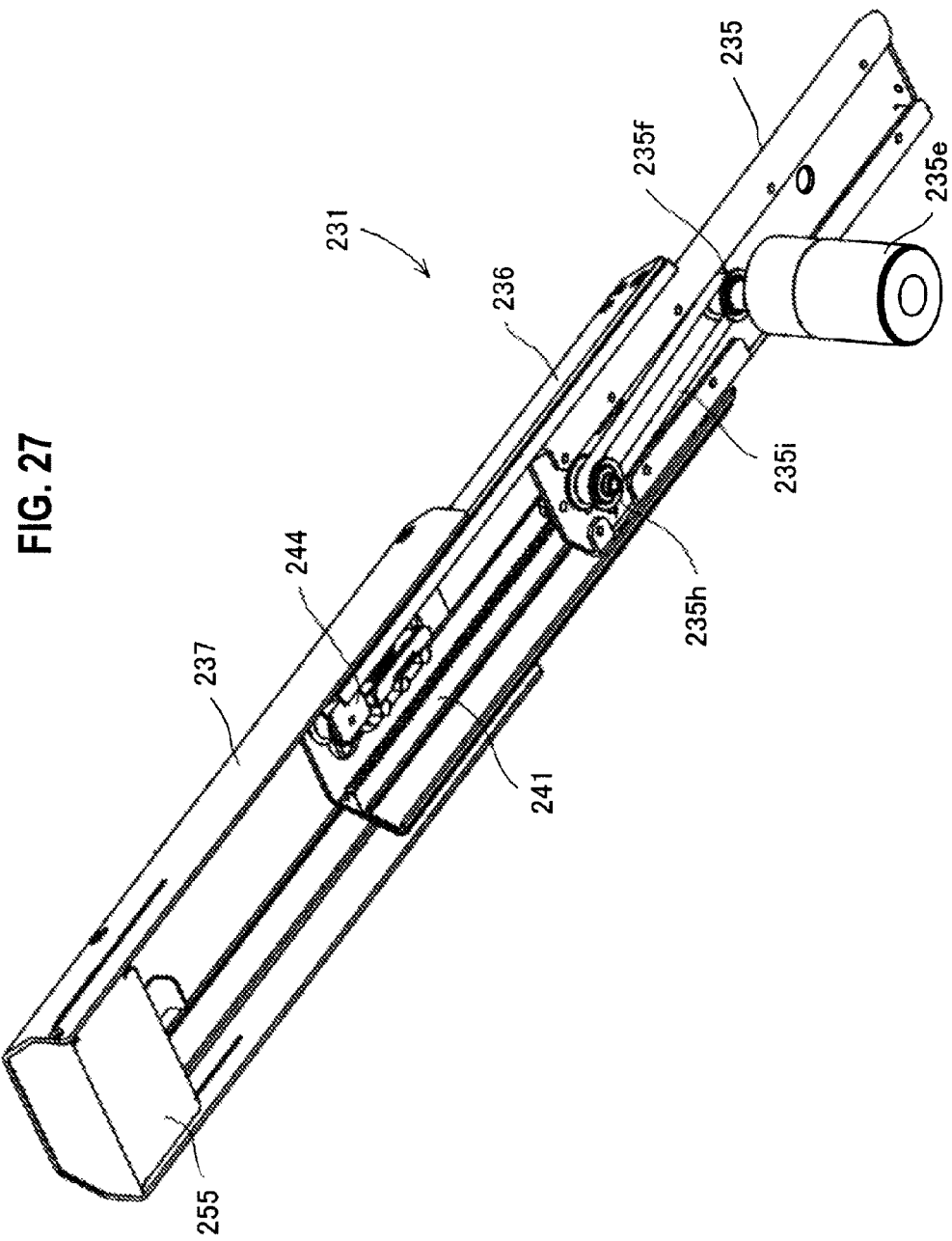
FIG. 27 is a lower perspective view of the medicine delivering unit of the transfer device shown in FIG. 25.

As shown in FIGS. 25 to 28, the first sliding body 236 is mounted on and covers the slide base 235 and is slidable in a lengthwise direction of the slide base 235. Further, the second sliding body 237 is mounted on and covers the first sliding body 236 and is slidable in a lengthwise direction of the first sliding body 236. Thus, as the medicine delivering unit 231 is drawn out away from the sliding base 235 by sliding the first sliding body 236 and the second sliding body 237 from the slide base 235 one after the other in a lengthwise direction, the medicine delivering unit can be expanded up to its overall length as shown in FIGS. 25 to 27. Further, as each of the first and the second sliding bodies 236, 237 is slid toward the slide base 235 from the expanded state shown in FIGS. 25 to 27, the medicine delivering unit decreases in its overall length and can be contracted to the extent of a length of the slide base 235.

More specifically, as shown in FIG. 29, the slide base 235 has the following: a top portion 235a; side portions 235b, 235b provided at both sides of the top portion 235a in a widthwise direction thereof; and a bottom portion 235c, 235c continuing to the side portions 235b, 235b parallel to the top portion 235a. The side portions 235b, 235b are inclined relative to the top portion 235a and the bottom portion 235c, and are linearly beveled outwardly in a widthwise direction from the top portion 235a toward the bottom portion 235c. Each of the side portions 235b, 235b is provided with a guide roller 235d rotatable about a shaft which is approximately vertically erected on the side portion 235b.

As shown in FIG. 29 (b), the slide base 235 has a drive motor 235e at a back side of the top portion 235a (below the top portion). A pulley 235f is coupled to a rotating shaft of the drive motor 235e. Further, a drive pulley 235h is coupled to one end of a shaft 235g, which is approximately vertical to the top portion 235a, at the back side of the top portion 235a and in a position corresponding to one end of the slide base 235 in its lengthwise direction (hereinafter, this may be referred to as a leading end, if necessary). The drive pulley 235h and the shaft 235f rotate integrally by power from the drive motor 235e transferred through a drive belt 253i wound between the drive pulley and the pulley 235f. Further, the shaft 235g approximately vertically passes through the top portion 235a of the slide base 235. As shown in FIG. 29 (a), a drive gear 235j is coupled to the other end of the shaft 235g (i.e. a portion protruding on a top surface of the top portion 235a). Thus, as the drive motor 235e operates, the drive gear 235j rotates about the shaft 235g by the rotational power of the drive motor 235e.

The slide base 235 has a belt fixing member positioned at the leading end of the top portion 235a and near one of the side portions 235b. The belt fixing member 235k is erected on a surface of the top portion 235a (on the top portion) and is fixed to engage a timing belt 248 which is described in detail below.

Figure 30:
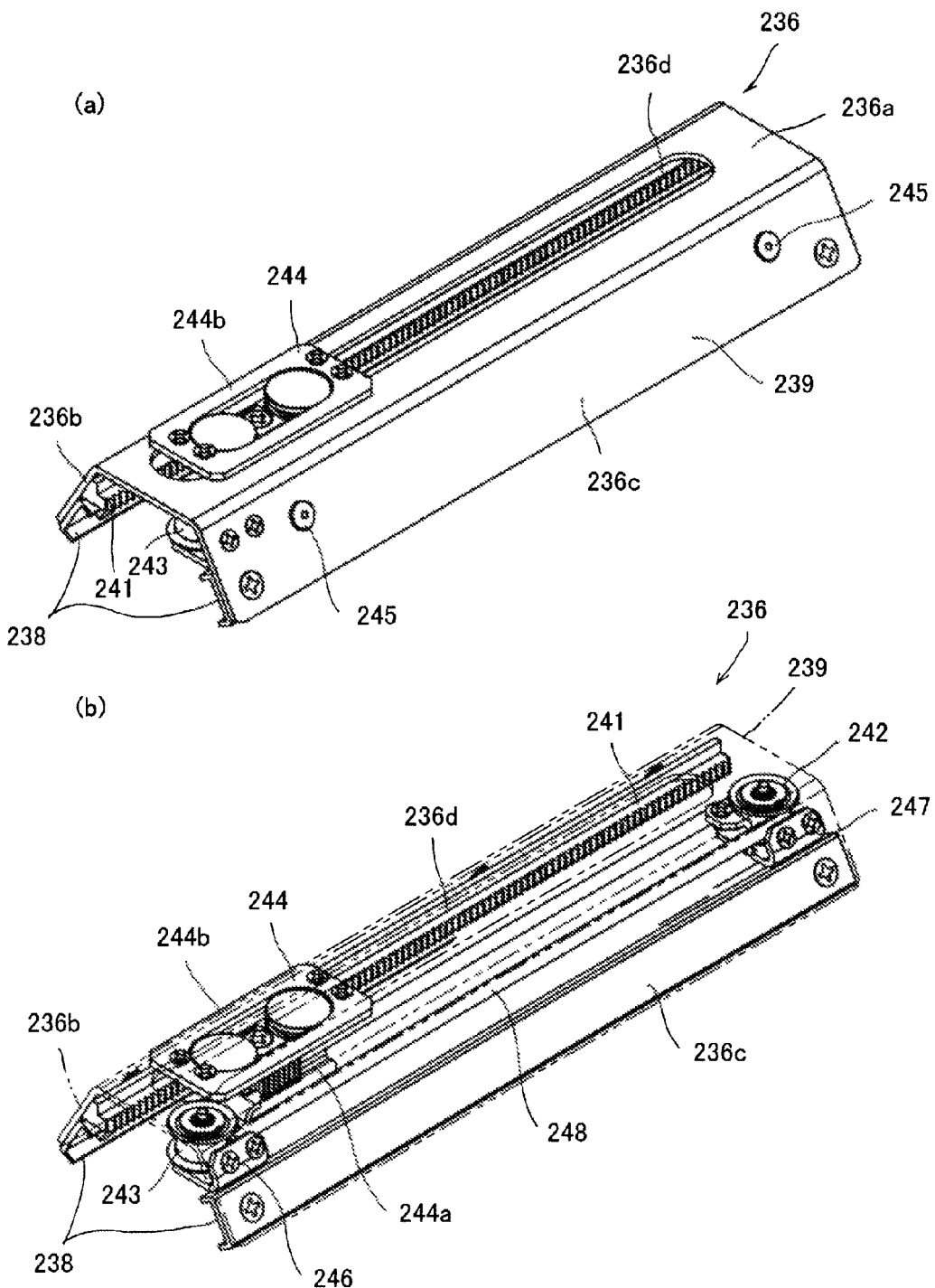
FIG. 30(a) is an upper perspective view of a first sliding body of the medicine delivering unit of the transfer device shown in FIG. 25.
FIG. 30(b) is a lower perspective view of the first sliding body.

As shown in FIG. 30, the first sliding body 236 is configured such that a guide rail 238, a driven rack gear 241, pulleys 242, 243, a slide member 244 and a guide roller 245 are assembled to a main body 239. Specifically, the main body 239 has a top portion 236a and side portions 236b, 236c. The top portion 236a has an elongated and flat plate shape and the side portions 236b, 236c are disposed at both sides of the top portion 236a in a widthwise direction thereof. The side portions 236b, 236c are provided throughout an entire length of the top portion 236a and are linearly beveled outwardly in the widthwise direction as being away from the top portion 235a. That is, the side portions 236b, 236c are opposite each other and are disposed in an inverted V shape in the back side of the top portion 236a. The top portion 236 is provided with an opening 236d extending in a lengthwise direction of the main body 239.

Figure 28:
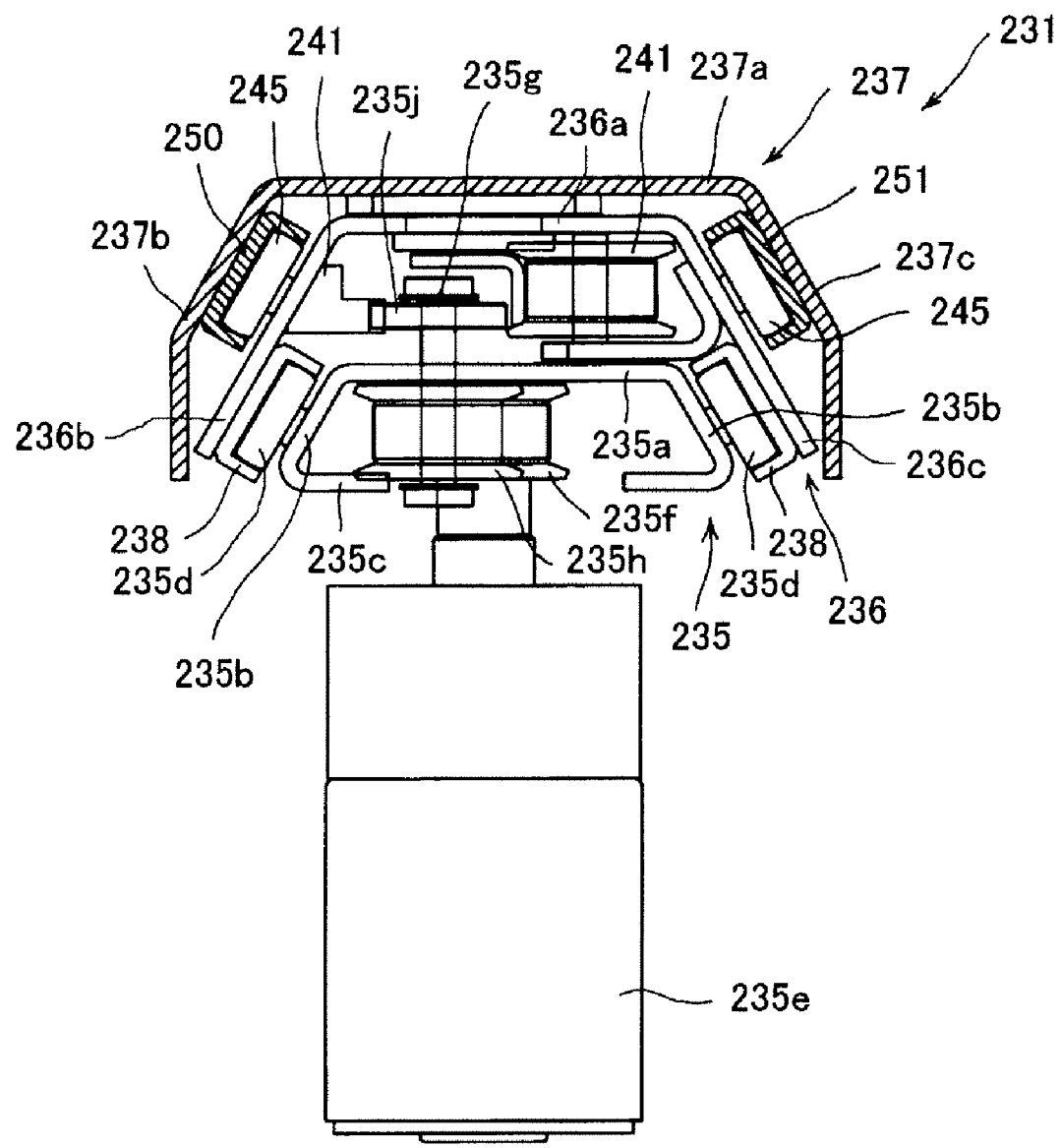
FIG. 28 is a section view of the medicine delivering unit of the transfer device shown in FIG. 25.

Guide rails 238, 238 are provided in an inside of the side portions 236b, 236c throughout an entire length of the side portion 236b, 236c. As shown in FIG. 28, guide rollers 235d, 235d provided in the side portions 235b, 235b of the slide base 235 are fitted to the guide rails 238, 238. Thus, the guide rollers 235d, 235d are linearly moved as guided by the guide rails 238, 238. Further, as shown in FIGS. 28 and 30, a driven rack gear 241 is provided throughout an entire length of the side portion 236b in the inside of the side portion 236b above the guide rail 238 (near the top portion 236a). As shown in FIGS. 26 and 28, when the medic delivering unit 231 is assembled, the driven rack gear 241 is meshed with the drive gear 235j provided in the top portion 235a of the slide base 235.

Meanwhile, in the first sliding body 236, pulley brackets 246, 247 are provided in the inside of the side portion 236c above the guide rail 238 (near the top portion 236a). Pulleys 242, 243 are provided in the pulley brackets. The pulley bracket 246 is positioned near one end of the first sliding body 236 (hereinafter, this may be referred to as a leading end, if necessary), while the pulley bracket 247 is positioned near the other end thereof (hereinafter, this may be referred to as a base end, if necessary). The pulleys 242, 243 are rotatably supported about shafts approximately vertically extending on the top portion 236a and fixed to the pulley brackets 246, 247. Further, a timing belt 248 is wound between the pulleys 242, 243. As shown in FIG. 26, the timing belt 248 is fitted and fixed to the belt fixing member 235k provided on the slide base 235.

The slide member 244 has a belt fixing portion 244a and a sliding body fixing portion 244b. The slide member 244 is fixed to the timing belt 248 by fitting the timing belt 248 to the belt fixing portion 244a. Further, the sliding body fixing portion 244b is exposed on the opening 236d of the first sliding body 236 toward the top surface of the top portion 236a (upwardly) and is linearly slidable along the opening 236d in a lengthwise direction of the first sliding body 236. The sliding body fixing portion 244b is fixed to a top portion 237a of the second sliding body 237, which will be described in detail, by screws and the like in one embodiment although other ways of affixing are possible.

The second sliding body 237 is provided to deliver medicines. As shown FIGS. 26 and 27, the second sliding body is disposed on and covers the first sliding body 236. The slide member 244 of the first sliding body 236 is fixed to one end of the second sliding body 237 in a lengthwise direction thereof (hereinafter, this may be referred to as a base end, if necessary) by screws and the like. Thus, the second sliding body 237 is connected to the first sliding body 236 via the slide member 244.

Figure 31:
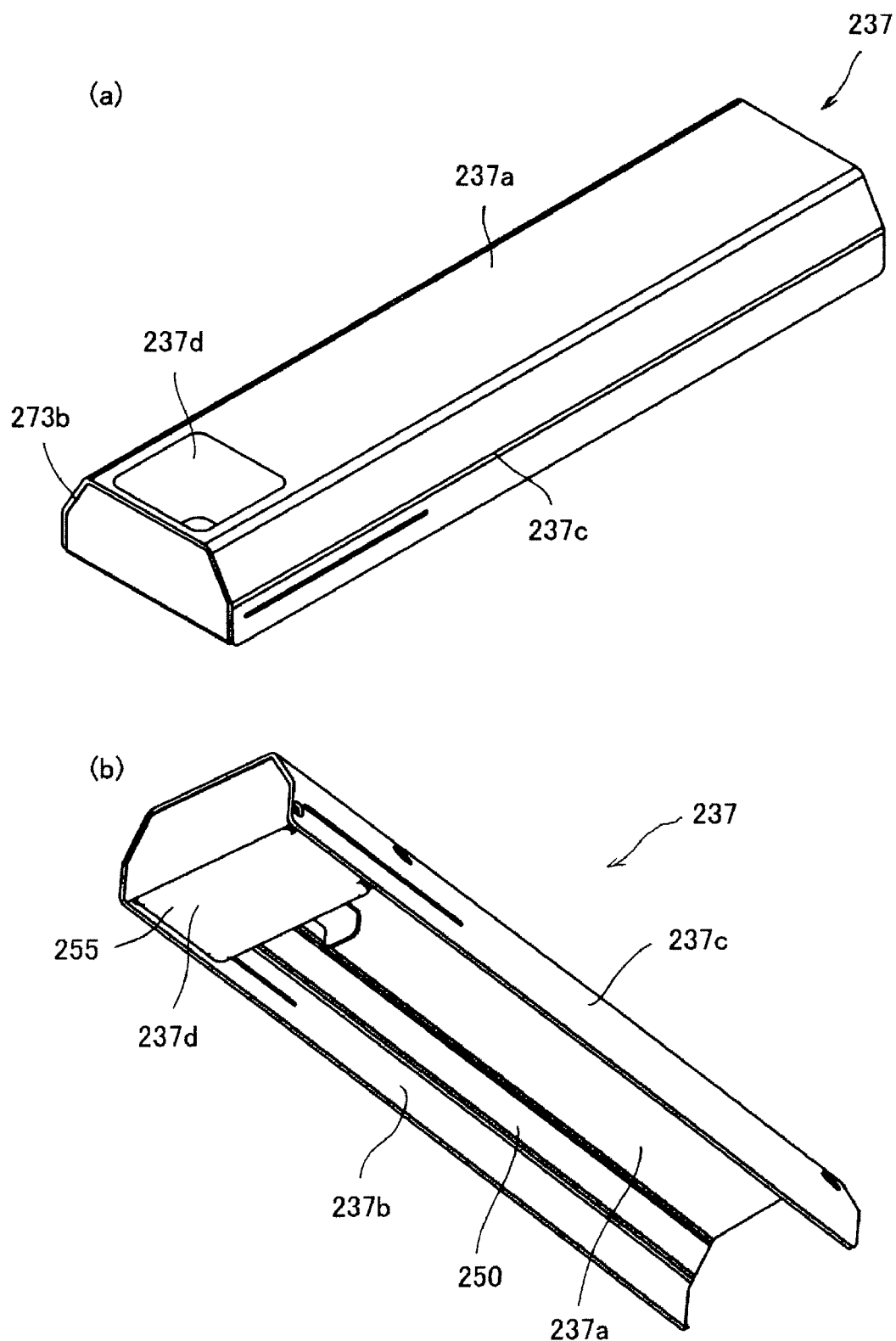
FIG. 31(a) is an upper perspective view of a second sliding body of the medicine delivering unit of the transfer device shown in FIG. 25.
FIG. 31(b) is a lower perspective view of the second sliding body.

As shown in FIGS. 28 and 31, the second sliding body 237 includes medicine receiving portion 237d in addition to the top portion 237a or side portions 237b, 237c. The top portion 237a is a portion having an elongated flat plate shape and the side portions 237b, 237c are disposed at both sides of the top portion 237a in a widthwise direction. The side portions 237b, 237c are opposite each other. Portions of side portions 237b, 237c between the top portion 236a and middle portion of the side portions 237b, 237c are beveled outwardly in a widthwise direction as being away from the top portion 236a. Guide rails 250, 251 are provided in said portions. The guide rails 250, 251 extend along a lengthwise direction of the second sliding body 237. As shown in FIG. 28, the guide rollers 245, 245 provided in the side portions 236b, 236c of the first sliding body 236 are fitted to the guide rails 250, 251. Thus, the second sliding body 237 can be relatively moved in the lengthwise direction of the first sliding body 236. Further, as described above, the second sliding body 237 is connected to the first sliding body 236 via the slide member 244. Thus, the second sliding body 237 is linearly moved relative to the first sliding body 236 along with sliding movement of the slide member 244.

The medicine receiving portion 237d is provided in one end of the second sliding body 237 in a lengthwise direction thereof (hereinafter, this may be referred to as a leading end, if necessary). The medicine receiving portion 237d has a shape of a measure with its top opened at the top portion 237a. A bottom surface of the medicine receiving portion 237d is blocked by a shutter 255. The shutter 255 is provided so as to be slidable in a lengthwise direction of the second sliding body 237. The medicines, which are received in the medicine receiving portion 237d, can be dispensed downwardly by opening the shutter 255.

Next, operations of the transfer device 210 will be described in detail. The transfer device 210 can turn each of the medicine delivering units 231 about the turning shaft 234 by operating the turn drive motor 225 provided on the support part 220. Further, by operating the drive motor 235e provided in each of the medicine delivering units 231, the transfer device 210 can linearly expand the slide base 235 and the first and second sliding bodies 236, 237 into a fully expanded state (hereinafter, this state is referred to as an expanded state) as shown in FIG. 25 (a), or pull the first and second sliding bodies 236, 237 toward the slide base 235 into an entirely contracted state (hereinafter, this state is referred to as a contracted state) as shown in FIG. 25 (b).

The operations of the medicine delivering unit 231 accompanied by the operation of the drive motor 235e are described in detail. As shown in FIG. 25 (b), if the drive motor 235e operates in the contracted state, the power therefrom is transferred to the drive pulley 235h by the drive belt 235i provided in the back side of the top portion 235a in the slide base 235 and the drive pulley 235h rotates together with the shaft 235g. Thus, the drive gear 235j provided on the surface of the top portion 235a is rotated. When the top portion 235a is viewed downwardly, if the drive gear 235j rotates counterclockwise, then the driven rack gear 241 of the first sliding body 236 meshed with the drive gear 235j is linearly transferred from the base end of the slide base 235 toward the leading end. Thus, the first sliding body 236 with the driven rack gear 241 slides from the base end of the slide base 235 toward the leading end.

In this case, as described above, the timing belt 248 wound between the pulleys 242, 243 in the first sliding body 236 is fixed to the belt fixing member 235k erected on the top portion 235a of the slide base 235. Further, since the slide member 244 is fixed to the timing belt 248, the slide member 244 and the timing belt 248 integrally operate. Further, when the transfer device 210 is in the contracted state, the slide member 244 is positioned near the base end of the first sliding body 236 (i.e. near the pulley 242). Meanwhile, the belt fixing member 235k is positioned near the leading end of the first sliding body 236 (i.e. near the pulley 234). That is, the belt fixing member 235k and the slide member 244 are obliquely (diagonally) opposed to each other with the timing belt 248 therebetween. Thus, if the first sliding body 236 slides from the base end of the slide base 235 toward the leading end, then the pulley 242 approaches the belt fixing member 235k. Meanwhile, the slide member 244 moves toward the pulley 243 (i.e. toward the leading end of the first sliding body 236) along the opening 236d provided in the top portion 236a of the first sliding body 236, while opposed to the belt fixing member 235k with the timing belt 248 therebetween.

If the slide member 244 moves to the leading end of the first sliding body 236, the second sliding body 237 integrally provided with the first sliding body via the slide member 244 also slides to the leading end of the first sliding body 236. Then, as shown in FIG. 26, if the slide member 244 reaches the leading end (the pulley 243) of the first sliding body 236, both the first and the second sliding bodies 236, 237 become in a state where the medicine delivering unit 231 is fully expanded in its lengthwise direction of (i.e. in the expanded state).

Meanwhile, when the first and second sliding bodies 236, 237 return to the slide base 235 from the expanded state shown in FIG. 26 to contract the overall length of the medicine delivering unit 231 (i.e. the contracted state), the medicine delivering unit 231 operates in reverse to the above-described operations. That is, in order to achieve the contracted state, the drive motor 235e operates such that its rotating shaft rotates in an opposite direction to the expanded state. Therefore, the power of the drive motor 235e is transmitted to the drive gear 235j by the timing belt 248, the drive pulley 235h and the shaft 235g. The drive gear 235j rotates in an opposite direction to a rotating direction wherein the medicine delivering unit 231 becomes in the expanded state. That is, when the top portion 235a is viewed downwardly, the drive gear 235j rotates clockwise. Thus, the driven rack gear 241 meshed with the drive gear 235j is linearly moved toward the base end of the slide base 235 and the first sliding body 236 slides from the base end of the slide base 235 toward the leading end.

If the first sliding body 236 slides as described above, the pulley 243 positioned at the leading end of the first sliding body 236 approaches the belt fixing member 235k. Also, the slide member 244, which is obliquely opposed to the belt fixing member 235k with the timing belt 248 therebetween, moves toward the pulley 242 positioned at the base end of the first sliding body 236 along the opening 236d provided in the top portion 236a of the first sliding body 236. Thus, the second sliding body 237 connected to the first sliding body 236 via the slide member 244 also slides toward the base end of the slide base 235 along with the first sliding body 236. Then, when the slide member 244 reaches the base end (the pulley 242) of the first sliding body 236, both the first and second sliding bodies 236, 237 become in the contracted state where the medicine delivering unit 231 is contracted in its lengthwise direction.

The transfer device 210 is disposed at the boundary between the main unit 2 and the sub unit 3 like the transfer device 5 employed in the foregoing embodiment. More specifically, as shown in FIG. 25, the transfer device 210 is positioned on the bottom surface of the housing constituting the sub unit 3 by screw-fixing the flange 223 thereto and adjacent to the communicating opening 4b provided in the wall surface 4a forming a boundary between the sub unit 3 and the main unit 2. Thus, in the transfer device 210, if the medicine delivering unit 231 is expanded when the lengthwise direction of the medicine delivering unit 231 is orthogonal to the wall surface 4a as shown in FIG. 25, the second sliding body 237 in one of the medicine delivering units 231 (hereinafter, this may be referred to as a delivering unit 231a) protrudes beyond the wall surface 4a toward the main unit 2. Further, the second-sliding body 237 of the other of the medicine delivering units 231 (hereinafter, this may be referred to as a delivering unit 231b) protrudes in the sub unit 3 in a direction opposite the above-described direction of the medicine delivering unit 231a.

If the second sliding body 237 of the medicine delivering unit 231a protrudes toward the main unit 2, the sub collecting hopper 87 connected to the medicine preparing part 80 of the main unit 2 is positioned under the medicine receiving portion 237d provided in the second sliding body 237. Thus, if the shutter 255 of the medicine delivering unit 231 positioned in the main unit 2 is opened in the state shown in FIG. 25 (a), the medicine received in the medicine receiving portion 237d can be dispensed to the medicine preparing part 80 of the main unit 2. On the other hand, if the second sliding body 237 of the medicine delivering unit 231b protrudes in the sub unit 3, the medicine receiving portion 237d is positioned just below the sub hopper 135 provided in the sub unit 3. Thus, if the medicines are dispensed from the sub medicine standby part 130 in such a state, then the medicines are inputted to the medicine receiving portion 237d.

Next, operations of a medicine dispensing system 1 employing the transfer device 210 will be described focusing on a medicine transferring sequence by the transfer device 210. As described above in the foregoing embodiment, the medicine dispensing system 1 dispenses the medicines dispensed from the main storage part 20 or the manual distributing unit 23 according to the prescription to each of the sections 81a of the section forming body 81 provided in the medicine preparing part 80 one pack at a time.

When the medicines to be prescribed are in sub unit 3, the medicines are dispensed from each of the cassettes 32 of the sub storage part 120 one pack at a time. The medicines dispensed from the sub storage part 120 are gathered in the sub medicine standby part 130. Meanwhile, the medicine delivering units 231a, 231b of the transfer device 210 go into an expanded state. Thus, the medicine receiving portion 237d provided in the second sliding body 237 of one of the medicine delivering units 231a, 231b (the medicine delivering unit 231b in FIG. 25 (a)) is positioned under the sub hopper 135. In this state, if the medicines are dispensed from sub medicine standby part 130, the medicines for one pack dispensed from the sub storage part 120 are received in the medicine receiving portion 237d.

If the medicines are inputted into the medicine receiving portion 237d, the medicine delivering unit 231a, 231b goes into a contracted state as shown in FIG. 25 (b). Then, the turn drive gear 226 provided in the base part 222 of the transfer device 210 operates to turn the medicine delivering units 231a, 231b about the turning shaft 234 by 180 degrees. Then, the medicine delivering units 231a, 231b goes into the expanded state. Thus, the medicine delivering unit 231b receiving the medicines from the sub unit 3 protrudes into the main unit 2 and thus the medicine receiving portion 237d is positioned above the sub collecting hoper 87 of the main unit 2. Further, the second sliding body 237 of the other medicine delivering unit 231a protrudes below the sub hopper 135 and is allowed to receive the next medicines for one pack.

If the medicine delivering units 231b, 231a are in an expanded state in the main unit and sub unit 3 respectively as described above, then the shutter 255 provided in the medicine receiving portion 237d of the medicine delivering unit 231b is opened and the medicines received from the sub unit 3 are dispensed to each of the sections 81a of the section forming body 81 provided in the medicine preparing part 80. Meanwhile, medicines for one pack are inputted from the sub medicine standby part 130 to the medicine receiving portion 237d of the medicine delivering unit 231a.

In case the medicine dispensing system 1 employs transfer device 210, the medicine dispensed in the sub unit 3 can be transferred to the main unit 2 by repeatedly expanding the medicine delivering units 231a, 231b sequentially and turning them in the expanded state. Thus, when a transfer device 210 is employed, the medicines dispensed in the sub unit 3 can be transferred to the main unit 2 and can be packed at the medicine packing part 21 together with the medicines dispensed in the main unit 2, similarly to the case of employing the transfer device 5.

As described above, since the transfer device 210 can turn the medicine delivering unit 231 in the contracted state, a space necessary for turning the medicine delivering unit 231 can be minimized. Further, since the transfer device 210 can expand the medicine delivering unit 231 into the expanded state, the medicines can be received or dispensed at a position apart from the transfer device 210. Thus, when the transfer device 210 is employed, the space inside the medicine dispensing system 1 can be effectively used and the medicine dispensing system 1 can be compactly configured.

Figure 32:
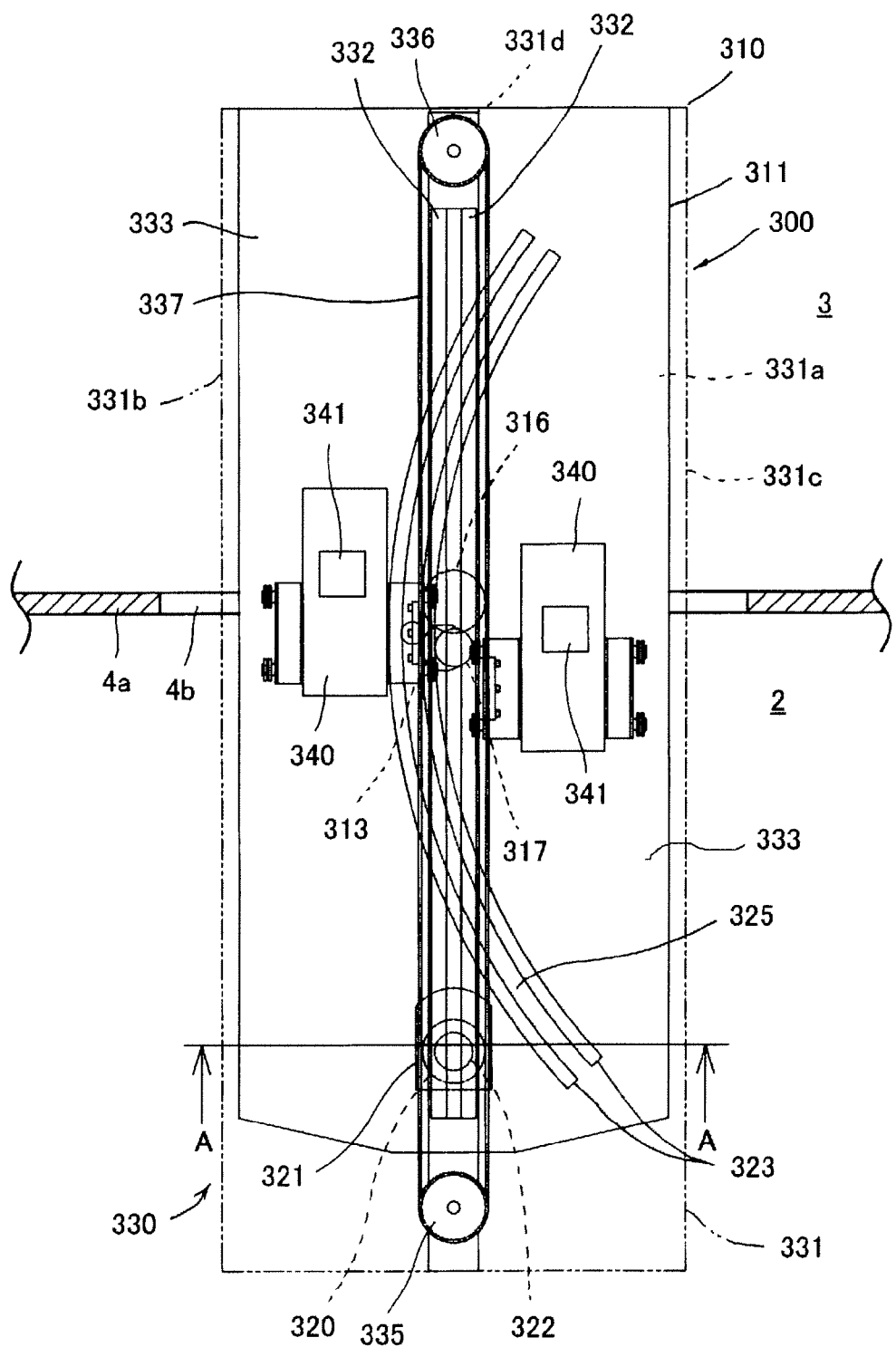
FIG. 32 is a front view showing a further variation of a transfer device.
Figure 33:
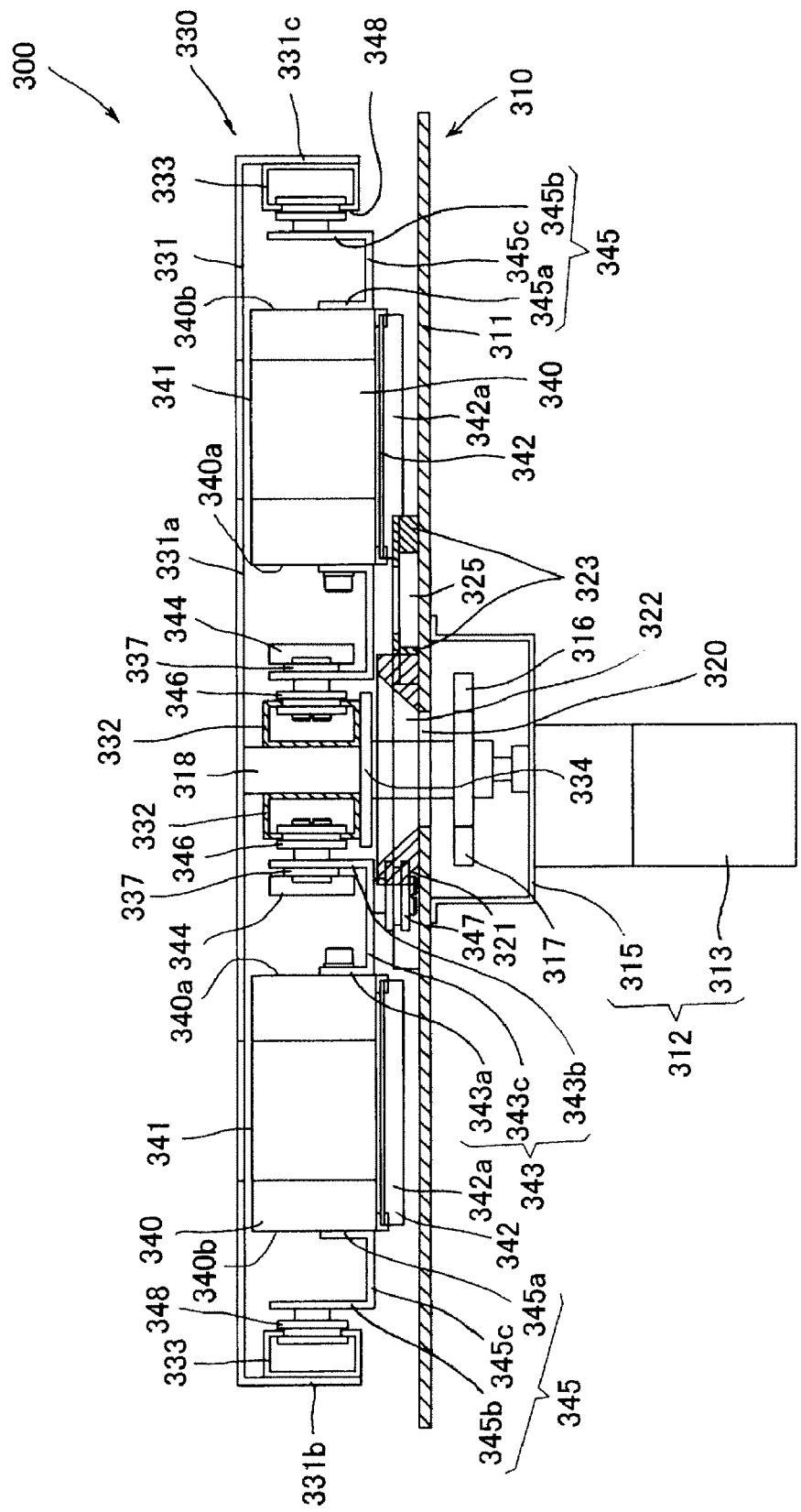
FIG. 33 is a section view taken along the ling A-A in FIG. 32.

The medicine dispensing system 1 may employ the above-described transfer device 5, 210. Further, the medicine dispensing system may employ a transfer device 300 shown in FIGS. 32 to 35. The transfer device 300 will be now described in detail with reference to the drawings. As shown in FIG. 33, the transfer device 300 has a base part 310 and a turn part 330 (conveyance part). The base part 310 has a base plate 311 having a flat plate shape and a drive unit 312. The drive unit 312 is provided at a back side of the base plate 311. The drive unit 312 has a drive motor 313 and a gear box 315 and serves as a direction adjusting means configured to adjust the direction of the turn part 330.

The gear box 315, which is positioned at an approximate central portion of the base plate 311, has a turn drive gear 316 and a turn driven gear 317 therein. The turn drive gear 316 of the gear box 315 is fixed to a rotating shaft of the drive motor 313. Further, the turn driven gear 316 is meshed with the turn drive gear 316. The turn driven gear 317 is fixed to a turning shaft 318 fixed to the turn part 330. Further, the turning shaft 318 is erected on an approximately central portion of the base part 311 while being rotatably supported thereon. Thus, as the turn motor 313 operates to rotate, the turn drive gear 316, the turn driven gear 317, the turning shaft 318 and the turn part 330 rotate together.

The base plate 311 has a dispensing opening 320 at its approximate center portion in its widthwise direction and at its one end in its lengthwise direction. Further, a contact member 321 is provided on a surface of the base plate 311 in a position corresponding to the dispensing opening 320. The contact member 321 has an opening 322 communicating with the dispensing opening 320. Further, as shown in FIG. 32, a pair of guide rails 323, 323 are fixed on the surface of the base plate 311 with a predetermined gap therebetween. The guide rails 323, 323 are curved members having a circular arc shape with a predetermined curvature. Thus, a groove 325 is formed between the guide rails 323, 323. The guide rails 323, 323 are disposed convexly toward one side in the widthwise direction of the base plate 311 (i.e. toward the left side in the example illustrated in FIG. 32).

Meanwhile, as shown in FIG. 32, the turn part 330 has a cover 331 which has a rectangular shape in a plan view. Further, as shown in FIG. 33, component members of the turn part 330 including medicine containers 340, 340 (medicine delivery container) are accommodated inside the cover 331. More specifically, the cover 331 is opened at its bottom side and is disposed above the base part 310. A receiving opening 331d is provided in a top surface 331a of the cover at one end of the cover in a lengthwise direction thereof. The cover 331 is disposed above the base plate 311 in such a manner that one end of the cover with the receiving opening 331d is opposite the dispensing opening 320 provided in the base plate 111 in the lengthwise direction of the top surface 331a and the top surface 331a is approximately parallel to the base plate 311.

The turning shaft 318 is integrally provided in the cover 331 at the approximately central portion of the top surface 331a. The turning shaft 318 is erected from the top surface 331a of the cover 331 and protrudes downward. The turning shaft 318 passes through an approximate center portion of the base plate 311 and extends into the gear box 315 provided in the back side of the base plate 311. The turning shaft is rotatably supported relative to the base plate 311. The turn driven gear 317 is coupled to the turning shaft 318 in the gear box 315. Thus, as the drive motor 313 operates to rotate the turn drive gear 316, the power therefrom rotates the turn driven gear 317 and the turning shaft 318 together and thus the turn part 330 including the cover 331 turns about the turning shaft 318.

As shown in FIG. 33, guide rails 332, 332 are provided in a middle portion of the turning shaft 318. Further, as shown in FIG. 32, the guide rails 332, 332 are provided to linearly extend in a lengthwise direction of the cover 331. The turning shaft 318 is fitted between the guide rails 332, 332 and the guide rails 332, 332 are fixed as supported by fixed supporting member 334 fixed to the middle portion of the turning shaft 318. Accordingly, the guide rails 332, 332 become integral with the turning shaft 318 and can rotate about the turning shaft 318.

Further, guide rails 333, 333 are attached to an inside of the cover 331 to linearly extend at long sides 331b, 331c formed along a lengthwise direction of the cover 331. The guide rails 333, 333 are opposite the guide rails 332, 332. The guide rails 333, 333 are combined with the opposite guide rails 322, 322 respectively to serve as a guide member for guiding medicine containers 340, 340, that will be described in detail below.

As shown in FIG. 32, timing pulleys 335, 336 are coupled to both ends of the cover 331 in a lengthwise direction thereof and at an approximate middle portion of the cover 331 in a widthwise direction thereof. The timing pulleys 335, 336 are provided adjacent to both ends of the guide rail 332 in the lengthwise direction thereof. Each of the timing pulleys 335, 336 can rotate freely about respective shafts, which are approximately vertical to the top surface 331a. A timing belt 337 is wound between the timing pulleys 335, 336.

The medicine container 340 is a box-shaped member with an opening at its top surface. As shown in FIG. 33, a shutter 342 is provided at a bottom surface of the medicine container 340. The medicines accommodated in the medicine container 340 can be dispensed downward when the shutter 342 is opened. The shutter 342 can be opened when a contact portion 342a is pressed and slid in a lengthwise direction of the medicine container 340. The shutter 342 is biased in a direction of closing the bottom of the medicine container 340 at normal times to thereby block the bottom of the medicine container. In the cover 331, the medicine container 340 is positioned between a pair of the guide rails 332, 333, which are provided at one side or the other side in a widthwise direction of the cover 331 relative to the turning shaft 318.

More specifically, the transfer device 300 has two medicine containers 340. One of the medicine containers 340 is provided at one side in a widthwise direction of the cover 331 relative to the turning shaft 318, while the other medicine container is provided at the other side in a widthwise direction of the cover 331 relative to the turning shaft. Side surfaces 340a, 340b of the medicine container 340 are located opposite guide rails 332, 333 and disposed between the guide rails 332, 333. Roller attaching members 343, 345 are attached to the side surfaces 340a, 340b. The roller attaching member 343 has: a fixing portion 343a fixed to the side surface 340a; a vertical portion 343b opposite thereto; and a horizontal portion 343c disposed between the fixing portion 343a and the vertical portion 343b and approximately parallel to the base plate 311.

A guide roller 346 is rotatably provided on the vertical portion 343b. The guide roller 346 is fitted to the guide rail 332 arranged along the turning shaft 318. Further, the sandwiching member 344 is mounted on the vertical portion 343b and the timing belt 337 is fitted between the sandwiching member 344 and the vertical portion 343b. This allows the medicine container 340 to be connected to the timing belt 338.

In this case, the transfer device 300 includes two medicine containers 340, 340 as described above. The medicine container 340 of said two medicine containers (a left medicine container 340 in an example illustrated in FIGS. 32 and 33) (hereinafter, this may be referred to as a drive side medicine container 340) has a guide roller 347 on the horizontal part 343c. The guide roller 347 is rotatably provided at a shaft approximately vertically fixed to the horizontal portion 343c and protruding downward therefrom. The guide roller 347 is fitted to the groove 325 formed between the guide rails 323, 323 provided on the surface of the base plate 311.

Meanwhile, a roller attaching member 345 is attached to the side surface 340b of the medicine container 340. The roller attaching member 345 has: a fixing portion 345a fixed to the side surface 340b; a vertical portion 345b opposed thereto; and a horizontal portion 345c connecting the fixing portion 345a and the vertical portion 345b. The vertical portion 345b is also opposite the guide rail 333 attached to the long side 331b, 331c of the cover 331. A guide roller 348 is rotatably attached to the vertical portion 345b and is fitted to the guide rail 333.

The transfer device 300 is configured as described above and is positioned as inserted to the communication opening 4b of the wall surface 4a between the main unit 2 and the sub unit 3. Specifically, the transfer device 300 is horizontally disposed with the base part 310 facing downward and the turn part 330 facing upward. Further, the transfer device 300 is disposed such that the receiving opening 331d provided in the cover 331 is located at the sub unit 3 and the dispensing opening 320 provided in the base plate 311 is located at the main unit 2.

Next, operation of the transfer device 300 will be described. The transfer device 300 can turn the turn part 330 about the turning shaft 318 while moving two medicine containers 340 provided in the turn part 330 along the guide rails 332, 333 by the power produced from the drive motor 313 provided in the base part 310. More specifically, if the drive motor 313 operates, the turn drive gear 316 coupled to the rotating shaft of the drive motor 313 and the turn driven gear 317 meshed with the turn drive gear 316 rotate. Thus, the turning shaft 318 with the turn driven gear 317 rotates and thus the entire turn part 330 rotate about the turning shaft 318.

In this case, as described above, the guide roller 347, which is rotatable about the shaft protruding downward, is provided in one of the two medicine containers 340, 340 (the drive side medicine container 340). The guide roller 347 is fitted to the groove 325 formed between the guide rails 323, 323 in the base part 310. Further, as shown in FIG. 32, the groove 325 is curved convexly toward one side in the width direction like the guide rails 323, 323. Thus, movements of the drive side medicine container 340 are restricted by the groove 325. Further, other component members for constituting the turn part 330 are assembled to the cover 331 like the drive side medicine container 340 and those are integrally rotatble about the turning shaft 318. Thus, when the turn part 330 rotates clockwise by the operation of the drive motor 313 in a state shown in FIG. 32, the entire turn part 330 is turned about the turning shaft 318 while guided by the groove 325 and the guide roller 347 and the drive side medicine container 340 advance toward the one end of the groove 325 (upward in FIG. 32). Also, as shown in FIG. 34, when the turn part 330 is turned at a predetermined angle about the turning shaft 318, the drive side medicine container 340 reach the vicinity of the timing pulley 336 disposed at the one end of the groove 325 (upper side in FIG. 34).

Further, as described above, the drive side medicine container 340 and the other medicine container 340 without the guide roller 347 (hereinafter, this may be referred to as a driven side medicine container 340) are fixed to the timing belt 337 respectively by the sandwiching member 344 attached to the vertical portion 343b of the roller attaching member 343. Thus, when the drive side medicine container 340 advance toward one end of the groove 325 along with the turning of the turn part 330, the driven side medicine container 340 advances toward the other end of the groove 325, that is, toward the timing pulley 335.

Figure 34:
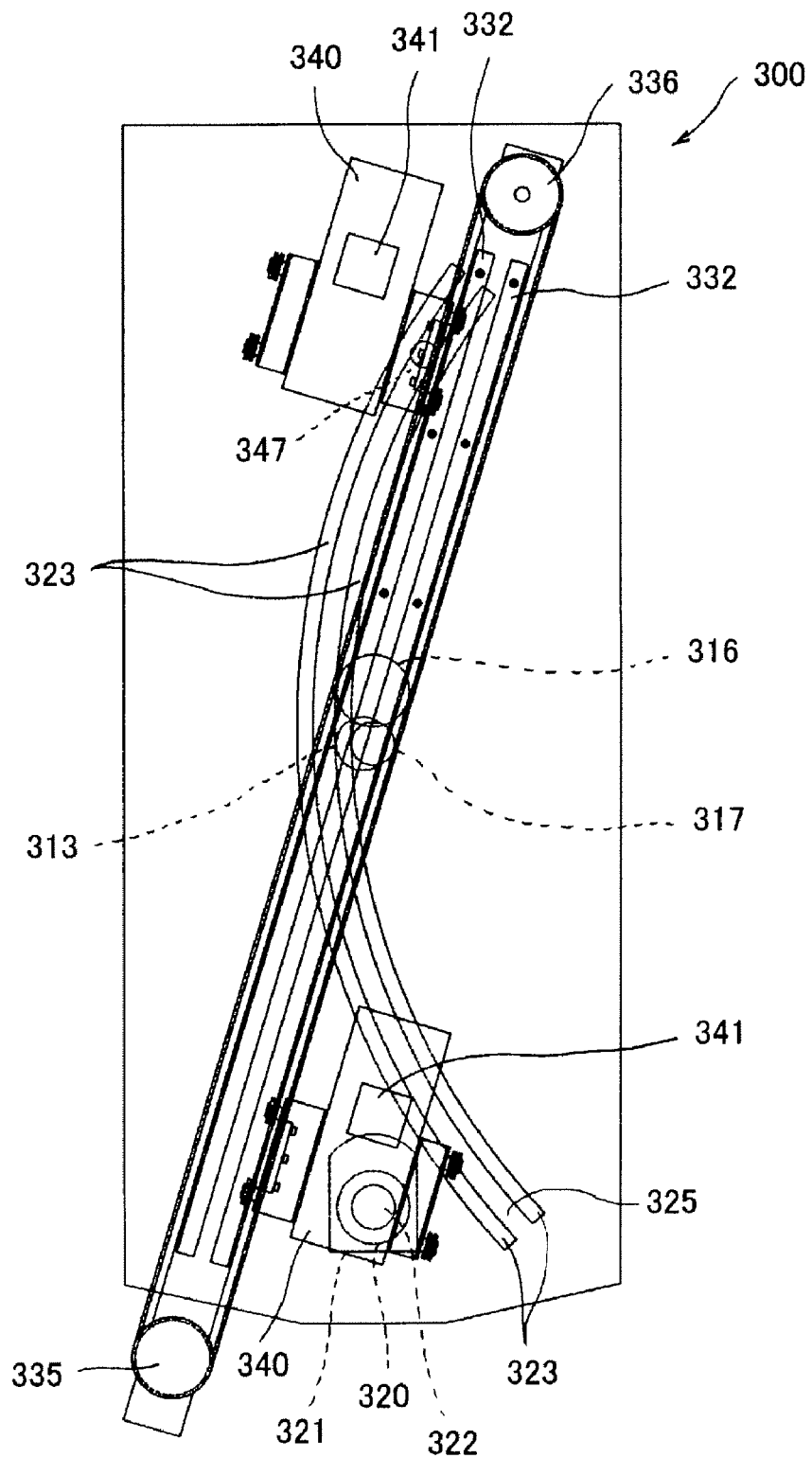
FIG. 34 is a front view showing one motion of the transfer device shown in FIG. 32.

Then, when the driven side medicine container 340 reaches the dispensing opening 320 provided in the base plate 311 as shown in FIG. 34, the contact portion 342a of the shutter 342 disposed at the bottom surface of the driven side medicine container 340 is brought into contact with the contact member 321 attached to the surface of the base plate 311. Thus, the shutter 342 is pushed and opened and thus the medicines therein are dispensed downward, that is, toward the sub collecting hopper 87 in the main unit 2. Meanwhile, in the state shown in FIG. 34, the drive side medicine container 340 reaches a position corresponding to the receiving opening 331d provided in the top surface 331a of the cover 331. Thus, in the state shown in FIG. 34, the medicine dispensed in the sub unit 3 can be inputted to the drive side medicine container 340 through the sub hopper 135.

Figure 35:
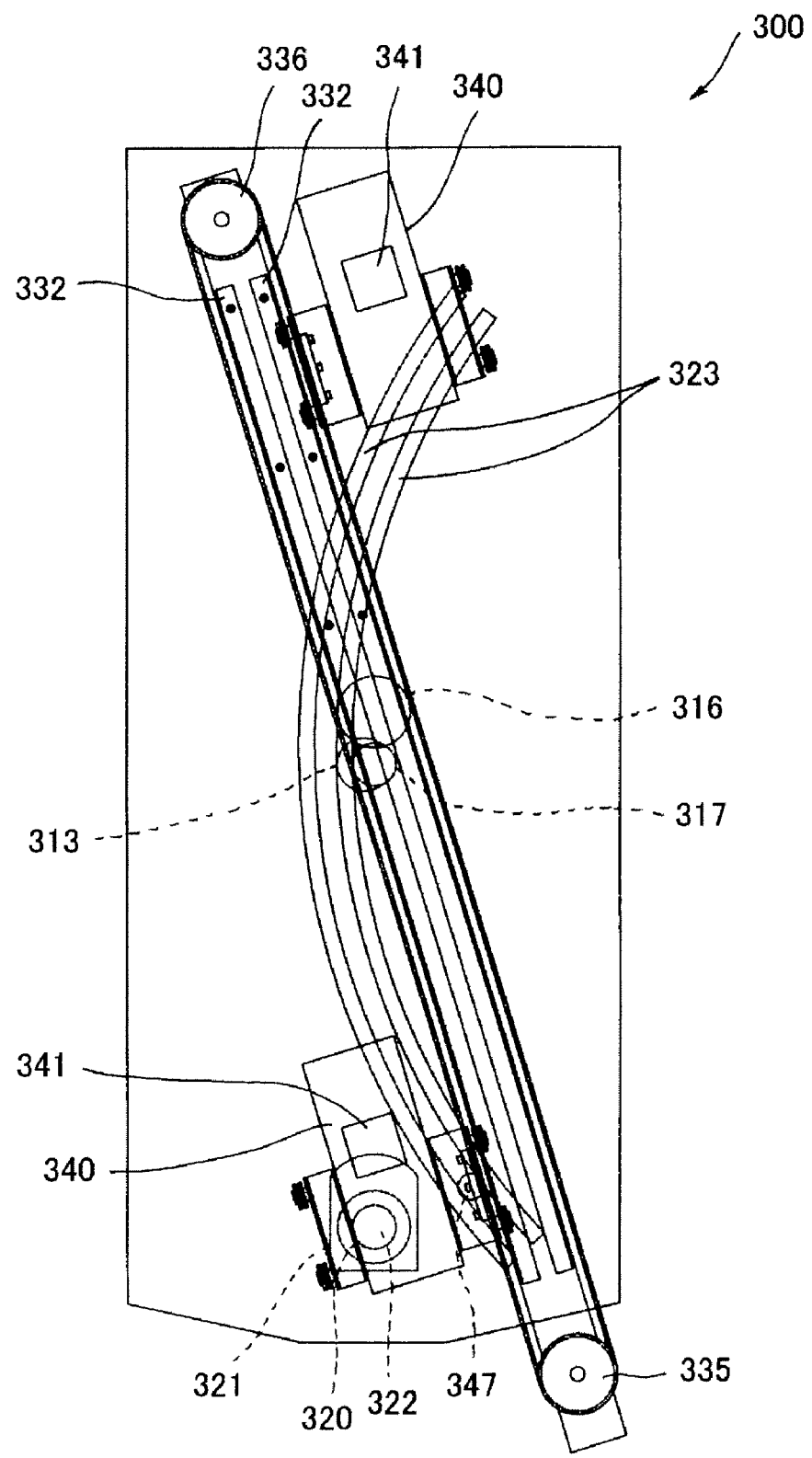
FIG. 35 is a front view showing the other motion of the transfer device shown in FIG. 32.

Meanwhile, in the states shown in FIGS. 32 and 34, if the drive motor 313 provided in the base part 310 operates so as to rotate the rotating shaft in a direction opposite to the above, the turn part 330 rotates counterclockwise about the turning shaft 318 (when viewed downwardly). Accordingly, the drive side medicine container 340 and the guide roller 347 attached thereto advance toward the dispensing opening 320 (downward in the state shown in FIGS. 32 and 34) while guided by the groove 325. Then, as shown in FIG. 35, if the turn part 330 rotates counterclockwise about the turning shaft 318 at a predetermined angle, the drive side medicine container 340 reaches a position corresponding to the dispensing opening 320. Thus, the shutter 342 disposed at an inside portion of the drive side medicine container 340 is opened and the medicines inputted thereto are dispensed to the sub collecting hopper 87 in the main unit 2 disposed below the shutter.

Meanwhile, the driven side medicine container 340 reaches the position corresponding to the receiving opening 331d concomitantly with the operation of the drive side medicine container 340. Thus, the medicines dispensed in the sub unit 3 can be inputted to the driven side medicine container 340.

The above-described transfer device 300 is configured to transfer the medicines between the main unit 2 and the sub unit 3 by turning the entire turn part 330 about the turning shaft 318 and by reciprocating each of the medicine containers 340, 340 in a lengthwise direction of the turn part 330 by means of power produced by the turning movement. Thus, when employing the transfer device 300, it is possible to provide a medicine dispensing system 1 that can transfer the medicines dispensed in the sub unit 3 to the main unit 3 to pack and dispense the same together with the medicines dispensed in the main unit 3, similarly to the case of employing the transfer device 5, 10.

The transfer device 300 obtains power for the turning movement of the turn part 330 and the reciprocating movement of the medicine containers 340 from the drive motor 313 provided in the base part 310. However, the present invention should not be limited to such configuration. For example, a power source for turning the turn part 330 and a power source for reciprocating the medicine containers 340 may be separately provided.

More specifically, the transfer device 300 may be configured such that the guide roller 347 provided in the drive side medicine container 340 and the guide rail 323 attached to the base plate 311 are omitted and at least one of the timing pulleys 335, 336 is rotated by a power source different from that of the drive motor 313. According to such configuration, the turn part 330 is turned by the drive motor 313, and the timing belt 337 wound between the timing pulleys 335, 336 is operated by the separately-provided power source, thereby reciprocating the medicine containers 340 between the dispensing opening 320 and receiving opening 331d.

Figure 36:
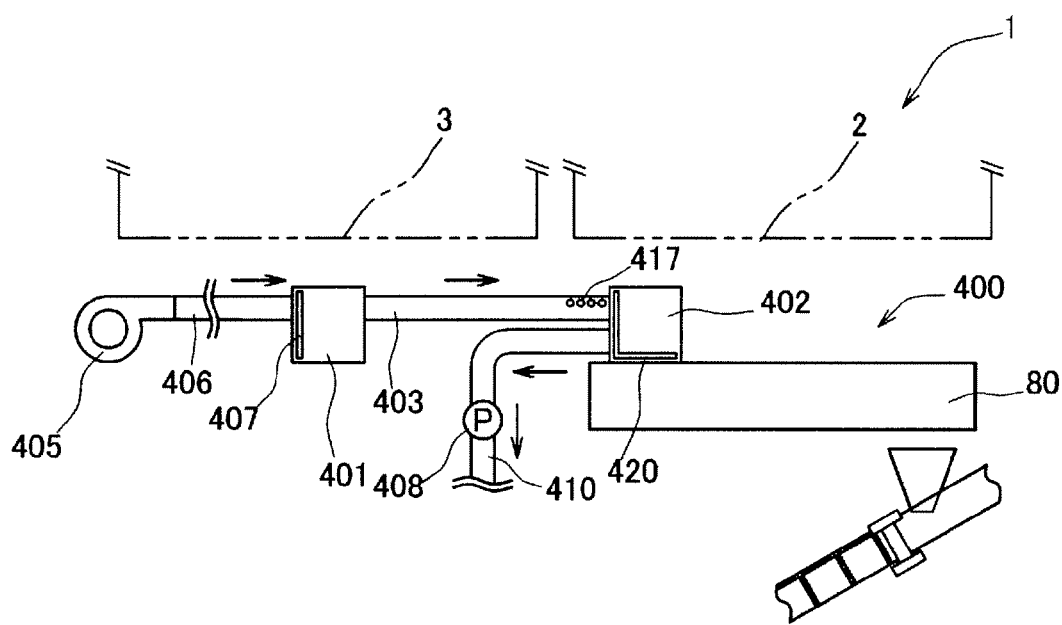
FIG. 36 is a front view schematically showing major parts of the internal structure of a medicine dispensing system including a transfer device according to another variation.

The medicine dispensing system 1 is not limited to employing the above-described transfer device 5, 210, 300 and may employ, for example, a transfer device 400 shown in FIG. 36. The transfer device 400 is configured similar to the above-described transfer device 5 in that the medicine dispensed in the sub unit 3 are transferred to the main unit 2 by means of an airflow. However, a device configuration and medicine transferring processes of the transfer device 400 are different from those of the transfer device 5. Specifically, the transfer device 400 has a medicine receiving part 401 for receiving the medicine dispensed in the sub unit 3, and a medicine dispensing part 402 for receiving and dispensing the medicines transferred from the sub unit 3. The medicine receiving part 401 and the medicine dispensing part 402 are a hollow member having a shape of a measure capable of storing medicines. Further, the transfer device 400 has a forward pipe line 403 configured to connect the medicine receiving part 401 and the medicine dispensing part 402.

The blower 405 is connected to the medicine receiving part 401 through a pipe 406. Further, a blower shutter 407 is provided at a connection portion between the medicine receiving part 401 and the pipe 406. Thus, when the blower 406 operates and the blower shutter 407 is opened, an airflow can be produced through the pipe 406 to the medicine receiving part 401.

A pump 408 is connected to the medicine dispensing part 402 through an exhaust pipe line 410. The transfer device 400 can introduce air into the medicine receiving part 401 through the pipe 406 and produce airflow flowing through the forward pipe line 403 from the medicine storing part 40 toward the medicine dispensing part 402 by operation of blower 405.

Further, the transfer device 400 can produce airflow flowing through the exhaust pipe line 410 from inside the medicine dispensing part 402 toward an outside portion thereof.

Figure 37:
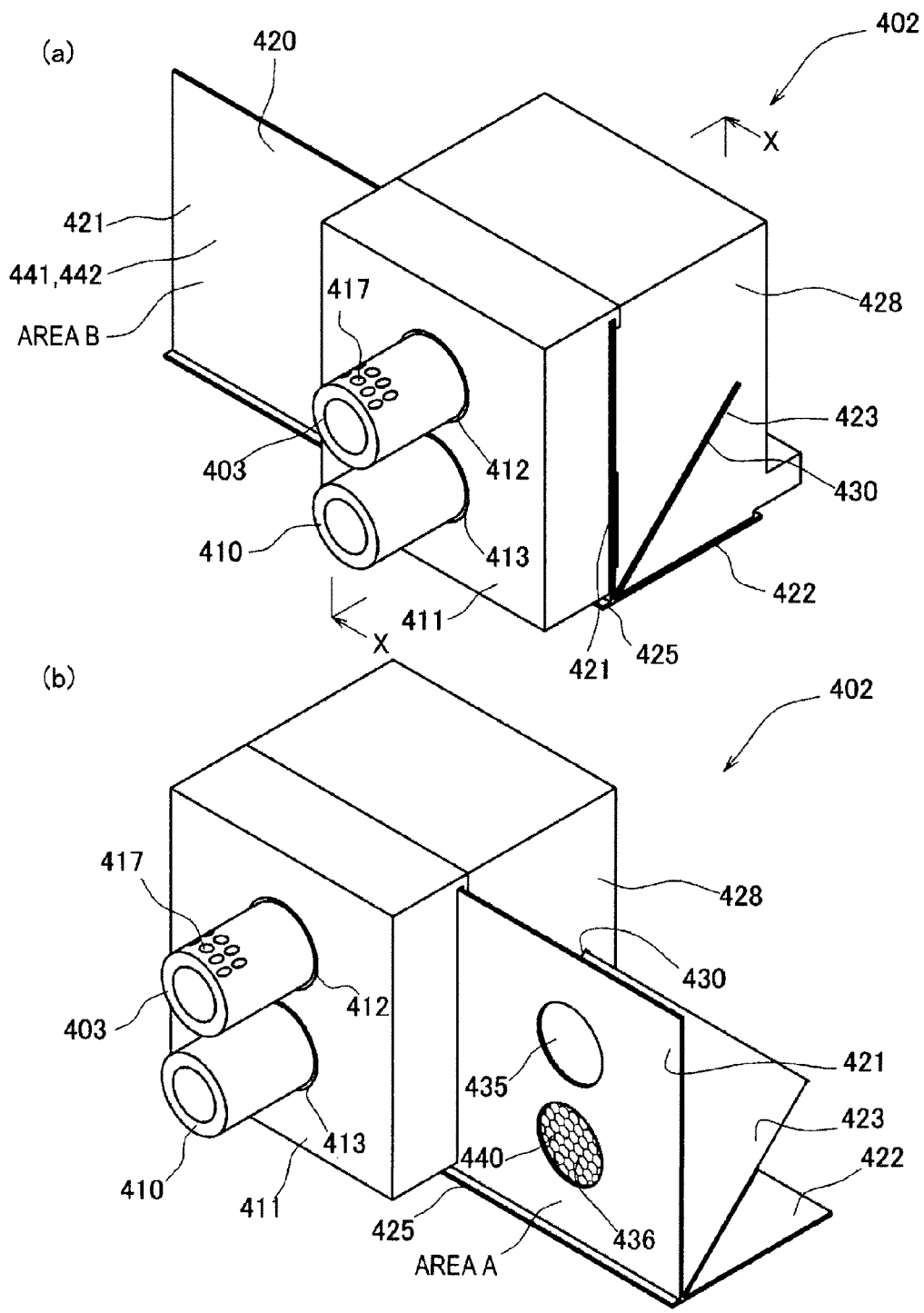
FIG. 37 is a perspective view showing the features of a medicine dispensing part employed in the transfer device shown in FIG. 36.
Figure 38:
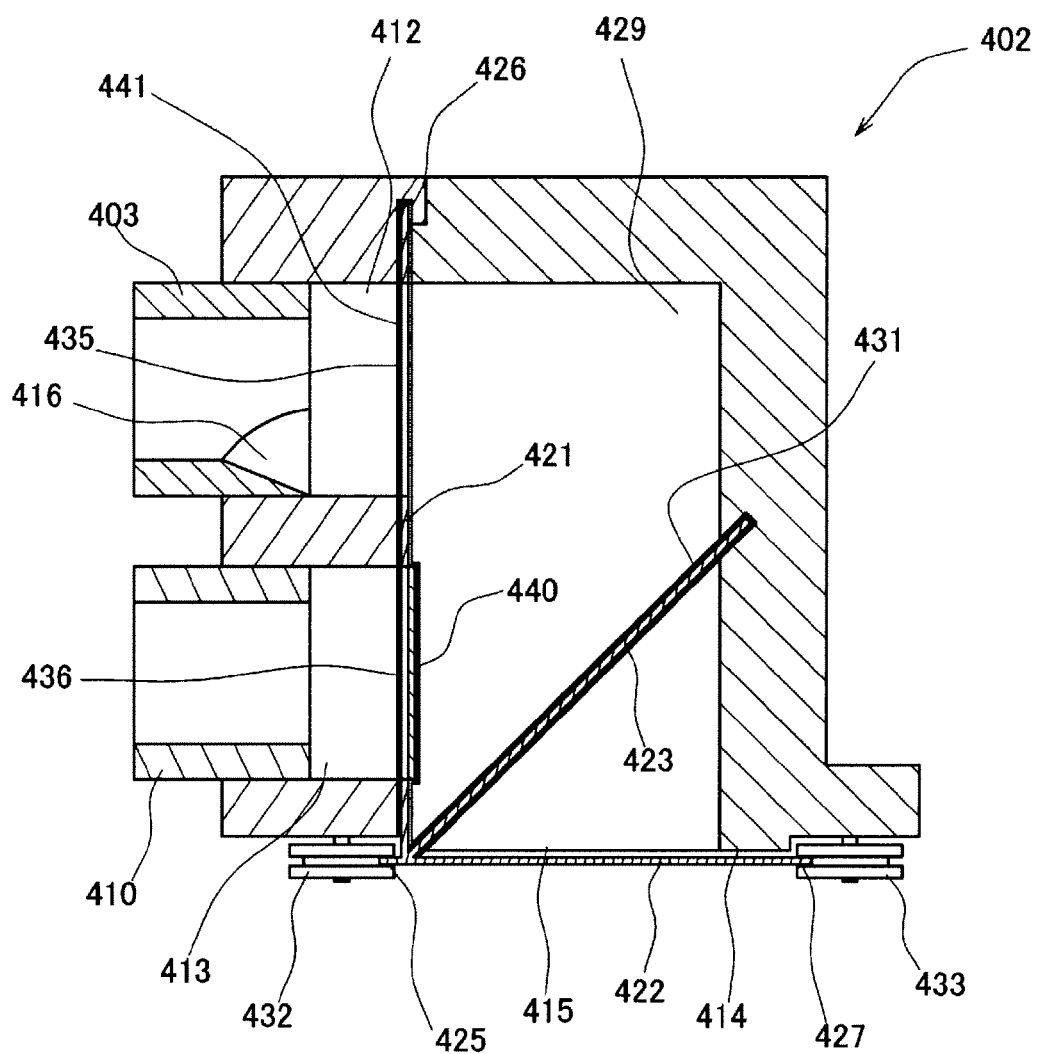
FIG. 38 is a sectional view taken along the line X-X in FIG. 37(a).

As shown in FIG. 37, the medicine dispensing part 402 is configured to be surrounded by peripheral surfaces and to be closed at a top surface. The medicine dispensing part 402 has an introducing opening 412 and an exhaust opening 413 at one of the peripheral surfaces of the medicine dispensing part 402 (hereinafter, this may be referred to as a peripheral surface 411) and a dispensing opening 415 at its bottom surface 414. The introducing opening 412 and the exhausting opening 413 are vertically juxtaposed. The forward pipe line 403 is connected to the introducing opening 412, while the exhaust pipe line 410 is connected to the exhaust opening 413. As shown in FIG. 38, the forward pipe line 403 has a staying portion 416 at its end portion, to which the introducing opening 412 is connected. The staying portion 416 is formed such that a peripheral surface of the forward pipe line 403 becomes thinner in thickness toward a forward end. The forward pipe line 403 is inserted and connected to the introducing opening 412 with the staying portion 416 facing downward. Thus, the medicines transferred through the forward pipe line 403 can stay in the staying portion 416.

Further, the forward pipe line 403 has air orifices 417 near the medicine dispensing part 402 and apart from an inserting portion to the introducing opening 412. The air orifices 417 are orifices for exhausting the airflow flowing within the forward pipe line 403. The air orifices 417 are much smaller than the medicines and are exposed outside the medicine dispensing part 402. Thus, even if the end portion of the forward pipe line 403 with the staying portion 416 becomes closed, the airflow flowing from the medicine receiving part 401 toward the medicine dispensing part 402 in the forward pipe line 403 can be produced through the operation of the blower 405.

Figure 39:
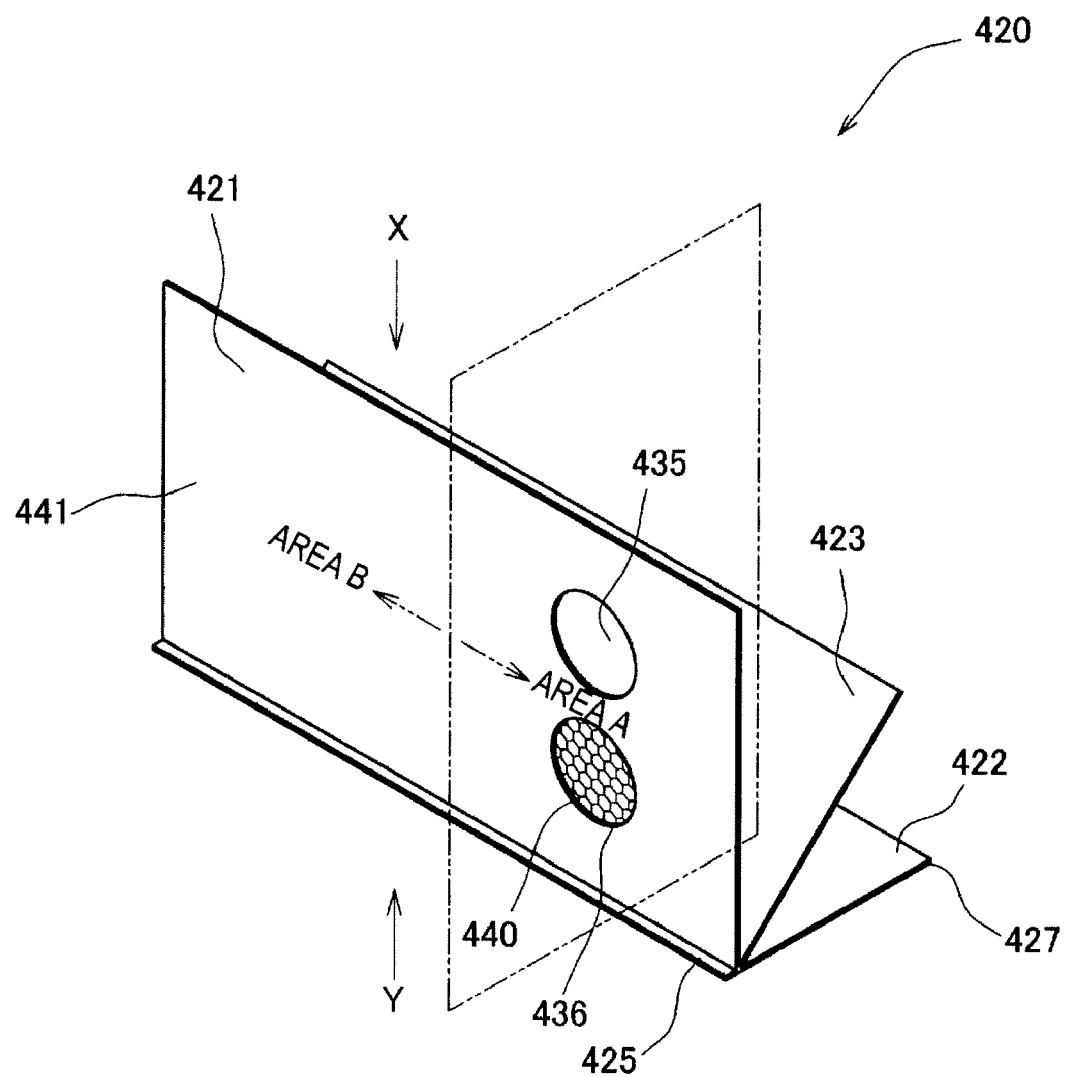
FIG. 39 is a perspective view showing the shutter provided in the medicine dispensing part shown in FIG. 37.

As shown in FIGS. 37 and 38, the medicine dispensing part 402 is provided with a shutter 420. As shown in FIG. 39, the shutter 420 includes a metallic plate having an L-shaped cross-section and an inclined plate integrally formed therewith. The shutter 420 is configured to open and close the introducing opening 412 and the exhaust opening 413 is provided in the peripheral surface 411 as well as the dispensing opening 415 formed on a bottom surface 414. More specifically, the shutter 420 includes: a first shutter surface 421; a second shutter surface 422 perpendicular to the first shutter surface 421; and an inclined surface 423 (i.e., a partitioning means) inclined relative to the first and second shutter surfaces 421, 422. Further, the second shutter surface 422 is provided with a protruding portion 425 which slightly protrudes beyond an intersection between the first shutter surface 421 and the second shutter surface 422.

The shutter 420 is positioned in such a manner that an upper end of the first shutter surface 421 is fitted to a groove 426 formed on a top surface of the medicine dispensing part 402 and the protrusion 425, and an edge portion 427 of the second shutter surface 422 are fitted to guide pulleys 432, 433 provided on the bottom surface 414 of the medicine dispensing part 402. Further, the shutter 420 is inserted to slits 430, 431 that are obliquely formed in another peripheral surfaces 428, 429 approximately perpendicular to the peripheral surface 414 of the medicine dispensing part 402. The shutter 420 is configured such that the first and second shutter surfaces 421, 422 can freely slide along the peripheral surface 411 and the bottom surface 414 of the medicine dispensing part 402 and the inclined surface 423 can freely slide as obliquely traversing an internal space of the medicine dispensing part 402 by a power from a power source (not shown).

In the shutter 420, a length in the above-described slide direction (a length in a lengthwise direction) is set to be about twice the width of the medicine dispensing part 402 (a widthwise length of the peripheral surface 411). The first and second shutter surfaces 421, 422 and the inclined surface 423 are configured differently in one area (in this case, this may be referred to as an area A) and the other area (in this case, this may be referred to as an area B) relative to half a length in a lengthwise direction. Specifically, the area A of the first shutter surface 421 is provided with two openings 435, 436, while the area B is not provided with any opening. The openings 435, 436 are vertically juxtaposed. The openings 435, 436 are positioned in a position where they can communicate with the introducing opening 412 and the exhaust opening 413 formed on the peripheral surface 411 of the medicine dispensing part 402 respectively. Further, an air-permeable filter 440 is provided in a position corresponding to the opening 436. Meanwhile, the area B of the first shutter surface 421 (e.g., a forward isolation portion 442), which is a portion for blocking the forward pipe line 403, is provided with a buffer material 441. The butter material 441 buffers an impact exerted on the medicine due to a collision of the medicine flowing in through the forward pipe line 403 while the introducing opening 412 is blocked by the first shutter surface 421. The buffer material 441 may include a rubber, a sponge, a foamed styrofoam, etc.

As shown in FIG. 40(b), the area B of the second shutter surface 422 is provided with an opening 437 which communicates with the dispensing opening 415 provided on the bottom surface 414 of the medicine dispensing part 402, while the area A is not provided with any opening. As shown in FIG. 40(a), the area B of the inclined surface 423 is provided with an opening 438, while the area A is not provided with any opening.

The shutter 420 is configured as described above. Thus, when the area A of the shutter 420 is positioned within the medicine dispensing part 402 and the area B is outwardly exposed as shown in FIG. 37(a), the internal space of the medicine dispensing part 402 is partitioned into two sections by the inclined surface 423 as shown in FIG. 38. Therefore, the forward pipe line 403 and the exhaust pipe line 410 communicate with each other through the introducing opening 412 and the exhaust opening 413 in the space above the inclined surface 423. Further, the dispensing opening 415 is blocked by the second shutter surface 422. Thus, the medicine transferred from the main unit 2 through the forward pipe line 403 is allowed to be received within the space above the inclined surface 423 in the medicine dispensing part 402.

When the area B of the shutter 420 is positioned within the medicine dispensing part 402 as shown in FIG. 37(b), the introducing opening 412 and the exhaust opening 413 are blocked by the first shutter surface 421. Meanwhile, the medicine stored within the medicine dispensing part 402 is capable of being dispensed from the dispensing opening 415 through the openings 437, 438 provided on the second shutter surface 422 and the inclined surface 423.

Next, operation of the transfer device 400 will be described. The transfer device 400 can transfer the medicine from the sub unit 3 to the main unit 2 by sequentially repeating a medicine transferring operation for transferring the medicine dispensed to the medicine receiving part 401 in the sub unit 3 to the vicinity of the medicine dispensing part 402 and a medicine introducing operation for introducing the medicine transferred by the medicine transferring operation into the medicine dispensing part 402.

When performing the medicine transferring operation, in the transfer device 400, a position of the shutter 420 is adjusted such that the area B is positioned in the position of the medicine dispensing part 402 as shown in FIG. 37(b). Therefore, a distal end of the forward pipe line 403 is blocked by the first shutter surface 421 of the shutter 420. When performing the medicine transferring operation, the blower 405 operates in such a state. Thus, an airflow flowing from the medicine receiving part 401 toward the medicine dispensing part 402 is produced within the forward pipe line 403. In this case, the airflow flowing within the forward pipe line 403 is enough to transfer the medicine. A flow rate and a flow velocity of the airflow are not so great. If the airflow is produced within the forward pipe line 403 as described above, the medicine, which is dispensed to the medicine receiving part 401 of the sub unit 3, flows to the main unit 2 to thereby be retained in the staying portion 416 provided in the vicinity of the introducing opening 412 of the medicine dispensing part 402. Thus, the medicine transferring operation is completed.

If the medicine transferring operation is completed as described above, the transfer device 400 proceeds with the medicine introducing operation. When performing the medicine introducing operation, as shown in FIG. 37(a), the position of the shutter 420 is adjusted such that the area A of the shutter 420 reaches a position corresponding to the medicine dispensing part 402. Thus, the introducing opening 412 and the exhausting opening 413 of the medicine dispensing part 402, which has been blocked by the first shutter surface 421, are opened, while the dispensing opening 415 is closed by the second shutter surface 422. Further, the internal space of the medicine dispensing part 402 is partitioned by the inclined surface 423. In this state, the pump 408 connected to the exhaust pipe line 410 operates and therefore the air within the medicine dispensing part 402 is sucked and exhausted. As a result, the medicine, which has been transferred to the staying portion 416 in the vicinity of the introducing opening 412 through the previously-performed medicine transferring operation, is introduced into the medicine dispensing part 402. The medicine introduced into the medicine dispensing part 402 is inhibited from flowing into the exhaust pipe line 410 by the filter 440 provided on the first shutter surface 421 of the shutter 420 and therefore stays within the medicine dispensing part 402. If the medicine transferred through the forward pipe line 403 is introduced into the medicine dispensing part 402 as described above, the medicine introducing operation is completed.

As described above, the transfer device 400 first transfers the medicine from the medicine dispensing part 402 to the medicine receiving part 401 through the medicine transferring operation and then can introduce the medicine transferred as such into the medicine receiving part 401 through the medicine introducing operation. Accordingly, in case of employing the transfer device 400, it is possible to deliver the medicine from the medicine dispensing part 402 to medicine receiving part 401 by repeating the medicine transferring operation and the medicine introducing operation, similar to the case of employing said transfer device 5, 210, 300.

Further, in the case of employing the transfer device 400, the medicine transferring operation and the medicine introducing operation are performed independently. Accordingly, the flow velocity of the airflow, which flows within the forward pipe line 403 by the operation of the blower 405 during the medicine transferring operation, is sufficient to transfer the medicine. It does not need to increase excessively. More specifically, the flow velocity of the airflow, which flows within the forward pipe line 403 by operation of the blower 405 in the medicine transferring operation, is equal to or lower than the flow velocity of the airflow flowing by the operation of the pump 408 during the medicine introducing operation. Accordingly, in the case of employing the transfer device 400, it is possible to prevent the medicine from breaking or chipping due to the collision between the medicines which are transferred from the main unit 2 to the sub unit 3 or between the medicines and the shutter 420.

Further, in the above-described transfer device 400, although the medicine transferred in the medicine transferring operation collides against the shutter 420, an impact on the medicine is buffered by the buffer material 441 provided on the shutter 420. Thus, according to the above-described configuration, it is possible to prevent the medicine from breaking or chipping due to the collision against the shutter 420 in the medicine transferring operation. Further, it is illustrated in the present embodiment that the buffer material 441 prevents the medicine from breaking or chipping. However, the present invention should not be limited to such a configuration. The buffer material 441 may not be employed.

As described above, the transfer device 400 has inclined surface 423 at the shutter 420 and can partition the internal space of the medicine dispensing part 402 by the inclined surface 423. Further, the inclined surface 423 is integrally formed in the shutter 420 and partitions the internal space of the medicine dispensing part 402 along with the open state of the introducing opening 412 or the exhaust opening 413. Therefore, a size of a space in which the exhaust pipe line 410 and the forward pipe line 403 communicates with each other (e.g., a space above the inclined surface 423) can be sufficiently smaller than a size of the internal space of the medicine dispensing part 402. Accordingly, the transfer device 400 can introduce the medicine transferred through the forward pipe line 403 into the medicine dispensing part 402 without significantly increasing an output (an exhaust capacity) of the pump 408 during the medicine introducing operation. Further, since there is no need to significantly increase the output of the pump 408 during the medicine introducing operation, the medicine is not subjected to great impact when introduced into the medicine dispensing part 402. As a result, it is possible to more surely prevent the medicine from breaking or chipping.

It is illustrated that the transfer device 400 has inclined surface 423 integrally mounted to the shutter 420. However, the present invention should not be limited to such a configuration. The inclined surface 423 may be configured to operate independently of the shutter 420. Further, the transfer device 400 has the inclined surface 423. However, the transfer device may not include the inclined surface 423.

As described above, the inclined surface 423 is disposed opposite the introducing opening 412 and the exhausting opening 413. Further, in the medicine dispensing part 402, a distance between the inclined surface 423 and the exhaust opening 413 positioned at downstream of the airflow flowing during transferring or introducing the medicine is narrower than a distance between the inclined surface 423 and the introducing opening 412 positioned upstream of the airflow. Thus, if the inclined surface 423 is disposed as described above, the air introduced from the introducing opening 413 into the medicine dispensing part 402 impinges against the inclined surface 423 and then changes its direction to flow smoothly toward the exhaust opening 413.

Figure 41:
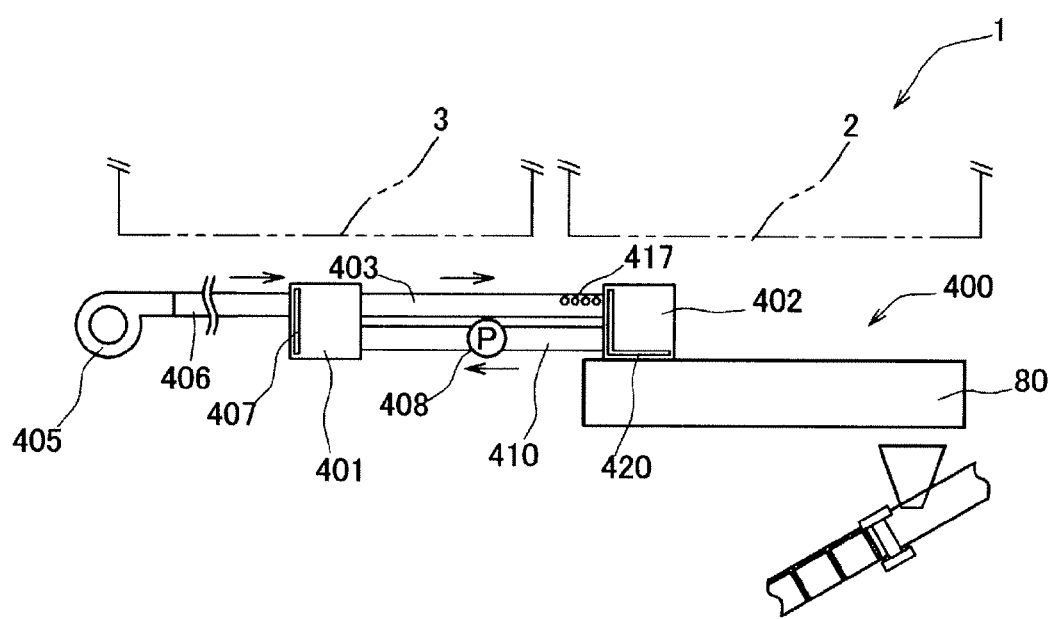
FIG. 41 is a front view showing a variation of the medicine dispensing system shown in FIG. 36.

Further, the above-described transfer device 400 is configured to head the air exhausted from the exhaust pipe line 410 outside. However, the present invention should not be limited to such a configuration. Specifically, as shown in FIG. 41, the exhaust pipe line 410 may be connected to the medicine receiving part 401 and the medicine dispensing part 402 in the same manner as the forward pipe line 403. According to such a configuration, a circulation system, which circulates the air between the medicine receiving part 401 and the medicine dispensing part 402, is formed.

Further, as shown in FIG. 41, when the exhaust pipe line 410 is connected to the medicine receiving part 401 to form the circulation system, the air circulates within the closed space generating heat. Therefore, in case of dealing with medicines which can be denatured by heat and connecting the exhaust pipe line 410 to the medicine receiving part 401, it is preferred that a cooling means for cooling the air may be disposed at a suitable place such as at a halfway point of the exhaust pipe line 410, and that the circulation system may be configured to appropriately introduce external air with low temperature.

The above-described transfer device 400 has a flow path, which runs from the medicine receiving part 401 through the forward pipe line 403 and the medicine dispensing part 402 to the exhaust pipe line 410 and produces airflow within the flow path along with the transfer of the medicine between the medicine receiving part 401 and medicine dispensing part 402. Further, similar to the case where the exhaust pipe line 410 is connected to the medicine receiving part 401 as shown in FIG. 41, the airflow is produced within the circulating flow path connecting the medicine receiving part 401 and medicine dispensing part 402 with the forward pipe line 403 and the exhaust pipe line 410. Since the above-described transfer device 400 includes the filter 440 provided on the medicine dispensing part 402 constituting a part of the flow path, it is preferred that the transfer device is configured to exactly detect a block of the filter 440 and to perform maintenance therefor. Thus, the transfer device 400 may include a flow-amount detecting means for detecting the amount of air flowing within the flow path and a clogging judging means. When the flow-amount detected by the flow-amount detecting means is less than a predetermined amount, the clogging judging means may decide that the filter 440 is clogged.

Further, in case of providing the flow-amount detecting means to judge the clogging of the filter 440 as described above, the medicine under transfer to the medicine dispensing part 402 provided in the main unit 2 may be transferred by increasing the output of one or both of the blower 405 and the pump 408 when the clogging occurs and then to stop transferring the medicine or notify the clogging of the filter 440. More specifically, the medicine under transfer may be completely transferred by increasing the output of one or both of the blower 405 and the pump 408 upon a condition that the flow-amount detected by the flow-amount detecting means decreases. Thereafter, based on the above-mentioned increases in the output of the blower 405 or the pump 408, the clogging of the filter 440 may be decided by the clogging judging means or transferring the next medicine may not be performed.

It is illustrated in the above-described embodiment that the filter 440 is provided in the flow path along which the airflow flows during the transfer of the medicine. However, the present invention should not be limited to such a configuration. A separate filter may be provided at any other place or the filter 440 may not be provided.

The medicine dispensing system 1 is not limited to employing the transfer device 5, 210, 300, 400 and may employ, for example a transfer device 500 shown in FIG. 42. The transfer device 500 includes: a forward pipe line 502; a blower 504 (an airflow producing means); a medicine dispensing part 510 (a delivering part); and a medicine receiving part 511. The transfer device 500 is configured similarly to the above-described transfer device 400 in that medicines are transferred by the airflow produced within the forward pipe line 502 by an operation of the blower 504. However, the transfer device 500 is configured differently from the above-described transfer device 400 in that it does not need the pump 408 or a pipe such as the exhaust pipe line 410 for exhausting the airflow introduced into the medicine dispensing part 510.

More specifically, the forward pipe line 502 of the transfer device 500 includes a pipe which connects a main storage part 20 and a sub storage part 120. The blower 504 is disposed so as to produce airflow from the sub unit 3 toward the main unit 2 within the forward pipe line 502.

As shown in FIGS. 44 to 47, the medicine dispensing part 510 is configured such that a delivery container 512 connected to the forward pipe line 502 is housed in a box-shaped outer container 530. The delivery container 512 is a hollow box-shaped member that is surrounded by side surfaces 512*a* to 512*d*. The delivery container includes a shutter 514 and a buffer means 522. The delivery container 512 includes an upper container body 524 and a lower container body 526, which are vertically combined. An inside portion of the delivery container 512 can be swept by removing the upper container body 524 of an upper side from the lower container body 526, if necessary.

As shown in FIGS. 46 and 47, the upper container body 524 is a hollow member constituting an upper portion of the delivery container 512. Further, the upper container body 524 is opened at a bottom portion coupled to the lower container body 526. When the delivery container 512 is assembled, the forward pipe line 502 is connected to a surface constituting the side surface 512*a* of the upper container body 524 via a joint pipe 540. The joint pipe 540 includes a pipe more flexible than the forward pipe line 502, such as a rubber pipe.

Further, a buffer means 522 is provided at the upper container body 524. The buffer means 522 includes a plate member, on which an elastic material such as rubber is provided or coated, or a rubber plate elastic in itself. The buffer means 522 is disposed opposite the surface 512*a* connected to the forward pipe line 502 within the upper container body 524. Specifically, the buffer means 522 is obliquely downwardly disposed across the side surface 512*d* and the top surface 512*e*.

In the upper container body 524, a surface, which crosses the surface (the side surface 512*a*) connected to the forward pipe line 502 (in the present embodiment, approximately crossing at a right angle) and constitutes the side surfaces 512*b*, 512*c* when the delivery container 512 is assembled, is formed with a plurality of exhausting holes 524*p*. In this case, the side surfaces 512*b*, 512*c* are surfaces laterally disposed relative to the airflow introduced into the delivery container 512 through the forward pipe line 502. Further, the exhausting holes 524*p* are disposed below a height of connection to the forward pipe line 502. More specifically, the exhausting holes 524*p* are disposed below a central axis LU centrally extending through an opening area of the forward pipe line 502. Thus, the airflow introduced through the forward pipe line 502 flows downward without being stagnant or forming a vortex within the upper section of the delivery container 512. Also, the airflow is directed so as to flow in a direction crossing direction the airflow is introduced into the delivery container 512.

As shown in FIGS. 46 and 47, the lower container body 526 is a hollow member constituting a lower portion of the delivery container 512. A bottom portion 518 of the lower container body 526 is formed with a dispensing opening 520 for dispensing the medicine toward the medicine preparing part 80. Further, the lower container body 526 is open at a top portion coupled to the upper container body 524. Accordingly, the lower container body 526 is integrally coupled to the upper container body 524 to thereby form a hollow internal space 516 within the upper and lower container bodies 524, 526.

In the lower container body 526, a surface, which constitutes the side surfaces 512b, 512c when the delivery container 512 is assembled, is formed with a plurality of exhausting holes 526p. That is, the exhausting holes 526p are formed in surfaces (the side surfaces 512b, 512c) laterally disposed relative to the airflow introduced into the delivery container 512 through the forward pipe line 502. Further, the exhausting holes 526p are positioned at a lower side of the lower container body 526. More specifically, the exhausting holes 526p are positioned below a reference plane LD passing through a position where a supporting shaft 552 of the shutter 514 is provided. Thus, in the airflow introduced into the upper container body 524 through the forward pipe line 502, the airflow, which flows downward to come to the lower container body 526, flows further downward within the lower container body 526. Also, the airflow is directed so as to flow in the direction crossing the introducing direction into the delivery container 512. Accordingly, the medicine, which has dropped to the lower container body 526, surely falls on the shutter 514.

Figure 46:
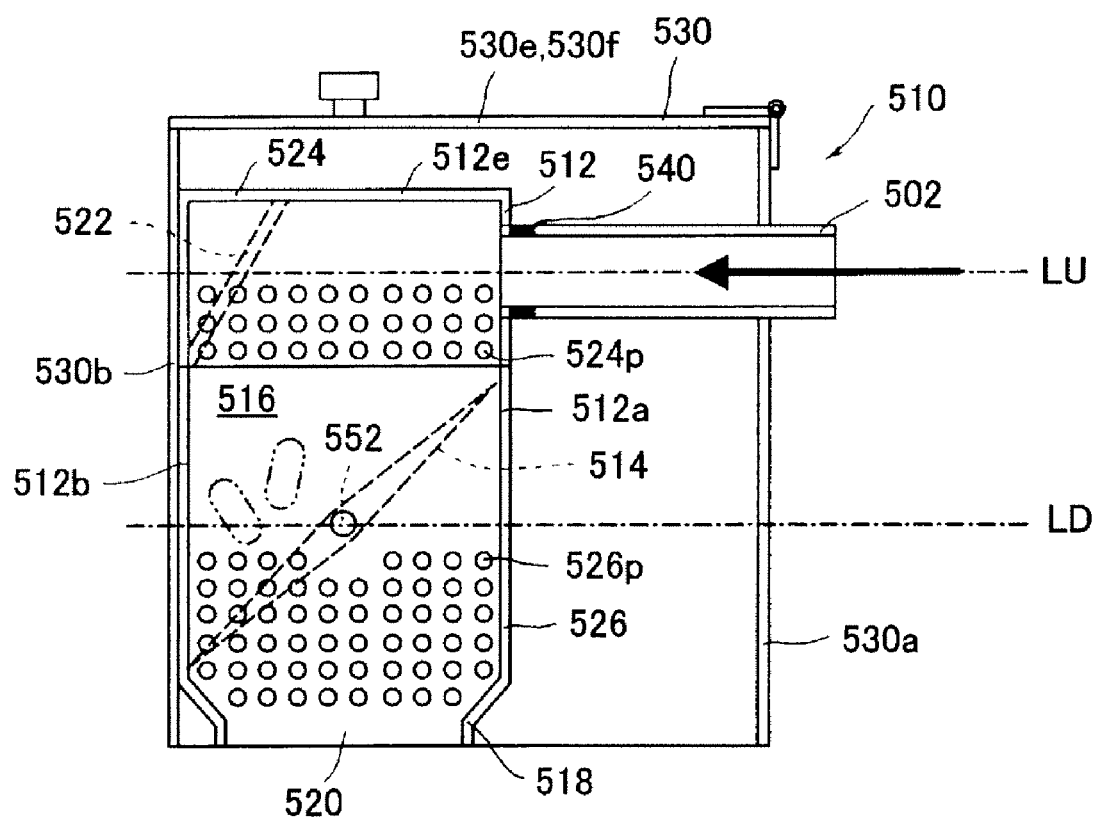
FIG. 46 is a sectional view showing the structure of the medicine dispensing part of the transfer device shown in FIG. 42 with a side portion of a delivery container cut away.
Figure 47:
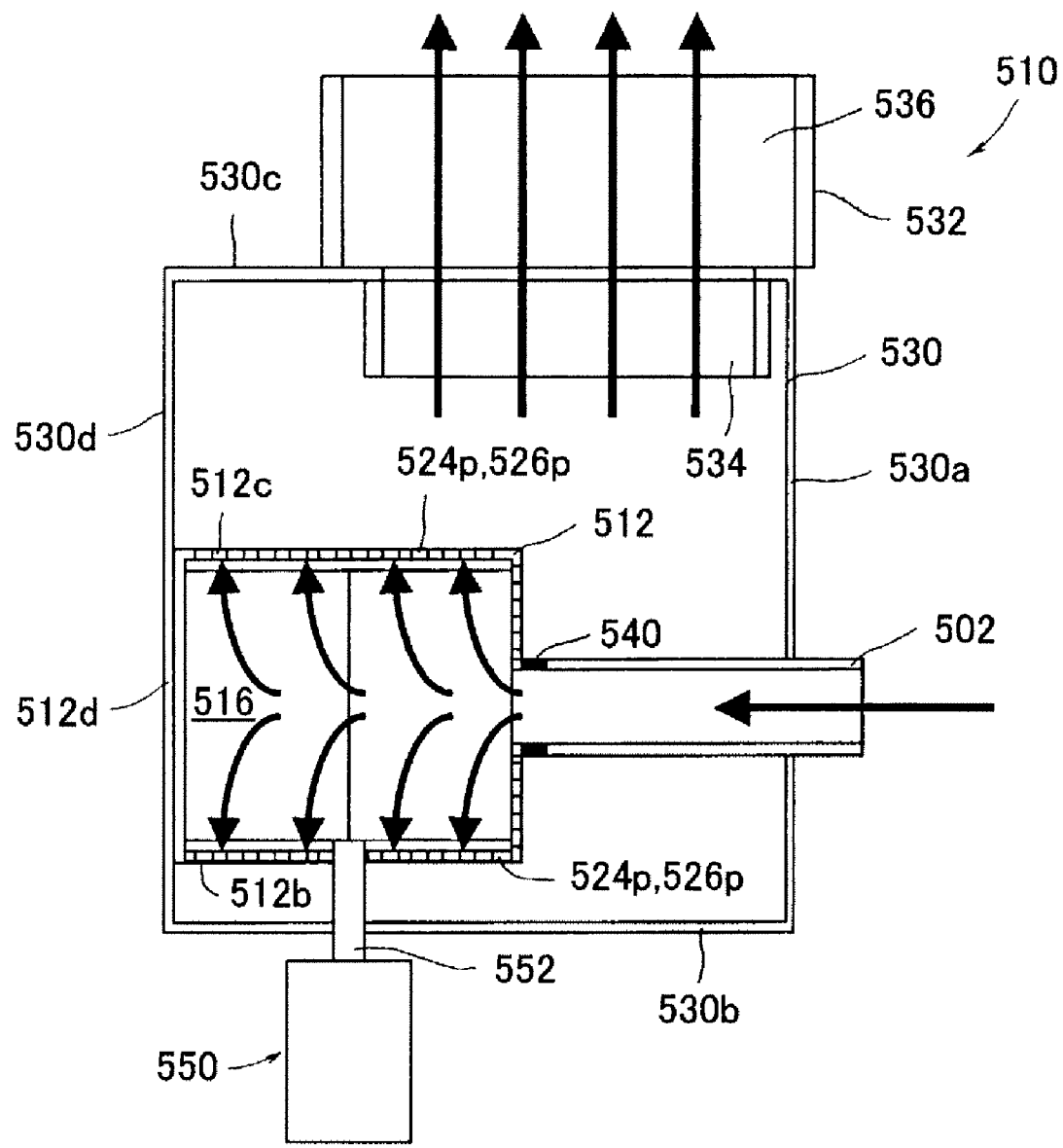
FIG. 47 is a sectional view showing the structure of the medicine dispensing part of the transfer device shown in FIG. 42 with a top portion of the delivery container cut away.

As shown in FIGS. 46 and 47, the shutter 514 serves to open and close the dispensing opening 520 provided at the bottom portions 518 and is positioned in the lower container body 526 of the delivery container 512. The shutter 514 includes a plate body having a cross section of a flat rhombus shape with pointed tips. A thickness of the plate body becomes gradually thinner as toward opposite ends of the plate body.

The shutter 514 is disposed rotatably about the supporting shaft 552 within the delivery container 512. The supporting shaft 552 is approximately perpendicular to the side surfaces 512b, 512c constituting the delivery container 512. The supporting shaft is connected to a drive device 550 provided outside of the outer container 530 of the medicine dispensing part 510. The drive device 550 includes a motor 550a and a power transmission mechanism 550b. A rotating power produced by the motor 550a is transmitted to the shutter 514 via the supporting shaft 552 to thereby change an orientation of the shutter 514.

The shutter 514 can vertically partition the internal space 516 of the delivery container 512 by placing its tip edges into contact with the side surfaces 512a, 512d of the delivery container 512. If the internal space 516 is vertically partitioned by the shutter 514, then the delivery container 512 goes into a state where the medicine is not allowed to be dispensed from the dispensing opening 520 (hereinafter, this state may be referred to as a closed state). Further, the internal space 516 of the delivery container 512 can vertically communicate by rotating the shutter 514 about the supporting shaft 552. If an inclination of the shutter becomes steeper than that in the closed state and the internal space 516 in which it vertically communicates, then the delivery container 512 goes into a state where the medicine is allowed to be dispensed from the dispensing opening 520 (hereinafter, this state may be referred to as an open sate). Therefore, as the inclination of the shutter 514 is changed by the operation of the drive device 550, the delivery container 512 can change between a closed state and the open state.

The delivery container 512 is housed in a space enclosed by the outer container 530. The outer container 530 is a hollow box-shaped body surrounded by four peripheral surfaces 530a to 530d. It is possible to sweep or maintain the delivery container 512 since a lid 530f provided on a top surface 530e of the outer container 530 is appropriately opened and closed.

Figure 44:
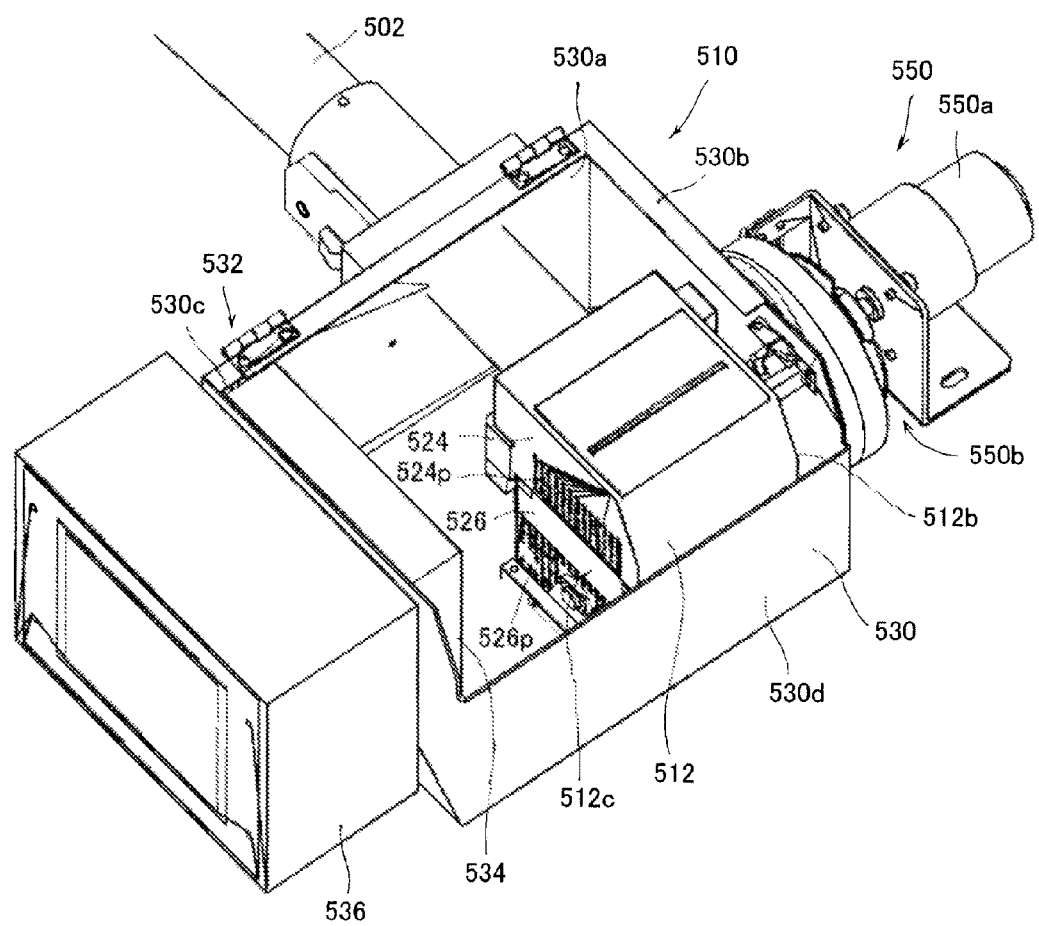
FIG. 44 is an enlarged perspective view of a medicine dispensing part of the transfer device shown in FIG. 42 with a lid of an outer container removed therefrom.
Figure 45:
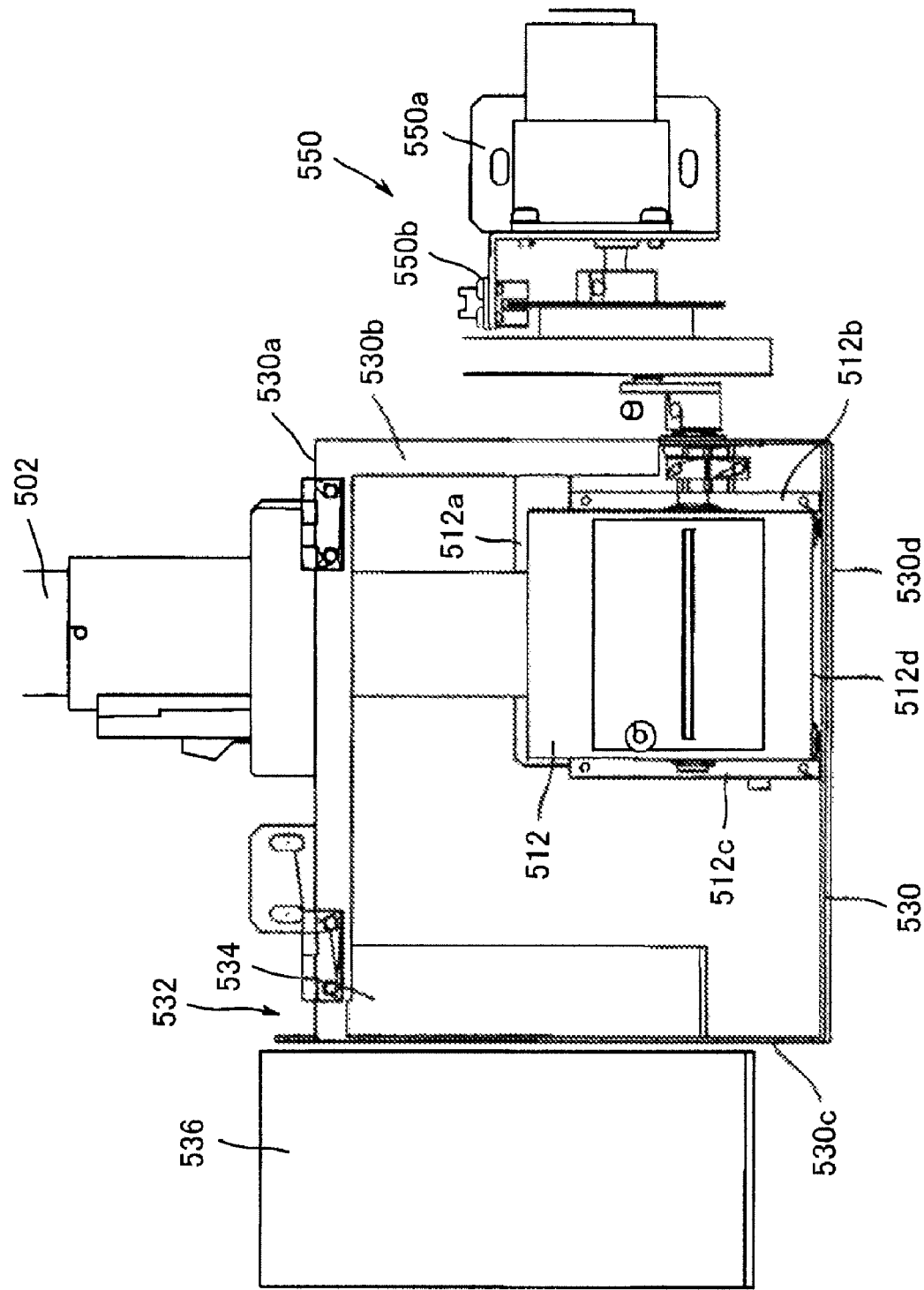
FIG. 45 is a top plan view of the medicine dispensing part of the transfer device shown in FIG. 42 with the lid of the outer container removed therefrom.

The peripheral surface 530a constituting the outer container 530 is penetrated by the forward pipe line 502 connected to the delivery container 512 housed in the outer container 530. Further, each of the peripheral surfaces 530b, 530c crosses the peripheral surface 530a (in the present embodiment, approximately crossing at a right angle), while the peripheral surface 530d is opposite the peripheral surface 530a. As shown in FIGS. 44, 45 and 47, the above-described delivery container 512 is positioned near a corner formed by the peripheral surfaces 530b, 530d in the space of the outer container 530. That is, the peripheral surfaces 530a, 530d are parallel to the side surfaces 512a, 512d of the delivery container 512, respectively, while distances between the peripheral surfaces 530a, 530d and the side surfaces 512a, 512d are different from each other. Specifically, the distance between the peripheral surface 530a and the side surface 512a is much larger than the distance between the peripheral surface 530d and the side surface 512d. Also, the peripheral surface 530d and the side surface 512d are positioned almost without a gap therebetween. Further, the distance between the peripheral surface 530b and the side surface 512b is smaller than the distance between the peripheral surface 530c and the side surface 512c.

The outer container 530 has an exhausting part 532 for exhausting the air flowing out from the exhausting holes 524p, 526p of the delivery container 512 at the peripheral surface 530c. The exhausting part 532 is positioned near the peripheral surface 530a of the outer container 530. The exhausting part 532 is provided with a primary filter 534 and a secondary filter 536 with meshes finer than those of the primary filter 534. The primary filter 534 and the secondary filter 536 can be detached separately for purposes of cleaning or replacement. The primary filter 534 with sparse meshes is disposed upstream in a flow direction of the air exhausted from the exhausting part 532 relative to the secondary filter 536 with fine meshes. In the present embodiment, the primary filter 534 is disposed in the exhausting part 532 inward of the outer container 530, while the secondary filter 536 is disposed outward of the outer container 530.

Figure 42:
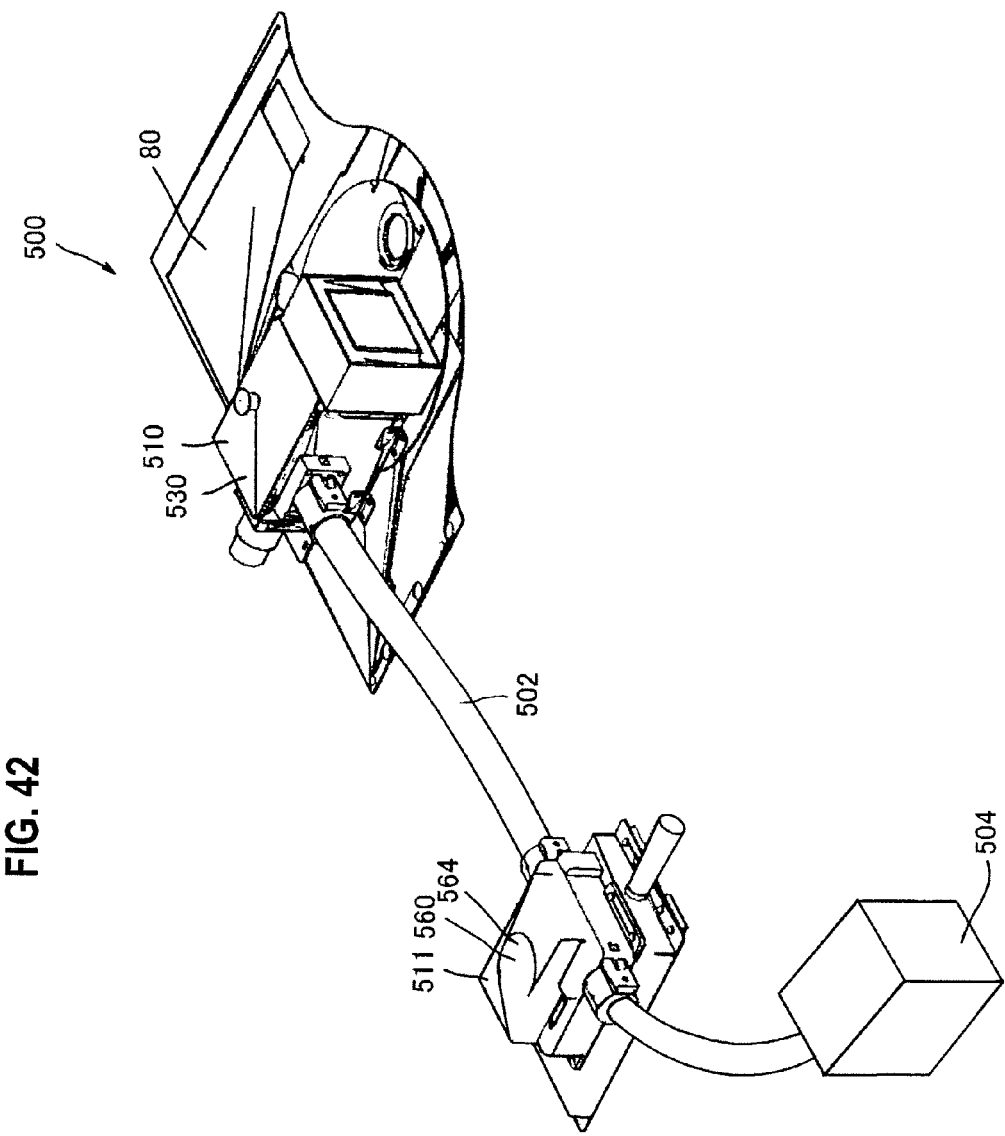
FIG. 42 is a perspective view showing yet another variation of a transfer device.
Figure 43:
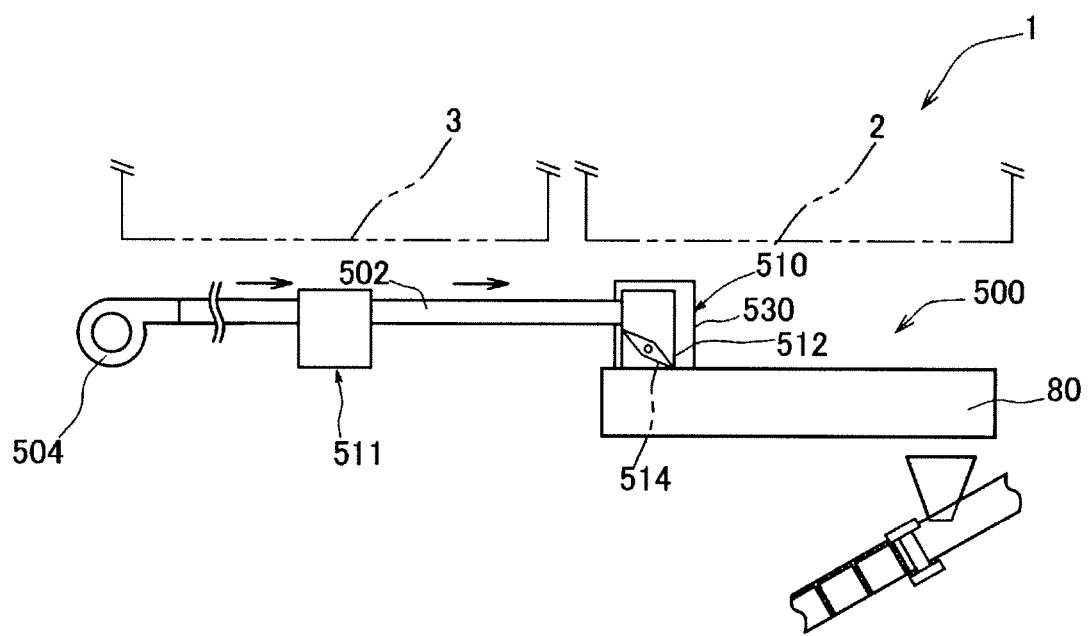
FIG. 43 schematically shows features of a transfer device shown in FIG. 42.
Figure 48:
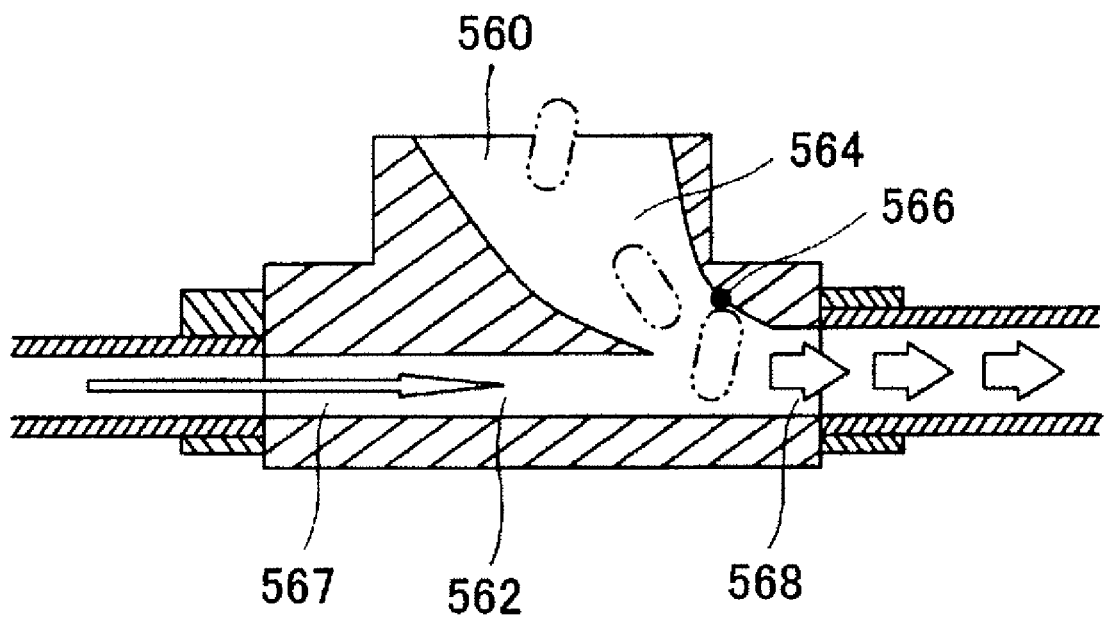
FIG. 48 is a sectional view showing a medicine receiving part of the transfer device shown in FIG. 42.

Meanwhile, as shown in FIG. 42, the medicine receiving part 511 provided in the sub unit 3 is comprised of a box-shaped body with an opened medicine input opening 560 at its top surface. The sub hopper 135 provided in the sub unit 3 is connected to the medicine input opening 560. The medicine dispensed from the sub storage part 120 is inputted into the medicine receiving part 511 through the medicine input opening 560. As shown in FIGS. 42 and 48, both the one end of the forward pipe line 502 and a blower pipe 566 connected to the blower 504 are connected to the medicine receiving part 511 to communicate with each other. A medicine transfer passage 562 and a medicine input passage 564 extending from the medicine input opening 560 to the forward pipe line 502 are provided within the medicine receiving part 511.

The forward pipe line 502 and the blower pipe 566 are connected to the medicine transfer passage 562. As indicated by an arrow in FIG. 48, as the blower 504 operates, airflow is produced toward the forward pipe line 502. The medicine transfer passage 562 joins the medicine input passage 564 at its halfway portion. The medicine transfer passage 562 has an enlarged diameter section 568, at which a cross section of the flow passage is enlarged, downstream of a junction 566 with the medicine input passage 564 (i.e., at a portion connected to the forward pipe line 502). A diameter of the enlarged diameter section 568 is enlarged toward the medicine input passage 564 (i.e., toward an upper side) within the medicine receiving part 511. In the present embodiment, the medicine transfer passage 562 is configured such that an inner diameter of the enlarged diameter section 568 is enlarged to be about 1.5 times larger than that of an upstream portion 567. Meanwhile, the medicine transfer passage 562 is configured such that a portion upstream of the junction 566 (hereinafter, this may be referred to as the upstream portion 567") and the enlarged diameter section 568 are flush with each other at a portion opposite the medicine input passage 564 (i.e., a bottom side of the medicine receiving part 511). Thus, the airflow flowing within the medicine transfer passage 564 smoothly flows toward the forward pipe line 502 without being stagnant or forming a vortex at the junction 566.

Further, the medicine input passage 564 is gently inclined downward from the medicine input opening 560 and is joined to the medicine transfer passage 562. Thus, if the airflow is produced by operation of the blower 504 within the medicine transfer passage 562, then a suction force from the medicine input opening 560 toward the medicine transfer passage 562 is produced at the medicine input passage 564. Accordingly, if the medicine is inputted into the medicine input opening 560, as indicated by a two dot chain line in FIG. 48, the medicine is sucked and introduced into the medicine transfer passage 562 and then is introduced to the forward pipe line 502.

Next, operation of the transfer device 500 will be described. The transfer device 500 starts transferring the medicine by dispensing the medicine from the sub storage part 120 of the sub unit 3. If the medicine dispensed from the sub storage part 120 is introduced into the forward pipe line 502 through the medicine receiving part 511, then the blower 504 operates to produce the airflow from the sub unit 3 toward the main unit 2 within the forward pipe line 502. Thus, the medicine flows to the medicine dispensing part 510 provided in the main unit 2. In this case, as shown in FIG. 46, the shutter 514 provided in the delivery container 512 in the medicine dispensing part 510 of the main unit 2 goes into the closed state.

When the medicine dispensed in the sub unit 3 reaches the medicine dispensing part 510, it is introduced into the delivery container 512. In this case, if the airflow is strong over the weight or quantity of the medicine, the medicine collides against the buffer means 522 and then drops downward in the internal space 516 of the delivery container 512. However, if the airflow is not so strong, the medicine drops downward in the internal space 516 without collision against the buffer means 522. Further, after the airflow introduced into the delivery container 512 through the forward pipe line 502 flows downward in the internal space 516, as indicated by an arrow in FIG. 47, it is exhausted from the exhausting holes 524p, 526p formed in the side surfaces 512b, 512c. Accordingly, the medicine transferred into the delivery container 512 drops smoothly. The medicine dropping within the delivery container 512 falls on the shutter 514 in the closed state.

If all the medicines transferred from the sub unit 3 falls on the shutter 514 as described above, the shutter 514 is changed into the open state. In such a case, the medicine falls along the surface of the shutter 514 which becomes gradually steeper and then is dispensed from the dispensing opening 520 provided on the bottom portion 518 of the delivery container 512. The medicine dispensed from the dispensing opening 520 is inputted into the medicine preparing part 80 provided below the medicine dispensing part 510 for packing in the medicine packing part 21 provided in the main unit 2. Thereafter, the medicines prepared in the medicine preparing part 80 are packed by the medicine packing part 21 one after another.

In case of employing the transfer device 500, it is possible to transfer the medicine from the sub unit 3 to main unit 2 to pack the same as described above, but also to sweep the inside of the medicine transfer path of the transfer device 500 by means of airflow produced by the blower 504. Specifically, when sweeping the inside of the medicine transfer path of the transfer device 500, the blower 504 operates as the shutter 514 is closed. In this case, the output of the blower 504 is set to be larger than the transfer of the medicine. Thus, dusts remaining within the medicine transfer path of the transfer device 500 are swept off and then expelled from the exhausting holes 524p, 526p of the delivery container 512. The dusts expelled from the exhausting holes 524p, 526p are captured by the primary filter 534 and the secondary filter 536 provided in the exhausting part 532 of the outer container 530.

As described above, the medicine dispensing system 1 employing the transfer device 500 can transfer the medicine from the sub unit 3 to the medicine dispensing part 510 provided in the main unit 2 along with the airflow produced by the operation of the blower 504. Further, after the medicine is transferred to the medicine dispensing part 510, the medicine can be dispensed for packing by changing the shutter 514 to the open state. Accordingly, in case of employing the transfer device 500, similarly to the case employing the above-described transfer device 5, 210, 300, 400, it is possible to pack the medicine dispensed in the sub unit 3 at the medicine packing part 21 provided in the main unit 2.

In the above-described transfer device 500, the exhausting holes 524p, 526p are formed below the connection position between the delivery container 512 and the forward pipe line 502. Thus, the airflow introduced into the delivery container 512 through the forward pipe line 502 flows downward. Further, in the above-described delivery container 512, the side surfaces 512b, 512c, which are disposed laterally to the side surface 512a connected to the forward pipe line 502, are provided approximately symmetrically. Thus, the airflow introduced into the delivery container 512 flows downward as described above and then is smoothly exhausted as bifurcated. As such, in the transfer device 500, the airflow introduced into the delivery container 512 smoothly flows downward and is exhausted without being stagnant at the upper side. Thus, the medicine introduced on the airflow drops smoothly without blowing within the delivery container 512 and is to be dispensed.

As described above, since the airflow smoothly flows and the medicine smoothly drops within the delivery container 512, the transfer device 500 does not need the pump 408 or the exhaust pipe line 410 for exhaust purposes as described in the transfer device 400. Accordingly, in case of employing the transfer device 500, a device configuration can be simplified when compared to the case of employing the transfer device 400.

It is illustrated in the present embodiment that the exhausting holes 524p, 526p are formed in the side surfaces 512b, 512c of the delivery container 512. However, an equivalent to the exhausting holes 524p, 526p may be formed on the side surfaces 512a, 512d. Further, an equivalent to the exhausting holes 524p, 526p may be formed in the side surfaces 512a, 512d instead of forming the exhausting holes 524p, 526p in the side surfaces 512b, 512c.

Further, it is illustrated in the present embodiment that the exhausting holes 524p, 526p are formed in both the upper container body 524 and the lower container body 526. However, the present invention should not be limited to such a configuration. One of the exhausting holes 524p, 526p may not be formed. Also, the number or the opening area of the openings 524p, 526p may be different. Further, in order to smoothly drop the medicine within the delivery container 512, the airflow, in some embodiments, is exhausted not in a halfway position in a height direction of the delivery container 512, but in a position as low as possible. Accordingly, in case of forming any one of the exhausting holes 524*p* and the exhausting holes 526*p*, it is preferred to form only the exhausting holes 526*p*. Further, in case of varying the number or the opening area of the exhausting holes 524*p*, 526*p*, the number or the opening area of the exhausting holes 524*p*, in some embodiments, is smaller than those of the exhausting holes 526*p*.

In the above-described transfer device 500, the buffer means 522 is provided within the delivery container 512 and is disposed opposite the side surface 512*a* connected to the forward pipe line 502 or an open end of the forward pipe line 502. Thus, although the medicine introduced from the forward pipe line 502 into delivery container 512 collide with the buffer means 522 from the force of the airflow, breakage or chipping of the medicine hardly occurs.

In the above-described transfer device 500, the shutter 514 is in the closed state and is inclined as it awaits the transfer of the medicine. Thus, when the medicine is transferred into the delivery container 512 and then falls on the shutter 514, a drop distance of the medicine is relatively short. Accordingly, an impact exerted to the medicine due to the drop within delivery container 512 is small. Further, once the medicine falls on the shutter 514, the medicine slides along the surface of the shutter 514 to drop downward. Thus, after the medicine falls on the shutter 514, no impact is exerted to the medicine until the medicine is dispensed. Therefore, according to the above-described configuration, it is possible to minimize the impact exerted on the medicine transferred from sub unit 3 to main unit 2.

As described above, it is possible to easily sweep or maintain the internal space of the outer container 530 or the delivery container 512 by opening the lid 530*f* provided on the top surface 530*e* of the outer container 530. Further, it is possible to divide the delivery container 512 by removing the upper container body 524 from the lower container body 526. Accordingly, it is possible to easily sweep or maintain the inside of the delivery container 512.

It is illustrated in the present embodiment that the openable and closable lid 530*f* is provided in the outer container 530 and the delivery container 512 is configured to be divided. However, the outer container and the delivery container are not necessarily configured as such. Further, the delivery container 512 is configured to be divide into two vertical members (the upper container body 524 and the lower container body 526). However, the delivery container may be divided into more members. Also, the delivery container may include an openable and closable lid in order to sweep the inside thereof, similar to the outer container 530.

Since the plurality of exhausting holes 524*p*, 526*p* are formed in the side surfaces 512*b*, 512*c* of the delivery container 512 in the above-described transfer device 500, the airflow is exhausted in different directions from the delivery container 512. However, in the transfer device 500, the delivery container 512 is disposed inside the outer container 530. The airflow exhausted from the delivery container 512 accumulates in a space between the outer container 530 and the delivery container 512 and is then exhausted from the exhausting part 532 separately provided in the outer container 530 through the primary filter 534 and the secondary filter 536. Thus, the transfer device 500 can prevent dusts from blowing within the main unit 2.

It is illustrated in the present embodiment that the outer container 530 for housing the delivery container 512 or the exhausting part 532 is provided in order to prevent the airflow from being exhausted from the transfer device 500 in different directions. However, if dust is unlikely to blow along with the exhaust of the airflow, or if the airflow may be exhausted a little from the transfer device 500, the outer container 530 may not be provided.

In the above-described outer container 530, the primary filter 534 and the secondary filter 536 are provided in the exhausting part 532. Thus, although the airflow exhausted into the outer container 530 contains dust, it is possible to prevent the dust from flowing out of the outer container 530. Further, since the primary filter 534 with sparse meshes is disposed upstream of the secondary filter 536 with fine meshes in the airflow flowing through the exhausting part 532, a service life of the secondary filter 536 can be extended. Furthermore, it is illustrated in the present embodiment that the primary filter 534 and the secondary filter 536 with different sized meshes are provided in the exhaust part 532. However, the present invention should not be limited to such configuration. In some embodiments only one of the primary filter and the secondary filter may be provided.

As described above, in the medicine dispensing part 510, the delivery container 512 and the forward pipe line 502 are connected to each other through the flexible joint pipe 540. Thus, although a certain stress is applied to the forward pipe line 502, such stress can be absorbed or relieved by the joint pipe 540, thereby preventing a joint portion between the delivery container 512 and the forward pipe line 502 from damaging. Further, it is illustrated in the present embodiment that the delivery container 512 and the forward pipe line 502 are connected to each other through the joint pipe 540. However, the present invention should not be limited to such a configuration. The joint pipe 540 and the delivery container 512 may be directly connected to each other. Further, in case a medicine transferring system is configured by connecting a pipe to another member in the same manner as the pipe line 540, the forward pipe line 403 and the exhaust pipe line 410 of the above-described transfer device 5, 400, a flexible member such as the joint pipe 540 may be interposed between a pipe and another member. Pipe line 140 or the forward pipe line 403, through which the medicine passes, may include a hard pipe for preventing the medicine from jamming in a halfway portion. Since a joint portion between a pipe and another member is apt to break because of stress, a connecting pipe 540 that is more flexible than the pipe at the joint portion between the piping and said other member may be used.

As described above, in case of employing the transfer device 500, in addition to the transfer of the medicine from the sub unit 3 to the main unit 2, it is possible to sweep off the dust remaining within the serial medicine transfer path extending from the medicine dispensing part 510 to the medicine receiving part 511 by means of airflow produced by the operation of the blower 504. Thus, in case of employing the transfer device 500, the medicine transfer path can be easily kept clean without performing large-scale work such as removal of the forward pipe line 502. Further, the timing of when to sweep the medicine transfer path by means of the airflow produced by the operation of the blower 504 may be appropriately set as, for example, a time after the predetermined quantity of medicine is packed, or a time when an operating means such as a separately-provided button is operated.

Further, in the present embodiment, when the medicine transfer path in the transfer device 500 is swept by the airflow produced by the operation of the blower 504, the output of the blower 504 is set to be larger than the output during the transfer of the medicine. Thus, dust, which does not flow from the airflow produced during the transfer of the medicine, can be swept off by performing a sweeping operation. Further, the output of the blower 504 during sweeping the transfer device 500 may not necessarily be increased. The output of the blower 504 may be equal to the output during the transfer of the medicine. Furthermore, the output of the blower 504 may be appropriately changed during sweeping.

Figure 49:
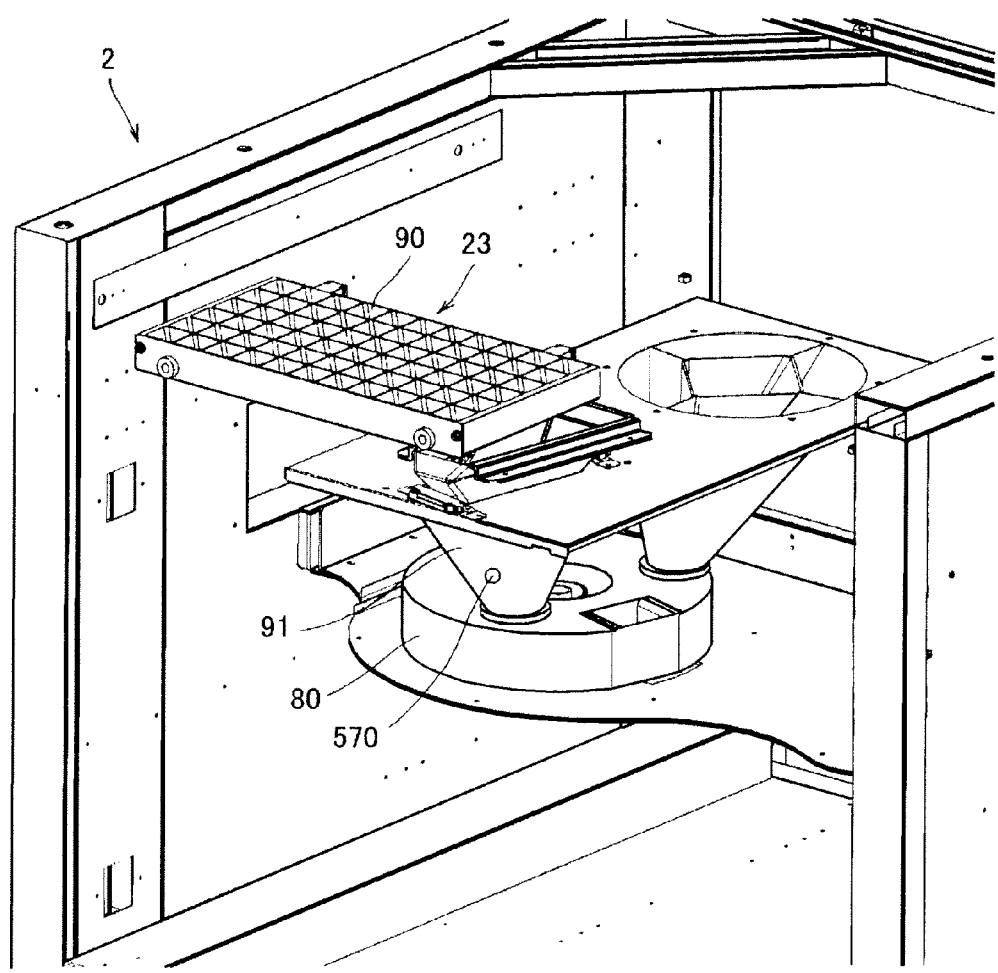
FIG. 49 is a perspective view showing the structure near a manual distributing unit in a main unit of a medicine dispensing system according to one embodiment of the present invention.
Figure 50:
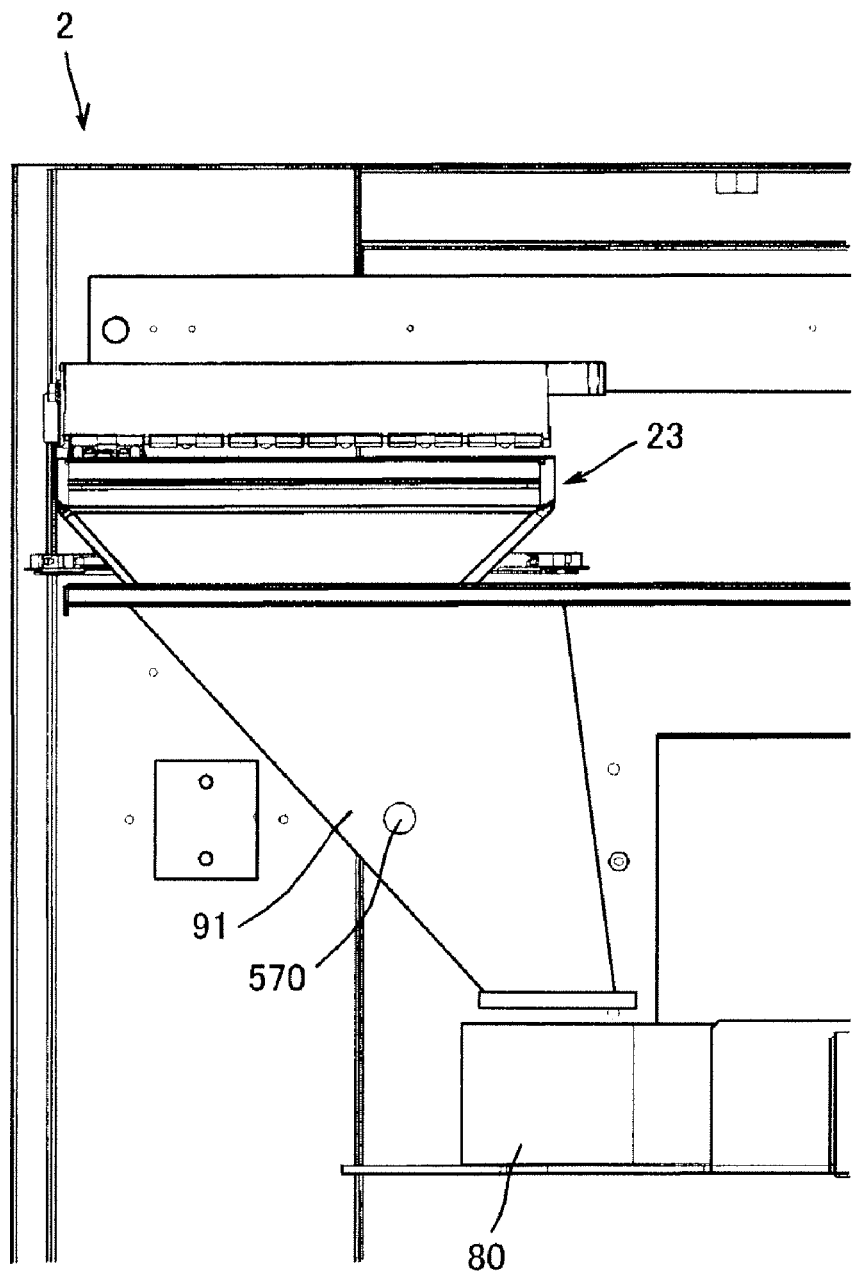
FIG. 50 is a side view showing the structure near the manual distributing unit in the main unit of the medicine dispensing system according to one embodiment of the present invention.

The above-described medicine dispensing system 1 is configured such that the medicine dispensed from the manual distributing unit 23 provided in the main unit 2 is inputted into the medicine preparing part 80 through the manual distributing hopper 91 provided below the manual distributing unit as shown in FIGS. 49 and 50. However, it is preferred that the medicine dispensing system is configured to detect whether the medicine is normally dispensed from the manual distributing unit 23. Meanwhile, the manual distributing unit 23 has a plurality of measures 90 and is configured to sequentially dispense the medicine from each of the measures 90. Thus, when a means for detecting a dispensing state of the medicine is provided in each of the measures 90, the structure of the manual distributing unit 23 becomes complicated. Accordingly, based on such knowledge, it is preferred that the above-described medicine dispensing system 1 includes a sensor capable of detecting the medicine midway in a path, through which the medicine dispensed from the manual distributing unit 23 passes. Specifically, as shown in FIGS. 49 and 50, it is preferred that a sensor 570 capable of detecting the medicine is provided in the manual distributing hopper 91 disposed between the manual distributing unit 23 and the medicine preparing part 80.

Next, other inventions will be explained hereinafter. There exists in the art a medicine dispensing device as disclosed in the below-mentioned reference Patent Document 2. A prior art medicine dispensing device has a storage part for storing a plurality kinds of medicines. Such a prior art medicine dispensing device is constructed to pack medicines removed from the storage part according to prescriptions into a packing paper sheet at a packing part and dispense the same. (see Patent Document 2: Japanese Laid-Open Patent Application No. 2006-130307)

A prior art medicine dispensing device disclosed in the above-mentioned Patent Document 2 includes: a packing part for packing medicines; and a packing paper sheet conveying part including a conveying means such as a conveyor for conveying the packing paper sheet, in which the medicines are packed, toward a removal opening. However, when abnormality in conveying a packing paper sheet occurs due to jamming caused by the packing paper sheet in the conveying part, the prior art device does not have a technique for rapidly and reliably detecting such abnormality. Further, in the prior art medicine dispensing device, a position of a dispensing opening for dispensing the packed medicine is determined under configuration of the conveying means and the packing part. Thus, there is a problem with the prior art device in that the packed medicine can be removed at a desired position.

Thus, there is a need for a medicine dispensing device, which is configured to rapidly and reliably detect abnormality in packing paper sheet transfer in a packing paper sheet conveying part, and a medicine dispensing system including the same. Further, there is a need to provide a medicine dispensing device and a medicine dispensing system, which are configured to remove medicine packed in a packing part at a desired position.

In one embodiment a medicine dispensing device includes a storage part configured to store and dispense medicine; a packing part configured to pack the medicine dispensed from the storage part into a packing paper sheet; and a packing paper sheet conveying part configured to convey a packing paper sheet into which the medicine is packed by the packing part. The packing paper sheet conveying part includes: a packing paper sheet conveying means configured to convey the packing paper sheet along a predetermined conveyance path through contact with the packing paper sheet; and a detecting means configured to contact the packing paper sheet passing through the conveyance path and operate independently of the packing paper sheet conveying means. It is detected upon a condition of not operating of the detecting means during operation of the packing paper sheet conveying means whether an abnormality in transferring a packing paper sheet occurs.

In another embodiment a medicine dispensing device includes, at the packing paper sheet conveying part, the detecting means contacting the packing paper sheet and operating independently of the packing paper sheet conveying means. The medicine dispensing device can detect whether or not the packing paper sheet transfer is normal through the detecting means. Further, the medicine dispensing device can rapidly and precisely detect an abnormality in the packing paper sheet transfer. Thus, the medicine dispensing device can perform appropriate measures such as stopping the packing paper sheet transfer, or stopping the dispensing of medicine to the packing paper sheet. Thus, it may be possible to minimize the amount of the packing paper sheet or the medicine wasted when an abnormality in the packing paper sheet transfer occurs.

Further the detecting means may include a roller independently rotatable of the packing paper sheet conveying means; and a rotation detecting means configured to detect a rotation of the roller.

According to such configuration, there can be provided a medicine dispensing device which can detect an abnormality in packing paper sheet transfer based on whether the rotation of the roller is detected by the rotation detecting means.

Further, the packing paper sheet conveying part may be configured to bend the conveyance path of the packing paper sheet.

According to such configuration, there can be provided a medicine dispensing device, which can remove the medicine packed in the packing part at a desired position by appropriately bending the conveyance path in the packing paper sheet conveying part.

In the medicine dispensing device according to the above-described embodiment, in order to rapidly detect the abnormality in packing paper sheet transfer, an abnormality in packing paper sheet transfer can be detected in a position as far upstream as possible in a conveyance direction of the packing paper sheet where the occurrence of the abnormality in packing paper sheet transfer can be accurately detected. Specifically, the abnormality in packing paper sheet transfer can be detected in a position as far upstream as possible in the conveyance direction of the packing paper sheet where a conveyance force acts on the packing paper sheet.

Thus, the detecting means may be situated upstream in the conveyance direction of the packing paper sheet in the packing paper sheet conveying means.

According to such configuration, there can be provided a medicine dispensing device, which can rapidly and accurately grasp an abnormality in packing paper sheet transfer when it occurs.

Further, the packing paper sheet conveying part may include a packing part for packing medicine. The packing paper sheet conveying means may be provided downstream in the conveyance direction of the packing paper sheet relative to the packing part. The packing paper sheet conveying means may include a receiving part receiving a packing paper sheet conveyed from the packing part; and a conveying part downstream of the conveying of the packing paper sheet received in the receiving part. The detecting means may be disposed near a boundary between the receiving part and the conveying part.

In the medicine dispensing device, the receiving part receiving the packing paper sheet is provided in the packing paper sheet conveying means. In the conveying part, a conveyance force acts on the packing paper sheet received in the receiving part to convey the packing paper sheet. Thus, where the detecting means is disposed near the boundary between the receiving part and the conveying part, similar to the medicine dispensing device of the present invention, an abnormality in packing paper sheet transfer can be rapidly and accurately detected.

Further, there is provided a medicine dispensing system including a main unit; one or more sub units; and a transfer device configured to connect the main unit and the sub units. The main unit includes the above-described medicine dispensing device. The sub unit includes a sub storage part configured to store and dispense a plurality kinds of medicines. The transfer device transfers the medicine dispensed from the sub storage part toward the main unit. The packing means of the main unit packs and dispenses the medicine.

The medicine dispensing system may include the main unit and the sub unit. It is configured such that the medicine dispensed from the sub storage part provided in the sub unit is transferred to the main unit through the transfer device and is packed and dispensed together with the medicine dispensed in the main unit. However, when the packing paper sheet conveying part provided in the main unit cannot rapidly and accurately detect an abnormality in packing paper sheet transfer, the medicine dispensed in the main unit as well as the medicine dispensed in the sub unit are not allowed to be properly packed. As a result, when the medicines dispensed from both the main unit and the sub unit are allowed to be packed together as described in the medicine dispensing system of the present invention, not detecting the abnormality in packing paper sheet transfer rapidly and accurately raises problems in that the wasted amount of the packing paper sheet and the medicine becomes excessive.

Thus, a medicine dispensing device in some embodiments may be employed as the main unit. Thus, when an abnormality in packing paper sheet transfer is detected in the main unit, such abnormality can be rapidly and accurately detected. Further, an abnormality in packing paper sheet transfer can be detected rapidly and accurately in some embodiments, the medicine dispensing device can perform appropriate measures such as stopping the packing paper sheet transfer, or stopping to dispense medicines to the packing paper sheet in case of the occurrence of an abnormality in packing paper sheet transfer. Thus, the wasted amount of the packing paper sheet and the medicine can be minimized.

There can be provided in other embodiments, a medicine dispensing device, which is configured to rapidly and reliably detect an abnormality in packing paper sheet transfer in a packing paper sheet conveying part, and the medicine dispensing system including the same. Further, there can be provided a medicine dispensing device and a medicine dispensing system, which are configured to remove a medicine packed in the packing part at a desired position.

Next, another embodiment will be explained hereinafter. There exists in the art a medicine dispensing device as disclosed in the below-mentioned reference Patent Document 3. A prior art medicine dispensing device has a medicine dispensing means. Such a prior art medicine dispensing device is configured to pack medicines dispensed from the medicine dispensing means according to prescriptions into a packing paper sheet at a packing means. Further, as disclosed in Patent Document 3, the prior art medicine dispensing device includes a printing means and is configured to print necessary information such as contents of the packed medicine on the packing paper sheet through the printing means. (see Patent Document 3: Japanese Laid-Open Patent Application No. 2006-130307).

In a packing work performed by the prior art medicine dispensing device disclosed in the Patent Document 3, pharmacists monitor whether medicines to be fed to the packing part and to be packed therein are accurately packed. The prior art medicine dispensing device disclosed in the Patent Document 3 is configured to assume that the medicines to be packed are fed to the packing part at a time when the medicines to be fed to the packing part and to be packed therein are ready and then to perform a printing operation to a packing paper sheet through the printing means. Thus, in the packing work performed by the prior art medicine dispensing device disclosed in the Patent Document 3, it cannot be judged by looking over the information printed on the packing paper sheet whether the medicines to be packed are accurately packed. Thus, it has a problem in that the examination work becomes complicated. Further, it has another problem in that the packing paper sheet, to which the printing operation is performed after the medicines are already packed, appears to be under a normally packed state. Further, in the prior art medicine dispensing device, even if the medicines to be packed are not ready due to an abnormality in feeding medicines to the packing part, the printing operation is performed to a packing paper sheet, thereby wasting the packing paper sheet.

Thus, in one embodiment a medicine dispensing device, which is configured to rapidly and precisely perform an examination work and to prevent the occurrence of wasted packing paper sheets, and a medicine dispensing system including the same.

In one embodiment a medicine dispensing device, which includes a medicine dispensing means configured to dispense a medicine according to a prescription; a medicine preparing means configured to receive a medicine dispensed from the medicine dispensing means and to dispense the same at a predetermined time; a packing means configured to pack a medicine dispensed from the medicine preparing means into a packing paper sheet; a packing paper sheet feeding means configured to feed a packing paper sheet to the packing means; and a printing means configured to print predetermined information on a packing paper sheet fed from the packing paper sheet feeding means to the packing means. The printing means is disposed upstream of the packing means in a flow direction of the packing paper sheet fed by the packing paper sheet feeding means. A length of a path, through which a packing paper sheet passes between the printing means and the packing means, is n times the length of a packing paper sheet necessary for packing a medicine for one pack. The medicine preparing means includes a plurality of sections configured to gather the medicine dispensed from the medicine dispensing means for one pack respectively and is configured to dispense the medicines gathered in the plurality of sections in a predetermined order. The printing means prints information corresponding to a section A of the plurality of sections on the packing paper sheet at a time earlier by a time period necessary for dispensing medicine for a section n from the medicine preparing means than a timing of dispensing a medicine gathered in section A.

In another embodiment, the length of the path, through which the packing paper sheet passes between the printing means and the packing means, is set to be n times the length of the packing paper sheet necessary for packing medicine for one pack. Further, the medicine preparing means includes a plurality of sections and is configured to dispense the medicine gathered in each of the sections in a predetermined order. Thus, the medicine dispensed from section A is packed into the packing paper sheet, which the printing means prints at a time earlier by a time period necessary for dispensing a medicine for the section n (i.e., equal to n packs) from the medicine preparing means toward the packing means than a time for dispensing a medicine gathered in the section A. That is, a medicine to be packed is supplied to section A at a time prior to performing the print operation corresponding to section A to the packing paper sheet. Further, a timing when the medicine gathered in the section A is dispensed to the packing part and a timing when a section of a packing paper sheet with the information corresponding to section A printed thereon reaches the packing part are coincidental. Thus, the medicine dispensing device of the present invention performs printing to a packing paper sheet when medicine to be packed is supplied to section A. Further, it can easily monitor whether or not a medicine to be packed is exactly supplied and resolve the waste of a packing paper sheet resulting from an abnormality in feeding a medicine.

Further, in the above-described medicine dispensing device, a printing operation to the packing paper sheet may be performed by the printing means upon a condition that the medicine is fed into section A up to a time earlier by the time period necessary for dispensing a medicine for the section n from the medicine preparing means than the time of dispensing a medicine gathered in the section A of the plurality of sections in the medicine preparing means.

Further, in the above-described medicine dispensing device, the medicine is dispensed from the medicine dispensing means to section A at a time earlier by a time period more than the time period necessary for dispensing a medicine for the section n from the medicine preparing means than the time of dispensing a medicine gathered in section A in the medicine preparing means. Thus, the information corresponding to section A is printed on the packing paper sheet after the medicine is fed into section A. Thus, the medicine dispensing device can easily monitor whether or not a medicine to be packed is accurately packed and resolve the waste of a packing paper sheet resulting from an abnormality in feeding a medicine.

Further a medicine dispensing device includes a medicine dispensing means configured to dispense a medicine according to a prescription; a medicine preparing means configured to receive a medicine dispensed from the medicine dispensing means and to dispense the same at a predetermined time; a packing means configured to pack a medicine dispensed from the medicine preparing means into a packing paper sheet; a packing paper sheet feeding means configured to feed a packing paper sheet to the packing means; and a printing means configured to print predetermined information on a packing paper sheet fed from the packing paper sheet feeding means to the packing means. The printing means is disposed upstream of the packing means in a flow direction of the packing paper sheet fed by the packing paper sheet feeding means. The medicine preparing means includes a plurality of sections configured to gather the medicine for one pack dispensed from the medicine dispensing means respectively. The medicine preparing means is configured to dispense the medicines gathered in the plurality of sections in a predetermined order. A medicine is dispensed from the medicine dispensing means into one section A of the plurality of sections at a time earlier by a timing Z as early as a time period Y when the packing paper sheet fed by the packing paper sheet feeding means moves from a position corresponding to the printing means to the packing means, than a timing X when the medicine in the section A is dispensed from the medicine dispensing means toward the packing means. Information corresponding to section A is printed on the packing paper sheet at the time Z by the printing means.

In the above-described medicine dispensing device, medicine is fed into section A of the medicine preparing means at a time earlier than the time Z. Further, the information corresponding to section A is printed on the packing paper sheet by the printing means at the time Z as early as the time period Y when the packing paper sheet fed by the packing paper sheet feeding means moves from the position corresponding to the printing means to the packing means, from the timing X when the medicine in section A is dispensed from the medicine dispensing means toward the packing means. That is, the information corresponding to section A is printed on a portion of the packing paper sheet, which is used for packing the medicine in section A, at the same time as, or later than a time for feeding the medicine into section A. Thus, the medicine dispensing device can perform the printing operation to the medicine dispensing device after ascertaining that the medicine to be packed is exactly fed into the section. Further, the medicine dispensing device can easily monitor whether or not the medicine to be packed is exactly fed and resolve the waste of a packing paper sheet resulting from an abnormality in feeding a medicine.

Further, the printing operation to the packing paper sheet may be performed upon a condition that the medicine is fed into section A at a time earlier than the time Z.

With such configuration, if the printing operation to the packing paper sheet is not performed, it can be judged that the medicine is not fed exactly before the time Z. Thus, examining whether or not the medicine is exactly packed can become easy. Further, according to such configuration, if the medicine is not fed into the section A before the time Z, the printing operation to the packing paper sheet stops, thereby preventing the occurrence of the wasted packing paper sheet in advance.

Further, a print purporting that the medicine to be packed runs short may be made on the packing paper sheet by the printing means upon a condition that the medicine to be packed is not inputted to section A until the time earlier than the time Z.

According to such configuration, it is ascertained through only looking over the print made on the packing paper sheet that the medicine to be packed runs short. Thus, the examination work can be performed more easily and reliably.

Further, in the above-described medicine dispensing device, the medicine preparing means may include a section forming body having a plurality of sections arranged circumferentially; and a dispensing opening. The section forming body may be configured to move relative to the dispensing opening. When the section reaches a position corresponding to the dispensing opening, the medicine gathered in the section may be disposed through the dispensing opening.

Further, there is provided a medicine dispensing system that includes a main unit; one or more sub units; and a transfer device configured to connect the main unit and the sub units. The main unit includes the above-described medicine dispensing device. The sub unit includes a sub storage part configured to store and dispense a plurality kinds of medicines. The transfer device transfers the medicine dispensed from the sub storage part toward the main unit and feeds the medicine into the section provided in the medicine preparing means. The packing part of the main unit packs and dispenses the medicine.

The medicine dispensing system includes the main unit and the sub unit. It is configured such that the medicine dispensed in the sub unit is transferred to the medicine preparing means provided in the main unit and is packed and dispensed together with the medicine dispensed in the main unit by the packing means. However, in the medicine dispensing system, there is a possibility that an abnormality in dispensing medicine to the medicine preparing means occurs in the main unit. In addition, there is another possibility that an abnormality in dispensing medicine occurs in the sub unit, and that troubles take place during transferring a medicine to the medicine preparing means through the transfer device. As such, where the main unit is provided, the medicine dispensing system may have many factors associated with the abnormality in dispensing medicine to the medicine preparing means. Accordingly, similar to the above-described medicine dispensing device of the present invention, it is preferred that the above-described medicine dispensing system may have some means so that it can easily monitor whether a packing operation is accurately performed and prevent the packing paper sheet from wasting concomitantly with the abnormality in dispensing a medicine to the medicine preparing means.

Thus, the medicine dispensing system, which is provided based on such knowledge, employs the above-described medicine dispensing device as the main unit. Thus, the medicine dispensing system can prevent the packing paper sheet from being wasting in conjunction with an abnormality in dispensing a medicine to the medicine preparing means.

According to another embodiment, there can be provided a medicine dispensing device, which is configured to easily and accurately perform the examination work regarding whether or not packing medicine is accurately performed and to prevent the packing paper sheet from wasting even if the medicine to be dispensed becomes unready due to an abnormality in feeding a medicine to the packing part. Further, there can be provided a medicine dispensing system that includes such a medicine dispensing device.

Next, another embodiment will be explained hereinafter. There exists in the art a medicine dispensing device as disclosed in the below-mentioned reference Patent Document 4. A prior art medicine dispensing device includes a plurality of medicine feeding containers configured to store medicine in a storage part and dispense the medicine. Such a prior art medicine dispensing device is configured to dispense the medicine from each of the medicine feeding container by the amount corresponding to a prescription and pack the same. (see Patent Document 4: Japanese Laid-Open Patent Application No. 2001-276183).

The prior art medicine dispensing device is used in such a manner that each of the medicine feeding containers accommodates different kinds of medicines. However, the prior art medicine dispensing device is not configured to simply and accurately grasp characteristic data of each medicine feeding container, such as a date and time when the medicine feeding container is filled with medicines, a user filling the medicine feeding container, data related to medicines accommodated in the medicine feeding container, etc. Further, as the number of the medicine feeding containers increases with an increase in the kinds of medicines to be dealt with, such a tendency becomes strong. Thus, the relevant art requires a medicine dispensing device configured to simply and accurately grasp characteristic data of each medicine feeding container. Similarly, a medicine dispensing system, which is constructed by combining a plurality of medicine dispensing devices, is required to be configured to simply and accurately grasp characteristic data of each medicine feeding container.

Thus, to satisfy the aforementioned demand, it is an object of the present invention to provide a medicine dispensing device and a medicine dispensing system, which are configured to simply and accurately grasp characteristic data of each medicine feeding container.

In on embodiment a medicine dispensing device, which includes a medicine feeding container configured to store a medicine, the medicine feeding container including an information recordable medium; a container mounting part configured to mount the medicine feeding container; and a control means. The medicine is allowed to be dispensed by mounting the medicine feeding container to the container mounting part. The control means is configured to perform data communication for a characteristic data of the medicine feeding container with the information recordable medium of the medicine feeding container.

According to such configuration, there can be provided a medicine dispensing device, which can perform the data communication for the characteristic data between the control means and the medicine feeding container having the information recordable medium and can simply and accurately grasp the characteristic data.

Further, a medicine dispensing device, which is provided based on the same knowledge, may include a storage means configured to store and dispense medicine; and a control means configured to data-communicate with an information recordable medium. The storage means may include a plurality of attachable/detachable medicine feeding containers configured to store and dispense the medicine. The information recordable medium may be provided in some or all of the medicine feeding containers. A data communication for the characteristic data of the medicine feeding container may be performed between the information recordable medium of the medicine feeding container and the control means.

The above-described medicine dispensing device includes a storage means configured to store and dispense medicine; and a control means configured to data-communicate with the information recordable medium. Herein, the storage means includes a shelf or drum, in which a plurality of medicine feeding container are removably provided (for example, this may be referred to as a main storage part or a sub storage part in embodiments described below). Further, in the medicine dispensing device, a plurality of medicine feeding containers configured to store and dispense a medicine are removably provided in the storage means, which includes a shelf or drum. Herein, the medicine feeding container corresponds to a feeder container in the below-described embodiments and a container capable of dispensing the medicine accommodated therein. The above-described storage means, which includes the medicine feeding container, can dispense the medicine dispensed from the medicine feeding container for the purpose of packing the same.

With the above-described constitution, there can be provided a medicine dispensing device, which can data communicate with the control means with respect to the characteristic data of each of the medicine feeding containers with the information recordable medium and thus can simply and accurately grasp the characteristic data.

Further, the control means may be configured to data communicate with an operator information recordable medium recording an operator information specifying an operator. The operator information read from the operator information recordable medium through the data communication may be recorded into the information recordable medium.

According to such constitution, information on an operator, who performs tasks relevant to the medicine feeding container, such as filling the medicine feeding container with medicines, may be recorded into the information recordable medium of each of the medicine feeding containers.

Further, the medicine dispensing device may be configured to operate in a plurality of operation modes. The operation mode may change in a predetermined operation mode selected from a plurality of operation modes upon a condition that the data communication is allowed between the control means and the information recordable medium of the medicine feeding container removed from a container mounting part.

In the medicine dispensing device, the operation mode changes upon a condition that the data communication is allowed between the control means and the information recordable medium of the medicine feeding container. That is, it can be used as a trigger for changing the operation modes that the information recordable medium provided in each of medicine feeding container is allowed to data communicate with the control means. Thus, efforts required to change the operation modes can be minimized and misoperation can be prevented.

Further, the medicine dispensing device may include a mark reading means for reading an identification mark assigned to each of the kinds of medicine. The kinds of medicine may be specified by the control means based on the identification mark read by the mark reading means. Information on the kinds of medicine may be recorded into the information recordable medium through data communication between the control means and the information recordable medium of the medicine feeding container removed from the container mounting part.

According to such configuration, if the mark reading means reads the identification mark assigned to each of the kinds of medicine when filling the medicine feeding container removed from the container mounting part with a medicine, the information on the kind of such a medicine can be recorded into the information recordable medium of the medicine feeding container through data communication. Thus, according to the medicine dispensing device of one embodiment, when the medicine feeding container is filled with a medicine, the information on the kinds of medicine can be easily and reliably recorded into the information recordable medium.

Further, the medicine dispensing device according to the above-described invention may further include a cassette placing part configured to place the medicine feeding container removed from the container mounting part; and an interface means wiredly or wirelessly connected to the control means. When the medicine feeding container is placed on the cassette placing part, the information recordable medium of the medicine feeding container may be allowed to data communicate with the control means via the interface means.

According to such configuration, efforts required to enable the data communication between the information recordable medium and the control means after removing the medicine feeding container from the container mounting part can be minimally saved.

Further, the medicine dispensing device may further include an interface means wiredly or wirelessly connected to the control means. The interface means may be configured to read and record data as not in contact with the information recordable medium.

According to such configuration, efforts required to enable the data communication between the information recordable medium and the control means after removing the medicine feeding container from the container mounting part can be saved.

The above-described medicine dispensing device can data-communicate with the information recordable medium of each of the medicine feeding containers with respect to the characteristic data of the medicine feeding container. Thus, the medicine dispensing device can be configured to dispense medicines for purposes of packing the same even if the medicine feeding container accommodating a predetermined medicine is situated at any location in the storage means. However, some medicine of the plurality kinds of medicines is prone to bound, roll over, break or chip due to drop impact at a dispensing portion while dispensed from the medicine feeding container. In case of dealing with such a medicine, it must be dealt with in a different manner from those for other medicines (for example, adjustment in dispensing timing regarding bound or roll, means for mitigating drop impact, etc.) so as not to cause an abnormality in dispensing medicine. Accordingly, the medicine feeding container accommodating medicine having such a particular characteristics is attached to a location capable of resolving the foregoing matter.

Thus, based on such knowledge, medicines may be sequentially dispensed based on prescription data inputted to the control means. A plurality of the container mounting parts configured to mount the medicine feeding container may be provided. The control means may include a correspondence relationship storing part defining and storing a correspondence relationship between the plurality of container mounting parts and the medicine feeding container to be attached to the plurality of the container mounting parts; and a judging part. The judging part may be configured to perform an error judgment operation for judging the following states, by comparing the correspondence relation storing part and the characteristic data of the medicine feeding container obtained from the data communication with the information recordable medium of the medicine feeding container mounted on the container mounting part: a right mount state where the medicine feeding container is properly mounted on the container mount part coinciding with the correspondence relationship regulated in the correspondence relationship storing part; and an erroneous mount state where the medicine feeding container is erroneously mounted on the container mounting part against the correspondence relationship regulated in the correspondence relationship storing part. Dispensing the medicines may continue from other medicine feeding containers excluding a erroneously mounted medicine feeding container upon a condition that it is judged by the error judgment operation that there is an erroneously mounted medicine feeding container, and that a medicine accommodated in the erroneously mounted medicine feeding container is not medicine to be dispensed according to the prescription data. Dispensing the medicines may stop upon a condition that it is judged by the error judgment operation that there is the erroneously mounted medicine feeding container, and that a medicine accommodated in the erroneously mounted medicine feeding container is a medicine to be dispensed according to the prescription data.

In the medicine dispensing device of one embodiment, the judging part of the control means performs an error judgment operation. Based on the correspondence relationship between the container mounting part and the medicine feeding container, which is regulated in the correspondence relationship storing part, it can be judged whether the medicine feeding container is properly mounted or erroneously mounted on the container mounting part dedicated for said medicine feeding container. Further, in the medicine dispensing device, where the medicine feeding container is erroneously mounted and such a medicine feeding container does not accommodate a medicine to be dispensed, even if dispensing a medicine does not intentionally stop in other medicine feeding containers, problems such as bound, roll, breakage, chipping, etc. of medicines do not occur. And, stopping to dispense a medicine leads to loss of work efficiency. Accordingly, in the medicine dispensing device, where the erroneously mounted medicine feeding container does not accommodate a medicine to be dispensed, dispensing a medicine continues and the erroneously mounted medicine feeding container can be dismounted without stopping to dispense medicine. Accordingly, in the medicine dispensing device, even if the erroneously mounted medicine feeding container exists, the loss of work efficiency resulting therefrom can be minimized.

By contrast, where the erroneously mounted medicine feeding container exists and such a medicine feeding container accommodates a medicine to be dispensed, continuing to dispense a medicine causes the aforementioned problems such as bound, roll, breakage, chipping, etc. of medicines. Accordingly, in such a case, the medicine dispensing device of in some embodiments is configured to stop to dispense a medicine. Thus, according to the medicine dispensing device in some embodiments, it is possible to prevent medicines from being dispensed from the erroneously mounted medicine feeding container.

Further, it is preferred that medicines prone to bound, roll over, break or chip due to drop impact at the dispensing portion are dispensed at a side as low as possible.

Thus, in the above-described medicine dispensing device provided based on such knowledge, the storage means may include a plurality of the container mounting parts configured to mount the medicine feeding container. The container mounting parts may be vertically arranged. It may be judged through the error judgment operation whether a medicine feeding container to be mounted on a container mounting part provided below a predetermined height is erroneously mounted on a container mounting part provided in a position above the predetermined height.

According to such configuration, it can be prevented that the medicine feeding container accommodating the medicine to be dispensed at a side as low as possible (i.e. the aforementioned medicine causing problems such as bound, roll, breakage or chipping concomitantly with drop) is erroneously mounted on the container mounting part situated in a position above the predetermined height.

Further, the above-described medicine dispensing device provided based on the same knowledge, the container mounting part configured to mount the medicine feeding container may be disposed in each of a plurality of container mounting regions defined along a height direction. The correspondence relationship storing part may regulate the correspondence relationship between the container mounting part and the medicine feeding container to be attached to the container mounting part as a relationship relative to the container mounting region located at a height corresponding to an upper attachment limit of a medicine feeding container that is determined according to a kind of medicine. The erroneous mount state may be judged through the error judgment operation when a medicine feeding container is mounted on a container mounting part of a container mounting region locating beyond a container mounting region located at a height corresponding to the upper attachment limit. The right mount state may be judged through the error judgment operation when a medicine feeding container is mounted on a container mounting part of a container mounting region located at a height below the upper attachment limit.

In the medicine dispensing device, the correspondence relationship storing part can regulate the correspondence relationship between the container mounting regions and the height corresponding to the upper attachment limit of the medicine feeding container at a plurality of steps in view of that bound, roll, breakage or chipping occurs at what level concomitantly with drop. Further, the erroneous mount state can be judged through the error judgment operation based on such a regulation, when a medicine feeding container is mounted on a container mounting part of a container mounting region located upward beyond a container mounting region located at a height corresponding to the upper attachment limit. Thus, it is possible to prevent the occurrence of trouble such as an abnormality in dispensing a medicine resulting from the erroneous mount state.

Further, the control means may be configured to perform a search operation for searching and selecting a container mounting part, on which the medicine feeding container judged to be in the erroneous mount state through the error judgment operation must be mounted.

According to such configuration, it can be easily determined through the search operation on which container mounting part the erroneously mounted medicine feeding container must be mounted.

Further, a search condition may be determined based on the characteristic data of the medicine feeding container obtained by the data communication with the information recordable medium, which the medicine feeding container judged to be in the erroneous mount state through the error judgment operation includes.

According to such configuration, even if an operator does not separately input a search condition in the search operation, the container mounting part on which the erroneously mounted medicine feeding container must be mounted can be selected. Thus, convenience in the search operation can be enhanced.

In the above-described invention, the storage means may be configured to move each of the container mounting parts to an attachment/detachment work position where an attachment/detachment work of the medicine feeding container can be performed. The container mounting part selected through the search operation may be moved to the attachment/detachment work position.

In such a medicine dispensing device, a container mounting part located at a proper position, in which the erroneously mounted medicine feeding container must be properly attached, is moved to the attachment/detachment work position. Thus, convenience in attaching the medicine feeding container in the proper position can be enhanced.

Further, there is provided a medicine dispensing system that includes a main unit; one or more sub units; and a transfer device configured to connect the main unit and the sub units. The main unit includes the above-described medicine dispensing device. The sub unit includes a sub storage means configured to store and dispense a plurality kinds of medicines. The sub storage means includes a plurality of attachable/detachable medicine feeding containers configured to store and dispense a medicine. The transfer device transfers the medicine dispensed from the sub storage means toward the main unit. The medicine is dispensed in the main unit.

Such a medicine dispensing system includes the main unit and the sub unit. A plurality of medicine feeding containers are removably attached to both the storage means of the main unit and the sub storage means of the sub unit. Accordingly, the medicine dispensing system has a large number of medicine feeding containers and thus needs to be configured to even more easily and reliably control the characteristic data of each of the medicine feeding containers. Thus, the medicine dispensing system, which is provided based on such knowledge, includes the above-described medicine dispensing device as the main unit. As a result, the medicine dispensing system can simply and accurately grasp and control the characteristic data through the data communication between the control means provided in the main unit and the information recordable medium of each of the medicine feeding containers provided in the main unit and the sub unit.

Thus, there can be provided a medicine dispensing device and a medicine dispensing system, which are configured to simply and accurately grasp the characteristic data of each medicine feeding container.

The invention claimed is:

1. A medicine dispensing system comprising:
   a main unit;
   one or more sub units; and
   a transfer device configured to connect the main unit and the sub unit,
   wherein the main unit comprises:
      a main storage part configured to store and dispense a plurality of kinds of medicines; and
      a packing part configured to pack the medicine dispensed from the main storage part,
   wherein the sub unit comprises a sub storage part configured to store and dispense a plurality of kinds of medicines,
   wherein the transfer device transfers the medicine dispensed from the sub storage part toward the main unit and the packing part of the main unit packs and dispenses the medicine, and
   wherein the transfer device comprises:
      a pipe line for connecting the main unit and the sub unit; and
      a transfer means configured to suck or pressure-send the medicine existing in the pipe line from the sub unit toward the main unit.

2. The medicine dispensing system of claim 1, wherein the transfer device comprises:
   a forward pipe line connecting the main storage part and the sub storage part;
   an airflow producing means configured to produce an air flow within the forward pipe line from the sub unit toward the main unit; and
   a delivery part connected to the forward pipe line and configured to receive and dispense the medicine transferred from the sub unit through the forward pipe line at the main unit, and
   wherein the delivery part comprises a delivery container and a shutter, the forward pipe line being connected to the delivery container,
   wherein the delivery container comprises an internal space and a dispensing opening, the internal space configured such that the medicine transferred through the forward pipe line freely falls therein, the dispensing opening being disposed at a bottom portion of the delivery container to dispense the medicine,
   wherein the shutter is configured to be changed between a dispensing-allowed state where the medicine is allowed to be dispensed from the dispensing opening, and a dispensing-unallowed state.

3. A medicine dispensing system comprising:
   a main unit;
   one or more sub units; and
   a transfer device configured to connect the main unit and the sub unit,
   wherein the main unit comprises:
      a main storage part configured to store and dispense a plurality of kinds of medicines; and
      a packing part configured to pack the medicine dispensed from the main storage part,
   wherein the sub unit comprises a sub storage part configured to store and dispense a plurality of kinds of medicines,
   wherein the transfer device transfers the medicine dispensed from the sub storage part toward the main unit and the packing part of the main unit packs and dispenses the medicine,
   wherein the transfer device comprises:
      a forward pipe line connecting the main storage part and the sub storage part;
      an airflow producing means configured to produce an air flow within the forward pipe line from the sub unit toward the main unit; and
      a delivery part connected to the forward pipe line and configured to receive and dispense the medicine transferred from the sub unit through the forward pipe line at the main unit,
   wherein the delivery part comprises a delivery container and a shutter, the forward pipe line being connected to the delivery container,
   wherein the delivery container comprises an internal space and a dispensing opening, the internal space configured such that the medicine transferred through the forward pipe line freely falls therein, the dispensing opening being disposed at a bottom portion of the delivery container to dispense the medicine, and
   wherein the shutter is configured to be changed between a dispensing-allowed state where the medicine is allowed to be dispensed from the dispensing opening, and a dispensing-unallowed state.

4. The medicine dispensing system of claim 3, wherein the delivery container further comprises an exhaust hole for exhausting an airflow flowing in through the forward pipe line, the exhaust hole being positioned downwardly of a connection position between the delivery container and the forward pipe line.

5. The medicine dispensing system of claim 4, wherein the delivery container comprises:
   a side portion (A) connected to the forward pipe line; and
   a pair of opposed side portions (B, C) crossing to the side portions, and wherein the exhaust hole is provided at each of the pair of the side portions (B, C).

6. The medicine dispensing system of claim 3, wherein a buffer means configured to buffer an impact caused by collision of the medicine is provided within the delivery container,
   wherein the forward pipe line is connected to a side portion of the delivery container, and
   wherein the buffer means is disposed opposite to the side portion to which the forward pipe line is connected.

7. The medicine dispensing system of claim 3, wherein the shutter is configured to change an inclination thereof in the delivery container,
   wherein the shutter becomes in the dispensing-unallowed state when the medicine is not dispensed from the dispensing opening when the shutter is situated to obliquely traverse the internal space of the delivery container, and
   wherein the shutter becomes in the dispensing-allowed state when the medicine is dispensed from the dispensing opening by changing the inclination of the shutter from the dispensing-unallowed state.

8. The medicine dispensing system of claim 3, wherein the delivery container is configured to divide into two or more sub container bodies.

9. The medicine dispensing system of claim 3, wherein the delivery part further comprises an outer container,
   wherein the delivery container is disposed in the outer container, and wherein the delivery container includes an exhausting part for exhausting an airflow exhausted from the delivery container into the outer container outwardly of the outer container.

10. The medicine dispensing system of claim 9, wherein the exhausting part includes:
a primary filter; and
a secondary filter disposed downstream of the primary filter in an exhaust flow direction, the secondary filter having meshes finer than the primary filter.

11. The medicine dispensing system of claim 3, wherein the delivery container and the forward pipe line are connected to each other via a flexible joint pipe.

12. The medicine dispensing system of claim 3, wherein while a transfer operation of a medicine from the sub unit to the main unit is completed and thereafter a next transfer operation is done, the shutter becomes in the dispensing-allowed state and the airflow producing means operates, thereby performing a sweeping operation for sweeping a medicine transfer passage formed in the transfer device.

13. A medicine dispensing device for a sub unit for constructing a medicine dispensing system, the medicine dispensing system comprising:
a main unit and one or more sub units, the main unit and the sub unit being configured to dispense a predetermined medicine by a predetermined quantity; and
a transfer device, wherein a medicine dispensed in the sub unit is transferred by the transfer device to the main unit and is dispensed in the main unit, and
a medicine dispensing device comprising:
a sub storage part configured to store and dispense a plurality of kinds of medicines; and
a transfer device configured to transfer a medicine dispensed from the sub storage part toward the main unit,
wherein the transfer device comprises:
a pipe line for connecting the main unit and the sub unit; and
a transfer means configured to suck or pressure-send the medicine existing in the pipe line from the sub unit toward the main unit.

14. The medicine dispensing device of claim 13, wherein the transfer device includes:
a forward pipe line in communication with the sub storage part and being configured to be connected to the main storage part;
an airflow producing means for producing an airflow from the sub unit toward the main unit within the forward pipe line; and
a delivery part, the forward pipe line being connected to the delivery part, the delivery part being configured to receive and dispense the medicine transferred from the sub unit through the forward pipe line in the main unit,
wherein the delivery part comprises a delivery container and a shutter, the forward pipe line being connected to the delivery container,
wherein the delivery container comprises an internal space and a dispensing opening, the internal space configured such that the medicine transferred through the forward pipe line freely falls therein, the dispensing opening being disposed at a bottom portion of the delivery container to dispense the medicine,
wherein the shutter is configured to be changed between a dispensing-allowed state where the medicine is permitted to be dispensed from the dispensing opening, and a dispensing-unallowed state.

15. The medicine dispensing device of claim 13, wherein the transfer device comprises:
a forward pipe line in communication with the sub storage part and configured to be connected to a main storage part provided in the main unit;
an airflow producing means configured to produce an airflow from the sub unit toward the main unit within the forward pipe line;
an exhaust pipe line configured to be connected to the main storage part;
a suction and exhaust means configured to suck and exhaust through the exhaust pipe line from an inside portion of the main storage part to an outside portion thereof; and
a shutter configured to close at least one of the forward pipe line and the exhaust pipe line,
wherein the transfer device is configured to perform the following:
a medicine transferring operation for moving a medicine to the main storage part by operating the airflow producing means in a closed state where the forward pipe line is closed by the shutter; and
a medicine introducing operation for introducing medicine from the forward pipe line to the main storage part by operating the suction and exhaust means in a communication state where the shutter is opened and the forward pipe line, the exhaust pipe line and the main storage part are in communication with one another.

16. The medicine dispensing device of claim 13, wherein the transfer device comprises:
a forward pipe line in communication with the sub storage part and configured to be connected to a main storage part provided in the main unit;
an airflow producing means configured to produce an air flow within the forward pipe line from the sub unit toward the main unit; and
a delivery part connected to the forward pipe line and configured to receive and dispense the medicine transferred from the sub unit through the forward pipe line at the main unit, and
wherein the delivery part comprises a delivery container and a shutter, the forward pipe line being connected to the delivery container,
wherein the delivery container comprises an internal space and a dispensing opening, the internal space configured such that the medicine transferred through the forward pipe line freely falls therein, the dispensing opening being disposed at a bottom portion of the delivery container to dispense the medicine,
wherein the shutter is configured to be changed between a dispensing-allowed state where the medicine is allowed to be dispensed from the dispensing opening, and a dispensing-unallowed state.

17. The medicine dispensing device of claim 16, wherein the delivery container further comprises an exhaust hole for exhausting an airflow flowing in through the forward pipe line, the exhaust hole being positioned downwardly of a connection position between the delivery container and the forward pipe line.

18. The medicine dispensing device of claim 17, wherein the delivery container comprises:
a side portion (A) connected to the forward pipe line; and
a pair of opposed side portions (B, C) crossing to the side portions, and
wherein the exhaust hole is provided at each of the pair of the side portions (B, C).

19. The medicine dispensing device of claim 16, wherein a buffer means configured to buffer an impact caused by collision of the medicine is provided within the delivery container, wherein the forward pipe line is connected to a side portion of the delivery container, and wherein the buffer means is disposed opposite to the side portion to which the forward pipe line is connected.

20. The medicine dispensing device of claim 16, wherein the shutter is configured to change an inclination thereof in the delivery container, wherein the shutter becomes in the dispensing-unallowed state when the medicine is not dispensed from the dispensing opening when the shutter is situated to obliquely traverse the internal space of the delivery container, and wherein the shutter becomes in the dispensing-allowed state when the medicine is dispensed from the dispensing opening by changing the inclination of the shutter from the dispensing-unallowed state.

21. The medicine dispensing device of claim 16, wherein the delivery container is configured to divide into two or more sub container bodies.

22. The medicine dispensing device of claim 16, wherein the delivery part further comprises an outer container, wherein the delivery container is disposed in the outer container, and wherein the delivery container includes an exhausting part for exhausting an airflow exhausted from the delivery container into the outer container outwardly of the outer container.

23. The medicine dispensing device of claim 22, wherein the exhausting part includes:

a primary filter; and a secondary filter disposed downstream of the primary filter in an exhaust flow direction, the secondary filter having meshes finer than the primary filter.

24. The medicine dispensing device of claim 16, wherein the delivery container and the forward pipe line are connected to each other via a flexible joint pipe.

25. The medicine dispensing device of claim 16, wherein while a transfer operation of a medicine from the sub unit to the main unit is completed and thereafter a next transfer operation is done, the shutter becomes in the dispensing-allowed state and the airflow producing means operates, thereby performing a sweeping operation for sweeping a medicine transfer passage formed in the transfer device.

* * * * *